(12) United States Patent
Vankayalapati et al.

(10) Patent No.: US 10,682,358 B2
(45) Date of Patent: Jun. 16, 2020

(54) SUBSTITUTED 2, 3-DIHYDRO-1H-INDEN-1-ONE RETINOIC ACID-RELATED ORPHAN NUCLEAR RECEPTOR ANTAGONISTS FOR TREATING MULTIPLE SCLEROSIS

(71) Applicant: Arrien Pharmaceuticals LLC, Salt Lake City, UT (US)

(72) Inventors: Hariprasad Vankayalapati, Draper, UT (US); Venkatakrishnareddy Yerramreddy, Andhra Pradesh (IN)

(73) Assignee: Arrien Pharmaceuticals LLC, Salt Lake City, UT (US)

( * ) Notice: Subject to any disclaimer, the term of this patent is extended or adjusted under 35 U.S.C. 154(b) by 0 days.

(21) Appl. No.: 16/239,869

(22) Filed: Jan. 4, 2019

(65) Prior Publication Data
US 2019/0209574 A1    Jul. 11, 2019

Related U.S. Application Data

(63) Continuation of application No. 15/087,811, filed on Mar. 31, 2016, now Pat. No. 10,172,866, which is a
(Continued)

(51) Int. Cl.
| | |
|---|---|
| *C07C 323/22* | (2006.01) |
| *C07C 211/14* | (2006.01) |
| *C07D 211/38* | (2006.01) |
| *C07C 211/58* | (2006.01) |
| *C07D 213/50* | (2006.01) |
| *C07D 231/12* | (2006.01) |
| *C07D 241/04* | (2006.01) |
| *C07D 277/42* | (2006.01) |
| *C07D 295/116* | (2006.01) |
| *C07D 295/135* | (2006.01) |
| *C07D 401/10* | (2006.01) |
| *C07D 413/10* | (2006.01) |
| *C07D 413/12* | (2006.01) |
| *A61K 31/5375* | (2006.01) |
| *C07D 211/14* | (2006.01) |
| *C07D 211/58* | (2006.01) |
| *A61P 17/06* | (2006.01) |
| *A61P 35/00* | (2006.01) |
| *A61P 37/00* | (2006.01) |
| *A61K 31/451* | (2006.01) |
| *A61K 31/4545* | (2006.01) |
| *A61K 31/495* | (2006.01) |
| *A61K 31/496* | (2006.01) |
| *A61K 31/5377* | (2006.01) |
| *A61K 31/122* | (2006.01) |

(Continued)

(52) U.S. Cl.
CPC ........ *A61K 31/5375* (2013.01); *A61K 31/122* (2013.01); *A61K 31/255* (2013.01); *A61K 31/44* (2013.01); *A61K 31/445* (2013.01); *A61K 31/451* (2013.01); *A61K 31/4545* (2013.01); *A61K 31/495* (2013.01); *A61K 31/496* (2013.01); *A61K 31/5377* (2013.01); *A61P 17/06* (2018.01); *A61P 35/00* (2018.01); *A61P 37/00* (2018.01); *C07C 323/22* (2013.01); *C07D 211/14* (2013.01); *C07D 211/38* (2013.01); *C07D 211/58* (2013.01); *C07D 213/50* (2013.01); *C07D 231/12* (2013.01); *C07D 241/04* (2013.01); *C07D 277/42* (2013.01); *C07D 295/116* (2013.01); *C07D 295/135* (2013.01); *C07D 401/10* (2013.01); *C07D 413/10* (2013.01); *C07D 413/12* (2013.01); *C07C 2602/08* (2017.05)

(58) Field of Classification Search
CPC ... C07C 323/22; C07D 211/14; C07D 211/38; C07D 211/58; C07D 213/50; C07D 531/12; C07D 241/04; C07D 277/42; C07D 295/116; C07D 295/135; C07D 401/10; C07D 413/10; C07D 413/12
See application file for complete search history.

(56) References Cited

U.S. PATENT DOCUMENTS

| | | | |
|---|---|---|---|
| 6,252,081 | B1 | 6/2001 | Iimura |
| 6,482,838 | B2 | 11/2002 | Pratt |

(Continued)

FOREIGN PATENT DOCUMENTS

| | | |
|---|---|---|
| EP | 0 296 560 A2 | 12/1988 |
| EP | 1 468 684 A1 | 10/2004 |

(Continued)

OTHER PUBLICATIONS

Ali, R. et al. (2013). Drugs in development for relapsing multiple sclerosis. Drugs 73(7): 625-650. PMID: 23609782.
CAS Registry No. 1424355-52-1; STN Entry Date Mar. 15, 2013.
CAS Registry No. 1424358-33-7; STN Entry Date Mar. 15, 2013.
CAS Registry No. 1424358-86-0; STN Entry Date Mar. 15, 2013.
CAS Registry No. 1424359-29-4; STN Entry Date Mar. 15, 2013.
CAS XP-002768234, Lee, Hiok-Huang, "Synthesis of the mangostins", Database accession No. 1982:527356 CAPLUS (1982).
Extended Search report for EP Application No. 14844892.1, 10 pages, dated Mar. 29, 2017.

(Continued)

*Primary Examiner* — Rebecca L Anderson
(74) *Attorney, Agent, or Firm* — Foley & Lardner LLP

(57) ABSTRACT

The present invention is directed to compounds, their synthesis, and their use as antagonists, inverse agonists, modulators and or inhibitors of the Retinoic acid-related orphan nuclear receptor γt (RORγt)/RORγ. The compounds of the present invention are useful for modulating RORγt)/RORγ activity and for treating diseases or conditions mediated by RORγt)/RORγ such as for example, disease states associated with immunopathology of human autoimmune diseases such as Multiple Sclerosis (MS), Rheumatoid Arthritis (RA), Inflammatory Colitis, Psoriasis, COPD, Pain, Obesity, Diabetes, Dyslipidemia, Osteoporosis, Asthma, Neurodegenerative diseases and Cancer.

17 Claims, 8 Drawing Sheets

Related U.S. Application Data continuation of application No. 14/469,900, filed on Aug. 27, 2014, now Pat. No. 9,359,315.

(60) Provisional application No. 61/876,099, filed on Sep. 10, 2013.

(51) Int. Cl.
*A61K 31/255* (2006.01)
*A61K 31/44* (2006.01)
*A61K 31/445* (2006.01)

(56) References Cited

U.S. PATENT DOCUMENTS

| | | |
|---|---|---|
| 7,087,599 B2 | 8/2006 | Parker et al. |
| 7,151,196 B2 | 12/2006 | Wilkening et al. |
| 9,359,315 B2 | 6/2016 | Vankayalapati et al. |
| 2002/0035129 A1 | 3/2002 | Pratt |
| 2003/0027840 A1 | 2/2003 | Parker et al. |
| 2006/0094779 A1 | 5/2006 | Wilkening et al. |
| 2008/0306271 A1 | 12/2008 | Neu et al. |

FOREIGN PATENT DOCUMENTS

| | | |
|---|---|---|
| JP | 64-079151 A | 3/1989 |
| JP | 02-169569 A | 6/1990 |
| JP | 2003-525903 A | 9/2003 |
| JP | 2003-531855 A | 10/2003 |
| JP | 2008-518960 A | 6/2008 |
| WO | WO-01/82923 A1 | 11/2001 |
| WO | WO-03/061658 A1 | 7/2003 |
| WO | WO-2006/050399 A2 | 5/2006 |
| WO | WO-2008/057309 A2 | 5/2008 |
| WO | WO-2012/158784 A2 | 11/2012 |

OTHER PUBLICATIONS

Fillion, E. et al., "Meldrum's Acids as Acylating Agents in the Catalytic Intramolecular Friedel-Crafts Reaction" Journal of Organic Chemistry, vol. 70, No. 4, pp. 1316-1327, 2005.
Fujita-Sato, S., (2011). Structural basis of digoxin that antagonizes RORgamma t receptor activity and suppresses Th17 cell differentiation and interleukin (IL)-17 production. J. Biol. Chem. 286(36), 31409-31417. PMID: 21733845.
Glass, C. K. And K. Saijo (2010). Nuclear receptor transrepression pathways that regulate inflammation in macrophages and T cells. Nat Rev Immunol 10(5): 365-376. PMID: 20414208.
Haworth, R. D. et al., "Galloflavin. Part I" Journal of the Chemical Society, pp. 1583-1589, 1952.
Hu, Y., et al. (2011). The IL-17 pathway as a major therapeutic target in autoimmune diseases. Ann NY Acad Sci 1217: 60-76. PMID: 21155836.
Huh, J.R, et al., (2013) Identification of Potent and Selective Diphenylpropanamide RORγ Inhibitors. ACS Med. Chem. Lett. 4 (1), 79-84.
International Search Report and Written Opinion for corresponding PCT Application No. PCT/US2014/053227, dated Mar. 25, 2015.
Isono F. et al., (2014) Inhibiting RORyt/Th17 axis for autoimmune disorders. Drug Discov Today. 19 (8): 1205-1211. PMID: 24792721.
Ivanov, I. I., et al. (2006). The orphan nuclear receptor RORgammat directs the differentiation program of proinflammatory IL-17 T helper cells. Cell 126(9): 1121-1133. PMID: 16990136.
Jin, L. et al., (2010). Structural basis for hydroxycholesterols as natural ligands of orphan nuclear receptor RORgamma. Mol Endocrinol 24(5): 923-929.
Kallaur, et al (2013). Cytokine profile in relapsing remitting multiple sclerosis patients and the association between progression and activity of the disease. Mol Med Rep 7(3): 1010-1020. PMID: 23292766.

Kamenecka, T. M, et al., (2013). Synthetic modulators of the retinoic acid receptor-related orphan receptors. Med. Chem. Commun. 4, 764-776.
Khan, P. M. et al., (2013). Small molecule amides as potent ROR-gamma selective modulators. Bioorganic & Medicinal Chemistry Letters 23(2): 532-536. PMID: 23232056.
Kieseier, B. C. and Hartung, H. (2003). Multiple paradigm shifts in multiple sclerosis. Curr Opin Neurol 16(3): 247-252. PMID: 22583433.
Kipp, M. van der Valk, P., Amor, S. (2012). Pathology of multiple sclerosis. CNS Neurol Disord—Drug Targets 11(5): 506-517. PMID: 12858058.
Kryczek, I., et al. (2007). Cutting edge: Th17 and regulatory T cell dynamics and the regulation by IL-2 in the tumor microenvironment. J. Immunol. 178, 6730-6733. PMID: 17513719.
Kumar, N. et al., (2012). Identification of SR2211: a potent synthetic RORgamma-selective modulator. ACS Chem Biol 7: 672-677. PMID: 22292739.
Kumar, N. st al., (2010). The benzenesulfoamide T0901317 [N-(2,2,2-trifluoroethyl)-N-[4-[2,2,2-trifluoro-1-hydroxy-1-(trifluoromethyl)ethyl]phenyl] benzenesulfonamide] is a novel retinoic acid receptor-related orphan receptor-alpha/gamma inverse agonist. Mol Pharmacology 77: 228-236. PMID: 19887649.
Lee, J. and Cua, D., (2014) The Emerging Landscape of RORγt Biology. Immunity, 40 (4) 451-452.
Lopez-Diego, R. S. and H. L. Weiner (2008). Novel therapeutic strategies for multiple sclerosis—a multifaceted adversary. Nat Rev Drug Discov 7(11): 909-925. PMID: 18974749.
Office Action for corresponding AU Application No. 2014318178, 8 pages, dated Jun. 23, 2016.
Office Action for corresponding CA Application No. 2916419, 3 pages, dated May 24, 2017.
Office Action for corresponding JP Application No. 2016-54200, 9 pages, dated Feb. 7, 2017, with English translation.
Pottgen, J. Dziobek, I. Reh, S. Heesen, C. Gold, S. M. (2013). Impaired social cognition in multiple sclerosis. JNeurol Neurosurg Psychiatry 84(5): 523-528. PMID: 23315621.
Pubchem. Compound Summary for CID 10451490. Create Date: Oct. 25, 2006. (retrieved on Mar. 5, 2015]. Retrieved from the Internet. <URL: https://pubchem.ncbi.nlm.nih.gov/compound/10451490>.
Pubchem. Compound Summary for CID 22988182. Create Date: Dec. 5, 2007. [retrieved on Mar. 4, 2015]. Retrieved from the Internet. <URL: https://pubchem.ncbi.nlm.nih.gov/compound/22988182>.
Ransohoff, R. M. (2012). Animal models of multiple sclerosis: the good, the bad and the bottom line. Nat Neurosci 15(8): 1074-1077. PMID: 22837037.
Rauen, T. et al., (2012). A novel isoform of the orphan receptor RORgammat suppresses IL-17 production in human T cells. Genes Immun 13: 346-350. PMID: 22237416.
Rolf W. Hartmann, et al., "Aromatase Inhibitors, Syntheses and Structure-Activity Studies of Novel Pyridyl-Substituted Indanones, Indans, and Tetralins" Journal of Medicinal Chemistry vol. 37, No. 9, pp. 1275-1281, 1994.
Sheridan, C. (2013). Footrace to clinic heats up for T-cell nuclear receptor inhibitors. Nature Biotechnology 31(5): 370. PMID: 23657373.
Skepner J, et al., (2014) Pharmacologic inhibition of RORγt regulates Th17 signature gene expression and suppresses cutaneous inflammation in vivo. J Immunol. 192(6):2564-2575. PMID: 24516292.
Solt, L. A., et al., (2011). Suppression of TH17 differentiation and autoimmunity by a synthetic ROR ligand. Nature 472, 491-494. PMID: 21499262.
Steinman, L. (1996). Multiple sclerosis: a coordinated immunological attack against myelin in the central nervous system. Cell 85, 299-302. PMID: 8616884.
Tesmer, L. A. et al., (2008). Th17 cells in human disease. Immunol Rev 223: 87-113. PMID: 18613831.
Vermersch, P., et al. (2012). Masitinib treatment in patients with progressive multiple sclerosis: a randomized pilot study. BMC Neurol 12: 36. PMID: 22691628.
Wang, Y., et al. (2010). Modulation of retinoic acid receptor-related orphan receptor alpha and gamma activity by 7-oxygenated sterol ligands. Journal of Biological Chemistry 285(7): 5013-5025. PMID: 19965867.

(56) References Cited

OTHER PUBLICATIONS

William Henry Perkin, CCXXII—Some Derivatives of Ortho-Vanillin, Journal of the Chemical Society, vol. 105 No. 0, pp. 2376-2392 (Jan. 1, 1914) XP055355002, GB ISSN:0368-1645, DOI: 10.1039/CT9140502376.

Wingerchuk D. M, and Carter J. L. (2014). Multiple sclerosis: current and emerging disease-modifying therapies and treatment strategies. Mayo Clin Proc. 89 (2):225-240. PMID: 24485135.

Xiao S., et al., (2014). Small-molecule RORgammat antagonists inhibit T helper 17 cell transcriptional network by divergent mechanisms. Immunity. 40 (4): 477-489. PMID: 24745332.

Yamamura, S. et al., "Studies in the Structure-Activity Relationship of Adrenergic Mimetic Benzylamine Derivatives. IV. 1) Aryl-substituted 1-Aminotetralins and 1-Aminoindans" Chemical & Pharmaceutical Bulletin, vol. 26, No. 12, pp. 3613-3623, 1978.

Yoshiyuki Kawakami, et al. , The rationale for E2020 as a Potent Acetylcholinesterase Inhibitor, Bioorganic & Medicinal Chemistry, vol. 4, No. 9, 1429-1446 (1996).

Zhang W, et al., (2012). Increasing human Th17 differentiation through activation of orphan nuclear receptor retinoid acid-related orphan receptor γ(RORγ) by a class of aryl amide compounds. Mol Pharmacol. 82 (4):583-590. PMID: 22700697.

SUBSTITUTED 2, 3-DIHYDRO-1H-INDEN-1-ONE RETINOIC ACID-RELATED ORPHAN NUCLEAR RECEPTOR ANTAGONISTS FOR TREATING MULTIPLE SCLEROSIS

CROSS-REFERENCE TO RELATED APPLICATIONS

This application is a continuation of U.S. patent application Ser. No. 15/087,811 filed Mar. 31, 2016, which is a continuation of U.S. patent application Ser. No. 14/469,900 filed Aug. 27, 2014 which claims the benefit of U.S. Provisional Patent Application 61/876,099 filed Sep. 10, 2013, the entireties of which are incorporated herein by reference

FIELD OF INVENTION

The present invention is directed to compounds, their synthesis, and their use as antagonists, inverse agonists, modulators and or inhibitors of the Retinoic acid-related Orphan nuclear Receptor γt (RORγt)/RORγ. In particular, the present invention is directed to substituted 2, 3-dihydro-1H-inden-1-one compounds that modulate (RORγt)/RORγ. The compounds of the present invention are useful for modulating (RORγt)/RORγ activity and for treating diseases or conditions mediated by (RORγt)/RORγ such as, for example, disease states associated with immunopathology of human autoimmune diseases such as Multiple Sclerosis (MS), Rheumatoid Arthritis (RA), Inflammatory Colitis, Psoriasis, Chronic Obstructive Pulmonary Disease (COPD), Pain, Obesity, Diabetes, Dyslipidemia, Osteoporosis, Asthma, Neurodegenerative diseases and Cancer.

BACKGROUND OF THE INVENTION

Multiple Sclerosis (MS) is an autoimmune inflammatory demyelinating disease of the CNS (central nervous system) that damages the fatty myelin sheaths around the axons of the brain and spinal cord. This damage, destruction, and loss or scarring of the myelin sheaths (sclerosis or plaques) results in a broad spectrum of symptoms. MS is a chronic, disabling disease that affects about 400,000 people in the United States and nearly 2.5 million people worldwide. MS substantially and adversely affects the quality of life of each individual, with symptoms that include loss of muscle control and strength, fatigue, weakness, loss of vision, spasticity, balance, sensation, bladder and bowel problems, numbness, vision loss, tremors, and adverse mental function such as depression. In the United States alone MS care is estimated to cost nearly $13 billion per year.

Inflammatory cytokines and its receptors have an important role in the progression of MS lesions, and pro- and anti-inflammatory cytokine levels have been found to correlate with changes in MS disease activity. Currently, available treatments usually focus on strategies to treat relapses (oral prednisone and i.v. methylprednisolone), manage symptoms and reduce the progress of the disease with Disease Modifying Drugs (DMDs). It includes relapsing-remitting MS (RRMS) drugs such as Immunomodulatory (β-interferons) therapeutics (Avonex, Betaseron, Rebif and Extavia), Monoclonal Antibodies (Tysabri, Lemtrada), other immunosuppressants (Mitoxantrone), Copaxone (glatiramer acetate injection) and oral agents; Teriflunomide, Fingolimod but none of these medications is a cure or prevent recurring symptoms. In addition to existing oral DMDs such as Fingolimod, and recently approved Tecfidera (BG-12 or Dimethyl Fumarate) and other experimental agents yet to be approved are in Phase III of clinical development such as Laquinimod, and Masitinib (oral immunomodulators) have been reported to cause opportunistic infections, antibody stimulation, liver and kidney toxicities. Target specific inhibitors or antagonists should promote myelination, neuronal repair, neuroprotection. Inhibiting the disease and halting neurodegeneration should eliminate many of these adverse events.

Presently, oral DMT drugs such as Fingolimod, Cladribine, and Tecfidera—as well as about 46 other experimental agents in various stages of clinical development such as Laquinimode, and Masitinib—have been reported to cause serious adverse events including opportunistic infections, antibody stimulation, and liver and kidney toxicities. Thus, there is a continuing need for effective MS drugs with better toxicity profiles. Target specific inhibitors or antagonists should promote myelination, neuronal repair, halting neurodegeneration, and should eliminate many of these adverse events.

The evidence supporting the risk-benefit profiles for available agents including emerging mAb (Alemtuzumab, Ocrelizumab and Daclizumab) DMTs is yet to fully emerge. Many of these approved and experimental agents yet to be approved create serious adverse events including opportunistic infections, antibody stimulation, and liver and kidney toxicities. Therefore, MS is still a significant target for innovative therapies that can have immunotherapeutic and/or neuroprotective effects on the disease. This opportunity has strengthened our research focus on clinically relevant RORγt, as an attractive target for the treatment of MS. RORγt as a nuclear hormone receptor that is a key regulator of T helper type 17 (Th17) cell differentiation. Th17 cells are normally produced in response to infection, but have been linked to the development of autoimmune diseases. A few pre-clinical stage lead RORγt and RORγ inverse agonists have been reported. For example, azole-type fungicides, T0901317, SR1001, ursolic acid, VPR-66, digoxin, and hexafluoro-substituted sulphamoyl thiazoles had efficacy in autoimmune encephalomyelitis (EAE) mice models. At least dozen companies; Lycera/Merck, Karo Bio/Pfizer, Phenex/J&J, Orphagen/JT (OR-1050/T0901317, 5 µM), Tempero/GSK (TMP-778, GSK-805), Exelixis/BMS, Teijin/Amgen, Cognoci (COG112), Innovimmune (INV-17), Visionary, 4SC Discovery and Genentech, have small molecule RORγt programs in preclinical stage of development. Identification of brain penetrant, RORγt specific antagonists that rescue myelin destruction, restore the axons of the brain and spinal cord following oral administration will be a significant approach for developing MS therapeutics. The substituted 2, 3-dihydro-1H-inden-1-one class of compounds claimed in Formula I discovered as potent, brain penetrant, orally available RORγt antagonist, and a small molecule candidate compounds as new drug entities for the treatment of such diseases claimed.

The present invention includes small molecule antagonists targeting Retinoic acid-related orphan nuclear receptor γt (RORγt)/RORγ. RORγt is the key transcription factor and is the master regulator of human Th17 (T helper 17) cells, a unique subset of CD4$^+$T cells. RORγt controls cellular differentiation, function and InterleukinIL-17 (IL-17 producing T-helper lymphocytes) release by Th17 cells and helps mediate the immunopathology of human autoimmune diseases such as Multiple Sclerosis (MS), Rheumatoid Arthritis (RA), Inflammatory Colitis, Psoriasis, COPD, Pain, Obesity, Diabetes, Dyslipidemia, Osteoporosis, Asthma, Neurodegenerative diseases and Cancer.

In addition, the substituted 2, 3-dihydro-1H-inden-1-one Retinoic acid-related orphan nuclear receptor γt (RORγt)/RORγ antagonists of the present invention may be useful in the treatment of multiple cancers, includes gastric, colon cancers, chronic myelogenic leukemia (CML), acute myelogenic leukemia (AML), squamous cell, and bladder carcinomas, medulloblastoma, hepatocellular carcinoma, multiple myeloma, bladder, glioblastoma multiform (GBM), breast and ovarian cancers, Ewing's sarcoma and bone associated cancer diseases. The methods of treatment of the claims of Formula I and its associated claims in the application comprise of administering a safe and effective dose of a compounds according to Formula I or a pharmaceutically-acceptable salt, formulations thereof to a human patients.

Induction of autoimmune MS conditions in mice using Myelin Oligodendrocyte Glycoprotein (MOG) or Proteolipid Protein (PLP) immunization causes RORγt activation and differentiation of Th17 cells that recruit proinflammatory cytokines IL-17A (IL-17), IL-17F, IL-21 and IL-22 leads to sclerotic myelin and damaged oligodendrocytes. Mice with RORγt deficient T cells have attenuated disease and lack tissue-infiltrating Th17 cells. Hence, RORγt is a key regulator of immune homeostasis and is a potential therapeutic target for Multiple Sclerosis. Using proprietary internal company proprietary Fragment-Field Drug Design (FFDD) based technology and uniquely designed specific RORγt isoform assays a novel, potent small molecule substituted 2, 3-dihydro-1H-inden-1-one series and are specific RORγt antagonist (inverse agonist) and demonstrated its RORγt activity in an RORγt-activated IL-17A Prom/LUC-Porter assay in HEK 293 cells, in IL-17 release from CD4$^+$T cells assays, as well as inhibition of IL-17 production in vivo in BALB/c mouse experiments and the effect of substituted 2, 3-dihydro-1H-inden-1-one series of Formula I compounds on $MOG_{35-55}$ induced in C57/BL6 or BALB/c mice, $PLP_{139-151}$ (Proteolipid Protein) induced in SJL/J mice and Theiler's Murine Encephalitis Virus-Induced Demyelinating Disease (TMEV-IDD) in female BALB/c mice induced Acute/Relapsing EAE model in female SJL/J mice is claimed in this application.

SUMMARY OF THE INVENTION

The present invention concerns compounds active on Nuclear hormone receptor superfamily, specifically RORγt and in general, including RORα, -β, and -γ (NR1F1-3 or RORA-C), its two isoforms, γ1 and γ2 (RORγt/ROR-γT) and any mutations of this Nuclear hormone receptor superfamily and the use thereof in treating disease and conditions associated with regulation of the activity of these Nuclear hormone receptor superfamily. More specifically the invention concerns compounds of Formula I as described below. Thus the invention provides novel use of compounds for therapeutic methods involving inhibition and or modulation of RORα, -β, and -γ specifically RORγt as novel compounds that can be used for the therapeutic methods involving modulation of the immunopathology of human autoimmune diseases such as Multiple Sclerosis (MS), Rheumatoid Arthritis (RA), Inflammatory Colitis, Psoriasis, COPD, Pain, Obesity, Diabetes, Dyslipidemia, Osteoporosis, Asthma, Neurodegenerative diseases and Cancer.

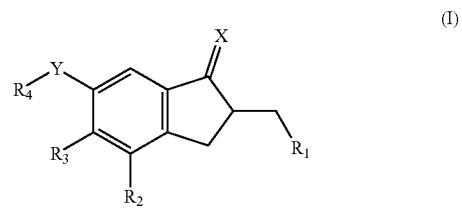

The present invention relates to compounds according to Formulas I: to pharmaceutically acceptable composition, salts thereof, their synthesis and their use as RORgt and RORg inhibitors including such compounds and methods of their use in the treatment of various immunopathology of human autoimmune diseases such as Multiple Sclerosis (MS), Rheumatoid Arthritis (RA), Inflammatory Colitis, Psoriasis, COPD, Pain, Obesity, Diabetes, Dyslipidemia, Osteoporosis, Asthma, Neurodegenerative diseases and Cancer.

DETAILED DESCRIPTION OF THE INVENTION

Figure 1:
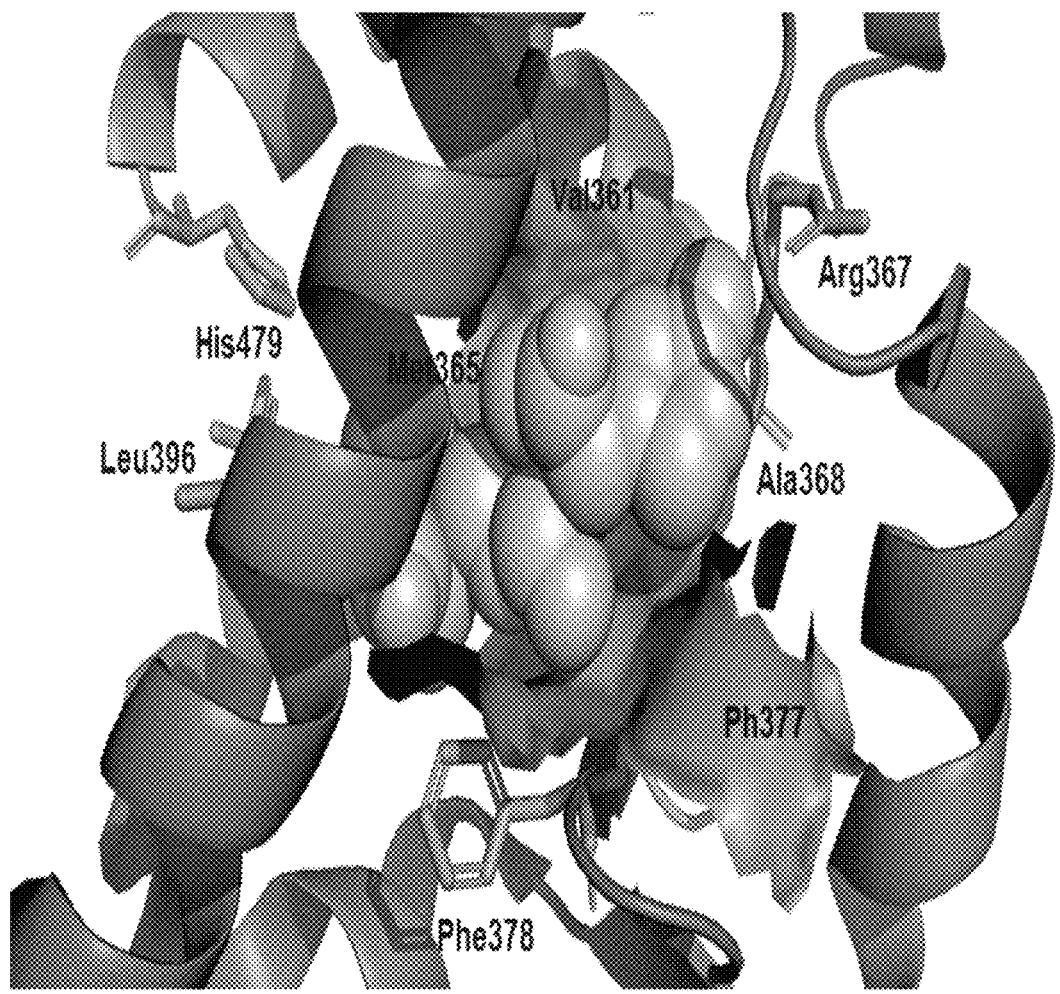
FIG. 1: X-ray crystal structure RORγ in complex with substituted 2, 3-dihydro-1H-inden-1-one containing RORγt antagonist.

Compounds of the present invention are described by Formula I:

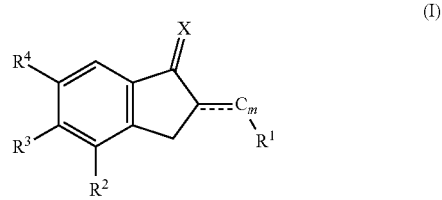

or pharmaceutically acceptable salts thereof, wherein:
X is O or S;
R$^1$ is

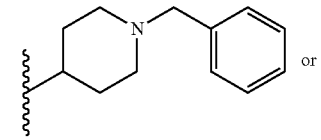 or

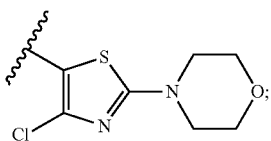

or

R¹ is $C_{1-4}$alkyl optionally substituted with 1-6 independent halo substituents; or R¹ is phenyl, pyridinyl, or pyrazolyl, each optionally substituted with 1-5 independent halo, trifluoromethyl, (trifluoromethyl)thio, trifluoromethoxy, 1,1,1,3,3,3,-hexafluoro-2-hydroxypropan-2-yl,

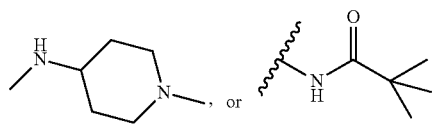

substituents;

m is 0 or 1;

the dotted line indicates an optional double bond when m=1;

R² or R³ each independently is halo, —OH, —CN, —OCH₃, —O—S(O)₂CH₂CH₃,

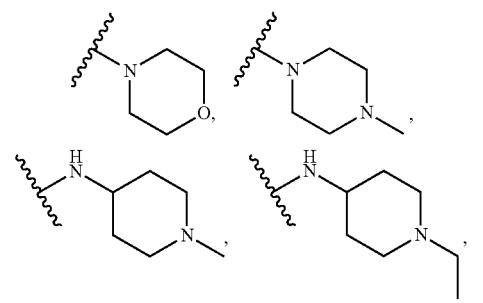

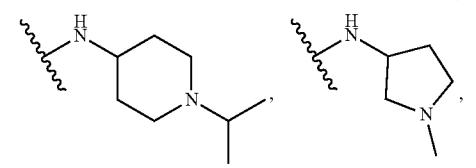

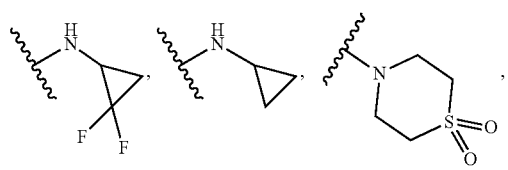

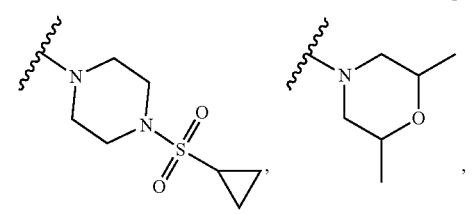

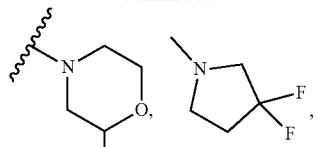

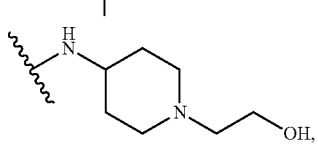

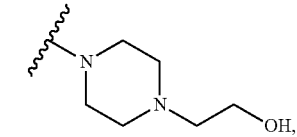

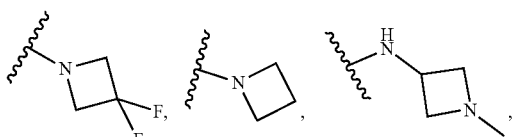

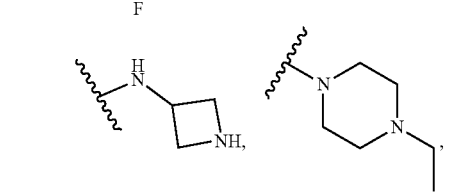

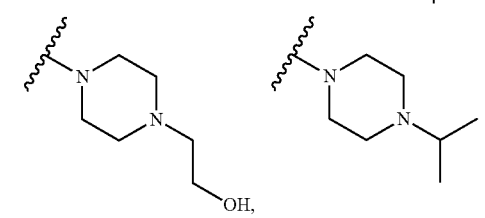

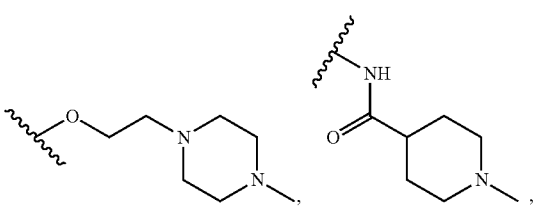

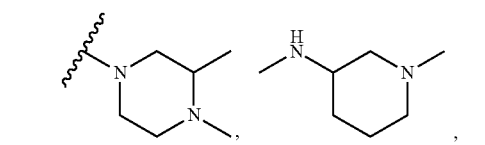

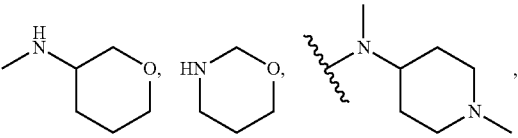

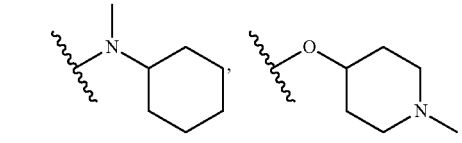

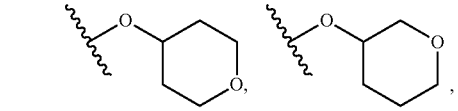

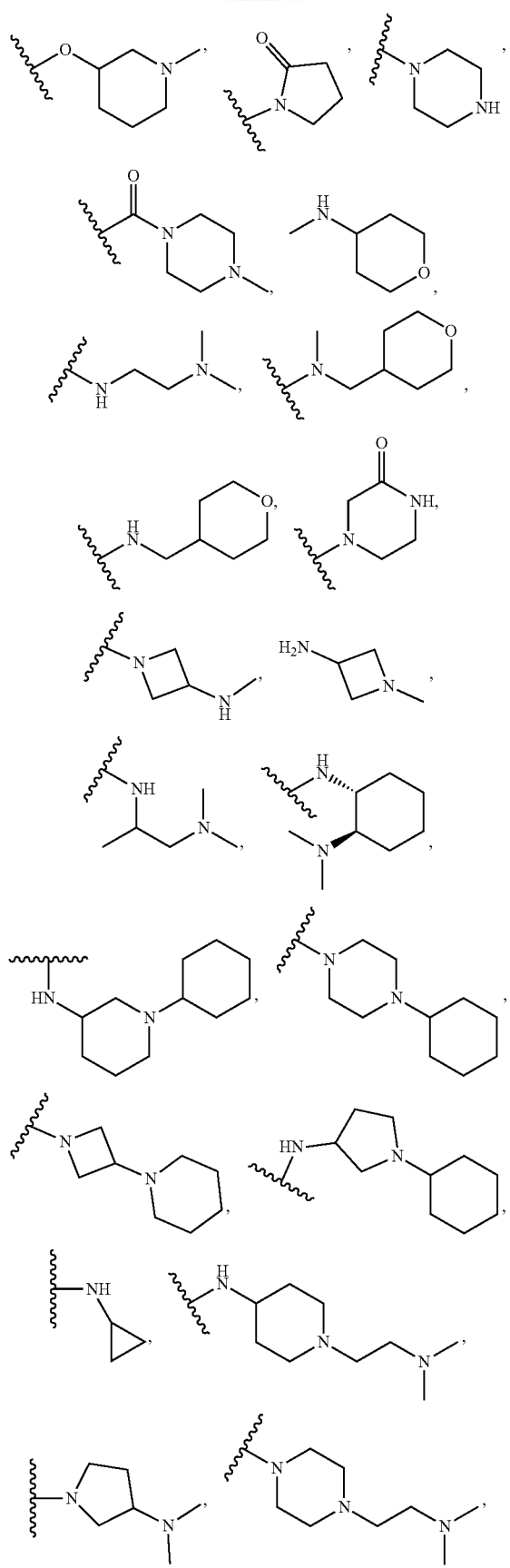
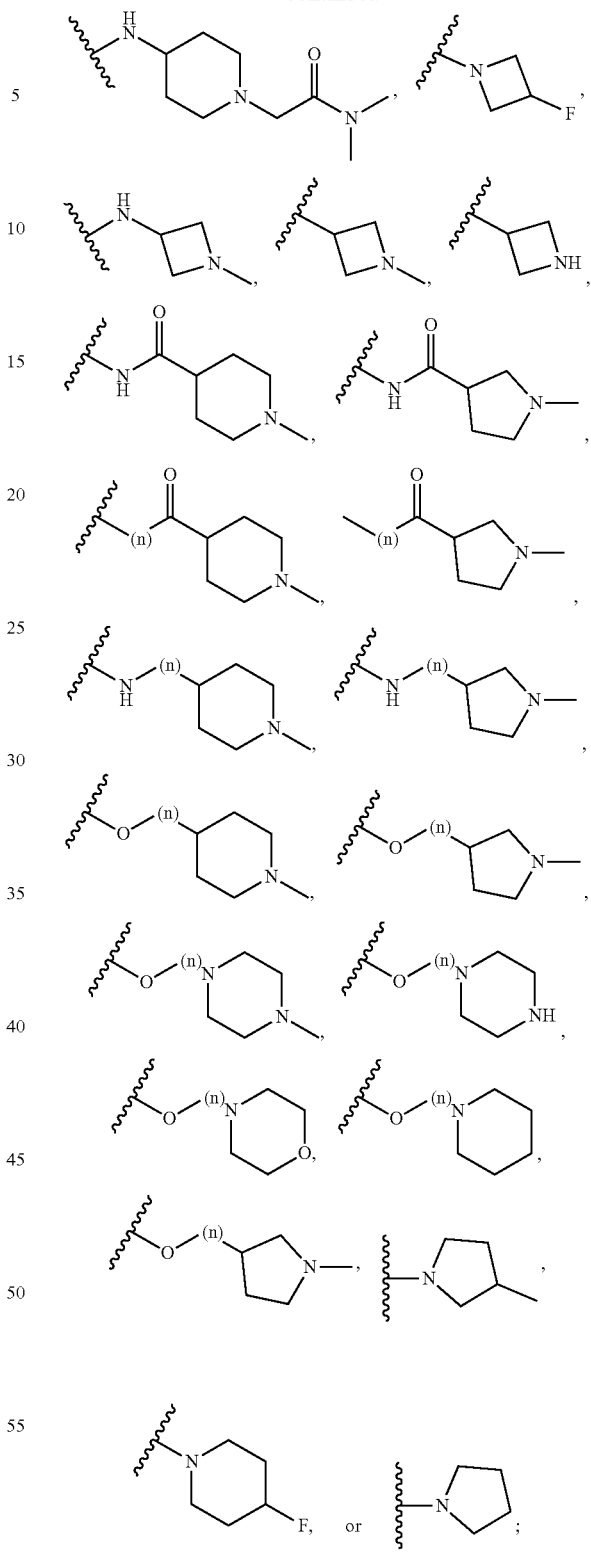
or $R^2$ or $R^3$ each independently is phenyl optionally substituted with 0-5 independent halo, trifluoromethoxy substituents;
n is 2 or 3 carbon chain; and
$R^4$ is H, OH, $OCH_3$, or $-O-S(O)_2CH_2CH_3$.

Compounds of the present invention can be made using the compounds

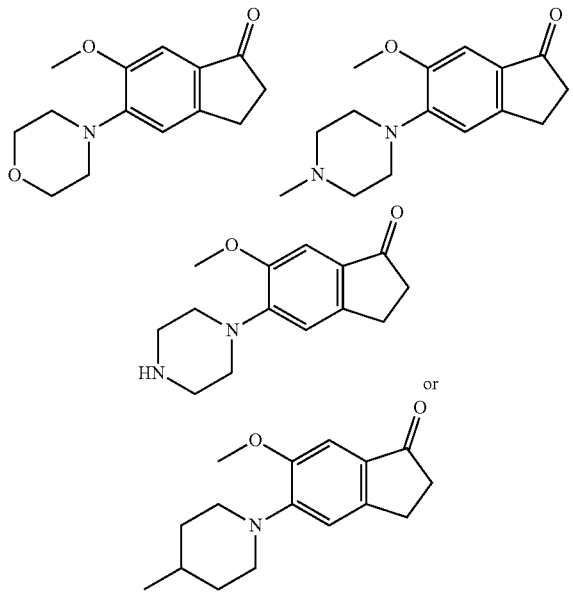

as an intermediate. Accordingly, the present invention includes these compounds.

In an aspect of the invention, compounds of the present invention are described by Formula (I) and pharmaceutically acceptable salts thereof, wherein X is O, and the other variables are as defined above for Formula (I).

In an embodiment of the aspect of the invention, compounds of the present invention are described by Formula (I) and pharmaceutically acceptable salts thereof, wherein
X is O, R¹ is

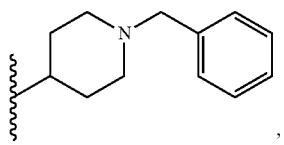 [SMILES: *C1CCN(Cc2ccccc2)CC1]

and the other variables are as defined above for Formula (I).

In another embodiment of the aspect of the invention, compounds of the present invention are described by Formula (I) and pharmaceutically acceptable salts thereof, wherein
X is O, R¹ is

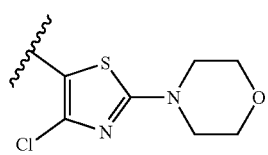 [SMILES: *c1sc(N2CCOCC2)nc1Cl]

and the other variables are as defined above for Formula (I).

In yet another embodiment of the aspect of the invention, compounds of the present invention are described by Formula (I) and pharmaceutically acceptable salts thereof, wherein X is O, R¹ is $C_{1-4}$alkyl optionally substituted with 1-6 independent halo substituents and the other variables are as defined above for Formula (I).

In still another embodiment of the aspect of the invention, compounds of the present invention are described by Formula (I) and pharmaceutically acceptable salts thereof, wherein X is O, R1 is phenyl, optionally substituted with 1-5 independent halo, trifluoromethyl, (trifluoromethyl)thio,

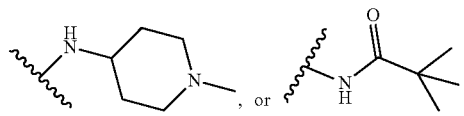

substituents, and the other variables are as defined above for Formula (I).

In another embodiment of the aspect of the invention, compounds of the present invention are described by Formula (I) and pharmaceutically acceptable salts thereof, wherein X is O, R1 is pyridinyl, optionally substituted with 1-5 independent halo, trifluoromethyl, (trifluoromethyl)thio,

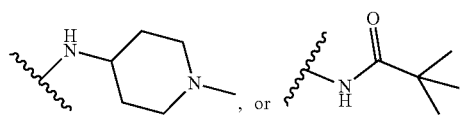

substituents, and the other variables are as defined above for Formula (I).

In still another embodiment of the aspect of the invention, compounds of the present invention are described by Formula (I) and pharmaceutically acceptable salts thereof, wherein X is O, R1 is pyrazolyl optionally substituted with 1-5 independent halo, trifluoromethyl, (trifluoromethyl)thio,

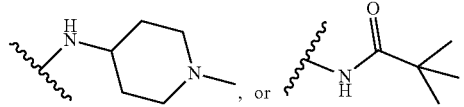

substituents, and the other variables are as defined above for Formula (I).

In an aspect of the present invention, compounds of the present invention are described by Formula (Ia) and pharmaceutically acceptable salts thereof,

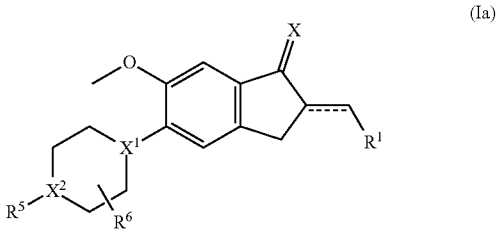

(Ia)

wherein
X is O or S;
R¹ is

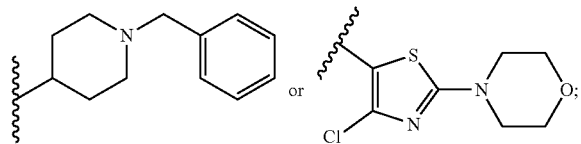 [SMILES: *C1CCN(Cc2ccccc2)CC1 ; *c1sc(N2CCOCC2)nc1Cl]

or

R¹ is $C_{1-4}$alkyl optionally substituted with 1-6 independent halo substituents; or R¹ is phenyl, pyridinyl, or pyrazolyl, each optionally substituted with 1-5 independent halo, trifluoromethyl, (trifluoromethyl)thio,

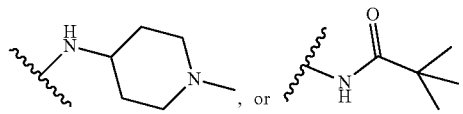

substituents;

the dotted line indicates an optional double bond;

$X^1$ and $X^2$ are independently C, N, or O; wherein at least one is not C;

$R^5$ is absent, halo, or $C_{0-4}$alkyl.

and $R^6$ is halo, or $C_{0-4}$alkyl.

In an aspect of the present invention, compounds of the present invention are described by Formula (Ia) and pharmaceutically acceptable salts thereof, (Ib)

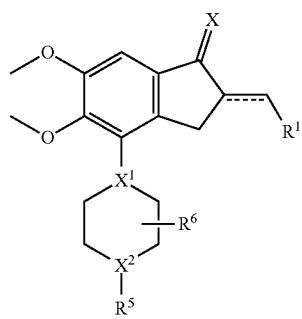

wherein
X is O or S;
R¹ is or

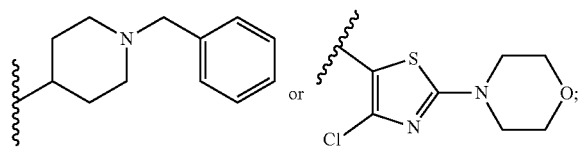 [SMILES: *C1CCN(Cc2ccccc2)CC1 ; *c1sc(N2CCOCC2)nc1Cl]

R¹ is $C_{1-4}$alkyl optionally substituted with 1-6 independent halo substituents; or R¹ is phenyl, pyridinyl, or pyrazolyl, each optionally substituted with 1-5 independent halo, trifluoromethyl, (trifluoromethyl)thio,

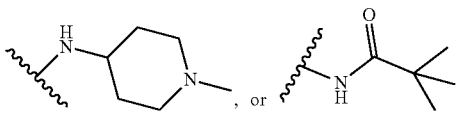

substituents;

the dotted line indicates an optional double bond $X^1$ and $X^2$ are independently C, N, or O; wherein at least one is not C;

$R^5$ is absent, halo, or $C_{0-4}$alkyl.

and $R^6$ is halo, or $C_{0-4}$alkyl.

In an aspect of the present invention, compounds of the present invention are described by Formula (Ia) and pharmaceutically acceptable salts thereof,

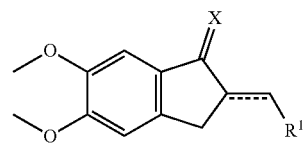

wherein
X is O or S;
R¹ is

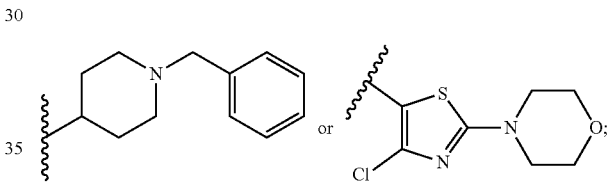

or

R¹ is $C_{1-4}$alkyl optionally substituted with 1-6 independent halo substituents; or R¹ is phenyl, pyridinyl, or pyrazolyl, each optionally substituted with 1-5 independent halo, trifluoromethyl, (trifluoromethyl)thio,

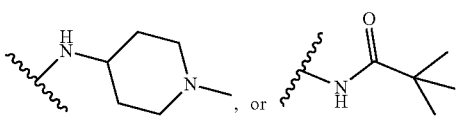

substituents;

the dotted line indicates an optional double bond.

The compounds of the present invention include:

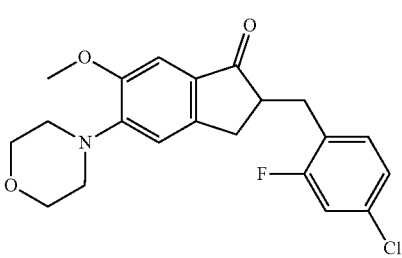

-continued
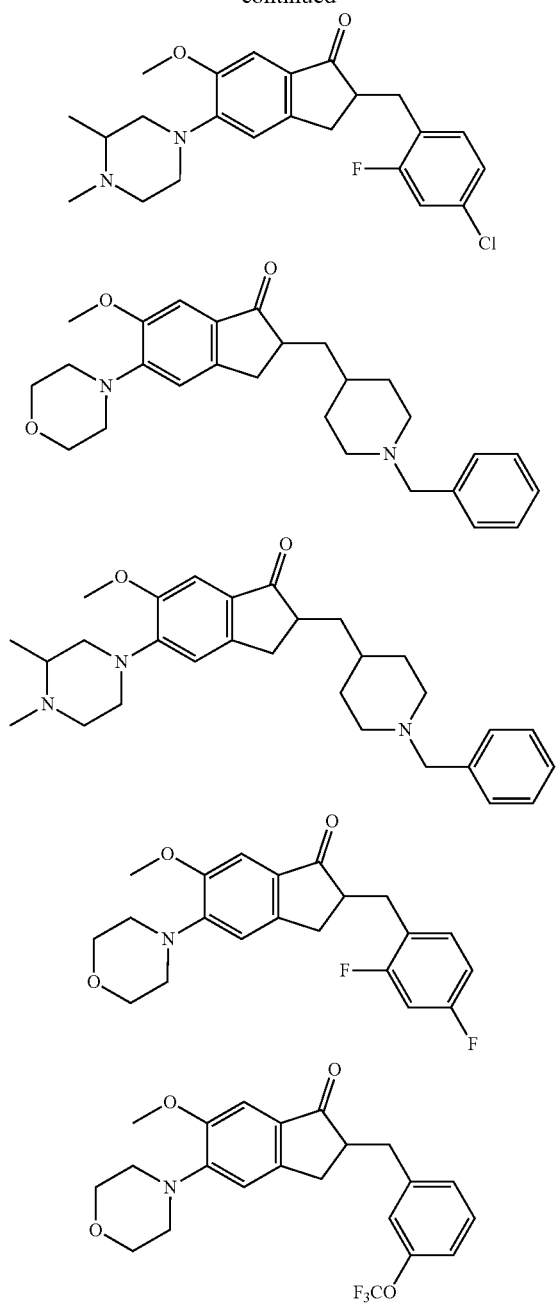
-continued
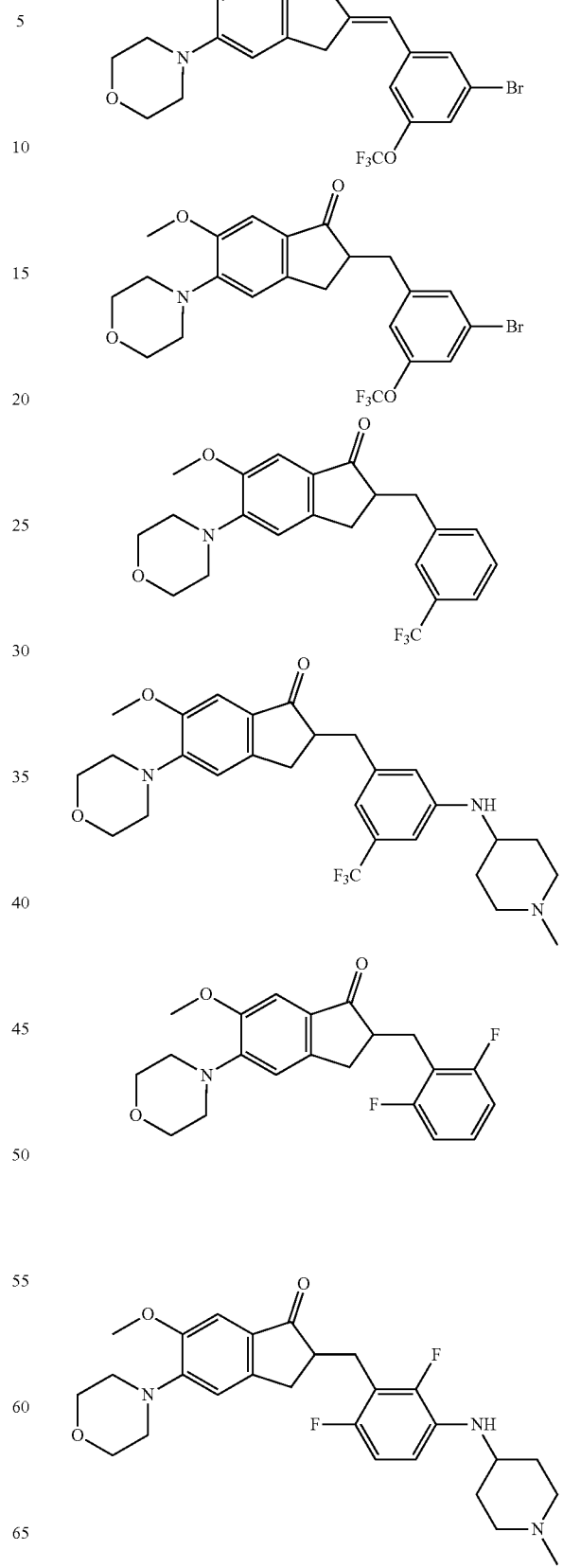

-continued
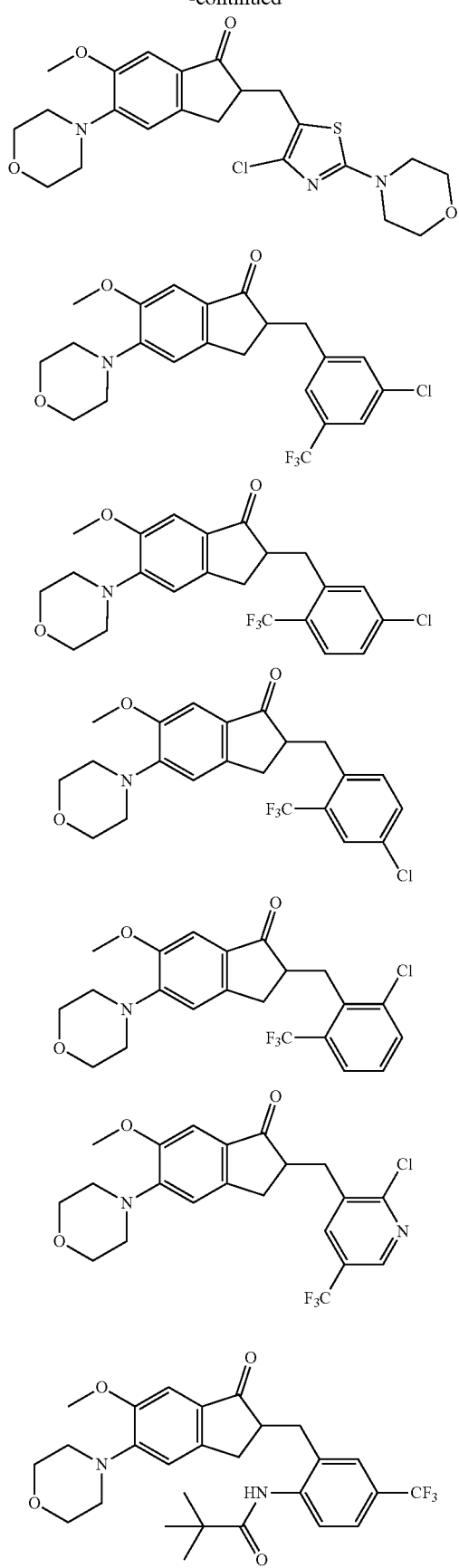
-continued
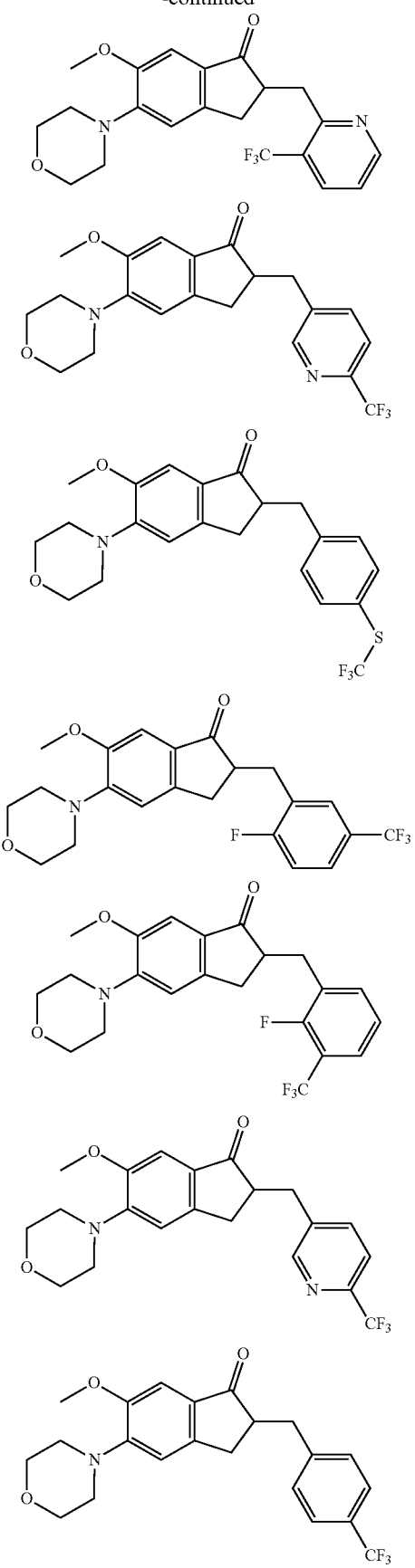

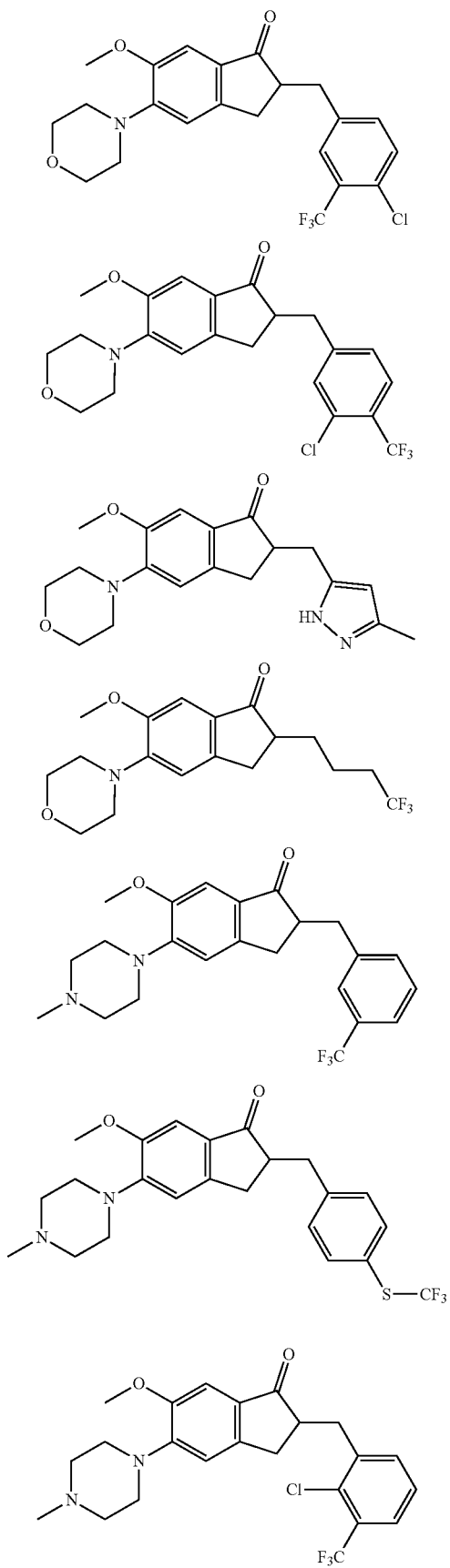
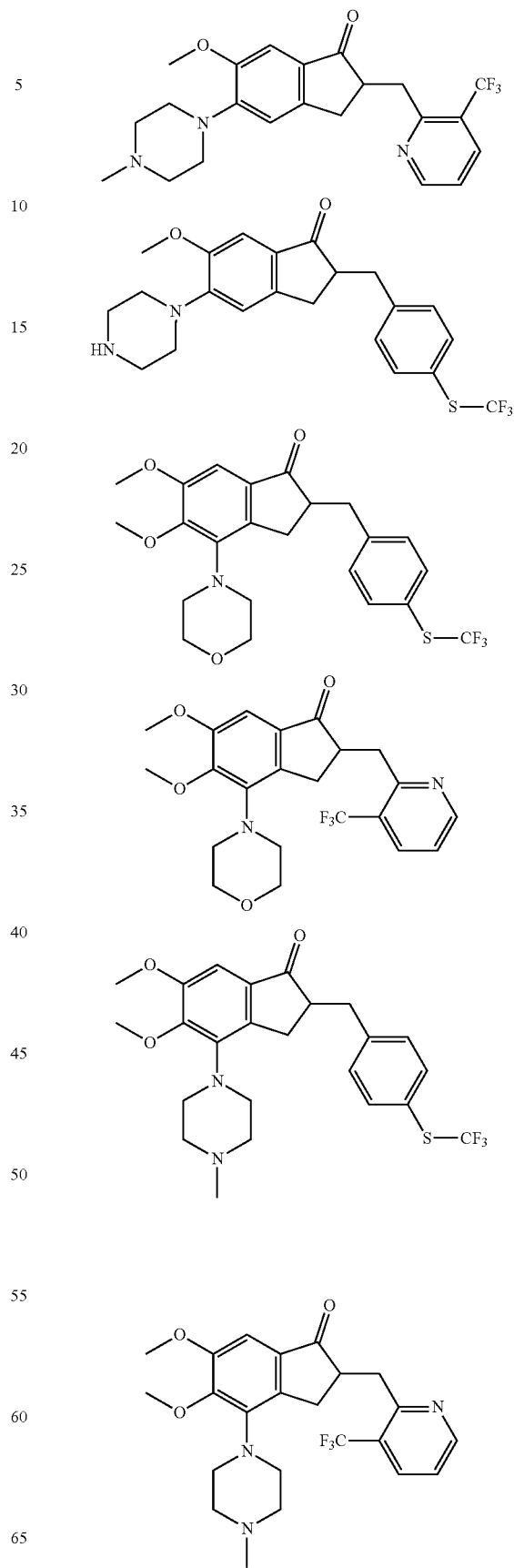

-continued
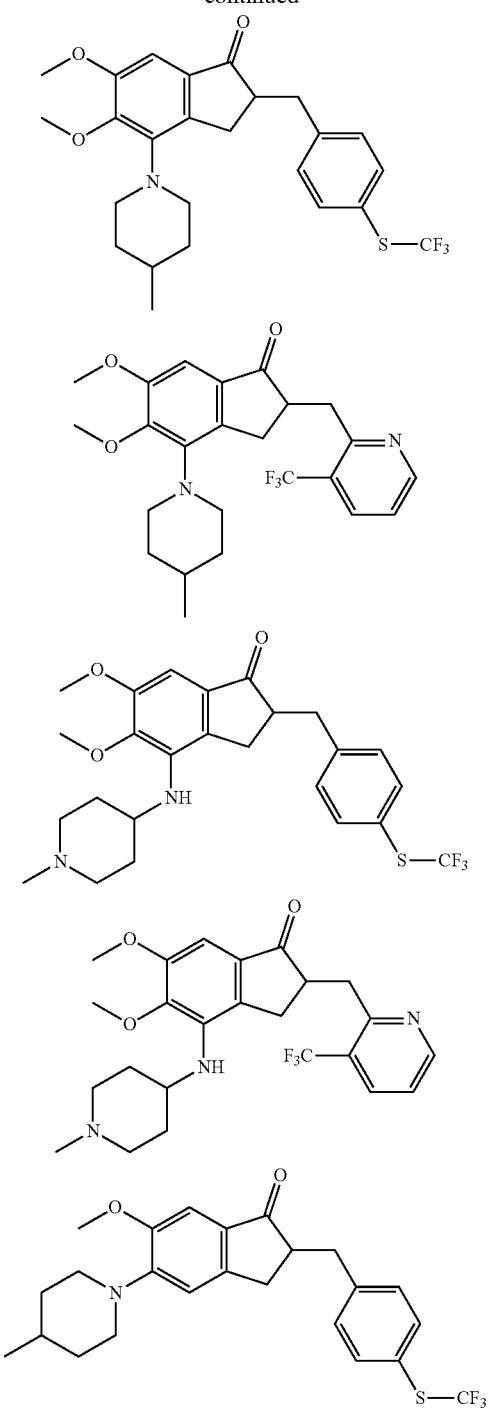
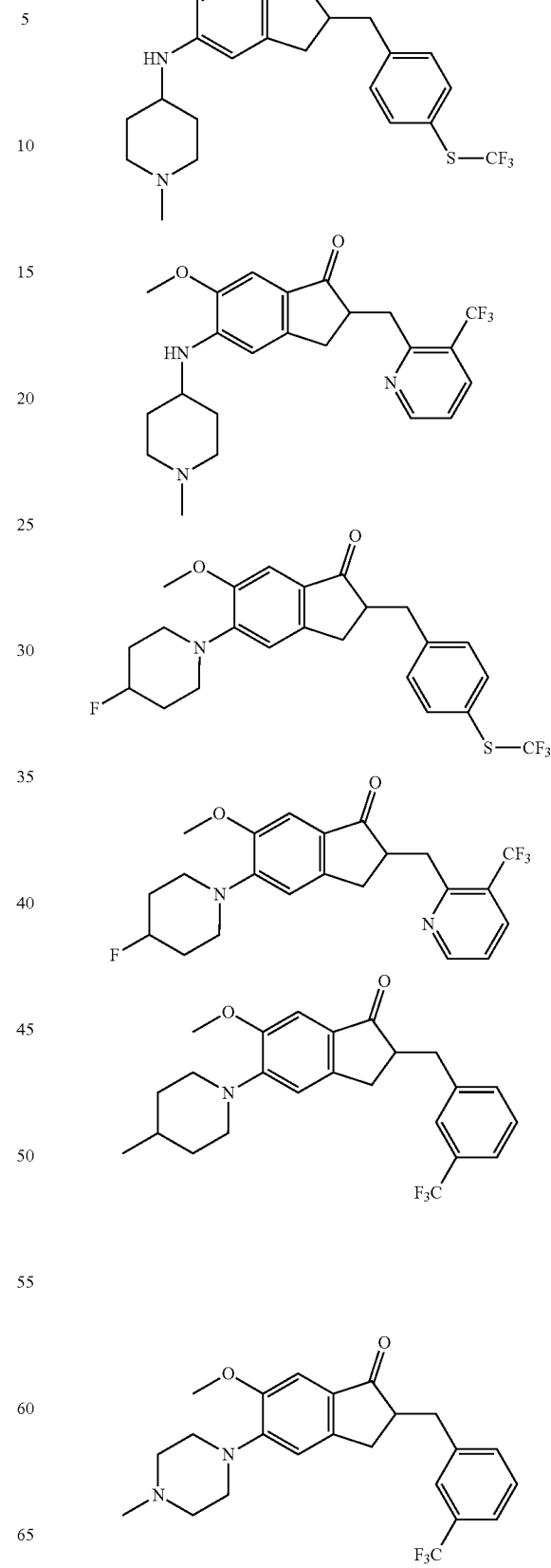

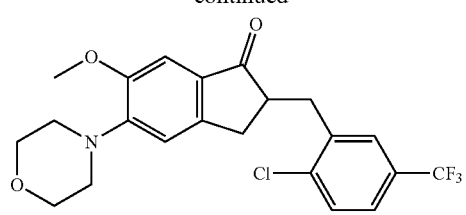
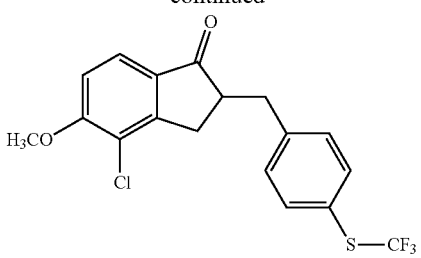
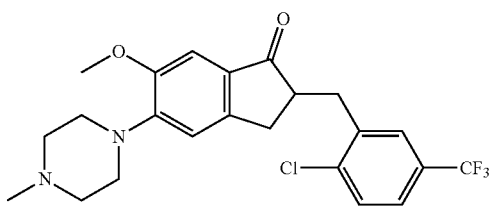
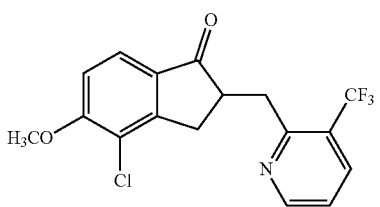
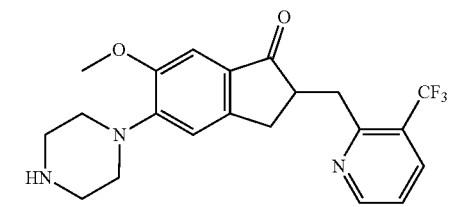
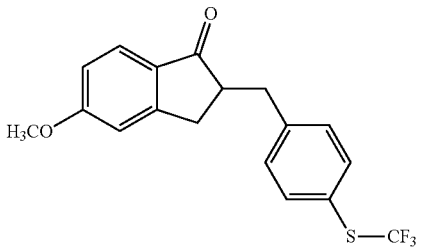
Compounds of the invention further include:
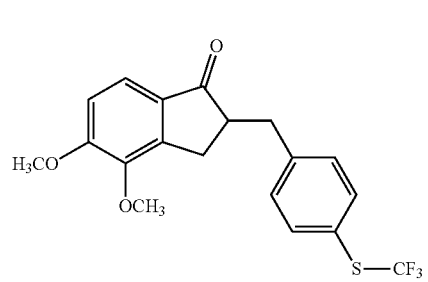
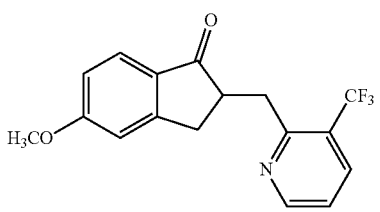
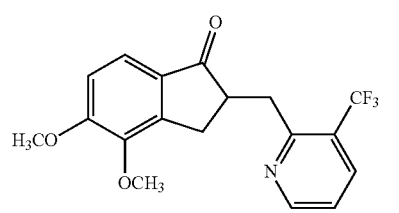
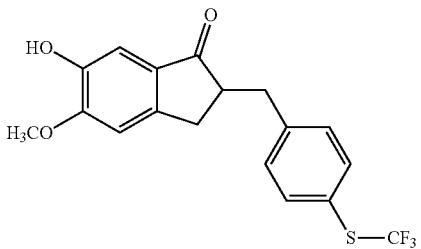
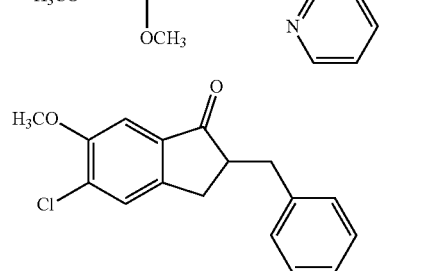
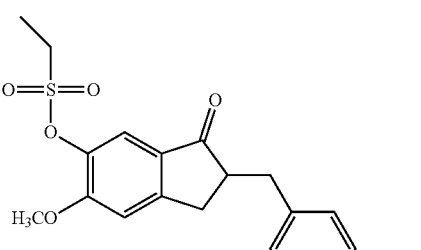
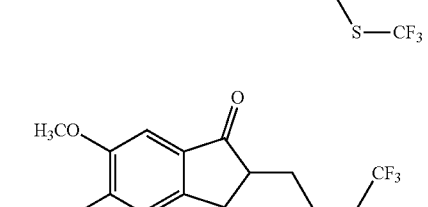
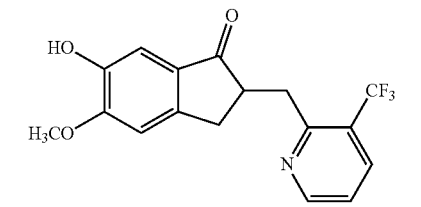
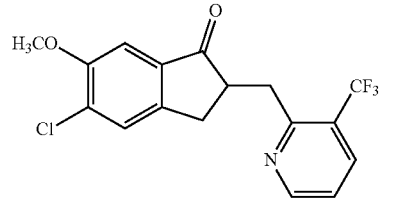

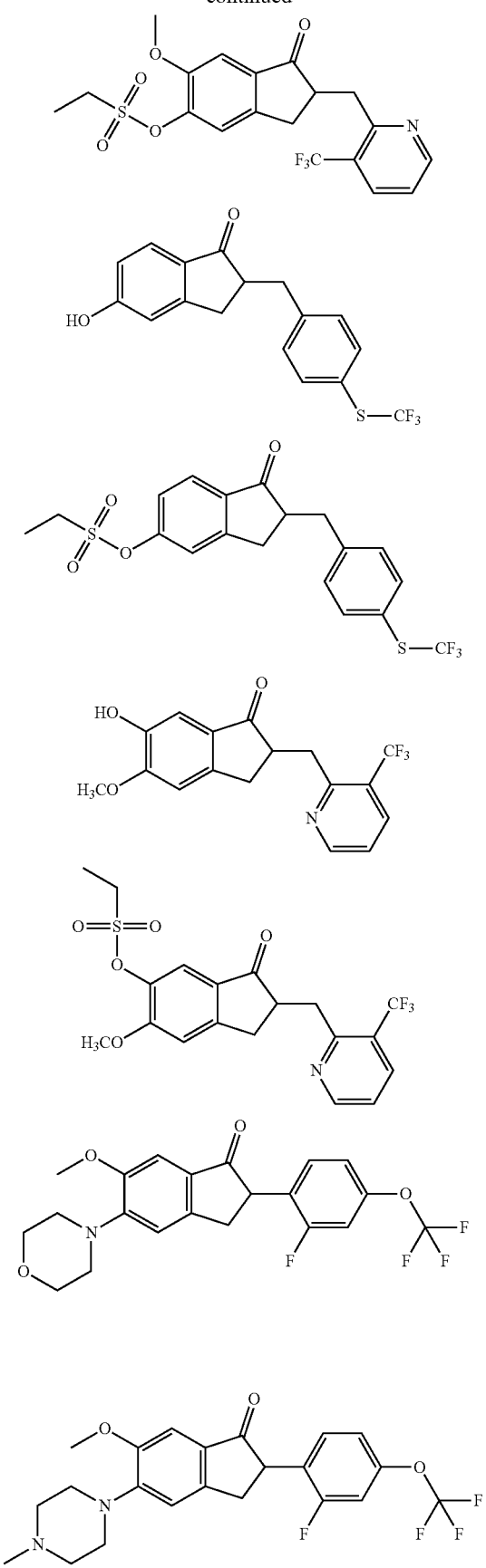
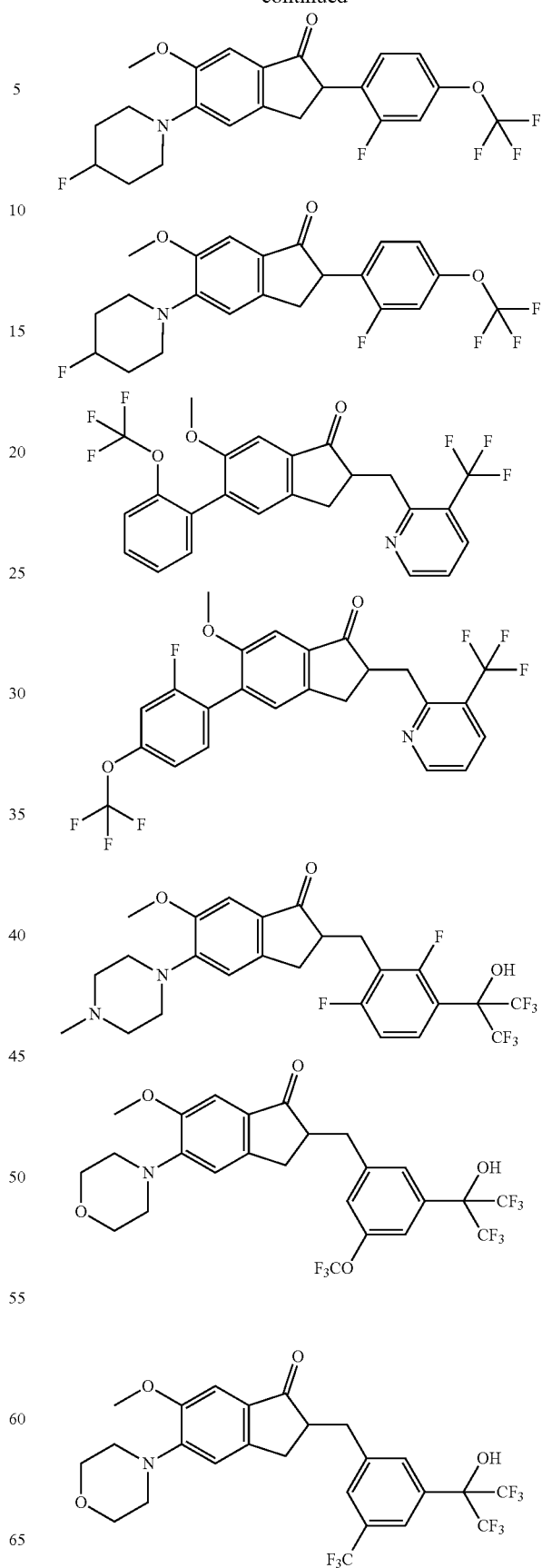

25
-continued

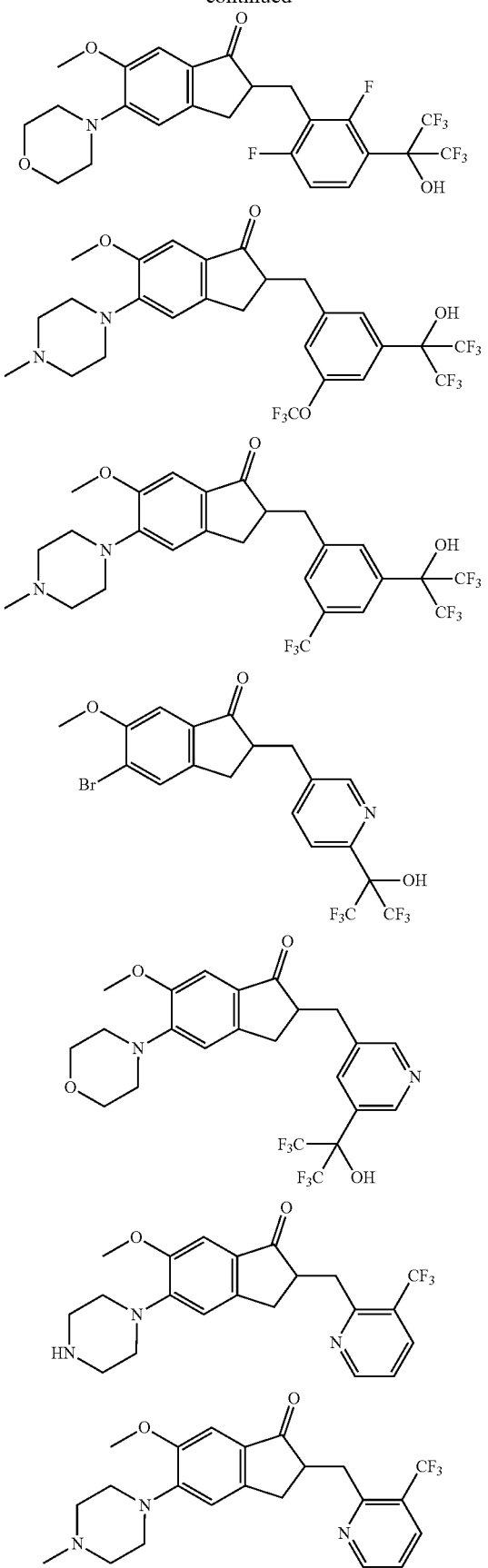

26
-continued

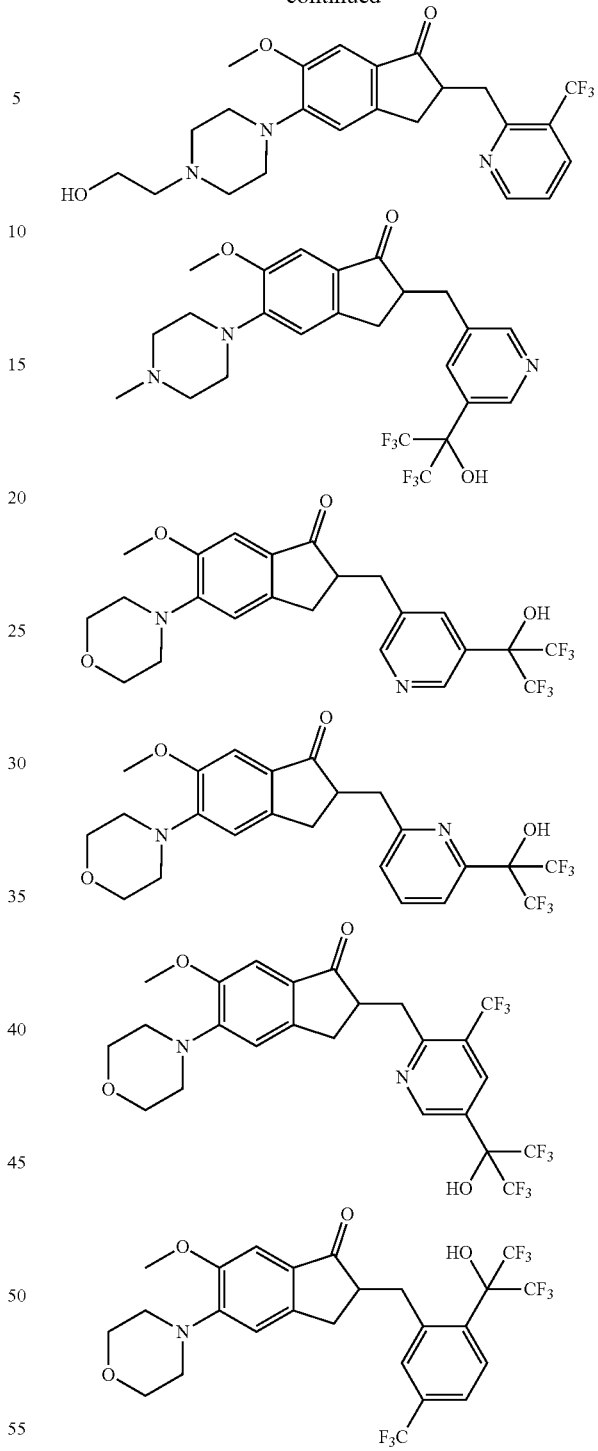

Unless otherwise stated the following terms used in the specification and claims have the meanings discussed below:

"Alkyl" refers to a saturated straight or branched hydrocarbon radical of one to six carbon atoms, preferably one to four carbon atoms, e.g., methyl, ethyl, propyl, 2-propyl, n-butyl, iso-butyl, tert-butyl, pentyl, hexyl, and the like, preferably methyl, ethyl, propyl, or 2-propyl. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Cyclic alkyls are referred to herein as a "cycloalkyl."

Unsaturated alkyls contain at least one double or triple bond between adjacent carbon atoms (referred to as an "alkenyl" or "alkynyl", respectively.) Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

"$C_{0-4}$alkyl" refers to an alkyl with 0, 1, 2, 3, or 4 carbon atoms. $C_{0-4}$alkyl with 0 carbon atoms is a hydrogen atom when terminal and is a direct bond when linking.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like, preferably methylene, ethylene, or propylene.

"Cycloalkyl" refers to a saturated cyclic hydrocarbon radical of three to eight carbon atoms, e.g., cyclopropyl, cyclobutyl, cyclopentyl or cyclohexyl.

"Alkoxy" means a radical —$OR_a$ where $R_a$ is an alkyl as defined above, e.g., methoxy, ethoxy, propoxy, butoxy and the like.

"Halo" means fluoro, chloro, bromo, or iodo, preferably fluoro and chloro.

"Haloalkyl" means alkyl substituted with one or more, preferably one, two or three, same or different halo atoms, e.g., —$CH_2Cl$, —$CF_3$, —$CH_2CF_3$, —$CH_2CCl_3$, and the like.

"Haloalkoxy" means a radical —$OR_b$ where $R_b$ is an haloalkyl as defined above, e.g., trifluoromethoxy, trichloroethoxy, 2,2-dichloropropoxy, and the like.

"Acyl" means a radical —$C(O)R_c$ where $R_c$ is hydrogen, alkyl, or haloalkyl as defined herein, e.g., formyl, acetyl, trifluoroacetyl, butanoyl, and the like.

"Aryl" refers to an all-carbon monocyclic or fused-ring polycyclic (i.e., rings which share adjacent pairs of carbon atoms) groups of 6 to 12 carbon atoms having a completely conjugated pi-electron system. Examples, without limitation, of aryl groups are phenyl, naphthyl and anthracenyl. The aryl group may be substituted or unsubstituted. Unless specifically stated otherwise, "substituted aryl" refers to the aryl group being substituted with one or more, more preferably one, two or three, even more preferably one or two substituents independently selected from the group consisting of alkyl (wherein the alkyl may be optionally substituted with one or two substituents), haloalkyl, halo, hydroxy, alkoxy, mercapto, alkylthio, cyano, acyl, nitro, phenoxy, heteroaryl, heteroaryloxy, haloalkyl, haloalkoxy, carboxy, alkoxycarbonyl, amino, alkylamino dialkylamino, aryl, heteroaryl, carbocycle or heterocycle (wherein the aryl, heteroaryl, carbocycle or heterocycle may be optionally substituted).

"Heteroaryl" refers to a monocyclic or fused ring (i.e., rings which share an adjacent pair of atoms) group of 5 to 12 ring atoms containing one, two, three or four ring heteroatoms selected from N, O, or S, the remaining ring atoms being C, and, in addition, having a completely conjugated pi-electron system. Examples, without limitation, of unsubstituted heteroaryl groups are pyrrole, furan, thiophene, imidazole, oxazole, thiazole, pyrazole, pyridine, pyrimidine, quinoline, isoquinoline, purine, triazole, tetrazole, triazine, and carbazole. The heteroaryl group may be unsubstituted or substituted, such as, for example, 5-methylthiazolyl. Unless specifically stated otherwise, "substituted heteroaryl" refers to the heteroaryl group being substituted with one or more, more preferably one, two or three, even more preferably one or two substituents independently selected from the group consisting of alkyl (wherein the alkyl may be optionally substituted with one or two substituents), haloalkyl, halo, hydroxy, alkoxy, mercapto, alkylthio, cyano, acyl, nitro, haloalkyl, haloalkoxy, carboxy, alkoxycarbonyl, amino, alkylamino dialkylamino, aryl, heteroaryl, carbocycle or heterocycle (wherein the aryl, heteroaryl, carbocycle or heterocycle may be optionally substituted).

"Carbocycle" refers to a saturated, unsaturated or aromatic ring system having 3 to 14 ring carbon atoms. The term "carbocycle", whether saturated or partially unsaturated, also refers to rings that are optionally substituted. The term "carbocycle" includes aryl. The term "carbocycle" also includes aliphatic rings that are fused to one or more aromatic or nonaromatic rings, such as in a decahydronaphthyl or tetrahydronaphthyl, where the radical or point of attachment is on the aliphatic ring. The carbocycle group may be substituted or unsubstituted. Unless specifically stated otherwise, "substituted carbocyle" refers to the carbocycle group being substituted with one or more, more preferably one, two or three, even more preferably one or two substituents independently selected from the group consisting of alkyl (wherein the alkyl may be optionally substituted with one or two substituents), haloalkyl, halo, hydroxy, alkoxy, mercapto, alkylthio, cyano, acyl, nitro, haloalkyl, haloalkoxy, carboxy, alkoxycarbonyl, amino, alkylamino dialkylamino, aryl, heteroaryl, carbocycle or heterocycle (wherein the aryl, heteroaryl, carbocycle or heterocycle may be optionally substituted).

"Heterocycle" refers to a saturated, unsaturated or aromatic cyclic ring system having 3 to 14 ring atoms in which one, two or three ring atoms are heteroatoms selected from N, O, or $S(O)_m$ (where m is an integer from 0 to 2), the remaining ring atoms being C, where one or two C atoms may optionally be replaced by a carbonyl group. The term "heterocycle" includes heteroaryl. Unless specifically stated otherwise, "substituted heterocyclyl" refers to the heterocyclyl ring being substituted independently with one or more, preferably one, two, or three substituents selected from alkyl (wherein the alkyl may be optionally substituted with one or two substituents), haloalkyl, cycloalkylamino, cycloalkyl or cycloalkyl-alkyl, cycloalkyl-aminoalkyl, cycloalkyl-alkyl amino-alkyl, cyanoalkyl, halo, nitro, cyano, hydroxy, alkoxy, amino, alkylamino, dialkylamino, hydroxyalkyl, carboxyalkyl, aminoalkyl, alkylaminoalkyl, dialkylaminoalkyl, aralkyl, heteroaralkyl, aryl, heteroaryl, carbocycle, heterocycle (wherein the aryl, heteroaryl, carbocycle or heterocycle may be optionally substituted), aralkyl, heteroaralkyl, saturated or unsaturated heterocycloamino, saturated or unsaturated heterocycloaminoalkyl, and —$COR_d$ (where $R_d$ is alkyl). More specifically the term heterocyclyl includes, but is not limited to, tetrahydropyranyl, 2,2-dimethyl-1,3-dioxolane, piperidino, N-methylpiperidin-3-yl, piperazino, N-methylpyrrolidin-3-yl, pyrrolidino, morpholino, 4-cyclopropylmethylpiperazino, thiomorpholino, thiomorpholino-1-oxide, thiomorpholino-1,1-dioxide, 4-ethyloxycarbonylpiperazino, 3-oxopiperazino, 2-imidazolidone, 2-pyrrolidinone, 2-oxohomopiperazino, tetrahydropyrimidin-2-one, and the derivatives thereof, including 2-methyl-4,5,6,7-tetrahydro-1H-pyrrolo[2,3-c]pyridinyl. In certain embodiments, the heterocycle group is optionally substituted with one or two substituents independently selected from halo, alkyl, alkyl substituted with carboxy, ester, hydroxy, alkylamino, saturated or unsaturated heterocycloamino, saturated or unsaturated heterocycloaminoalkyl, or dialkylamino.

"Optional" or "optionally" means that the subsequently described event or circumstance may but need not occur, and that the description includes instances where the event or circumstance occurs and instances in which it does not. For example, "heterocyclic group optionally substituted with an alkyl group" means that the alkyl may but need not be present, and the description includes situations where the heterocycle group is substituted with an alkyl group and situations where the heterocycle group is not substituted with the alkyl group.

Lastly, unless specifically stated otherwise, the term "substituted" as used herein means any of the above groups (e.g., alkyl, aryl, heteroaryl, carbocycle, heterocycle, etc.) wherein at least one hydrogen atom is replaced with a substituent. In the case of an oxo substituent ("=O") two hydrogen atoms are replaced. "Substituents" within the context of this invention, if not specified, include halogen, hydroxy, oxo, cyano, nitro, amino, alkylamino, dialkylamino, alkyl, alkoxy, thioalkyl, haloalkyl (e.g., —$CF_3$), hydroxyalkyl, aryl, substituted aryl, arylalkyl, substituted arylalkyl, heteroaryl, substituted heteroaryl, heteroarylalkyl, substituted heteroarylalkyl, heterocycle, substituted heterocycle, heterocyclealkyl, substituted heterocyclealkyl, —$NR_eR_f$, —$NR_eC(=O)R_f$, —$NR_eC(=O)NR_eR_f$, —$NR_eC(=O)OR_f$, —$NR_eSO_2R_f$, —$OR_e$, —$C(=O)R_e$—$C(=O)OR_e$, —$C(=O)NR_eR_f$, —$OC(=O)NR_eR_f$, —SH, —$SR_e$, —$SOR_e$, —$S(=O)_2R_e$, —$OS(=O)_2R_e$, —$S(=O)_2OR_e$, wherein $R_e$ and $R_f$ are the same or different and independently hydrogen, alkyl, haloalkyl, substituted alkyl, aryl, substituted aryl, arylalkyl, substituted arylalkyl, heteroaryl, substituted heteroaryl, heteroarylalkyl, substituted heteroarylalkyl, heterocycle, substituted heterocycle, heterocyclealkyl or substituted heterocyclealkyl.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups; a pair of enantiomers is possible. An enantiomer can be characterized by the absolute configuration of its asymmetric center and is described by the R- and S-sequencing rules of Cahn and Prelog (Cahn, R., Ingold, C., and Prelog, V. Angew. Chem. 78:413-47, 1966; Angew. Chem. Internat. Ed. Eng. 5:385-415, 511, 1966), or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Ch. 4 of ADVANCED ORGANIC CHEMISTRY, 4$^{th}$ edition, March, J., John Wiley and Sons, New York City, 1992).

The compounds of the present invention may exhibit the phenomena of tautomerism and structural isomerism. This invention encompasses any tautomeric or structural isomeric form and mixtures thereof which possess the ability to modulate (RORγt)/RORγ activity and is not limited to, any one tautomeric or structural isomeric form.

It is contemplated that a compound of the present invention would be metabolized by enzymes in the body of the organism such as human being to generate a metabolite that can modulate the activity of the protein kinases. Such metabolites are within the scope of the present invention.

A compound of the present invention or a pharmaceutically acceptable salt thereof can be administered as such to a human patient or can be administered in pharmaceutical compositions in which the foregoing materials are mixed with suitable carriers or excipient(s). Techniques for formulation and administration of drugs may be found, for example, in REMINGTON'S PHARMACOLOGICAL SCIENCES, Mack Publishing Co., Easton, Pa., latest edition.

A "pharmaceutical composition" refers to a mixture of one or more of the compounds described herein or pharmaceutically acceptable salts or prodrugs thereof, with other chemical components, such as pharmaceutically acceptable excipients. The purpose of a pharmaceutical composition is to facilitate administration of a compound to an organism.

"Pharmaceutically acceptable excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

"Pharmaceutically acceptable salt" refers to those salts which retain the biological effectiveness and properties of the parent compound. Such salts may include: (1) acid addition salt which is obtained by reaction of the free base of the parent compound with inorganic acids such as hydrochloric acid, hydrobromic acid, nitric acid, phosphoric acid, sulfuric acid, and perchloric acid and the like, or with organic acids such as acetic acid, oxalic acid, (D)- or (L)-malic acid, maleic acid, methanesulfonic acid, ethanesulfonic acid, p-toluenesulfonic acid, salicylic acid, tartaric acid, citric acid, succinic acid or malonic acid and the like, preferably hydrochloric acid or (L)-malic acid; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

The compound of the present invention may also act, or be designed to act, as a prodrug. A "prodrug" refers to an agent, which is converted into the parent drug in vivo. Prodrugs are often useful because, in some situations, they may be easier to administer than the parent drug. They may, for instance, be bioavailable by oral administration whereas the parent drug is not. The prodrug may also have improved solubility in pharmaceutical compositions over the parent drug. An example, without limitation, of a prodrug would be a compound of the present invention, which is, administered as an ester (the "prodrug"), phosphate, amide, carbamate, or urea.

"Therapeutically effective amount" refers to that amount of the compound being administered which will relieve to some extent one or more of the symptoms of the disorder being treated. In reference to the treatment of MS, a therapeutically effective amount refers to that amount which has the effect of: (1) ameliorating loss of muscle control and strength, (2) lessoning fatigue or weakness, (3) stabilizing loss of vision, (4) decreasing spasticity, (5) increased balance, (6) lessoning bladder and bowel problems, (7) decreasing numbness, or relieving one or more symptoms associated with MS.

The term "disease", as used herein, means any disease or other deleterious condition in which Retinoic acid-related orphan nuclear receptor γt (RORγt)/RORγ is known to play a role. The term "disease" also means those diseases or conditions that are alleviated by treatment with (RORγt)/RORγ modulators.

The term "(RORγt)/RORγ activity-mediated condition" or "disease", as used herein, means any disease or other deleterious condition in which (RORγt)/RORγ activity is known to play a role. The term "(RORγt)/RORγ activity-mediated condition" also means those diseases or conditions that are alleviated by treatment with a (RORγt)/RORγ inhibitor.

As used herein, "administer" or "administration" refers to the delivery of an inventive compound or of a pharmaceutically acceptable salt thereof or of a pharmaceutical composition containing an inventive compound or a pharmaceutically acceptable salt thereof of this invention to an organism for the purpose of prevention or treatment of a (RORγt)/RORγ related disorder.

Suitable routes of administration may include, without limitation, oral, rectal, transmucosal or intestinal administration or intramuscular, subcutaneous, intramedullary, intrathecal, direct intraventricular, intravenous, intravitreal, intraperitoneal, intranasal, or intraocular injections. In certain embodiments, the preferred routes of administration are oral and intravenous.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention may be formulated in any conventional manner using one or more physiologically acceptable carriers comprising excipients and auxiliaries which facilitate processing of the active compounds into preparations which can be used pharmaceutically. Proper formulation is dependent upon the route of administration chosen.

For injection, the compounds of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the compounds can be formulated by combining the active compounds with pharmaceutically acceptable carriers well known in the art. Such carriers enable the compounds of the invention to be formulated as tablets, pills, lozenges, dragees, capsules, liquids, gels, syrups, slurries, suspensions and the like, for oral ingestion by a patient. Pharmaceutical preparations for oral use can be made using a solid excipient, optionally grinding the resulting mixture, and processing the mixture of granules, after adding other suitable auxiliaries if desired, to obtain tablets or dragee cores. Useful excipients are, in particular, fillers such as sugars, including lactose, sucrose, mannitol, or sorbitol, cellulose preparations such as, for example, maize starch, wheat starch, rice starch and potato starch and other materials such as gelatin, gum tragacanth, methyl cellulose, hydroxypropylmethyl-cellulose, sodium carboxymethylcellulose, and/or polyvinyl-pyrrolidone (PVP). If desired, disintegrating agents may be added, such as cross-linked polyvinyl pyrrolidone, agar, or alginic acid. A salt such as sodium alginate may also be used.

Dragee cores are provided with suitable coatings. For this purpose, concentrated sugar solutions may be used which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, a binder such as starch, and/or a lubricant such as talc or magnesium stearate and, optionally, stabilizers. In soft capsules, the active compounds may be dissolved or suspended in suitable liquids, such as fatty oils, liquid paraffin, or liquid polyethylene glycols. Stabilizers may be added in these formulations, also. Pharmaceutical compositions which may also be used include hard gelatin capsules. The capsules or pills may be packaged into brown glass or plastic bottles to protect the active compound from light. The containers containing the active compound capsule formulation are preferably stored at controlled room temperature (15-30° C.).

For administration by inhalation, the compounds for use according to the present invention may be conveniently delivered in the form of an aerosol spray using a pressurized pack or a nebulizer and a suitable propellant, e.g., without limitation, dichlorodifluoromethane, trichlorofluoromethane, dichlorotetra-fluoroethane or carbon dioxide. In the case of a pressurized aerosol, the dosage unit may be controlled by providing a valve to deliver a metered amount. Capsules and cartridges of, for example, gelatin for use in an inhaler or insufflator may be formulated containing a powder mix of the compound and a suitable powder base such as lactose or starch.

The compounds may also be formulated for parenteral administration, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulating materials such as suspending, stabilizing and/or dispersing agents.

Pharmaceutical compositions for parenteral administration include aqueous solutions of a water soluble form, such as, without limitation, a salt, of the active compound. Additionally, suspensions of the active compounds may be prepared in a lipophilic vehicle. Suitable lipophilic vehicles include fatty oils such as sesame oil, synthetic fatty acid esters such as ethyl oleate and triglycerides, or materials such as liposomes. Aqueous injection suspensions may contain substances which increase the viscosity of the suspension, such as sodium carboxymethyl cellulose, sorbitol, or dextran. Optionally, the suspension may also contain suitable stabilizers and/or agents that increase the solubility of the compounds to allow for the preparation of highly concentrated solutions.

Alternatively, the active ingredient may be in powder form for constitution with a suitable vehicle, e.g., sterile, pyrogen-free water, before use.

The compounds may also be formulated in rectal compositions such as suppositories or retention enemas, using, e.g., conventional suppository bases such as cocoa butter or other glycerides.

In addition to the formulations described previously, the compounds may also be formulated as depot preparations. Such long acting formulations may be administered by implantation (for example, subcutaneously or intramuscularly) or by intramuscular injection. A compound of this invention may be formulated for this route of administration with suitable polymeric or hydrophobic materials (for instance, in an emulsion with a pharmacologically acceptable oil), with ion exchange resins, or as a sparingly soluble derivative such as, without limitation, a sparingly soluble salt.

A non-limiting example of a pharmaceutical carrier for the hydrophobic compounds of the invention is a cosolvent system comprising benzyl alcohol, a nonpolar surfactant, a water-miscible organic polymer and an aqueous phase such as the VPD cosolvent system. VPD is a solution of 3% w/v benzyl alcohol, 8% w/v of the nonpolar surfactant polysorbate 80, and 65% w/v polyethylene glycol 300, made up to volume in absolute ethanol. The VPD cosolvent system (VPD: D5W) consists of VPD diluted 1:1 with a 5% dextrose in water solution. This cosolvent system dissolves hydrophobic compounds well, and itself produces low toxicity upon systemic administration. Naturally, the proportions of such a cosolvent system may be varied considerably without destroying its solubility and toxicity characteristics. Furthermore, the identity of the cosolvent components may be varied: for example, other low-toxicity nonpolar surfactants may be used instead of polysorbate 80, the fraction size of polyethylene glycol may be varied, other biocompatible polymers may replace polyethylene glycol, e.g., polyvinyl pyrrolidone, and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. In addition, certain organic solvents such as dimethylsulfoxide also may be employed, although often at the cost of greater toxicity.

Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions herein also may comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

Many of the (RORγt)/RORγ modulating compounds of the invention may be provided as physiologically acceptable salts wherein the claimed compound may form the negatively or the positively charged species. Examples of salts in which the compound forms the positively charged moiety include, without limitation, quaternary ammonium (defined elsewhere herein), salts such as the hydrochloride, sulfate, carbonate, lactate, tartrate, malate, maleate, succinate wherein the nitrogen atom of the quaternary ammonium group is a nitrogen of the selected compound of this invention which has reacted with the appropriate acid. Salts in which a compound of this invention forms the negatively charged species include, without limitation, the sodium, potassium, calcium and magnesium salts formed by the reaction of a carboxylic acid group in the compound with an appropriate base (e.g. sodium hydroxide (NaOH), potassium hydroxide (KOH), calcium hydroxide ($Ca(OH)_2$), etc).

Pharmaceutical compositions suitable for use in the present invention include compositions wherein the active ingredients are contained in an amount sufficient to achieve the intended purpose, e.g., the modulation of protein kinase activity and/or the treatment or prevention of a protein kinase-related disorder.

More specifically, a therapeutically effective amount means an amount of compound effective to prevent, alleviate or ameliorate symptoms of disease or prolong the survival of the subject being treated.

Determination of a therapeutically effective amount is well within the capability of those skilled in the art, especially in light of the detailed disclosure provided herein.

For any compound used in the methods of the invention, the therapeutically effective amount or dose can be estimated initially from cell culture assays. Then, the dosage can be formulated for use in animal models so as to achieve a circulating concentration range that includes the $IC_{50}$ as determined in cell culture (i.e., the concentration of the test compound which achieves a half-maximal inhibition of the (RORγt)/RORγ, or surrogate marker activity). Such information can then be used to more accurately determine useful doses in humans.

Toxicity and therapeutic efficacy of the compounds described herein can be determined by standard pharmaceutical procedures in cell cultures or experimental animals, e.g., by determining the $IC_{50}$ and the $LD_{50}$ (both of which are discussed elsewhere herein) for a subject compound. The data obtained from these cell culture assays and animal studies can be used in formulating a range of dosage for use in humans. The dosage may vary depending upon the dosage form employed and the route of administration utilized. The exact formulation, route of administration and dosage can be chosen by the individual physician in view of the patient's condition. (See, e.g., GOODMAN & GILMAN'S THE PHARMACOLOGICAL BASIS OF THERAPEUTICS, Ch. 3, $9^{th}$ ed., Ed. by Hardman, J., and Limbard, L., McGraw-Hill, New York City, 1996, p. 46.)

Dosage amount and interval may be adjusted individually to provide plasma levels of the active species which are sufficient to maintain the kinase modulating effects. These plasma levels are referred to as minimal effective concentrations (MECs). The MEC will vary for each compound but can be estimated from in vitro data, e.g., the concentration necessary to achieve 50-90% inhibition of (RORγt)/RORγ, or surrogate marker may be ascertained using the assays described herein. Dosages necessary to achieve the MEC will depend on individual characteristics and route of administration. HPLC assays or bioassays can be used to determine plasma concentrations.

Dosage intervals can also be determined using MEC value. Compounds should be administered using a regimen that maintains plasma levels above the MEC for 10-90% of the time, preferably between 30-90% and most preferably between 50-90%.

At present, the therapeutically effective amounts of compounds of the present invention may range from approximately 2.5 mg/m² to 1500 mg/m² per day. Additional illustrative amounts range from 0.2-1000 mg/qid, 2-500 mg/qid, and 20-250 mg/qid.

In cases of local administration or selective uptake, the effective local concentration of the drug may not be related to plasma concentration, and other procedures known in the art may be employed to determine the correct dosage amount and interval.

The amount of a composition administered will, of course, be dependent on the subject being treated, the severity of the affliction, the manner of administration, the judgment of the prescribing physician, etc.

The compositions may, if desired, be presented in a pack or dispenser device, such as an FDA approved kit, which may contain one or more unit dosage forms containing the active ingredient. The pack may for example comprise metal or plastic foil, such as a blister pack. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions or of human or veterinary administration. Such notice, for example, may be of the labeling approved by the U.S. Food and Drug Administration for prescription drugs or of an approved product insert. Compositions comprising a compound of the invention formulated in a compatible pharmaceutical carrier may also be prepared, placed in an appropriate container, and labeled for treatment of an indicated condition. Suitable conditions indicated on the label may include treatment of a tumor, inhibition of angiogenesis, treatment of fibrosis, diabetes, and the like.

As mentioned above, the compounds and compositions of the invention will find utility in a broad range of diseases and conditions mediated by protein kinases, including diseases and conditions mediated by (RORγt)/RORγ activity. Such diseases may include by way of example and not limitation, Multiple Sclerosis (MS), Rheumatoid Arthritis (RA), Inflammatory Colitis, Psoriasis, COPD, Pain, Obesity, Diabetes, Dyslipidemia, Osteoporosis, Asthma, Neurodegenerative diseases and Cancer.

The invention will be further understood upon consideration of the following non-limiting Examples. In other aspects or embodiments include any of the compounds in TABLE 1A and 1B that fall with in the scope of any of the embodiments described above of the compounds of Formula I or pharmaceuticals acceptable salts thereof

TABLE 1A

Substituted 2,3-dihydro-1H-inden-1-one containing RORγ Antagonists

| Example ID | Structure | Name | MW |
|---|---|---|---|
| 16 | 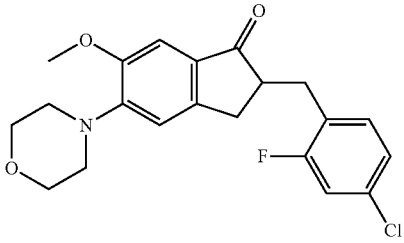 [SMILES: COc1cc2c(cc1N1CCOCC1)CC(Cc1ccc(Cl)cc1F)C2=O] | 2-(4-chloro-2-fluorobenzyl)-6-methoxy-5-morpholino-2,3-dihydro-1H-inden-1-one | 389.8* |
| 20 | 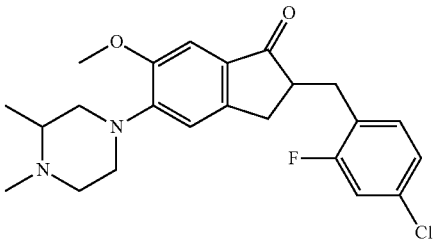 [SMILES: COc1cc2c(cc1N1CCN(C)C(C)C1)CC(Cc1ccc(Cl)cc1F)C2=O] | 2-(4-chloro-2-fluorobenzyl)-5-(3,4-dimethylpiperazin-1-yl)-6-methoxy-2,3-dihydro-1H-inden-1-one | 414.9 |
| 23 | 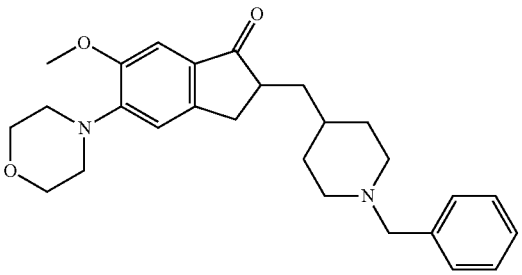 [SMILES: COc1cc2c(cc1N1CCOCC1)CC(CC1CCN(Cc3ccccc3)CC1)C2=O] | 2-((1-benzylpiperidin-4-yl)methyl)-6-methoxy-5-morpholino-2,3-dihydro-1H-inden-1-one | 435.2* |

TABLE 1A-continued

Substituted 2,3-dihydro-1H-inden-1-one containing RORγ Antagonists

| Example ID | Structure | Name | MW |
|---|---|---|---|
| 25 | 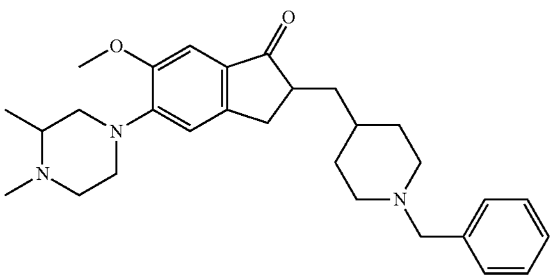 [SMILES: COc1cc2c(cc1N1CCN(C)C(C)C1)CC(CC1CCN(Cc3ccccc3)CC1)C2=O] | 2-((1-benzylpiperidin-4-yl)methyl)-5-(3,4-dimethylpiperazin-1-yl)-6-methoxy-2,3-dihydro-1H-inden-1-one | 461.6 |
| 28 | 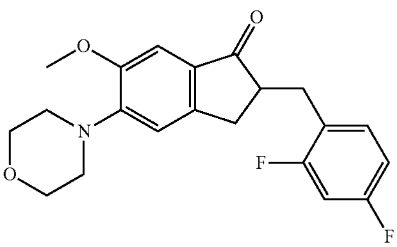 [SMILES: COc1cc2c(cc1N1CCOCC1)CC(Cc1ccc(F)cc1F)C2=O] | 2-(2,4-difluorobenzyl)-6-methoxy-5-morpholino-2,3-dihydro-1H-inden-1-one | 373.9* |
| 31 | 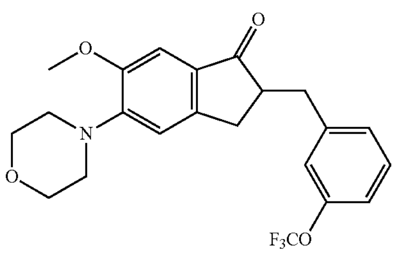 [SMILES: COc1cc2c(cc1N1CCOCC1)CC(Cc1cccc(OC(F)(F)F)c1)C2=O] | 6-methoxy-5-morpholino-2-(3-(trifluoromethoxy)benzyl)-2,3-dihydro-1H-inden-1-one | 422.1* |
| 34 | 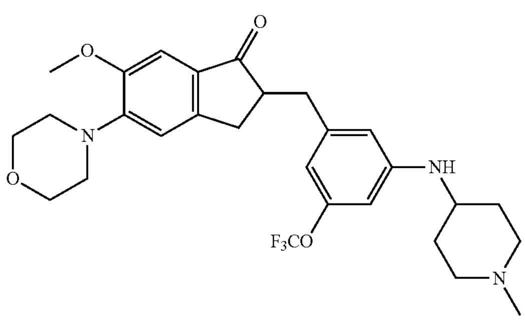 [SMILES: COc1cc2c(cc1N1CCOCC1)CC(Cc1cc(NC3CCN(C)CC3)cc(OC(F)(F)F)c1)C2=O] | 6-methoxy-2-(3-((1-methylpiperidin-4 yl)amino)-5 (trifluoromethoxy)benzyl)-5-morpholino-2,3-dihydro-1H-inden-1-one | 533.2 |
| 30 | 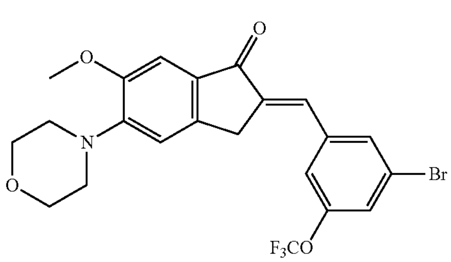 [SMILES: COc1cc2c(cc1N1CCOCC1)C/C(=C\c1cc(Br)cc(OC(F)(F)F)c1)C2=O] | (E)-2-(3-bromo-5-(trifluoromethoxy)benzylidene)-6-methoxy-5-morpholino-2,3-dihydro-1H-inden-1-one | 498.2 |

TABLE 1A-continued

Substituted 2,3-dihydro-1H-inden-1-one containing RORγ Antagonists

| Example ID | Structure | Name | MW |
|---|---|---|---|
| 32 | 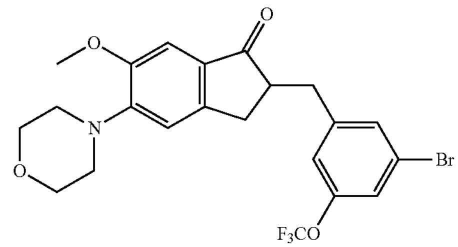 [SMILES: COc1cc2c(cc1N1CCOCC1)CC(Cc1cc(Br)cc(OC(F)(F)F)c1)C2=O] | 2-(3-bromo-5-(trifluoromethoxy)benzyl)-6-methoxy-5-morpholino-2,3-dihydro-1H-inden-1-one | 500.3 |
| 37 | 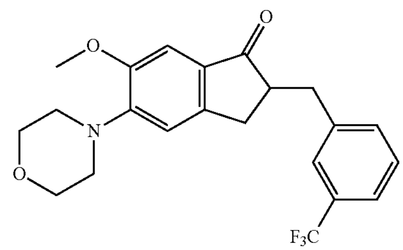 | 6-methoxy-5-morpholino-2-(3-(trifluoromethyl)benzyl)-2,3-dihydro-1H-inden-1-one | 406.0* |
| 39 | 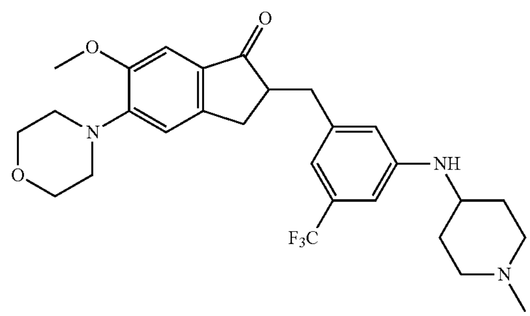 [SMILES: COc1cc2c(cc1N1CCOCC1)CC(Cc1cc(NC3CCN(C)CC3)cc(C(F)(F)F)c1)C2=O] | 6-methoxy-2-(3-((1-methylpiperidin-4-yl)amino)-5-(trifluoromethyl)benzyl)-5-morpholino-2,3-dihydro-1H-inden-1-one | 517.26 |
| 42 | 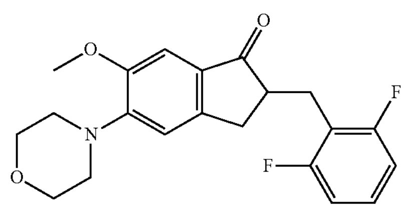 [SMILES: COc1cc2c(cc1N1CCOCC1)CC(Cc1c(F)cccc1F)C2=O] | 2-(2,6-difluorobenzyl)-6-methoxy-5-morpholino-2,3-dihydro-1H-inden-1-one | 374.0* |
| 44 | 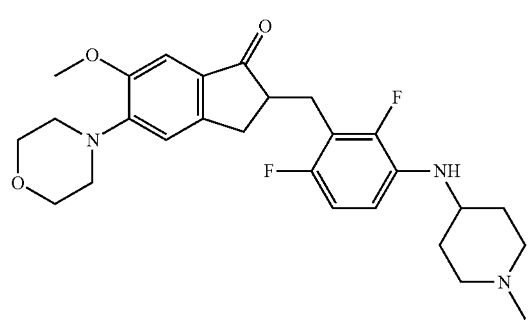 [SMILES: COc1cc2c(cc1N1CCOCC1)CC(Cc1c(F)ccc(NC3CCN(C)CC3)c1F)C2=O] | 2-(2,6-difluoro-3-((1-methylpiperidin-4-yl)amino)benzyl)-6-methoxy-5-morpholino-2,3-dihydro-1H-inden-1-one | 485.25 |

TABLE 1A-continued

Substituted 2,3-dihydro-1H-inden-1-one containing RORγ Antagonists

| Example ID | Structure | Name | MW |
|---|---|---|---|
| 47 | 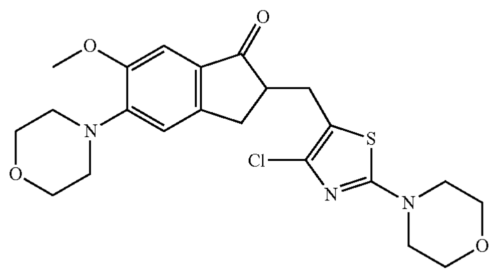 [SMILES: COc1cc2c(cc1N1CCOCC1)CC(Cc1sc(N3CCOCC3)nc1Cl)C2=O] | 2-((4-chloro-2-morpholinothiazol-5-yl)methyl)-6-methoxy-5-morpholino-2,3-dihydro-1H-inden-1-one | 463.98 |
| 50 | 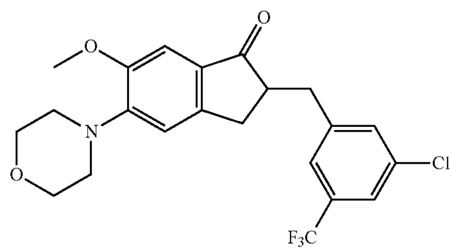 [SMILES: COc1cc2c(cc1N1CCOCC1)CC(Cc1cc(Cl)cc(C(F)(F)F)c1)C2=O] | 2-(3-chloro-5-(trifluoromethyl)benzyl)-6-methoxy-5-morpholino-2,3-dihydro-1H-inden-1-one | 440.0* |
| 53 | 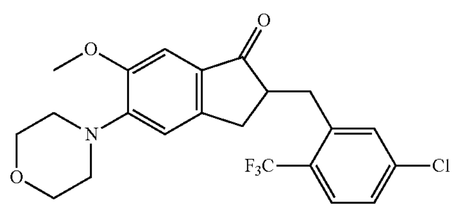 [SMILES: COc1cc2c(cc1N1CCOCC1)CC(Cc1cc(Cl)ccc1C(F)(F)F)C2=O] | 2-(5-chloro-2-(trifluoromethyl)benzyl)-6-methoxy-5-morpholino-2,3-dihydro-1H-inden-1-one | 440.0* |
| 56 | 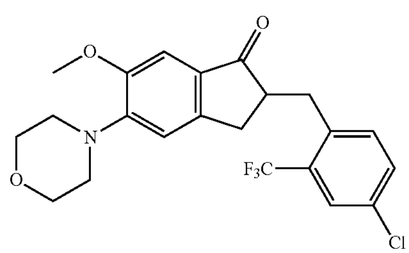 | 2-(4-chloro-2-(trifluoromethyl)benzyl)-6-methoxy-5-morpholino-2,3-dihydro-1H-inden-1-one | 439.8 |
| 59 | 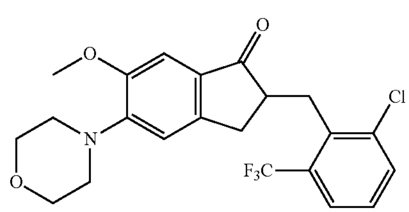 [SMILES: COc1cc2c(cc1N1CCOCC1)CC(Cc1c(Cl)cccc1C(F)(F)F)C2=O] | 2-(2-chloro-6-(trifluoromethyl)benzyl)-6-methoxy-5-morpholino-2,3-dihydro-1H-inden-1-one | 439.8 |
| 62 | 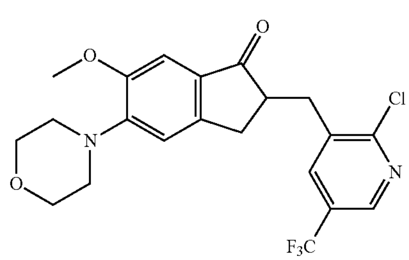 [SMILES: COc1cc2c(cc1N1CCOCC1)CC(Cc1cc(C(F)(F)F)cnc1Cl)C2=O] | 2-((2-chloro-5-(trifluoromethyl)pyridin-3-yl)methyl)-6-methoxy-5-morpholino-2,3-dihydro-1H-inden-1-one | 440.8 |

TABLE 1A-continued

Substituted 2,3-dihydro-1H-inden-1-one containing RORγ Antagonists

| Example ID | Structure | Name | MW |
|---|---|---|---|
| 65 | 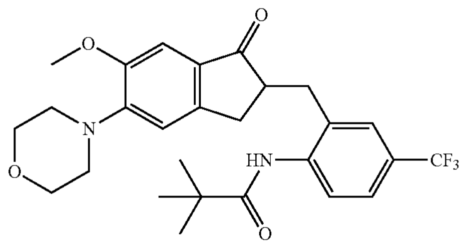 [SMILES: COc1cc2c(cc1N1CCOCC1)CC(Cc1cc(C(F)(F)F)ccc1NC(=O)C(C)(C)C)C2=O] | N-(2-((6-methoxy-5-morpholino-1-oxo-2,3-dihydro-1H-inden-2-yl)methyl)-4-(trifluoromethyl)phenyl)pivalamide | 504.5 |
| 68 | 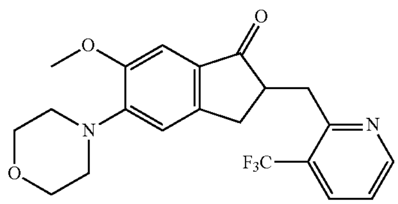 [SMILES: COc1cc2c(cc1N1CCOCC1)CC(Cc1ncccc1C(F)(F)F)C2=O] | 6-methoxy-5-morpholino-2-((3-(trifluoromethyl)pyridin-2-yl)methyl)-2,3-dihydro-1H-inden-1-one | 407.0* |
| 71 | 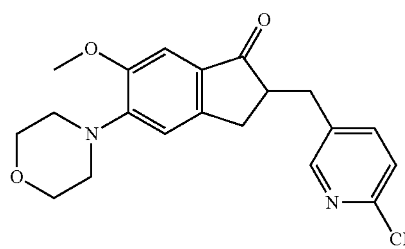 | 6-methoxy-5-morpholino-2-((6-(trifluoromethyl)pyridin-3-yl)methyl)-2,3-dihydro-1H-inden-1-one | 407.0* |
| 74 | 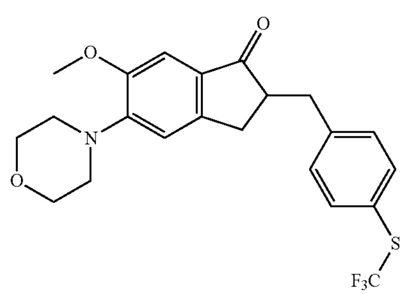 [SMILES: COc1cc2c(cc1N1CCOCC1)CC(Cc1ccc(SC(F)(F)F)cc1)C2=O] | 6-methoxy-5-morpholino-2-(4-((trifluoromethyl)thio)benzyl)-2,3-dihydro-1H-inden-1-one | 438.0* |
| 77 | 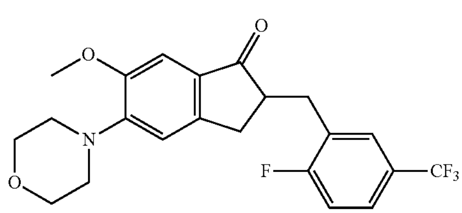 [SMILES: COc1cc2c(cc1N1CCOCC1)CC(Cc1cc(C(F)(F)F)ccc1F)C2=O] | 2-(2-fluoro-5-(trifluoromethyl)benzyl)-6-methoxy-5-morpholino-2,3-dihydro-1H-inden-1-one | 424.0* |
| 80 | 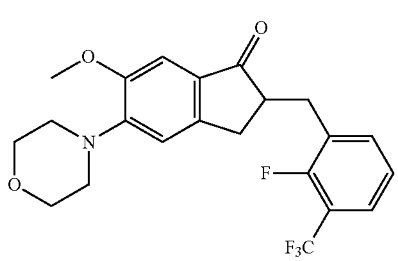 [SMILES: COc1cc2c(cc1N1CCOCC1)CC(Cc1cccc(C(F)(F)F)c1F)C2=O] | 2-(2-fluoro-3-(trifluoromethyl)benzyl)-6-methoxy-5-morpholino-2,3-dihydro-1H-inden-1-one | 424.0 |

TABLE 1A-continued

Substituted 2,3-dihydro-1H-inden-1-one containing RORγ Antagonists

| Example ID | Structure | Name | MW |
|---|---|---|---|
| 83 | 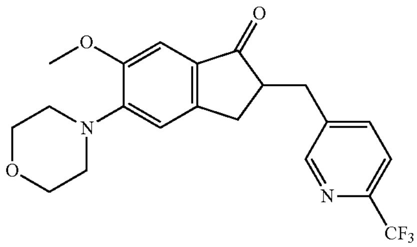 | 6-methoxy-5-morpholino-2-((6-(trifluoromethyl)pyridin-3-yl)methyl)-2,3-dihydro-1H-inden-1-one | 406.4 |
| 86 | 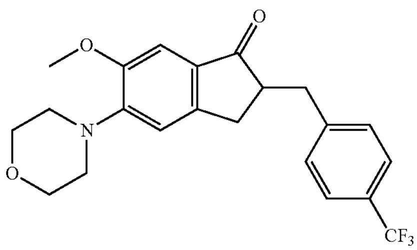 [SMILES: COc1cc2c(cc1N1CCOCC1)CC(Cc1ccc(C(F)(F)F)nc1)C2=O] | 6-methoxy-5-morpholino-2-(4-(trifluoromethyl)benzyl)-2,3-dihydro-1H-inden-1-one | 406.0* |
| 89 | 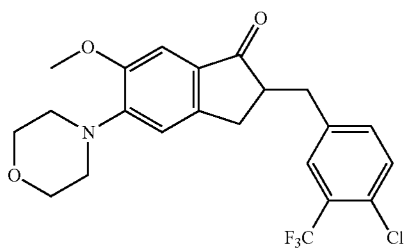 [SMILES: COc1cc2c(cc1N1CCOCC1)CC(Cc1ccc(Cl)c(C(F)(F)F)c1)C2=O] | 2-(4-chloro-3-(trifluoromethyl)benzyl)-6-methoxy-5-morpholino-2,3-dihydro-1H-inden-1-one | 439.9* |
| 92 | 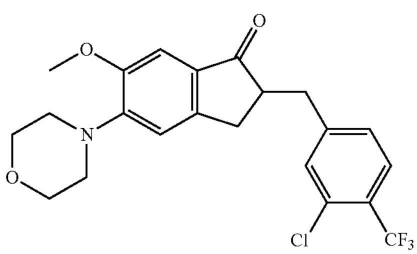 [SMILES: COc1cc2c(cc1N1CCOCC1)CC(Cc1ccc(C(F)(F)F)c(Cl)c1)C2=O] | 2-(3-chloro-4-(trifluoromethyl)benzyl)-6-methoxy-5-morpholino-2,3-dihydro-1H-inden-1-one | 440.0* |
| 95 | 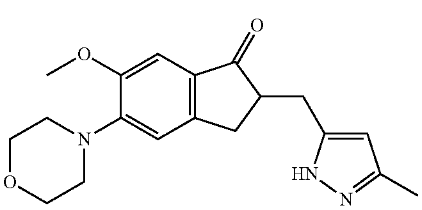 [SMILES: COc1cc2c(cc1N1CCOCC1)CC(Cc1cc(C)n[nH]1)C2=O] | 6-methoxy-2-((3-methyl-1H-pyrazol-5-yl)methyl)-5-morpholino-2,3-dihydro-1H-inden-1-one | 342.0* |
| 98 | 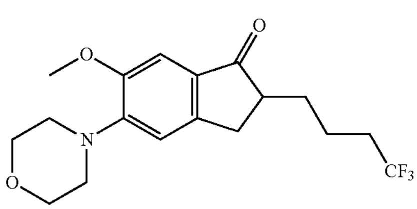 [SMILES: COc1cc2c(cc1N1CCOCC1)CC(CCCC(F)(F)F)C2=O] | 6-methoxy-5-morpholino-2-(4,4,4-trifluorobutyl)-2,3-dihydro-1H-inden-1-one | 357.3 |

TABLE 1A-continued

Substituted 2,3-dihydro-1H-inden-1-one containing RORγ Antagonists

| Example ID | Structure | Name | MW |
|---|---|---|---|
| 103 | 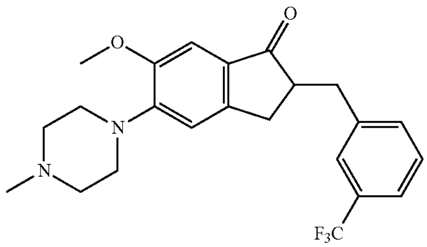 [SMILES: COc1cc2c(cc1N1CCN(C)CC1)CC(Cc1cccc(C(F)(F)F)c1)C2=O] | 6-methoxy-5-(4-methylpiperazin-1-yl)-2-(3-(trifluoromethyl)benzyl)-2,3-dihydro-1H-inden-1-one | 418.4 |
| 106 | 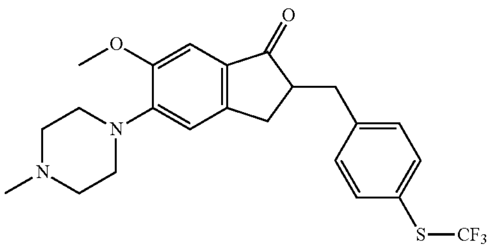 | 6-methoxy-5-(4-methylpiperazin-1-yl)-2-(3-((trifluoromethyl)thio)benzyl)-2,3-dihydro-1H-inden-1-one | 451.0* |
| 110 | 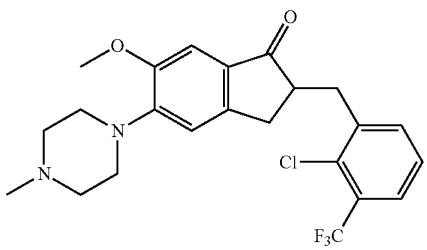 [SMILES: COc1cc2c(cc1N1CCN(C)CC1)CC(Cc1cccc(C(F)(F)F)c1Cl)C2=O] | 2-(2-chloro-3-(trifluoromethyl)benzyl)-6-methoxy-5-(4-methylpiperazin-1-yl)-2,3-dihydro-1H-inden-1-one | 452.9 |
| 113 | 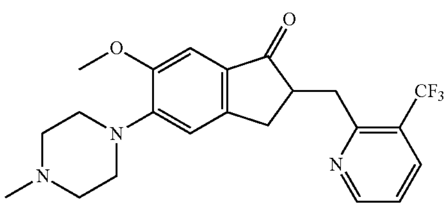 | 6-methoxy-5-(4-methylpiperazin-1-yl)-2-((3-(trifluoromethyl)pyridin-2-yl)methyl)-2,3-dihydro-1H-inden-1-one | 419.4 |
| 117 | 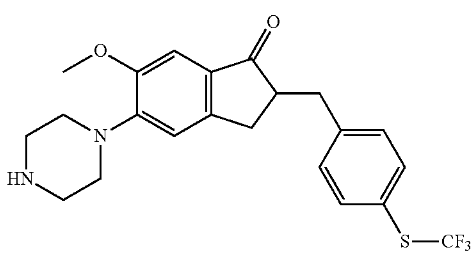 [SMILES: COc1cc2c(cc1N1CCNCC1)CC(Cc1ccc(SC(F)(F)F)cc1)C2=O] | 6-methoxy-5-(piperazin-1-yl)-2-(4-((trifluoromethyl)thio)benzyl)-2,3-dihydro-1H-inden-1-one | 436.5 |
| 120 | 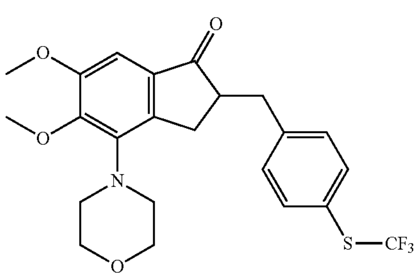 [SMILES: COc1cc2c(c(N3CCOCC3)c1OC)CC(Cc1ccc(SC(F)(F)F)cc1)C2=O] | 5,6-dimethoxy-4-morpholino-2-(4-((trifluoromethyl)thio)benzyl)-2,3-dihydro-1H-inden-1-one | 467.5 |

TABLE 1A-continued

Substituted 2,3-dihydro-1H-inden-1-one containing RORγ Antagonists

| Example ID | Structure | Name | MW |
|---|---|---|---|
| 123 | 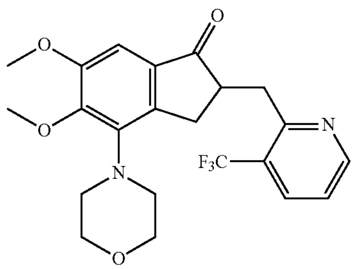 [SMILES: COc1cc2c(c(N3CCOCC3)c1OC)CC(Cc1ncccc1C(F)(F)F)C2=O] | 5,6-dimethoxy-4-morpholino-2-((3-(trifluoromethyl)pyridin-2-yl)methyl)-2,3-dihydro-1H-inden-1-one | 436.4 |
| 125 | 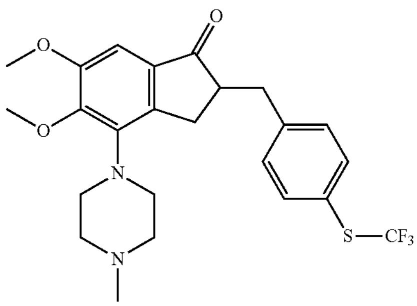 [SMILES: COc1cc2c(c(N3CCN(C)CC3)c1OC)CC(Cc1ccc(SC(F)(F)F)cc1)C2=O] | 5,6-dimethoxy-4-(4-methylpiperazin-1-yl)-2-(4-((trifluoromethyl)thio)benzyl)-2,3-dihydro-1H-inden-1-one | 480.5 |
| 128 | 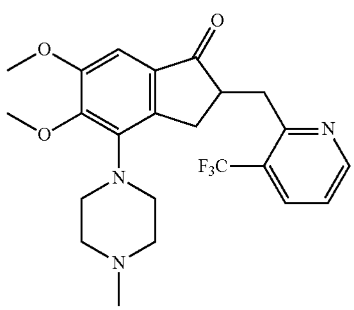 [SMILES: COc1cc2c(c(N3CCN(C)CC3)c1OC)CC(Cc1ncccc1C(F)(F)F)C2=O] | 5,6-dimethoxy-4-(4-methylpiperazin-1-yl)-2-((3-(trifluoromethyl)pyridin-2-yl)methyl)-2,3-dihydro-1H-inden-1-one | 449.4 |
| 131 | 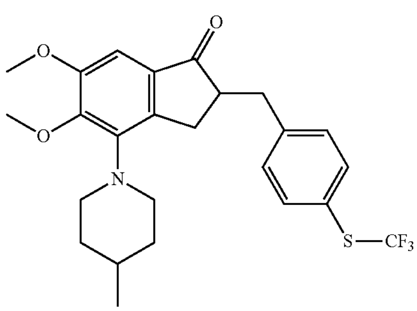 [SMILES: COc1cc2c(c(N3CCC(C)CC3)c1OC)CC(Cc1ccc(SC(F)(F)F)cc1)C2=O] | 5,6-dimethoxy-4-(4-methylpiperidin-1-yl)-2-(4-((trifluoromethyl)thio)benzyl)-2,3-dihydro-1H-inden-1-one | 479.5 |
| 133 | 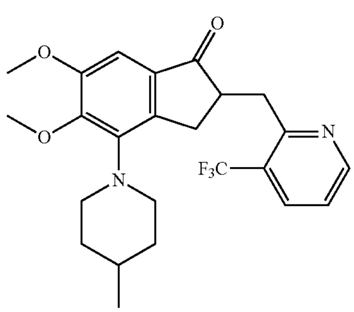 [SMILES: COc1cc2c(c(N3CCC(C)CC3)c1OC)CC(Cc1ncccc1C(F)(F)F)C2=O] | 5,6-dimethoxy-4-(4-methylpiperidin-1-yl)-2-((3-(trifluoromethyl)pyridin-2-yl)methyl)-2,3-dihydro-1H-inden-1-one | 448.5 |

TABLE 1A-continued

Substituted 2,3-dihydro-1H-inden-1-one containing RORγ Antagonists

| Example ID | Structure | Name | MW |
|---|---|---|---|
| 136 | 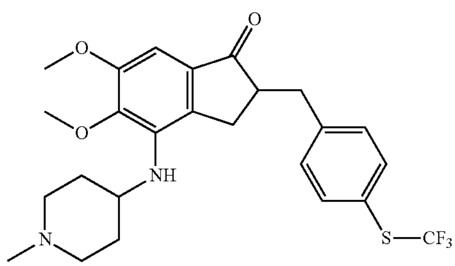 [SMILES: COc1cc2c(c(NC3CCN(C)CC3)c1OC)CC(Cc1ccc(SC(F)(F)F)cc1)C2=O] | 5,6-dimethoxy-4-((1-methylpiperidin-4-yl)amino)-2-(4-((trifluoromethyl)thio)benzyl)-2,3-dihydro-1H-inden-1-one | 494.5 |
| 138 | 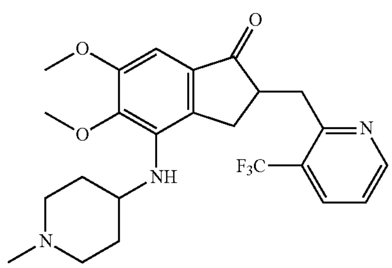 [SMILES: COc1cc2c(c(NC3CCN(C)CC3)c1OC)CC(Cc1ncccc1C(F)(F)F)C2=O] | 5,6-dimethoxy-4-((1-methylpiperidin-4-yl)amino)-2-((3-(trifluoromethyl)pyridin-2-yl)methyl)-2,3-dihydro-1H-inden-1-one | 463.5 |
| 140 | 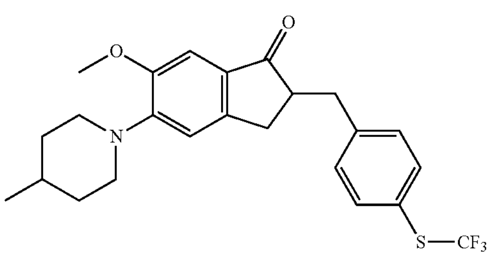 [SMILES: COc1cc2c(cc1N1CCC(C)CC1)CC(Cc1ccc(SC(F)(F)F)cc1)C2=O] | 6-methoxy-5-(4-methylpiperidin-1-yl)-2-(4-((trifluoromethyl)thio)benzyl)-2,3-dihydro-1H-inden-1-one | 450.1* |
| 142 | 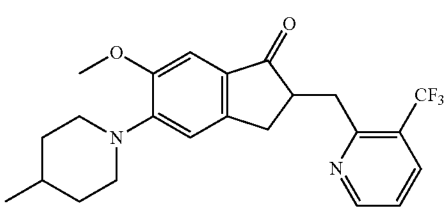 [SMILES: COc1cc2c(cc1N1CCC(C)CC1)CC(Cc1ncccc1C(F)(F)F)C2=O] | 6-methoxy-5-(4-methylpiperidin-1-yl)-2-((3-(trifluoromethyl)pyridin-2-yl)methyl)-2,3-dihydro-1H-inden-1-one | 418.4 |
| 144 | 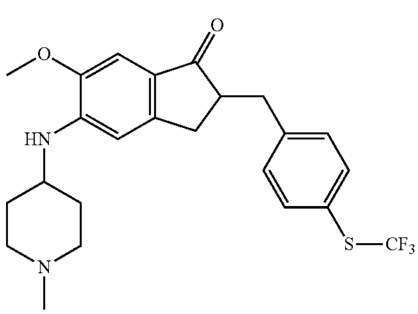 [SMILES: COc1cc2c(cc1NC1CCN(C)CC1)CC(Cc1ccc(SC(F)(F)F)cc1)C2=O] | 6-methoxy-5-((1-methylpiperidin-4-yl)amino)-2-(4-((trifluoromethyl)thio)benzyl)-2,3-dihydro-1H-inden-1-one | 464.5 |

TABLE 1A-continued

Substituted 2,3-dihydro-1H-inden-1-one containing RORγ Antagonists

| Example ID | Structure | Name | MW |
|---|---|---|---|
| 146 | 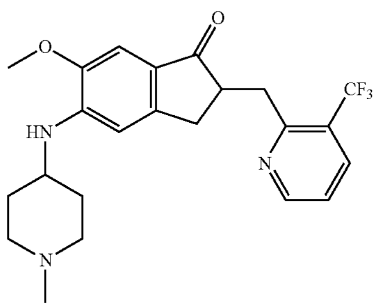 [SMILES: COc1cc2c(cc1NC1CCN(C)CC1)CC(Cc1ncccc1C(F)(F)F)C2=O] | 6-methoxy-5-((1-methylpiperidin-4-yl)amino)-2-((3-(trifluoromethyl)pyridin-2-yl)methyl)-2,3-dihydro-1H-inden-1-one | 433.4 |
| 149 | 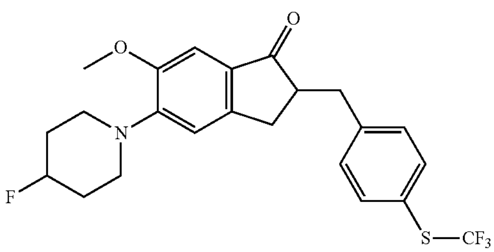 [SMILES: COc1cc2c(cc1N1CCC(F)CC1)CC(Cc1ccc(SC(F)(F)F)cc1)C2=O] | 5-(4-fluoropiperidin-1-yl)-6-methoxy-2-(4-((trifluoromethyl)thio)benzyl)-2,3-dihydro-1H-inden-1-one | 453.5 |
| 151 | 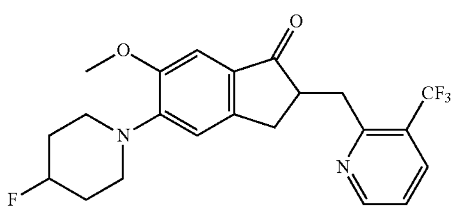 [SMILES: COc1cc2c(cc1N1CCC(F)CC1)CC(Cc1ncccc1C(F)(F)F)C2=O] | 5-(4-fluoropiperidin-1-yl)-6-methoxy-2-((3-(trifluoromethyl)pyridin-2-yl)methyl)-2,3-dihydro-1H-inden-1-one | 422.4 |
| 154 | 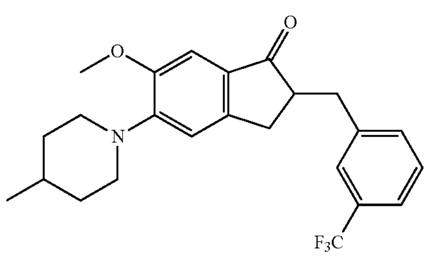 [SMILES: COc1cc2c(cc1N1CCC(C)CC1)CC(Cc1cccc(C(F)(F)F)c1)C2=O] | 6-methoxy-5-(4-methylpiperidin-1-yl)-2-(3-(trifluoromethyl)benzyl)-2,3-dihydro-1H-inden-1-one | 418.* |
| 156 | 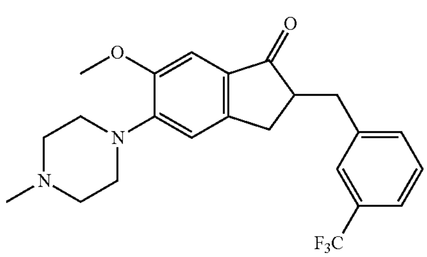 | 6-methoxy-5-(4-methylpiperazin-1-yl)-2-(3-(trifluoromethyl)benzyl)-2,3-dihydro-1H-inden-1-one | 419.0* |
| 158 | 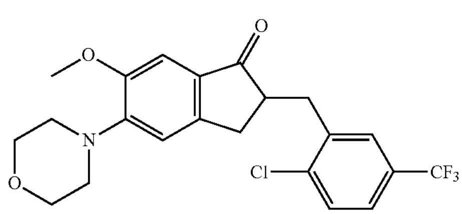 [SMILES: COc1cc2c(cc1N1CCOCC1)CC(Cc1cc(C(F)(F)F)ccc1Cl)C2=O] | 2-(2-chloro-5-(trifluoromethyl)benzyl)-6-methoxy-5-morpholino-2,3-dihydro-1H-inden-1-one | 440.0* |

TABLE 1A-continued

Substituted 2,3-dihydro-1H-inden-1-one containing RORγ Antagonists

| Example ID | Structure | Name | MW |
|---|---|---|---|
| 161 | 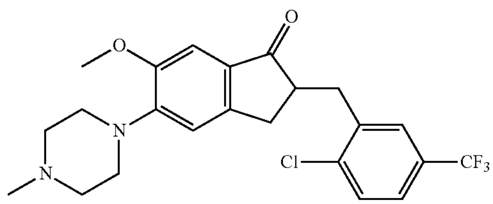 [SMILES: COc1cc2c(cc1N1CCN(C)CC1)CC(Cc1cc(C(F)(F)F)ccc1Cl)C2=O] | 2-(2-chloro-5-(trifluoromethyl)benzyl)-6-methoxy-5-(4-methylpiperazin-1-yl)-2,3-dihydro-1H-inden-1-one | 452.9 |
| 164 | 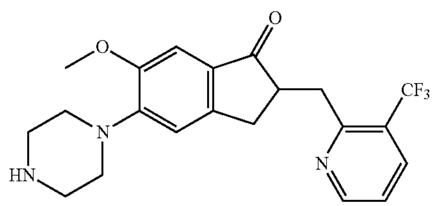 [SMILES: COc1cc2c(cc1N1CCNCC1)CC(Cc1ncccc1C(F)(F)F)C2=O] | 6-methoxy-5-(piperazin-1-yl)-2-((3-(trifluoromethyl)pyridin-2-yl)methyl)-2,3-dihydro-1H-inden-1-one | 405.4 |

*MS (ESI) m/z (M + H)

TABLE 1B

Substituted 2,3-dihydro-1H-inden-1-one containing RORγ Antagonists

| Example ID | Structure | Name | MW |
|---|---|---|---|
| 167 | 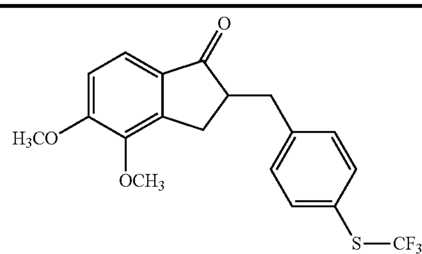 | 4,5-dimethoxy-2-(4-((trifluoromethyl)thio)benzyl)-2,3-dihydro-1H-inden-1-one | 382.40 |
| 169 | 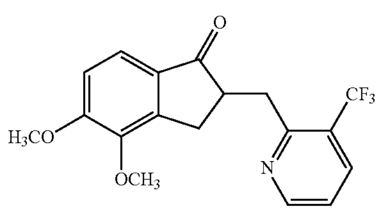 [SMILES: COc1ccc2c(c1OC)CC(Cc1ncccc1C(F)(F)F)C2=O] | 4,5-dimethoxy-2-((3-(trifluoromethyl)pyridin-2-yl)methyl)-2,3-dihydro-1H-inden-1-one | 351.32 |
| 172 | 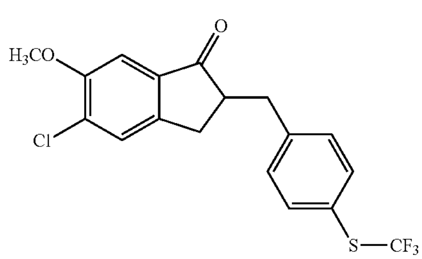 [SMILES: COc1cc2c(cc1Cl)CC(Cc1ccc(SC(F)(F)F)cc1)C2=O] | 5-chloro-6-methoxy-2-(4-((trifluoromethyl)thio)benzyl)-2,3-dihydro-1H-inden-1-one | 386.82 |
| 174 | 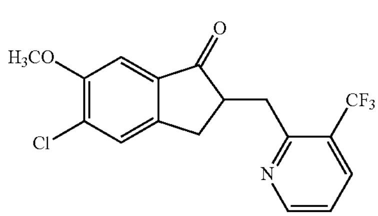 [SMILES: COc1cc2c(cc1Cl)CC(Cc1ncccc1C(F)(F)F)C2=O] | 5-chloro-6-methoxy-2-((3-(trifluoromethyl)pyridin-2-yl)methyl)-2,3-dihydro-1H-inden-1-one | 355.74 |

TABLE 1B-continued

Substituted 2,3-dihydro-1H-inden-1-one containing RORγ Antagonists

| Example ID | Structure | Name | MW |
|---|---|---|---|
| 177 | 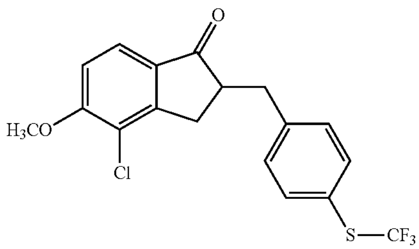 [SMILES: COc1ccc2c(c1Cl)CC(Cc1ccc(SC(F)(F)F)cc1)C2=O] | 4-chloro-5-methoxy-2-(4-((trifluoromethyl)thio)benzyl)-2,3-dihydro-1H-inden-1-one | 386.84 |
| 179 | 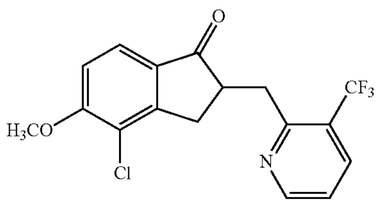 [SMILES: COc1ccc2c(c1Cl)CC(Cc1ncccc1C(F)(F)F)C2=O] | 4-chloro-5-methoxy-2-((3-(trifluoromethyl)pyridin-2-yl)methyl)-2,3-dihydro-1H-inden-1-one | 355.06 |
| 182 | 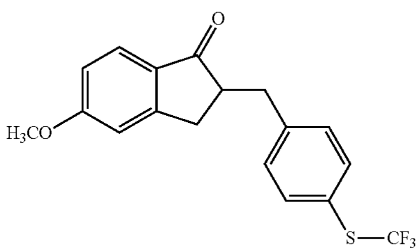 [SMILES: COc1ccc2c(c1)CC(Cc1ccc(SC(F)(F)F)cc1)C2=O] | 5-methoxy-2-(4-((trifluoromethyl)thio)benzyl)-2,3-dihydro-1H-inden-1-one | 352.07 |
| 184 | 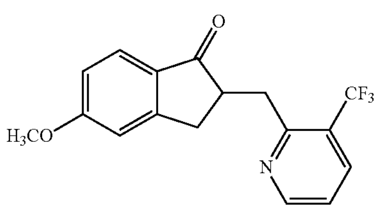 [SMILES: COc1ccc2c(c1)CC(Cc1ncccc1C(F)(F)F)C2=O] | 5-methoxy-2-((3-(trifluoromethyl)pyridin-2-yl)methyl)-2,3-dihydro-1H-inden-1-one | 321.10 |
| 187 | 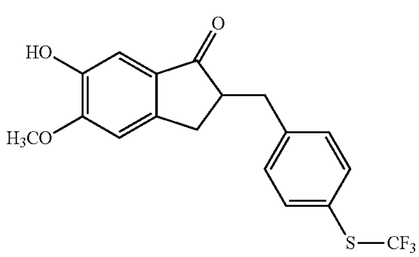 [SMILES: COc1cc2c(cc1O)C(=O)C(Cc1ccc(SC(F)(F)F)cc1)C2] | 6-hydroxy-5-methoxy-2-(4-((trifluoromethyl)thio)benzyl)-2,3-dihydro-1H-inden-1-one | 368.01 |
| 188 | 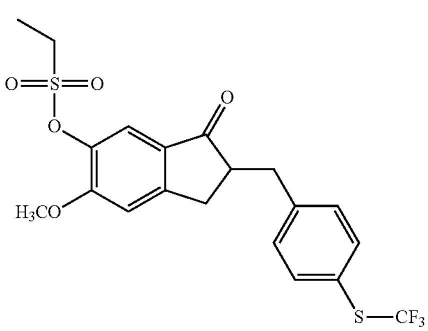 [SMILES: CCS(=O)(=O)Oc1cc2c(cc1OC)CC(Cc1ccc(SC(F)(F)F)cc1)C2=O] | 6-methoxy-3-oxo-2-(4-((trifluoromethyl)thio)benzyl)-2,3-dihydro-1H-inden-5-yl ethanesulfonate | 460.06 |

TABLE 1B-continued

Substituted 2,3-dihydro-1H-inden-1-one containing RORγ Antagonists

| Example ID | Structure | Name | MW |
|---|---|---|---|
| 190 | 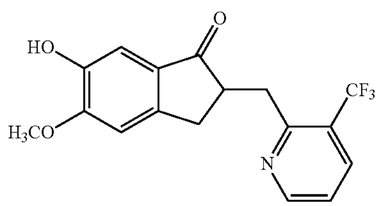 [SMILES: COc1cc2c(cc1O)C(=O)C(Cc1ncccc1C(F)(F)F)C2] | 6-hydroxy-5-methoxy-2-((3-(trifluoromethyl)pyridin-2-yl)methyl)-2,3-dihydro-1H-inden-1-one | 337.09 |
| 191 | 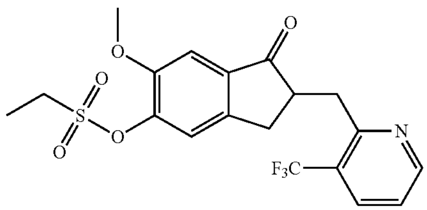 [SMILES: CCS(=O)(=O)Oc1cc2c(cc1OC)C(=O)C(Cc1ncccc1C(F)(F)F)C2] | 6-methoxy-3-oxo-2-((3-(trifluoromethyl)pyridin-2-yl)methyl)-2,3-dihydro-1H-inden-5-yl ethanesulfonate | 429.09 |
| 193 | 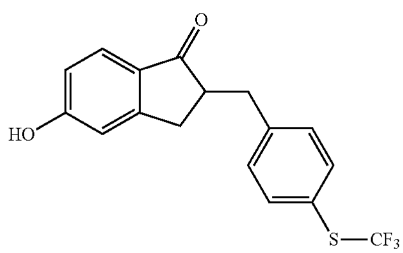 [SMILES: O=C1c2ccc(O)cc2CC1Cc1ccc(SC(F)(F)F)cc1] | 5-hydroxy-2-(4-((trifluoromethyl)thio)benzyl)-2,3-dihydro-1H-inden-1-one | 338.06 |
| 194 | 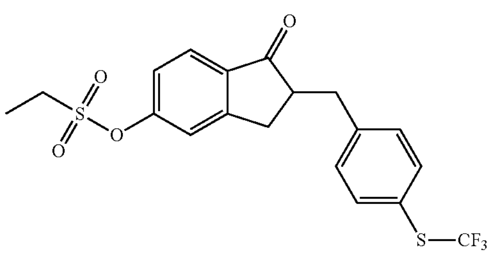 [SMILES: CCS(=O)(=O)Oc1ccc2c(c1)CC(Cc1ccc(SC(F)(F)F)cc1)C2=O] | 1-oxo-2-(4-((trifluoromethyl)thio)benzyl)-2,3-dihydro-1H-inden-5-yl ethanesulfonate | 430.05 |
| 196 | 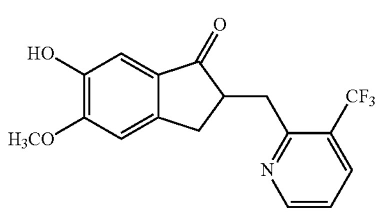 [SMILES: COc1cc2c(cc1O)C(=O)C(Cc1ncccc1C(F)(F)F)C2] | 6-hydroxy-5-methoxy-2-((3-(trifluoromethyl)pyridin-2-yl)methyl)-2,3-dihydro-1H-inden-1-one | 337.09 |
| 197 | 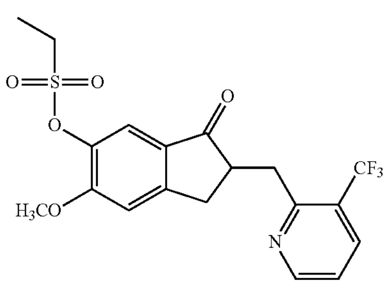 [SMILES: CCS(=O)(=O)Oc1cc2c(cc1OC)CC(Cc1ncccc1C(F)(F)F)C2=O] | 6-methoxy-3-oxo-2-((3-(trifluoromethyl)pyridin-2-yl)methyl)-2,3-dihydro-1H-inden-5-yl ethanesulfonate | 429.09 |

TABLE 1B-continued

Substituted 2,3-dihydro-1H-inden-1-one containing RORγ Antagonists

| Example ID | Structure | Name | MW |
|---|---|---|---|
| 200 | 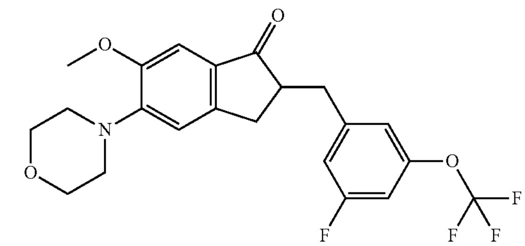 [SMILES: COc1cc2c(cc1N1CCOCC1)CC(Cc1cc(F)cc(OC(F)(F)F)c1)C2=O] | 2-(2-fluoro-4-(trifluoromethoxy)phenyl)-6-methoxy-5-morpholino-2,3-dihydro-1H-inden-1-one | 425.13 |
| 202 | 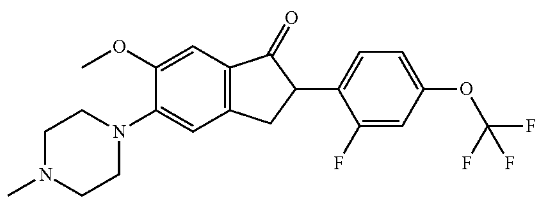 [SMILES: COc1cc2c(cc1N1CCN(C)CC1)CC(c1ccc(OC(F)(F)F)cc1F)C2=O] | 2-(2-fluoro-4-(trifluoromethoxy)phenyl)-6-methoxy-5-(4-methylpiperazin-1-yl)-2,3-dihydro-1H-inden-1-one | 438.16 |
| 206 | 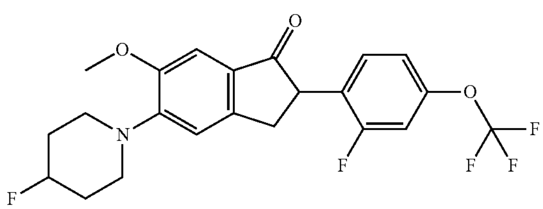 [SMILES: COc1cc2c(cc1N1CCC(F)CC1)CC(c1ccc(OC(F)(F)F)cc1F)C2=O] | 2-(2-fluoro-4-(trifluoromethoxy)phenyl)-5-(4-fluoropiperidin-1-yl)-6-methoxy-2,3-dihydro-1H-inden-1-one | 441.14 |
| 209 | 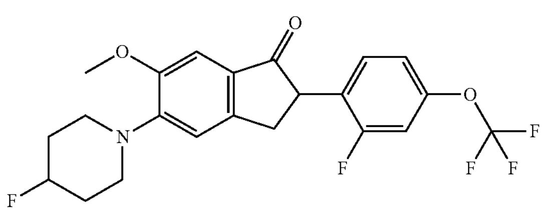 [SMILES: COc1cc2c(cc1N1CCC(F)CC1)CC(c1ccc(OC(F)(F)F)cc1F)C2=O] | 2-(2-fluoro-4-(trifluoromethoxy)phenyl)-5-(4-fluoropiperidin-1-yl)-6-methoxy-2,3-dihydro-1H-inden-1-one | 441.14 |
| 213 | 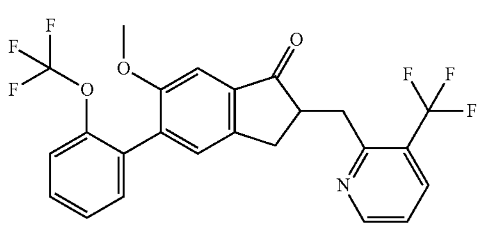 [SMILES: COc1cc2c(cc1-c1ccccc1OC(F)(F)F)CC(Cc1ncccc1C(F)(F)F)C2=O] | 6-methoxy-5-(2-(trifluoromethoxy)phenyl)-2-((3-(trifluoromethyl)pyridin-2-yl)methyl)-2,3-dihydro-1H-inden-1-one | 481.11 |
| 216 | 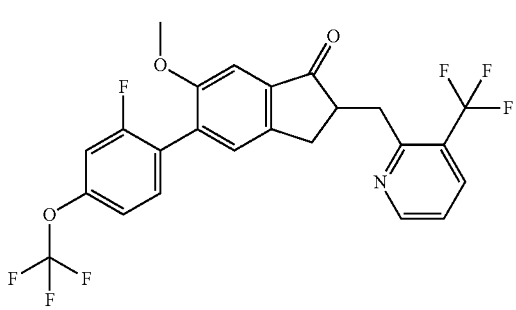 [SMILES: COc1cc2c(cc1-c1ccc(OC(F)(F)F)cc1F)CC(Cc1ncccc1C(F)(F)F)C2=O] | 5-(2-fluoro-4-(trifluoromethoxy)phenyl)-6-methoxy-2-((3-(trifluoromethyl)pyridin-2-yl)methyl)-2,3-dihydro-1H-inden-1-one | 499.10 |

TABLE 1B-continued

Substituted 2,3-dihydro-1H-inden-1-one containing RORγ Antagonists

| Example ID | Structure | Name | MW |
|---|---|---|---|
| 220 | 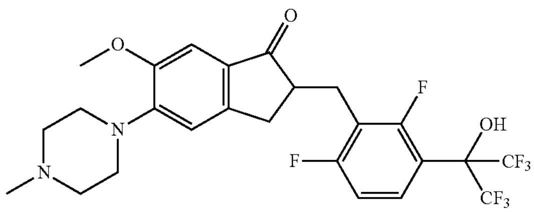 [SMILES: COc1cc2c(cc1N1CCN(C)CC1)CC(Cc1c(F)ccc(C(O)(C(F)(F)F)C(F)(F)F)c1F)C2=O] | 2-(2,6-difluoro-3-(1,1,1,3,3,3-hexafluoro-2-hydroxypropan-2-yl)benzyl)-6-methoxy-5-(4-methylpiperazin-1-yl)-2,3-dihydro-1H-inden-1-one | 552.17 |
| 225 | 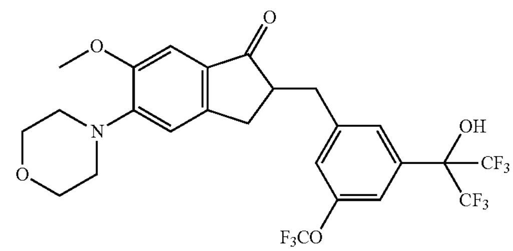 [SMILES: COc1cc2c(cc1N1CCOCC1)CC(Cc1cc(OC(F)(F)F)cc(C(O)(C(F)(F)F)C(F)(F)F)c1)C2=O] | 2-(3-(1,1,1,3,3,3-hexafluoro-2-hydroxypropan-2-yl)-5-(trifluoromethoxy)benzyl)-6-methoxy-5-morpholino-2,3-dihydro-1H-inden-1-one | 587.14 |
| 229 | 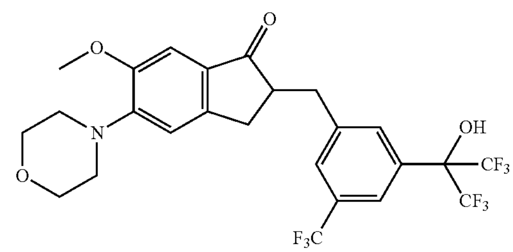 [SMILES: COc1cc2c(cc1N1CCOCC1)CC(Cc1cc(C(F)(F)F)cc(C(O)(C(F)(F)F)C(F)(F)F)c1)C2=O] | 2-(3-(1,1,1,3,3,3-hexafluoro-2-hydroxypropan-2-yl)-5-(trifluoromethyl)benzyl)-6-methoxy-5-morpholino-2,3-dihydro-1H-inden-1-one | 571.14 |
| 232 | 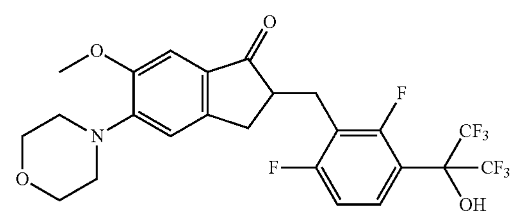 [SMILES: COc1cc2c(cc1N1CCOCC1)CC(Cc1c(F)ccc(C(O)(C(F)(F)F)C(F)(F)F)c1F)C2=O] | 2-(2,6-difluoro-3-(1,1,1,3,3,3-hexafluoro-2-hydroxypropan-2-yl)benzyl)-6-methoxy-5-morpholino-2,3-dihydro-1H-inden-1-one | 539.13 |
| 236 | 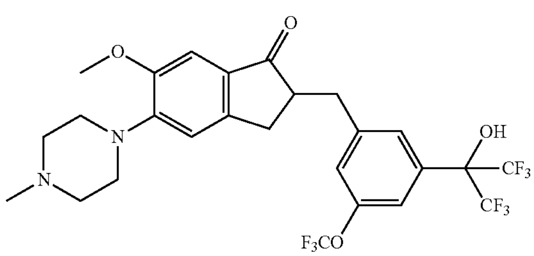 [SMILES: COc1cc2c(cc1N1CCN(C)CC1)CC(Cc1cc(OC(F)(F)F)cc(C(O)(C(F)(F)F)C(F)(F)F)c1)C2=O] | 2-(3-(1,1,1,3,3,3-hexafluoro-2-hydroxypropan-2-yl)-5-(trifluoromethoxy)benzyl)-6-methoxy-5-(4-methylpiperazin-1-yl)-2,3-dihydro-1H-inden-1-one | 600.17 |
| 240 | 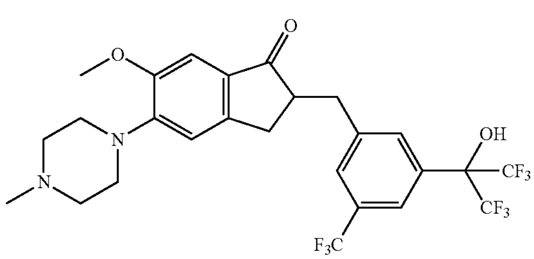 [SMILES: COc1cc2c(cc1N1CCN(C)CC1)CC(Cc1cc(C(F)(F)F)cc(C(O)(C(F)(F)F)C(F)(F)F)c1)C2=O] | 2-(3-(1,1,1,3,3,3-hexafluoro-2-hydroxypropan-2-yl)-5-(trifluoromethyl)benzyl)-6-methoxy-5-(4-methylpiperazin-1-yl)-2,3-dihydro-1H-inden-1-one | 584.17 |

TABLE 1B-continued

Substituted 2,3-dihydro-1H-inden-1-one containing RORγ Antagonists

| Example ID | Structure | Name | MW |
|---|---|---|---|
| 242 | 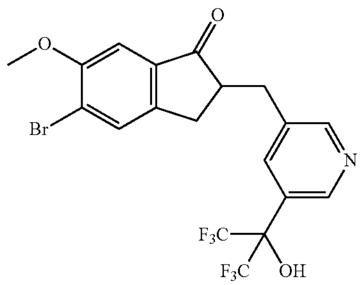 [SMILES: COc1cc2c(cc1Br)CC(Cc1cncc(C(O)(C(F)(F)F)C(F)(F)F)c1)C2=O] | 5-bromo-2-((6-(1,1,1,3,3,3-hexafluoro-2-hydroxypropan-2-yl)pyridin-3-yl)methyl)-6-methoxy-2,3-dihydro-1H-inden-1-one | 497.01 |
| 245 | 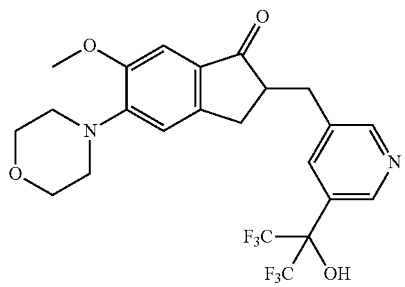 [SMILES: COc1cc2c(cc1N1CCOCC1)CC(Cc1cncc(C(O)(C(F)(F)F)C(F)(F)F)c1)C2=O] | 2-((6-(1,1,1,3,3,3-hexafluoro-2-hydroxypropan-2-yl)pyridin-3-yl)methyl)-6-methoxy-5-morpholino-2,3-dihydro-1H-inden-1-one | 504.15 |
| 249 | 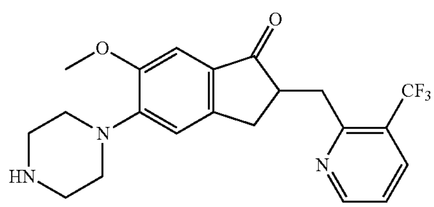 [SMILES: COc1cc2c(cc1N1CCNCC1)CC(Cc1ncccc1C(F)(F)F)C2=O] | 6-methoxy-5-(piperazin-1-yl)-2-((3-(trifluoromethyl)pyridin-2-yl)methyl)-2,3-dihydro-1H-inden-1-one | 405.41 |
| 250 | 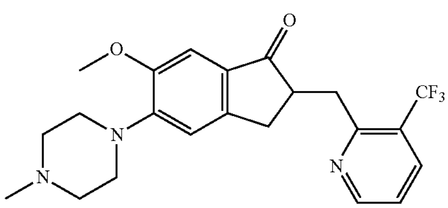 | 6-methoxy-5-(4-methylpiperazin-1-yl)-2-((3-(trifluoromethyl)pyridin-2-yl)methyl)-2,3-dihydro-1H-inden-1-one | 419.18 |
| 251 | 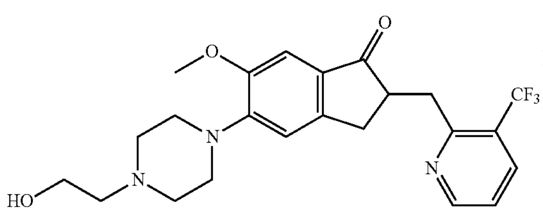 [SMILES: COc1cc2c(cc1N1CCN(CCO)CC1)CC(Cc1ncccc1C(F)(F)F)C2=O] | 5-(4-(2-hydroxyethyl)piperazin-1-yl)-6-methoxy-2-((3-(trifluoromethyl)pyridin-2-yl)methyl)-2,3-dihydro-1H-inden-1-one | 449.19 |
| 256 | 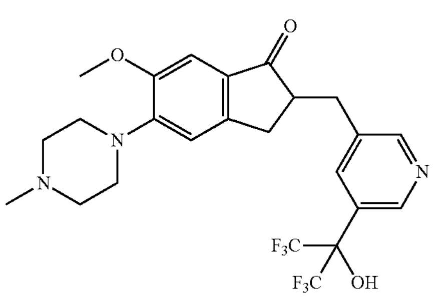 [SMILES: COc1cc2c(cc1N1CCN(C)CC1)CC(Cc1cncc(C(O)(C(F)(F)F)C(F)(F)F)c1)C2=O] | 2-((6-(1,1,1,3,3,3-hexafluoro-2-hydroxypropan-2-yl)pyridin-3-yl)methyl)-6-methoxy-5-(4-methylpiperazin-1-yl)-2,3-dihydro-1H-inden-1-one | 517.18 |

TABLE 1B-continued

Substituted 2,3-dihydro-1H-inden-1-one containing RORγ Antagonists

| Example ID | Structure | Name | MW |
|---|---|---|---|
| 264 | 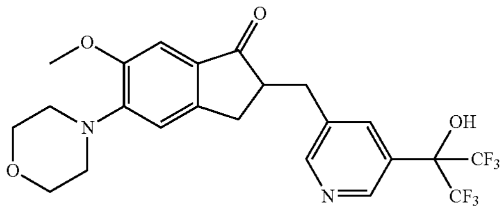 | 2-((5-(1,1,1,3,3,3-hexafluoro-2-hydroxypropan-2-yl)pyridin-3-yl)methyl)-6-methoxy-5-morpholino-2,3-dihydro-1H-inden-1-one | 504.42 |
| 266 | 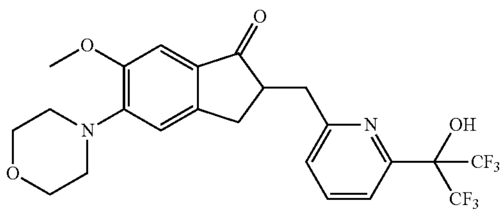 [SMILES: COc1cc2c(cc1N1CCOCC1)CC(Cc1cccc(C(O)(C(F)(F)F)C(F)(F)F)n1)C2=O] | 2-((5-(1,1,1,3,3,3-hexafluoro-2-hydroxypropan-2-yl)pyridin-3-yl)methyl)-6-methoxy-5-morpholino-2,3-dihydro-1H-inden-1-one | 504.42 |
| 268 | 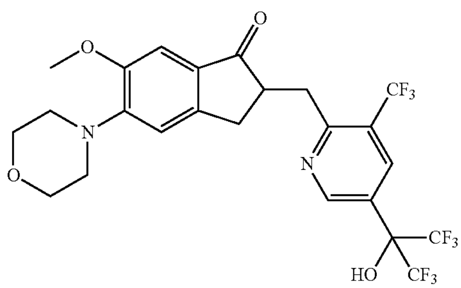 [SMILES: COc1cc2c(cc1N1CCOCC1)CC(Cc1ncc(C(O)(C(F)(F)F)C(F)(F)F)cc1C(F)(F)F)C2=O] | 2-((5-(1,1,1,3,3,3-hexafluoro-2-hydroxypropan-2-yl)-3-(trifluoromethyl)pyridin-2-yl)methyl)-6-methoxy-5-morpholino-2,3-dihydro-1H-inden-1-one | 572.42 |
| 270 | 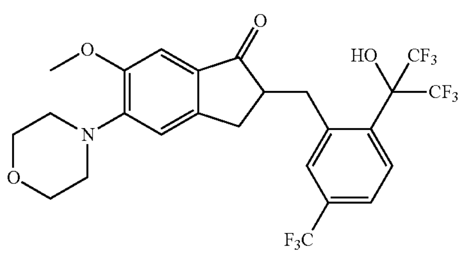 [SMILES: COc1cc2c(cc1N1CCOCC1)CC(Cc1cc(C(F)(F)F)ccc1C(O)(C(F)(F)F)C(F)(F)F)C2=O] | 2-(2-(1,1,1,3,3,3-hexafluoro-2-hydroxypropan-2-yl)-5-(trifluoromethyl)benzyl)-6-methoxy-5-morpholino-2,3-dihydro-1H-inden-1-one | 571.43 |

*MS (ESI) m/z (M + H)

TABLE 2

List of abbreviation and meaning used through out this application

| Abbreviation | Meaning |
|---|---|
| CHCl3 | Chloroform - $CHCl_3$ |
| CDCl3 | Chloroform deuterated solvent - $CDCl_3$ |
| DCM | Dichloromethane - $CH_2Cl_2$ |
| DME | 1,2-Dimethoxyethane |
| DMF | N,N-Dimethylformamide |
| DMSO | Dimethylsulfoxide |
| DMSO-$d_6$ | Dimethylsulfoxide deuterated solvent |
| Pd2(pda)3 | Tris(dibenzylideneacetone)dipalladium(0) |
| Pd(PH3)4 | Tetrakis(trifluorophosphine)palladium(0) |
| PTSA | p-Toluene Sulfonic Acid |
| THF | Tetrahydrofuran |
| ±BINAP | rac 2.2'-Bis(diphenylphosphino)-9,9-dimethylxanthene |
| Xantphos | 4,5-Bis(diphenylphosphino)-9,9-dimethylxanthene |
| Pd(dppf)Cl$_2$•CH$_2$Cl$_2$ | [1,1'-bis(diphenylphosphino)ferrocene]dichloropalladium II DCM |
| Et | Ethyl |
| Me | Methyl |

TABLE 2-continued

List of abbreviation and meaning used through out this application

| Abbreviation | Meaning |
|---|---|
| MeOH | Methanol |
| EtOH | Ethanol |
| EtOAc | Ethylacetate |
| AcCN/MeCN | Acetonitrile |
| DIPEA | Diisopropylethylamine |
| IP | Isopropanol |
| $Na_2CO_3$ | Sodium Carbonate |
| $K_2CO_3$ | Potassium Carbonate |
| $Cs_2CO_3$ | Cesium Carbonate |
| TFA | Trifluoroacetic acid |
| EDC HCl | N-Ethyl-N'-(3-dimethylaminopropyl)carbodiimide HCl |
| HOBT | 1-Hydroxybenzotgriazole hydrate |
| HOAc | Acetic Acid |
| Et | Ethyl |
| TMS | Trimethylsilyl |
| NBS | N-Bromosuccinamide |
| NCS | N-Chlorosuccinamide |
| PG | Protecting Group |
| g, gm | Gram(s) |
| mg | Milligram(s) |
| h, hr | Hour |
| min | Minute(s) |
| M | Molar, molarity |
| mM | Millimolar |
| μM | Micromolar |
| nM | Nanomolar |
| L, l | Liter(s) |
| mL, mL | Milliliter(s) |
| μL | Microliter(s) |
| RM | Reaction Mixture or Reaction Mass |
| SM | Starting Material |
| RT, rt | Room Temperature |
| HPLC | High-Performance Liquid Chromatography |
| LCMS | Liquid Chromatography Mass Spectrometry |
| MS or ms | Mass Spectrometry |
| NMR | Nuclear Magnetic Resonance Spectroscopy |
| TLC | Thin Layer Chromatography |
| UV | Ultra-Violet Spectrometry |
| s | Singlet |
| d, Dt, dt | Doublet, doublet of doublet |
| t, tr | Triplet |
| m | Multiplet |

Methods of Preparation of Compounds

In certain embodiments, the Examples below are compounds prepared according to general procedures given in the following sections. Although the synthetic methods and Schemes depict the syntheses of certain compounds of the present invention, the methods and other methods known to one of ordinary skill in the art can be applied to all the compounds of the genus, the genus sub-class and species of each of these compounds as described herein. Aspects of this invention can be understood from the following general Schemes 1 and 2. The following are exemplary and are not intended to limit the scope of the invention.

Scheme 1

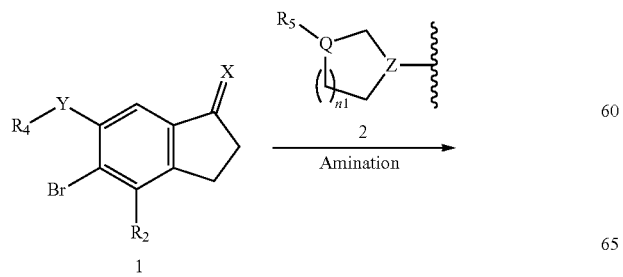

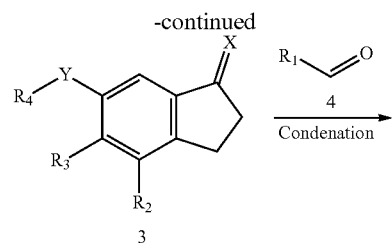

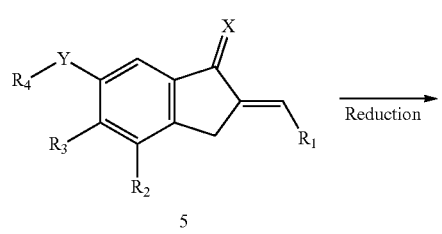

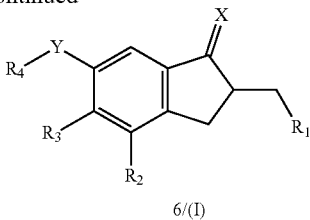

6/(I)

Scheme 2

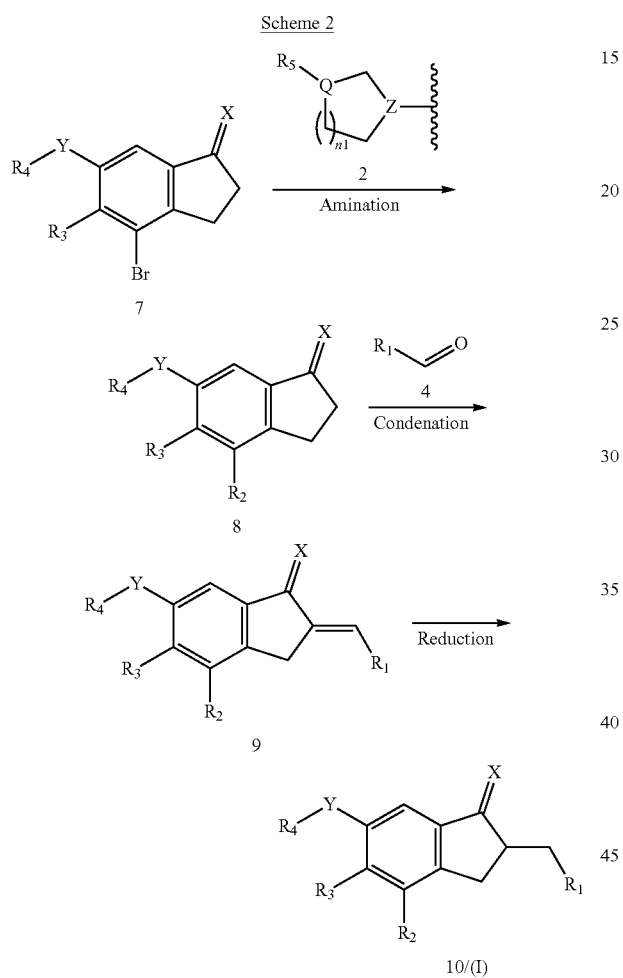

10/(I)

EXAMPLES

Experimental Details and Examples

Melting points were determined in a MP-96 digital Polmon apparatus. $^1$H NMR and $^{13}$C NMR spectra were recorded at RT in CDCl$_3$ or DMSO-d6 at Jeol 400-MHz NMR spectrophotometer using solvent peaks for CDCl$_3$: 7.27 and DMSO-d6 2.50 (D) as internal references. The assignment of chemical shifts is based on standard NMR experiments (1H, 13C). Mass spectra were recorded on a Shimadzu LCMS LC-210EV spectrometer with an API-ES ionization source. Jasco-FTIR-4100 was used to record the IR spectra. TLC analyses were performed on silica F254 and detection by UV light at 254 nm, or by spraying with phosphomolybdic-H$_2$SO$_4$ dyeing reagent, KMNO$_4$ or iodine. Column chromatography were performed on silica Gel 60 (230 mesh). Purifications and separations were performed on a standard silica flash chromatography system. The purity of the samples has been determined by HPLC for the % area peak corresponding to the retention of compound and elemental analysis for C, H, N and O was carried out using Perkin-Elmer 2400 elemental analyser and chloride analysis performed using calorimetric titration at the Intertek USA Inc., QTI.

General synthetic methodology

The compounds of this invention are prepared in general by methods such as those depicted in the Schemes below, and the preparative examples that follow.

Preparation of Examples

Example 1: 6-methoxy-5-morpholino-2, 3-dihydro-1H-inden-1-one (13)

Scheme 3

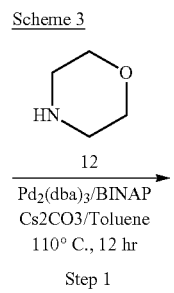

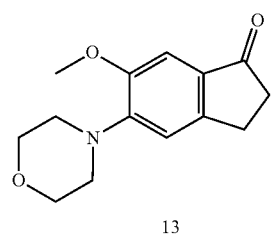

13

Step 1: A solution of 5-bromo-6-methoxy-2,3-dihydro-1H-inden-1-one (11) (1 g, 4.149 mmol) and morpholine (0.36 g, 4.149 mmol) in toluene 15 mL was added cesium carbonate (2.69 g, 8.298 mmol). The reaction was degassed and purged with nitrogen for 10 min. Pd$_2$ (dba)$_3$ (189.3 mg, 0.207 mmol) and BINAP (64.5 mg, 0.103 mmol) was added, degassed and purged and with nitrogen for another 10 min. The reaction was heated to 110° C. overnight under sealed microwave vial. After completion of the starting material, the reaction was diluted with chloroform and filtered through celite bed. The organic layer was concentrated to get the crude compound 13 and the resulting crude was purified through flash chromatography by using 100-200 mesh silica gel eluting the compound at 25% ethyl acetate in hexane as pale yellow coloured solid 6-methoxy-5-morpholino-2,3-dihydro-1H-inden-1-one 13. $^1$HNMR (400 MHz, CDCl$_3$) δ ppm 7.70 (s, 1H), 7.20 (s, 1H), 3.93 (s, 3H), 3.06 (m, 2H), 2.72 (m, 2H); MS (ESI) m/z 247.9 (M+H).

Example 2: 2-(4-chloro-2-fluorobenzyl)-6-methoxy-5-morpholino-2, 3-dihydro-1H-inden-1-one (16)

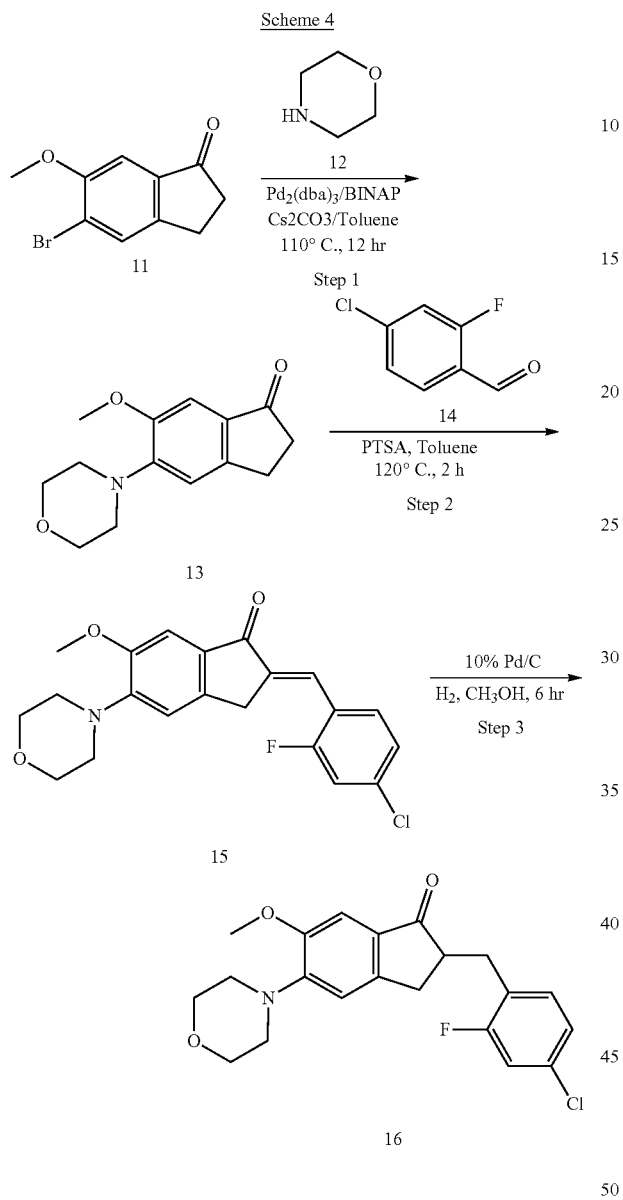

Step 2: To a solution of compound 13 (150 mg, 0.607 mmol) in toluene 15 mL was added 14 (86.2 mg, 0.607 mmol). p-Toluene sulphonic acid (PTSA) (230.9 mg, 1.214 mmol) was added to the reaction mixture, and stirred at 120° C. for 6h. The reaction mass was diluted with ethyl acetate and washed with water (3×25 mL). The organic layer was dried over sodium sulphate and concentrated to get the crude compound 15. The crude compound 15 was purified through flash chromatography by using 100-200 mesh silica gel. The compound (E)-2-(4-chloro-2-fluorobenzylidene)-6-methoxy-5-morpholino-2,3-dihydro-1H-inden-1-one 15 was eluted at 28% ethyl acetate in hexane to afford a yellow coloured solid.

Step 3: Compound 15 (45 mg, 0.121 mmol) was dissolved in methanol and was added Pd/C 20 mg and stirred the reaction under hydrogen balloon for 6h. The reaction was filtered through celite bed and washed with excess methanol. The organic layer was concentrated to get the crude compound 16. The crude 16 was purified by flash chromatography using 100-200 mesh silica gel. Compound 16 was eluted at 23% ethyl acetate in hexane as half white coloured solid 2-(4-chloro-2-fluorobenzyl)-6-methoxy-5-morpholino-2,3-dihydro-1H-inden-1-one 16. $^1$HNMR (400 MHz, CDCl$_3$) δ ppm 7.18 (m, 2H), 6.82 (m, 3H), 3.88 (m, 3H), 3.86 (m, 4H), 3.31 (m, 1H), 3.16 (m, 4H), 3.06 (m, 1H), 2.95 (m, 1H), 2.73 (m, 2H); MS (ESI) m/z 389.8 (M+H).

Example 3: 2-(4-chloro-2-fluorobenzyl)-5-(3, 4-dimethylpiperazin-1-yl)-6-methoxy-2,3-dihydro-1H-inden-1-one (20)

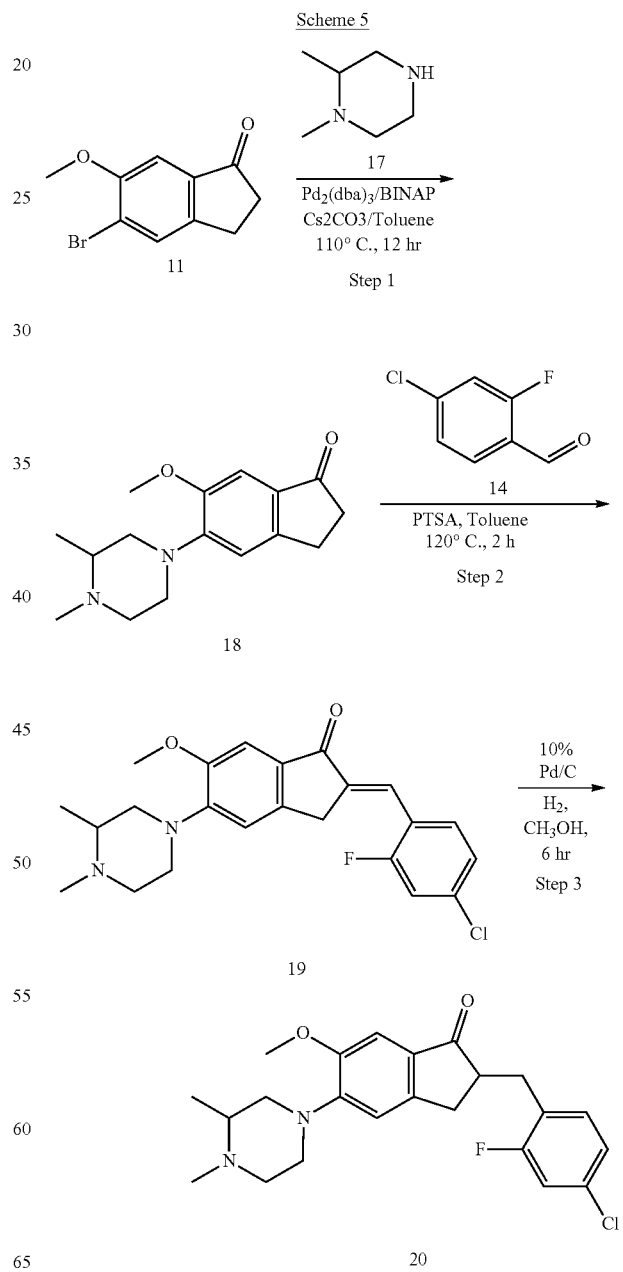

Example 4: 2-((1-benzylpiperidin-4-yl) methyl)-6-methoxy-5-morpholino-2,3-dihydro-1H-inden-1-one (23)

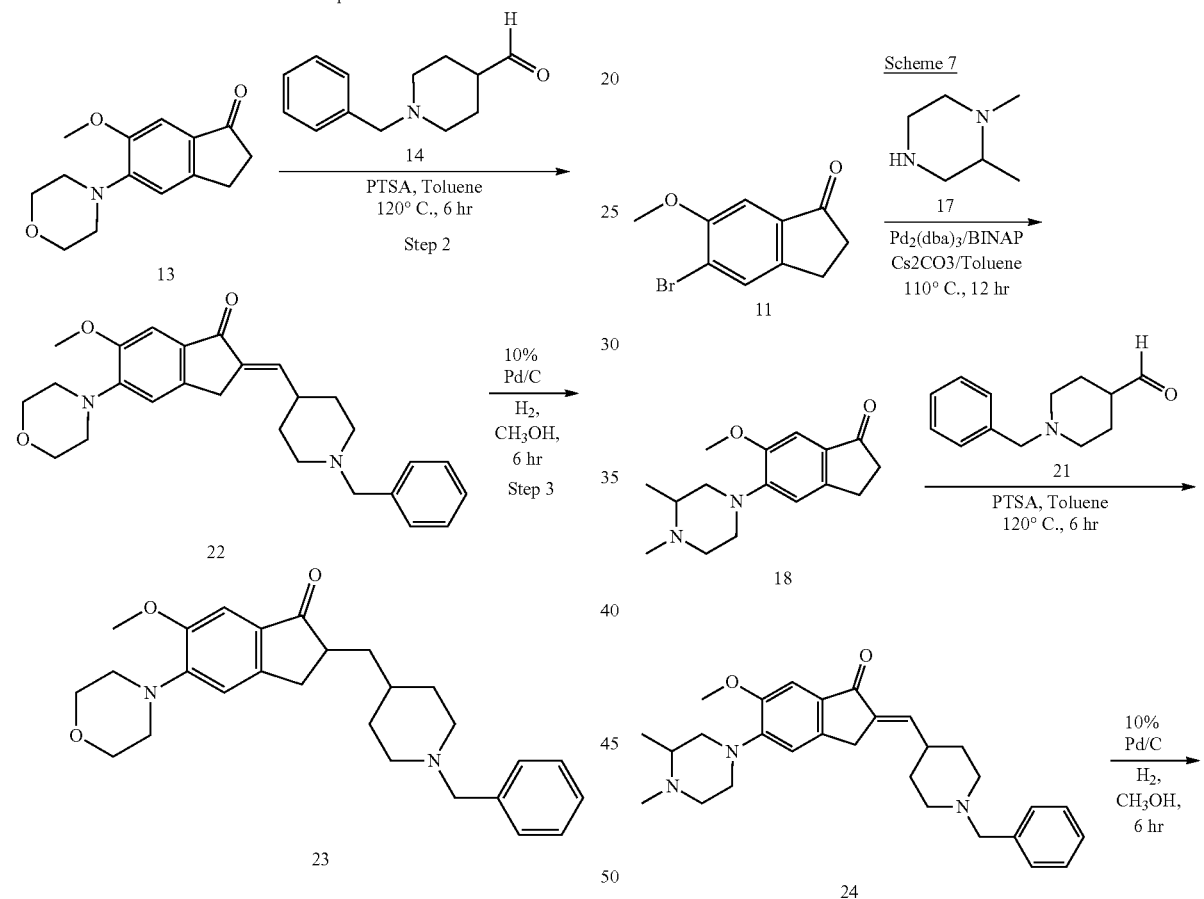

Step 1: To a solution of 13 (150 mg, 0.607 mmol) in toluene 15 mL was added 1-benzylpiperidine-4-carbaldehyde 21 (123.4 mg, 0.607 mmol). p-Toluene sulphonic acid (PTSA) (230.9 mg, 1.214 mmol) was added to the reaction mixture, and stirred at 120° C. for 6h. The reaction mass was diluted with ethyl acetate and washed with water (3×25 mL). The organic layer was dried over sodium sulphate and concentrated to get the crude material, which was purified through flash chromatography using 100-200 mesh silica gel. Eluting at 30% ethyl acetate in hexane gave yellow coloured solid (E)-2-((1-benzylpiperidin-4-yl) methylene)-6-methoxy-5-morpholino-2, 3-dihydro-1H-inden-1-one 22.

Step 2: Compound 22 (85 mg, 0.195 mmol) was dissolved in methanol 25 mL, added Pd/C 40 mg and stirred under hydrogen balloon for 6h. The reaction was filtered through celite bed and washed with excess methanol. The organic layer was concentrated to get the crude compound 23. The crude material was purified by flash chromatography using 100-200 mesh silica gel. The compound was eluted with 20% ethyl acetate in hexane to give half white coloured solid compound 2-((1-benzylpiperidin-4-yl)methyl)-6-methoxy-5-morpholino-2,3-dihydro-1H-inden-1-one 23. $^1$HNMR (400 MHz, CDCl$_3$) δ ppm 7.31 (m, 5H), 7.15 (bs, 1H), 6.85 (bs, 1H), 3.88 (m, 7H), 3.51 (bs, 2H), 3.22 (m, 4H), 2.90 (m, 2H), 2.65 (m, 2H), 1.90 (m, 3H), 1.64 (m, 2H), 1.58 (bs, 4H); MS (ESI) m/z 435.2 (M+H).

Example 5: 2-((1-benzylpiperidin-4-yl) methyl)-5-(3, 4-dimethylpiperazin-1-yl)-6-methoxy-2, 3-dihydro-1H-inden-1-one (25)

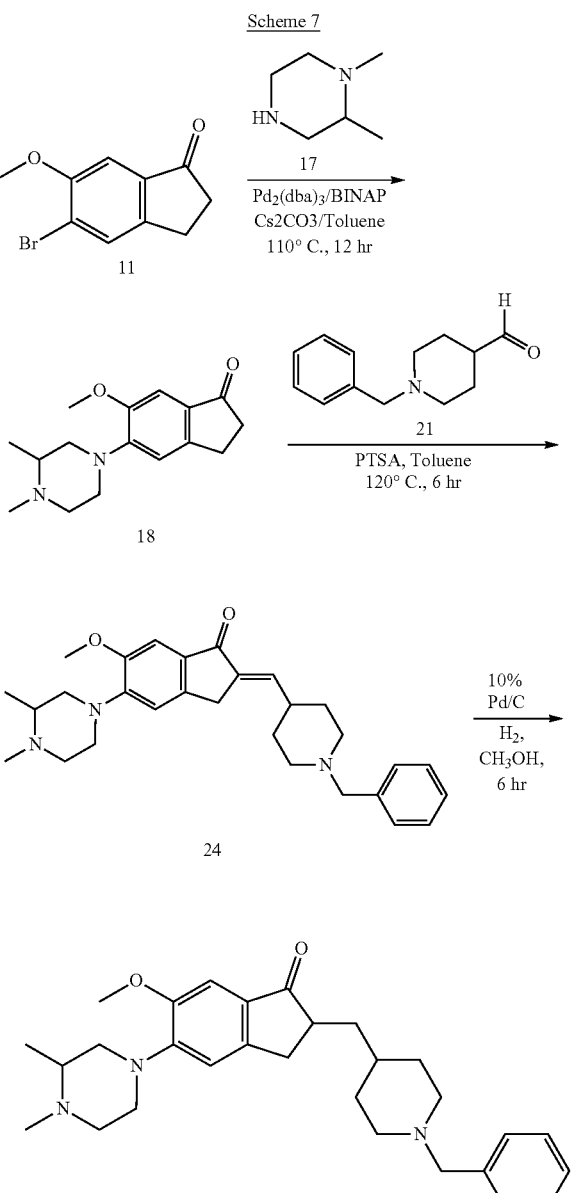

Example 6: 2-(2, 4-difluorobenzyl)-6-methoxy-5-morpholino-2,3-dihydro-1H-inden-1-one (28)

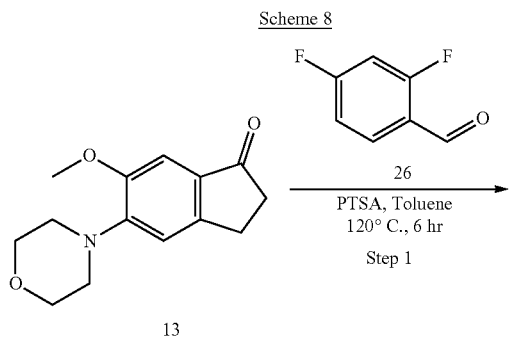

Scheme 8

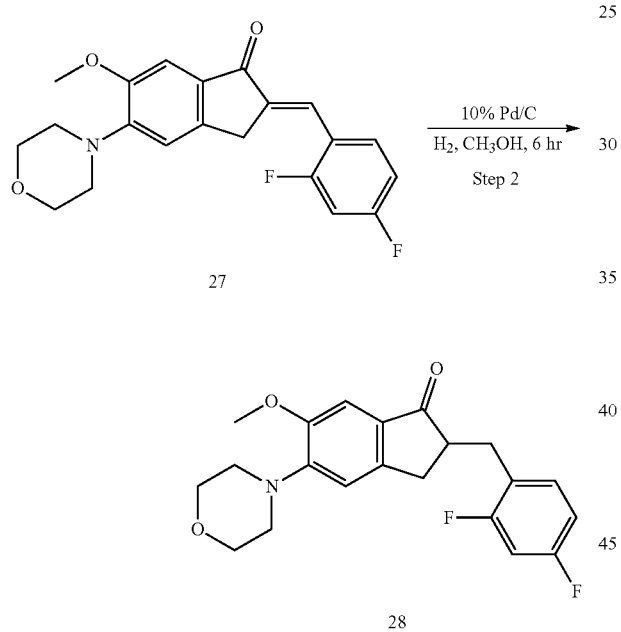

Step 1: To a solution of compound 13 (150 mg, 0.607 mmol) in toluene 15 mL was added 26 (86.2 mg, 0.607 mmol), then PTSA (230.9 mg, 1.214 mmol) was added and stirred at 120° C. for 6h. The resulting mixture was diluted with ethyl acetate and washed with water (3×25 mL). The organic layer was dried over sodium sulphate and concentrated to get the crude compound 27, which was purified through flash chromatography using 100-200 mesh silica gel. Eluting at 28% ethyl acetate in hexane gave yellow coloured solid compound (E)-2-(2,4-difluorobenzylidene)-6-methoxy-5-morpholino-2,3-dihydro-1H-inden-1-one 27.

Step 2: To 27 (45 mg, 0.121 mmol), dissolved in methanol, was added Pd/C 20 mg and stirred under hydrogen balloon for 6h. The reaction was filtered through celite bed and washed with excess methanol. The organic layer was concentrated to get the crude, which was purified by flash chromatography using 100-200 mesh silica gel. The compound was eluted at 23% ethyl acetate in hexane as half white coloured solid compound 2-(2,4-difluorobenzyl)-6-methoxy-5-morpholino-2,3-dihydro-1H-inden-1-one 28. $^1$HNMR (400 MHz, CDCl$_3$) δ ppm 7.18 (m, 2H), 6.82 (m, 3H), 3.88 (m, 3H), 3.86 (m, 4H), 3.31 (m, 1H), 3.16 (m, 4H), 3.06 (m, 1H), 2.95 (m, 1H), 2.73 (m, 2H); MS (ESI) m/z 373.9 (M+H).

Example 7: 6-methoxy-5-morpholino-2-(3-(trifluoromethoxy) benzyl)-2, 3-dihydro-1H-inden-1-one (31)

Scheme 9

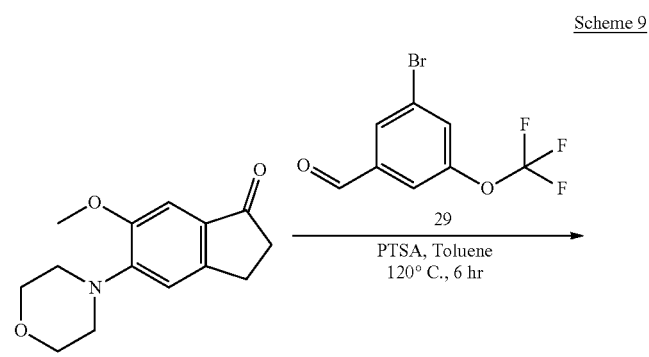

-continued

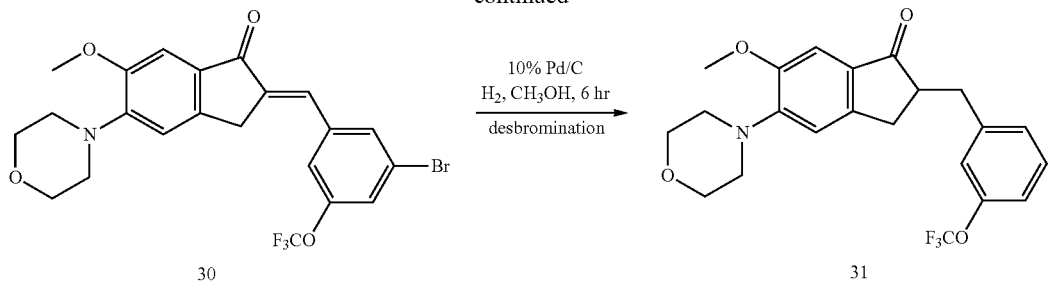

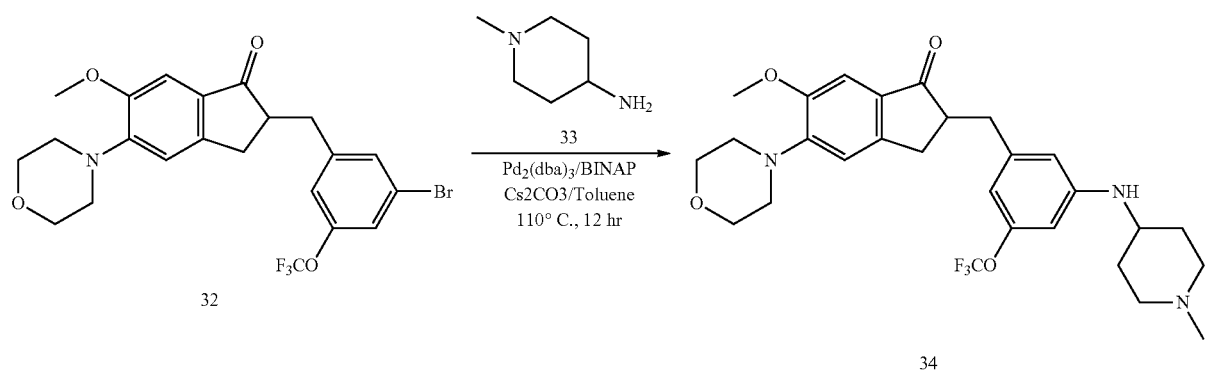

To a solution of compound 13 (150 mg, 0.607 mmol) in toluene 15 mL was added 3-bromo-5-(trifluoromethoxy) benzaldehyde 29 (115.4 mg, 0.607 mmol). PTSA (230.9 mg, 1.214 mmol) was added to the reaction mixture, then stirred at 120° C. for 6h. The reaction mixture was diluted with ethyl acetate and washed with water (3×25 mL). The organic layer was dried over sodium sulphate and concentrated to get the crude compound (E)-2-(3-bromo-5-(trifluoromethoxy) benzylidene)-6-methoxy-5-morpholino-2, 3-dihydro-1H-inden-1-one 30, which was purified through flash chromatography by using 100-200 mesh silica gel. Compound 30 was eluted at 25% ethyl acetate in hexane to afford a yellow coloured solid. To 30 (45 mg, 0.107 mmol), dissolved in methanol 20 mL, was added Pd/C 20 mg and stirred under hydrogen balloon for 6h. The reaction was filtered through celite bed and washed with excess methanol. The organic layer was concentrated to get the crude desbrominated compound 31. The crude 31 was purified by flash chromatography using 100-200 mesh silica gel. Compound 31 was eluted as des-brominated compound at 25% ethyl acetate in hexane as half white coloured solid compound 6-methoxy-5-morpholino-2-(3-(trifluoromethoxy) benzyl)-2,3-dihydro-1H-inden-1-one 31. $^1$HNMR (400 MHz, CDCl$_3$) δ ppm 7.43 (m, 4H), 7.18 (s, 1H), 6.81 (s, 1H), 3.89 (m, 3H), 3.87 (m, 4H), 3.43 (m, 1H), 3.17 (m, 4H), 3.06 (m, 1H), 2.97 (m, 1H), 2.69 (m, 2H); MS (ESI) m/z 422.1 (M+H).

Example 8: 6-methoxy-5-morpholino-2-(3-(trifluoromethyl) benzyl)-2, 3-dihydro-1H-inden-1-one (37)

Scheme 10

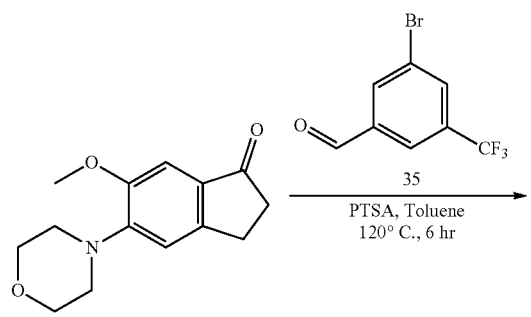

81                                                                  82

-continued

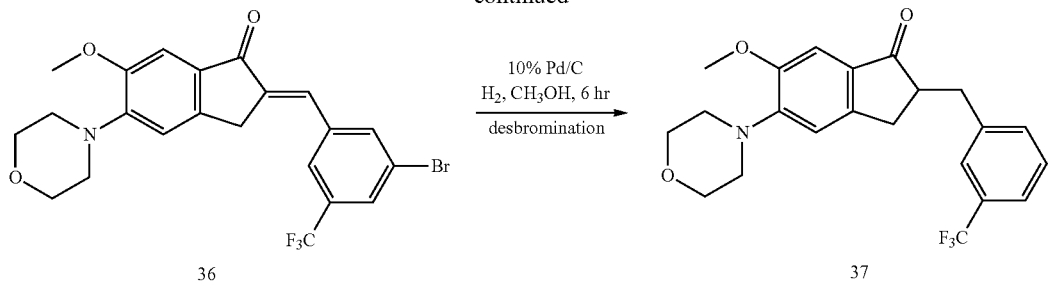

To a solution of 13 (450 mg, 1.819 mmol) in toluene 10 mL was added 3-bromo-5-(trifluoromethyl) benzaldehyde 35 (316.8 mg, 1.819 mmol). PTSA (692.2 mg, 3.639 mmol) was added to the reaction mixture, then stirred at 120° C. for 6h. The reaction mass was diluted with ethyl acetate and washed with water (3×25 mL). The organic layer was dried over sodium sulphate and concentrated to get the crude 36, which was purified through flash chromatography by using 100-200 mesh silica gel. The compound (E)-2-(3-bromo-5-(trifluoromethyl)benzylidene)-6-methoxy-5-morpholino-2,3-dihydro-1Hinden-1-one 36 was eluted at 30% ethyl acetate in hexane to afford yellow coloured solid.

The 36 (570 mg, 1.413 mmol) was dissolved in methanol and was added Pd/C (350 mg), and stirred under hydrogen balloon for 6h. The reaction was filtered through celite bed and washed with excess methanol. The organic layer was concentrated to get the crude 37, which was purified by flash chromatography using 100-200 mesh silica gel. The compound 6-methoxy-5-morpholino-2-(3-(trifluoromethyl)benzyl)-2,3-dihydro-1H-inden-1-one 37 was eluted as des-brominated compound at 28% ethyl acetate in hexane as half white coloured solid. ¹HNMR (400 MHz, CDCl₃) δ ppm 7.47 (m, 4H), 7.18 (s, 1H), 6.81 (s, 1H), 3.89 (m, 3H), 3.87 (m, 3H), 3.40 (m, 1H), 3.17 (m, 4H), 3.06 (m, 1H), 2.97 (m, 1H), 2.69 (m, 2H); MS (ESI) m/z 406.0 (M+H).

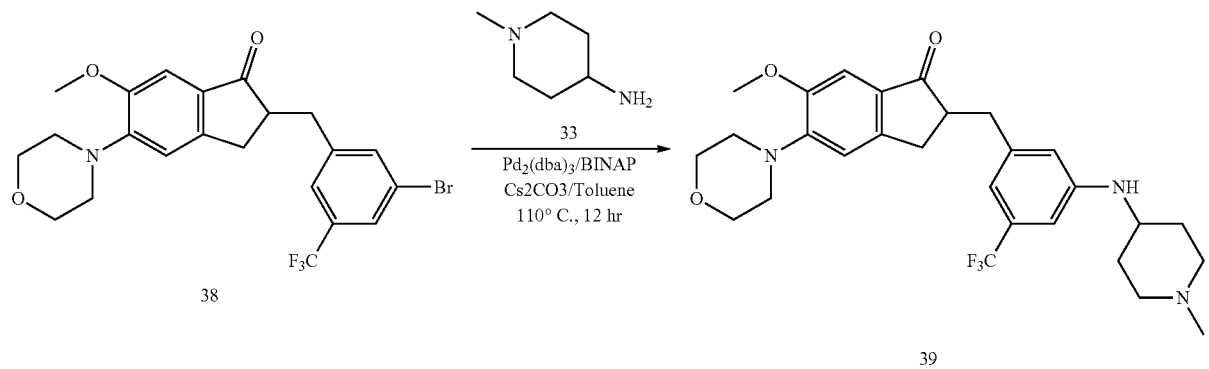

Example 9: 2-(2, 6-difluorobenzyl)-6-methoxy-5-morpholino-2, 3-dihydro-1H-inden-1-one (42)

Scheme 11

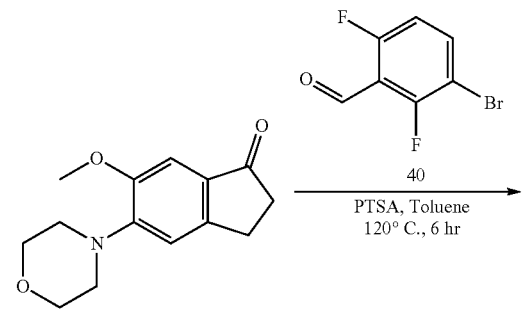

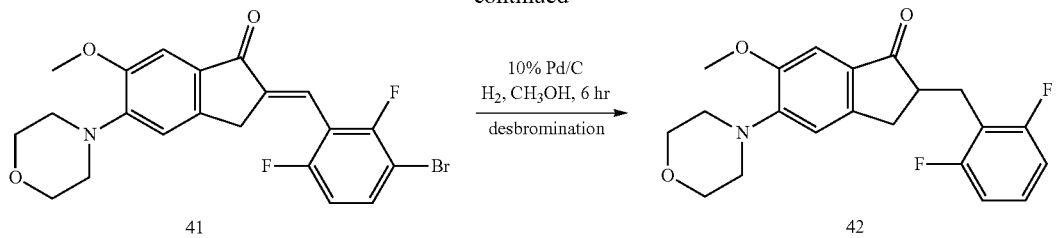

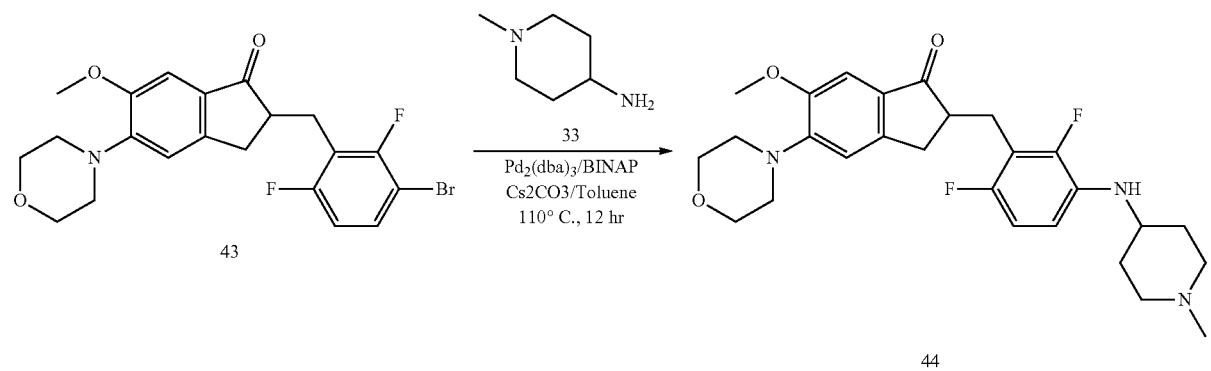

To a solution of 13 (150 mg, 0.607 mmol) in toluene 15 mL was added 3-bromo-2, 6-difluorobenzaldehyde 40 (81.4 mg, 0.607 mmol) and subsequently PTSA (230.9 mg, 1.214 mmol) was added, and stirred at 120° C. for 6h. The reaction mass was diluted with ethyl acetate and washed with water (3×25 mL). The organic layer was dried over sodium sulphate and concentrated to get the crude compound 41. The crude 41 was purified through flash chromatography by using 100-200 mesh silica gel. The compound (E)-2-(3-bromo-2,6-difluorobenzylidene)-6-methoxy-5-morpholino-2,3-dihydro-1H-inden-1-one 41 was eluted at 32% ethyl acetate in hexane to afford yellow coloured solid.

The 41 (40 mg, 0.088 mmol) was dissolved in methanol 15 mL and added Pd/C 20 mg and stirred under hydrogen balloon for 6h. The reaction was filtered through elite bed and washed with excess methanol. The organic layer was concentrated to get the crude compound 42, which was purified by flash chromatography using 100-200 mesh silica gel. The compound 2-(2,6-difluorobenzyl)-6-methoxy-5-morpholino-2,3-dihydro-1H-inden-1-one 42 was eluted as des-brominated compound at 26% ethyl acetate in hexane as half white coloured solid. $^1$HNMR (400 MHz, CDCl$_3$) δ ppm 7.17 (m, 2H), 6.89 (m, 3H), 3.89 (m, 7H), 3.35 (m, 1H), 3.19 (m, 4H), 3.06 (m, 2H), 2.76 (m, 2H); MS (ESI) m/z 374.0 (M+H).

Example 10: 2-((4-chloro-2-morpholinothiazol-5-yl)methyl)-6-methoxy-5-morpholino-2,3-dihydro-1H-inden-1-one (47)

Scheme 12

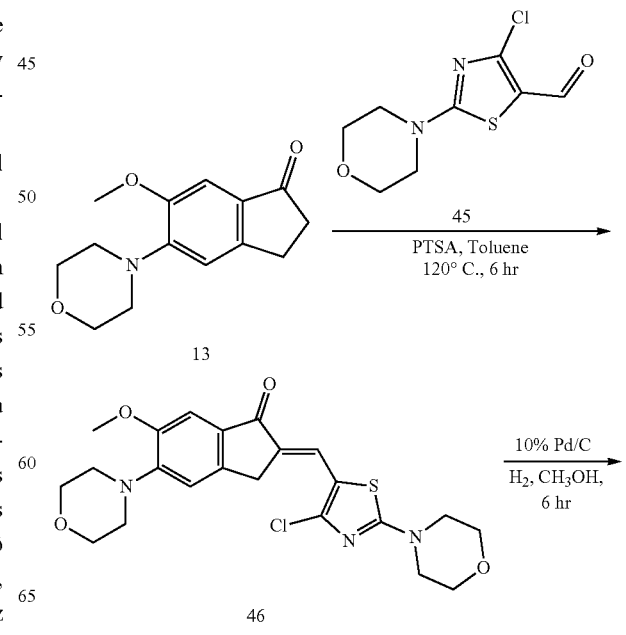

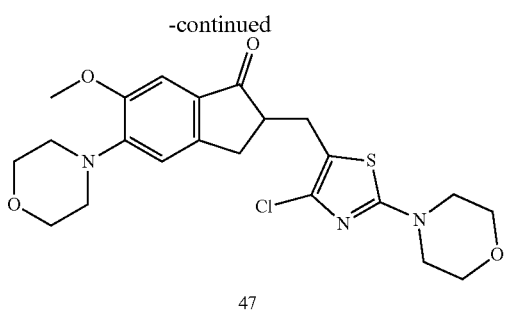

47

Example 11: 2-(3-chloro-5-(trifluoromethyl) benzyl)-6-methoxy-5-morpholino-2, 3-dihydro-1H-inden-1-one (50)

The 49 (30 mg, 0.068 mmol) was dissolved in methanol 20 mL, Pd/C 10 mg added and stirred under hydrogen balloon for 6h. The reaction was filtered through celite bed and washed with excess methanol. The organic layer was concentrated to get the crude compound 50. The crude 50 was purified by flash chromatography using 100-200 mesh silica gel. The compound 2-(3-chloro-5-(trifluoromethyl)benzyl)-6-methoxy-5-morpholino-2,3-dihydro-1H-inden-1-one 50 was eluted at 28% ethyl acetate in hexane as half white coloured solid. $^1$HNMR (400 MHz, CDCl$_3$) δ ppm 7.43 (m, 3H), 7.18 (s, 1H), 6.82 (s, 1H), 3.90 (m, 3H), 3.87 (m, 4H), 3.37 (m, 1H), 3.17 (m, 4H), 3.09 (m, 1H), 2.96 (m, 1H), 2.70 (m, 2H); MS (ESI) m/z 440.0 (M+H).

Example 12: 2-(5-chloro-2-(trifluoromethyl) benzyl)-6-methoxy-5-morpholino-2, 3-dihydro-1H-inden-1-one (53)

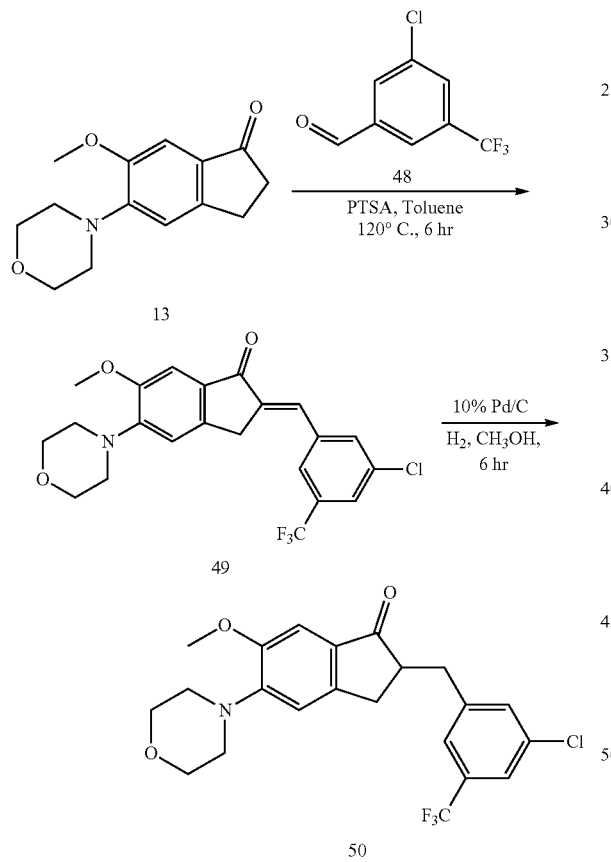

Scheme 13

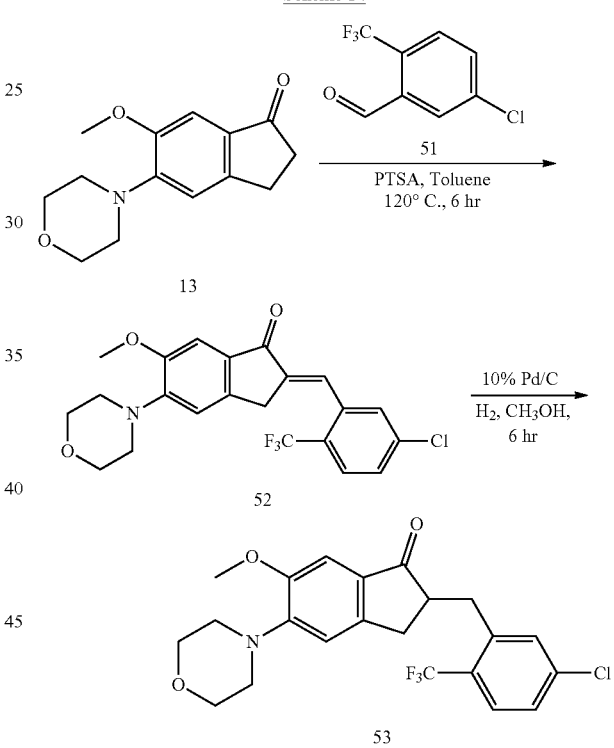

Scheme 14

To a solution of 13 (100 mg, 0.404 mmol) in toluene 5 mL was added 3-chloro-5-(trifluoromethyl) benzaldehyde 48 (84.4 mg, 0.404 mmol). PTSA (153.9 mg, 0.809 mmol) was added to the reaction mass, then stirred at 120° C. for 6h. The reaction mass was diluted with ethyl acetate and washed with water (3×25 mL). The organic layer was dried over sodium sulphate and concentrated to get the crude compound 49, which was purified through flash chromatography by using 100-200 mesh silica gel. The compound (E)-2-(3-chloro-5-(trifluoromethyl)benzylidene)-6-methoxy-5-morpholino-2,3-dihydro-1H-inden-1-one 49 was eluted at 35% ethyl acetate in hexane to afford yellow coloured solid.

To a solution of 13 (100 mg, 0404 mmol) in toluene 5 mL was added 5-chloro-2-(trifluoromethyl) benzaldehyde 51 (84.4 mg, 0.404 mmol) and PTSA (153.9 mg, 0.809 mmol). The reaction was stirred at 120° C. for 6h. The reaction mixture was diluted with ethyl acetate and washed with water (3×25 mL). The organic layer was dried over sodium sulphate and concentrated to get the crude compound 52. The crude 52 was purified through flash chromatography by using 100-200 mesh silica gel. The compound (E)-2-(5-chloro-2-(trifluoromethyl)benzylidene)-6-methoxy-5-morpholino-2,3-dihydro-1H-inden-1-one 52 was eluted at 28% ethyl acetate in hexane to afford yellow coloured solid.

Compound 52 (50 mg, 0.114 mmol) was dissolved in methanol 30 mL, Pd/C 17 mg added and the reaction stirred under hydrogen balloon for 6h. The reaction was filtered through celite bed and washed with excess methanol. The organic layer was concentrated to get the crude, which was purified by flash chromatography using 100-200 mesh silica gel. The compound 53 was eluted at 24% ethyl acetate in hexane as half white coloured solid compound 2-(5-chloro-2-(trifluoromethyl)benzyl)-6-methoxy-5-morpholino-2,3-dihydro-1H-inden-1-one 53. ¹HNMR (400 MHz, CDCl₃) δ ppm 7.43 (m, 3H), 7.18 (s, 1H), 6.82 (s, 1H), 3.90 (m, 3H), 3.87 (m, 4H), 3.48 (d, 1H), 3.38 (m, 1H), 3.17 (m, 4H), 3.09 (m, 1H), 2.95 (m, 1H), 2.67 (m, 2H); MS (ESI) m/z 440.0 (M+H).

Example 13: 2-(4-chloro-2-(trifluoromethyl) benzyl)-6-methoxy-5-morpholino-2, 3-dihydro-1H-inden-1-one (56)

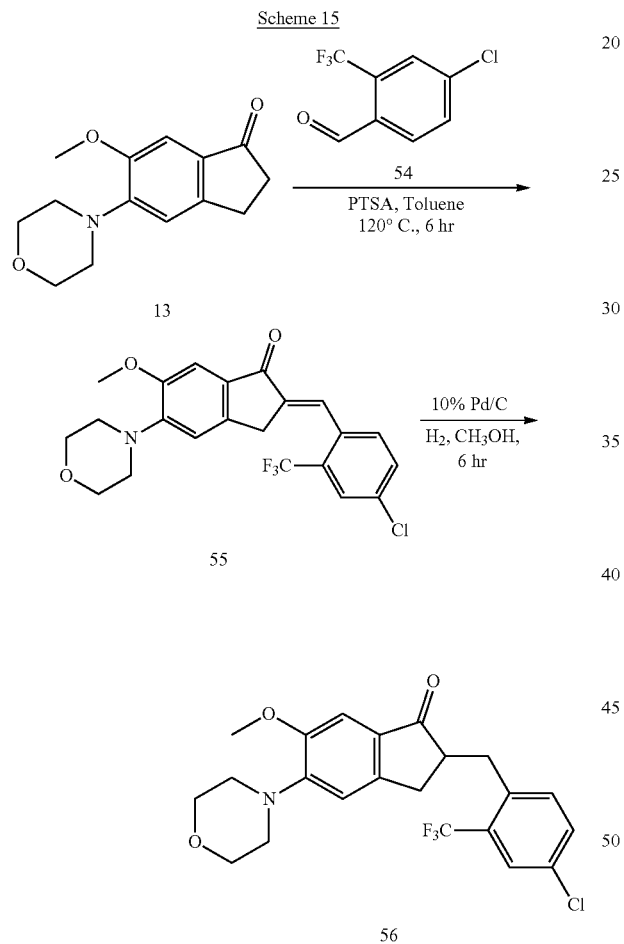

To a solution of 13 (100 mg, 0404 mmol) in toluene 5 mL was added compound 4-chloro-2-(trifluoromethyl)benzaldehyde 54 (84.4 mg, 0.404 mmol). PTSA (153.9 mg, 0.809 mmol) was added to the reaction mass and stirred at 120° C. for 6h. The reaction mass was diluted with ethyl acetate and washed with water (3×25 mL). The organic layer was dried over sodium sulphate and concentrated to get the crude compound 55, which was purified through flash chromatography by using 100-200 mesh silica gel. The compound 55 was eluted at 28% ethyl acetate in hexane to afford a yellow coloured solid.

Compound 55 (40 mg, 0.104 mmol) was dissolved in methanol 30 mL, Pd/C 14 mg added and the reaction stirred under hydrogen balloon for 6h. The reaction was filtered through celite bed and washed with excess methanol. The organic layer was concentrated to get the crude 56. Which was purified by flash chromatography using 100-200 mesh silica gel. The compound was eluted at 24% ethyl acetate in hexane as half white coloured solid 2-(4-chloro-2-(trifluoromethyObenzyl)-6-methoxy-5-morpholino-2,3-dihydro-1H-inden-1-one 56. ¹HNMR (400 MHz, CDCl₃) δ pp 7.64 (m, 1H), 7.44 (m, 2H), 7.19 (m, 2H), 6.81 (s, 1H), 4.00 (bs, 2H), 3.48 (d, 1H), 3.89 (m, 7H), 3.48 (m, 4H), 3.17 (m, 5H), 2.90 (m, 1H), 2.64 (m, 1H).

Example 14: 2-(2-chloro-6-(trifluoromethyl) benzyl)-6-methoxy-5-morpholino-2,3-dihydro-1H-inden-1-one (59)

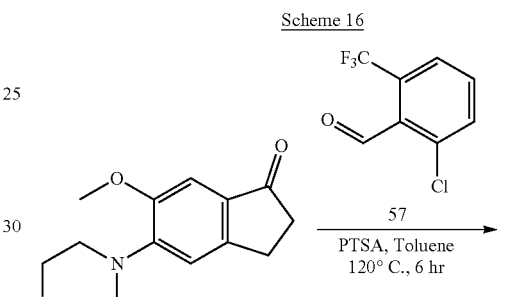

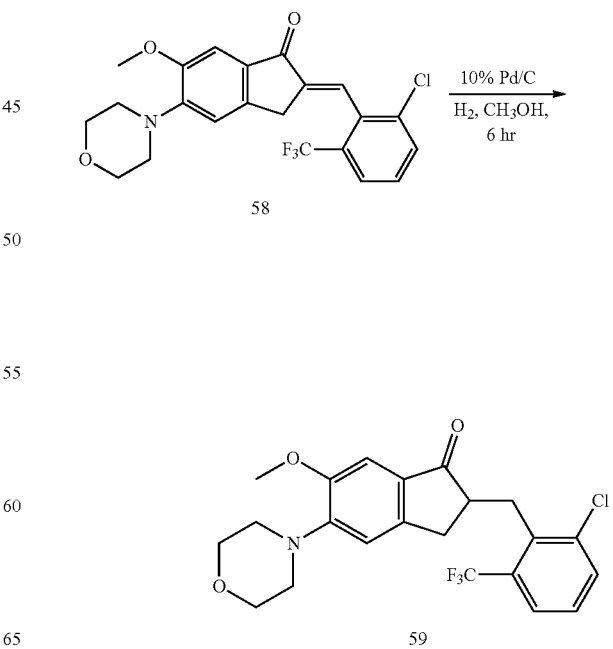

Example 15: 2-((2-chloro-5-(trifluoromethyl) pyridin-3-yl) methyl)-6-methoxy-5-morpholino-2, 3-dihydro-1H-inden-1-one (62)

Scheme 17

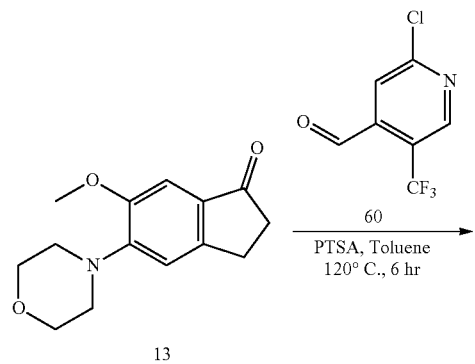

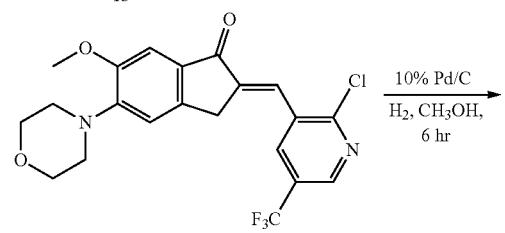

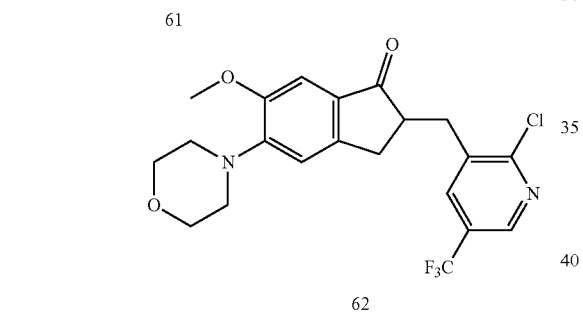

Example 16: N-(2-((6-methoxy-5-morpholino-1-oxo-2, 3-dihydro-1H-inden-2-yl) methyl)-4-(trifluoromethyl) phenyl) pivalamide (65)

Scheme 18

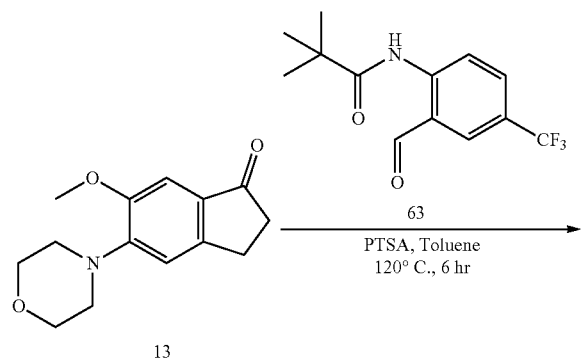

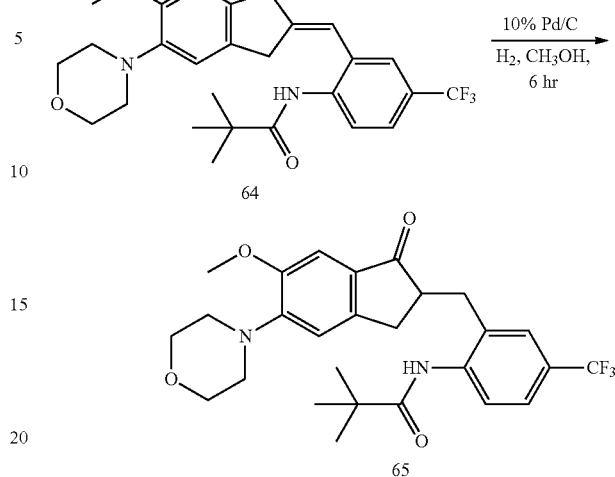

Example 17: 6-methoxy-5-morpholino-2-((3-(trifluoromethyl)pyridin-2-yl)methyl)-2,3-dihydro-1H-inden-1-one (68)

Scheme 19

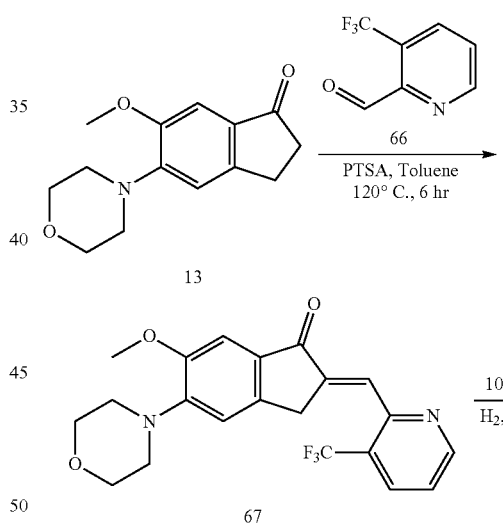

To a solution of 13 (250 mg, 1.010 mmol) in toluene 10 mL was added 3-(trifluoromethyl) picolinaldehyde (177.0 mg, 1.010 mmol). PTSA (384.5 mg, 2.021 mmol) was added to the reaction mixture and stirred at 120° C. for 6h. The reaction mass was diluted with ethyl acetate and washed with water (3×25 mL). The organic layer was dried over sodium sulphate and concentrated to get the crude compound (E)-6-methoxy-5-morpholino-2-((3-(trifluoromethyl)pyridin-2-yl)methylene)-2,3-dihydro-1H-inden-1-one 67. The compound 67 was purified through flash chromatography by using 100-200 mesh silica gel. The compound was eluted at 34% ethyl acetate in hexane to afford yellow coloured solid.

Compound 67 (80 mg, 0.197 mmol) was dissolved in methanol 15 mL, Pd/C 50 mg added, and the reaction stirred under hydrogen balloon for 6h. The reaction was filtered through celite bed and washed with excess methanol. The organic layer was concentrated to get the crude. The crude was purified by flash chromatography using 100-200 mesh silica gel. The compound was eluted at 26% ethyl acetate in hexane as half white coloured solid compound 68. $^1$HNMR (400 MHz, CDCl$_3$) δ ppm 8.64 (d, 1H), 7.91 (d, 1H), 7.22 (d, 2H), 6.83 (s, 1H), 3.89 (m, 7H), 3.65 (dd, 1H), 3.44 (m, 1H), 3.16 (m, 6H), 2.72 (dd, 1H); MS (ESI) m/z 407.0 (M+H).

Example 18: 6-methoxy-5-morpholino-2-((6-(trifluoromethyl) pyridin-3-yl) methyl)-2,3-dihydro-1H-inden-1-one (71)

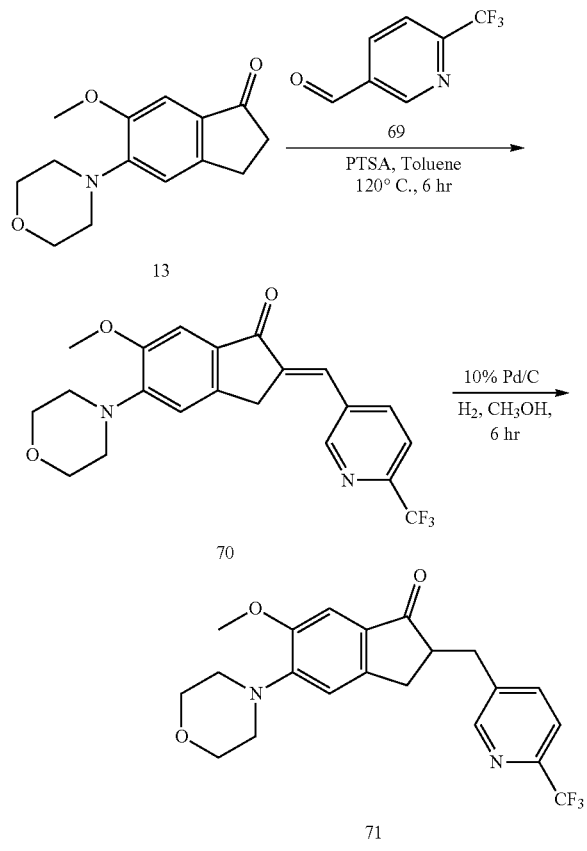

To a solution of 13 (100 mg, 0.404 mmol) in toluene 5 ml was added 6-(trifluoromethyl) nicotinaldehyde 69 (70.8 mg, 0.404 mmol). PTSA (154 mg, 0.808 mmol) was added, and the reaction mixture stirred at 120° C. for 6h. The reaction mass was diluted with ethyl acetate and washed with water (3×25 mL). The organic layer was dried over sodium sulphate and concentrated to get the crude compound (E)-6-methoxy-5-morpholino-2-((6-(trifluoromethyl)pyridin-3-yl)methylene)-2,3-dihydro-1H-inden-1-one 70. The crude 70 was purified through flash chromatography by using 100-200 mesh silica gel. The compound was eluted at 32% ethyl acetate in hexane to afford yellow coloured solid 70.

Compound 70 (55 mg, 0.136 mmol) was dissolved in methanol 20 mL, Pd/C 35 mg added, and the reaction stirred under hydrogen balloon for 6h. The reaction was filtered through celite bed and washed with excess methanol. The organic layer was concentrated to get the crude compound 71. The crude 71 was purified by flash chromatography using 100-200 mesh silica gel. The compound was eluted at 28% ethyl acetate in hexane as half white coloured solid compound 6-methoxy-5-morpholino-2-((6-(trifluoromethyl)pyridin-3-yl)methyl)-2,3-dihydro-1H-inden-1-one 71. $^1$HNMR (400 MHz, CDCl$_3$) δ ppm 8.61 (s, 1H), 7.74 (d, 1H), 7.59 (d, 1H), 7.17 (s, 1H), 6.80 (s, 1H), 3.89 (m, 3H), 3.86 (m, 4H), 3.39 (dd, 1H), 3.17 (m, 4H), 3.11 (m, 1H), 2.98 (m, 1H), 2.83 (m, 1H), 2.71 (m, 1H); MS (ESI) m/z 407.0 (M+H).

Example 19: 6-methoxy-5-morpholino-2-(4-((trifluoromethyl) thio) benzyl)-2, 3-dihydro-1H-inden-1-one (74)

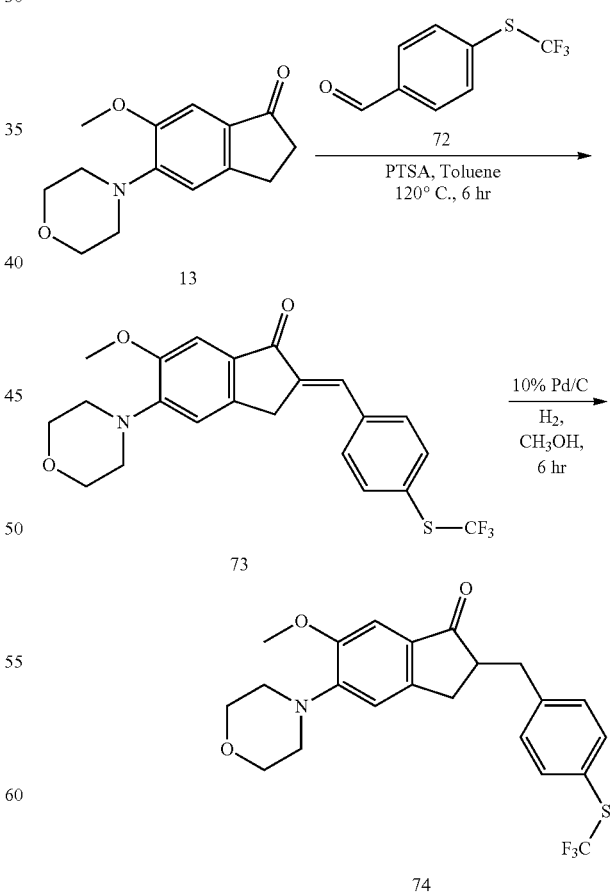

To a solution of 13 (1.2 g, 4.858 mmol) in toluene 40 mL was added 4-((trifluoromethyl)thio)benzaldehyde 72 (1 g, 4.858 mmol). PTSA (1.84 g, 9.716 mmol) was added and the reaction mixture was stirred at 120° C. for 6h. The reaction mass was diluted with ethyl acetate and washed with water (3×25 mL). The organic layer was dried over sodium sulphate and concentrated to get the crude compound 73, which was purified through flash chromatography by using 100-200 mesh silica gel. The compound (E)-6-methoxy-5-morpholino-2-(4-(((trifluoromethyl)thio)benzylidene)-2,3-dihydro-1H-inden-1-one 73 was eluted at 37% ethyl acetate in hexane to afford yellow coloured solid.

Compound 73 (1.0 g, 2.296 mmol) was dissolved in methanol 250 mL, Pd/C 400 mg was added, and the reaction was stirred under hydrogen balloon for 6h. The result was filtered through celite bed and washed with excess methanol. The organic layer was concentrated to get the crude compound 74, which was purified by flash chromatography using 100-200 mesh silica gel. The compound was eluted at 30% ethyl acetate in hexane as half white coloured solid 6-methoxy-5-morpholino-2-(4-(((trifluoromethyl)thio)benzyl)-2,3-dihydro-1H-inden-1-one 74. $^1$HNMR (400 MHz, CDCl$_3$) δ ppm 7.56 (d, 2H), 7.28 (d, 2H), 7.18 (s, 1H), 6.81 (s, 1H), 3.89 (m, 3H), 3.87 (m, 4H), 3.37 (dd, 1H), 3.15 (m, 4H), 3.06 (m, 1H), 2.96 (m, 1H), 2.66 (m, 2H); MS (ESI) m/z 438.0 (M+H).

Example 20: 2-(2-fluoro-5-(trifluoromethyl) benzyl)-6-methoxy-5-morpholino-2, 3-dihydro-1H-inden-1-one (77)

reaction mass was diluted with ethyl acetate and washed with water (3×25 mL). The organic layer was dried over sodium sulphate and concentrated to get the crude compound 76 which was purified through flash chromatography by using 100-200 mesh silica gel. The compound (E)-2-(2-fluoro-5-(trifluoromethyl)benzylidene)-6-methoxy-5-morpholino-2,3-dihydro-1H-inden-1-one 76 was eluted at 34% ethyl acetate in hexane to afford yellow coloured solid.

Compound 76 (50 mg, 0.118 mmol) was dissolved in methanol 20 mL, Pd/C 30.6 mg added, and the reaction stirred under hydrogen balloon for 6h. The result was filtered through celite bed and washed with excess methanol. The organic layer was concentrated to get the crude which was purified by flash chromatography using 100-200 mesh silica gel. The compound was eluted at 26% ethyl acetate in hexane as half white coloured solid compound 2-(2-fluoro-5-(trifluoromethyl)benzyl)-6-methoxy-5-morpholino-2,3-dihydro-1H-inden-1-one 77. $^1$HNMR (400 MHz, CDCl$_3$) δ ppm 7.51 (dd, 1H), 7.48 (m, 1H), 7.15 (m, 2H), 6.82 (s, 1H), 3.89 (m, 3H), 3.87 (m, 4H), 3.40 (m, 1H), 3.17 (m, 4H), 3.11 (m, 1H), 3.02 (m, 1H), 2.70 (m, 2H); MS (ESI) m/z 424.0 (M+H).

Example 21: 2-(2-fluoro-5-(trifluoromethyl) benzyl)-6-methoxy-5-morpholino-2, 3-dihydro-1H-inden-1-one (80)

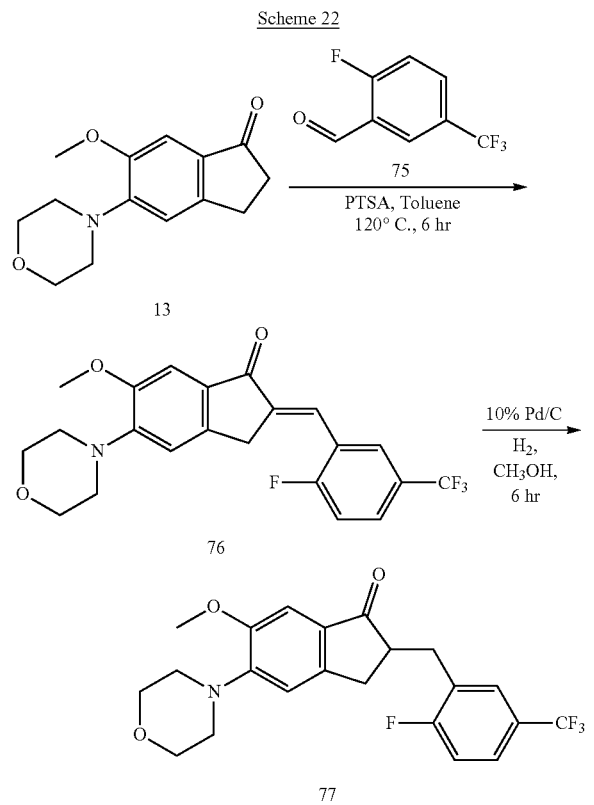

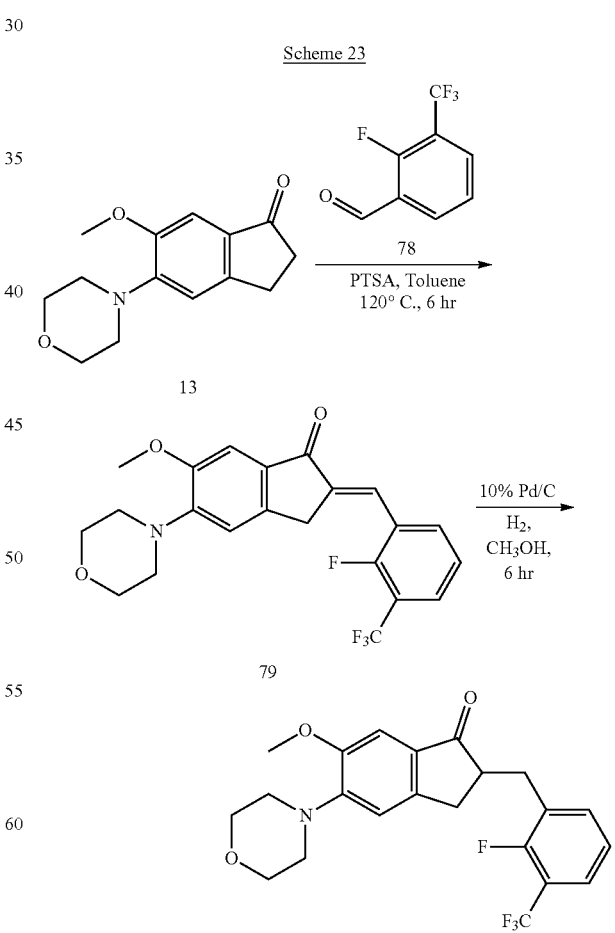

To a solution of 13 (100 mg, 0.404 mmol) in toluene 10 mL was added 2-fluoro-5-(trifluoromethyl) benzaldehyde 75 (77.7 mg, 0404 mmol). PTSA (153.8 mg, 0809 mmol) was added and the reaction mixture stirred at 120° C. for 6h. The To a solution of 13 (100 mg, 0.404 mmol) in toluene 10 mL was added 2-fluoro-3-(trifluoromethyl) benzaldehyde 78 (77.7 mg, 0.404 mmol). PTSA (153.8 mg, 0.809 mmol) was added to the reaction mixture and stirred at 120° C. for 6h. The reaction mass was diluted with ethyl acetate and washed with water (3×25 mL). The organic layer was dried over sodium sulphate and concentrated to get the crude compound 79 which was purified through flash chromatography by using 100-200 mesh silica gel. The compound (E)-2-(2-fluoro-3-(trifluoromethyl)benzylidene)-6-methoxy-5-morpholino-2,3-dihydro-1H-inden-1-one 79 was eluted at 34% ethyl acetate in hexane to afford yellow coloured.

Compound 79 (40 mg, 0.094 mmol) was dissolved in methanol 15 mL, Pd/C 25 mg, added, and the reaction stirred under hydrogen balloon for 6h. The reaction was filtered through celite bed and washed with excess methanol. The organic layer was concentrated to get the crude 80 which was purified by flash chromatography using 100-200 mesh silica gel. The compound was eluted at 30% ethyl acetate in hexane as half white coloured solid compound 2-(2-fluoro-3-(trifluoromethyObenzyl)-6-methoxy-5-morpholino-2,3-dihydro-1H-inden-1-one 80. $^1$HNMR (400 MHz, CDCl$_3$) δ ppm 7.48 (m, 2H), 7.33 (m, 1H), 7.15 (m, 1H), 6.82 (s, 1H), 3.88 (m, 3H), 3.86 (m, 4H), 3.47 (dd, 1H), 3.14 (m, 4H), 3.08 (m, 1H), 2.83 (m, 1H), 2.55 (m, 2H); MS (ESI) m/z 424.0 (M+H).

Example 22: 6-methoxy-5-morpholino-2-((6-(trifluoromethyl) pyridin-3-yl) methyl)-2, 3-dihydro-1H-inden-1-one (83)

Scheme 24

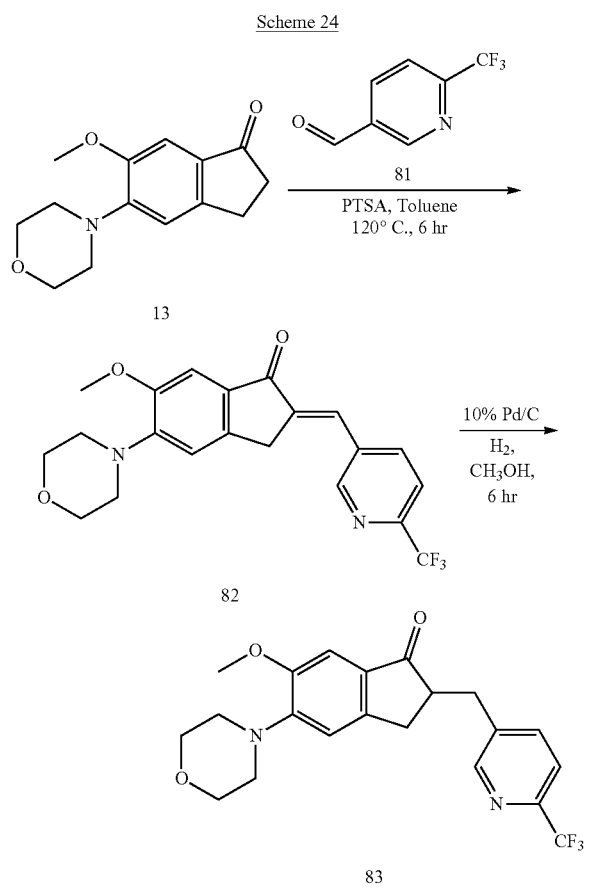

Example 23: 6-methoxy-5-morpholino-2-(4-(trifluoromethyl) benzyl)-2, 3-dihydro-1H-inden-1-one (86)

Scheme 25

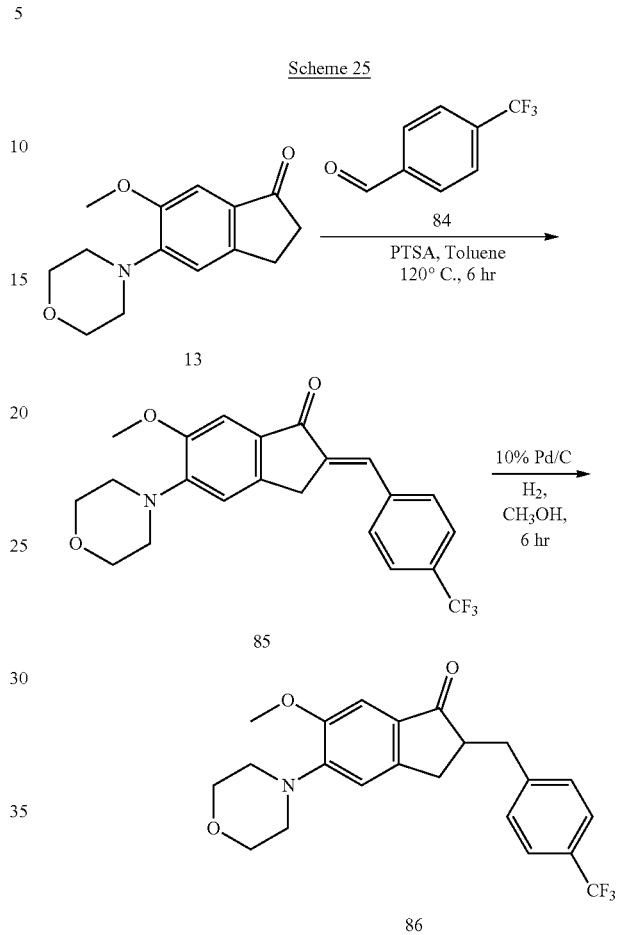

To a solution of 13 (100 mg, 04048 mmol) in toluene 10 mL was added 4-(trifluoromethyl) benzaldehyde 84 (70.4 mg, 0.404 mmol). PTSA (153.9 mg, 0.809 mmol) was added to the reaction mass, then stirred at 120° C. for 6h. The reaction mass was diluted with ethyl acetate and washed with water (3×25 mL). The organic layer was dried over sodium sulphate and concentrated to get the crude 85 which was purified through flash chromatography by using 100-200 mesh silica gel. The compound 85 was eluted at 28% ethyl acetate in hexane to afford yellow coloured solid compound (E)-6-methoxy-5-morpholino-2-(4-(trifluoromethyl)benzylidene)-2,3-dihydro-1H-inden-1-one 85.

The 85 (50 mg, 0.123 mmol) was dissolved in methanol 20 mL, Pd/C 20 mg added, and the reaction stirred under hydrogen balloon for 6h, then filtered through celite bed and washed with excess methanol. The organic layer was concentrated to get the crude 86 which was purified by flash chromatography using 100-200 mesh silica gel. The compound 86 was eluted at 25% ethyl acetate in hexane as half white coloured solid compound 6-methoxy-5-morpholino-2-(4-(trifluoromethyl)benzyl)-2,3-dihydro-1H-inden-1-one 86. $^1$HNMR (400 MHz, CDCl$_3$) δ ppm 7.53 (d, 2H), 7.34 (d, 2H), 7.18 (s, 1H), 6.80 (s, 1H), 3.89 (m, 3H), 3.86 (m, 4H), 3.38 (m, 1H), 3.15 (m, 4H), 3.08 (m, 1H), 2.96 (m, 1H), 2.68 (m, 2H); MS (ESI) m/z 406.0 (M+H).

97

Example 24: 2-(4-chloro-3-(trifluoromethyl) benzyl)-6-methoxy-5-morpholino-2,3-dihydro-1H-inden-1-one (89)

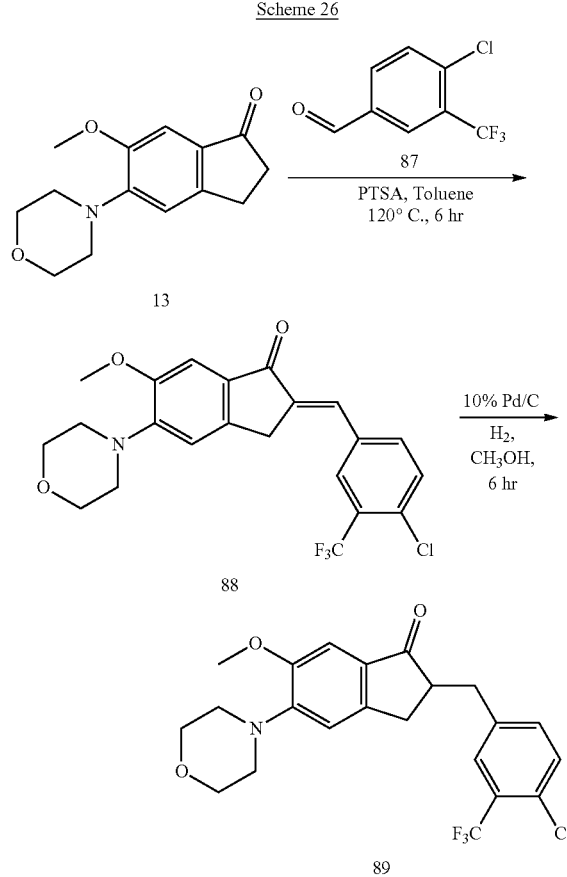

Scheme 26

To a solution of 13 (100 mg, 0.404 mmol) in toluene 10 mL was added 4-chloro-3-(trifluoromethyl) benzaldehyde 87 (84.4 mg, 0.404 mmol). PTSA (153.8 mg, 0.808 mmol) was added and the reaction was stirred at 120° C. for 6h. The reaction mass was diluted with ethyl acetate and washed with water (3×25 mL). The organic layer was dried over sodium sulphate and concentrated to get the crude 88 which was purified through flash chromatography by using 100-200 mesh silica gel. The compound (E)-2-(4-chloro-3-(trifluoromethyl)benzylidene)-6-methoxy-5-morpholino-2,3-dihydro-1H-inden-1-one 88 was eluted at 31% ethyl acetate in hexane to afford yellow coloured solid.

The 88 (65 mg, 0.148 mmol) was dissolved in ethyl acetate 50 mL, Pd/C 15 mg added, and the reaction stirred under hydrogen balloon for 6h, then filtered through celite bed and washed with excess methanol. The organic layer was concentrated to get the crude compound 89. The crude was purified by flash chromatography using 100-200 mesh silica gel. The compound 89 was eluted at 25% ethyl acetate in hexane as half white coloured solid compound 2-(4-chloro-3-(trifluoromethyl)benzyl)-6-methoxy-5-morpholino-2,3-dihydro-1H-inden-1-one 89. $^1$HNMR (400 MHz, CDCl$_3$) δ ppm 7.55 (d, 1H), 7.41 (d, 1H), 7.34 (dd, 1H), 7.17 (s, 1H), 6.81 (s, 1H), 3.87 (m, 7H), 3.33 (dd, 1H), 3.17 (m, 4H), 3.06 (m, 1H), 2.93 (m, 1H), 2.66 (m, 2H); MS (ESI) m/z 439.9 (M+H).

98

Example 25: 2-(3-chloro-4-(trifluoromethyl) benzyl)-6-methoxy-5-morpholino-2,3-dihydro-1H-inden-1-one (92)

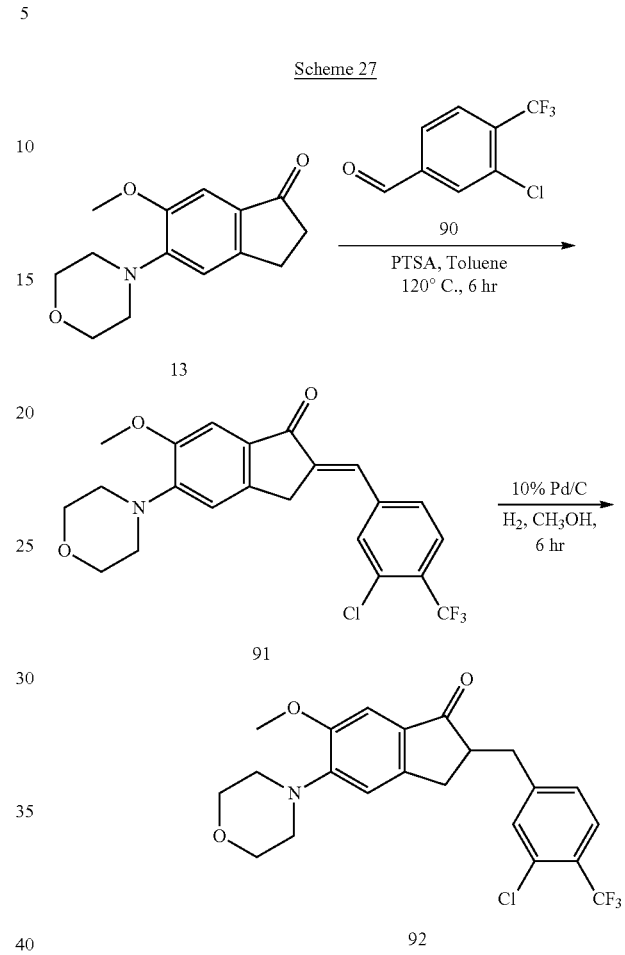

Scheme 27

To a solution of 13 (550 mg, 2.226 mmol) in toluene 25 mL was added 3-chloro-4-(trifluoromethyl) benzaldehyde 90 (464.2 mg, 2.226 mmol). PTSA (846.7 mg, 4.452 mmol) was added to the reaction, and stirred at 120° C. for 6h, then diluted with ethyl acetate and washed with water (3×25 mL). The organic layer was dried over sodium sulphate and concentrated to get the crude compound 91 which was purified through flash chromatography by using 100-200 mesh silica gel. The compound was eluted at 30% ethyl acetate in hexane to afford yellow coloured solid compound (E)-2-(3-chloro-4-(trifluoromethyl)benzylidene)-6-methoxy-5-morpholino-2,3-dihydro-1H-inden-1-one 91.

The 91 (220 mg, 0.502 mmol) was dissolved in ethyl acetate 150 mL, Pd/C 100 mg added, and the reaction stirred under hydrogen balloon for 6h, then filtered through celite bed and washed with excess methanol. The organic layer was concentrated to get the crude 92 which was purified by flash chromatography using 100-200 mesh silica gel. The compound was eluted at 28% ethyl acetate in hexane as half white coloured solid compound 2-(3-chloro-4-(trifluoromethyObenzyl)-6-methoxy-5-morpholino-2,3-dihydro-1H-inden-1-one 92. ¹HNMR (400 MHz, CDCl₃) δ ppm 7.59 (d, 1H), 7.49 (d, 1H), 7.31 (m, 1H), 7.19 (s, 1H), 6.83 (s, 1H), 3.89 (m, 3H), 3.87 (m, 4H), 3.53 (m, 1H), 3.17 (m, 4H), 3.07 (m, 2H), 2.91 (m, 1H), 2.73 (m, 1H); MS (ESI) m/z 440.0 (M+H).

Example 26: 6-methoxy-2-((3-methyl-1H-pyrazol-5-yl) methyl)-5-morpholino-2, -dihydro-1H-inden-1-one (95)

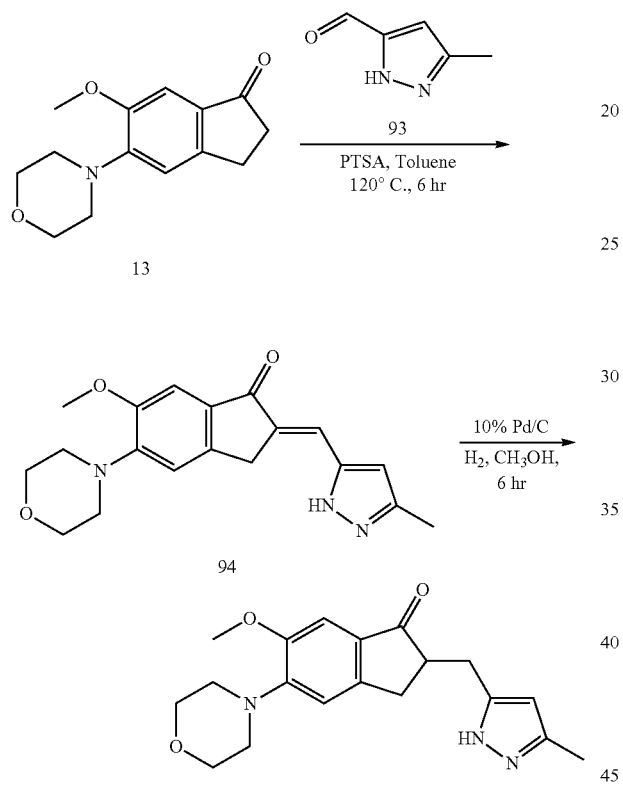

To a solution of 13 (100 mg, 0.404 mmol) in toluene 10 mL was added 3-methyl-1H-pyrazole-5-carbaldehyde 93 (70.8 mg, 0.404 mmol). PTSA (153.8 mg, 0.808 mmol) was added to the reaction mass, then stirred at 120° C. for 6h, diluted with ethyl acetate and washed with water (3×25 mL). The organic layer was dried over sodium sulphate and concentrated to get the crude 94 and was purified through flash chromatography by using 100-200 mesh silica gel eluting at 2% MeOH in DCM to afford yellow coloured solid compound (E)-6-methoxy-2-((3-methyl-1H-pyrazol-5-yl) methylene)-5-morpholino-2, 3-dihydro-1H-inden-1-one 94.

The 94 (85 mg, 0.250 mmol) was dissolved in methanol 50 mL, Pd/C 55 mg added, and the reaction stirred under hydrogen balloon for 6h, filtered through celite bed and washed with excess methanol. The organic layer was concentrated to get the crude 95 and was purified by flash chromatography using 100-200 mesh silica gel. The compound 95 was eluted at 2% MeOH in DCM as half white coloured solid compound 6-methoxy-2-((3-methyl-1H-pyrazol-5-yl)methyl)-5-morpholino-2,3-dihydro-1H-inden-1-one 95. ¹HNMR (400 MHz, CDCl₃) δ ppm 7.17 (s, 1H), 6.82 (s, 1H), 5.86 (s, 1H), 3.88 (m, 3H), 3.86 (m, 4H), 3.18 (m, 6H), 2.97 (m, 1H), 2.81 (m, 1H), 2.77 (m, 1H); MS (ESI) m/z 342.0 (M+H).

Example 29: 6-methoxy-5-(4-methylpiperazin-1-yl)-2-(4-((trifluoromethyl) thio)benzyl)-2,3-dihydro-1H-inden-1-one (106)

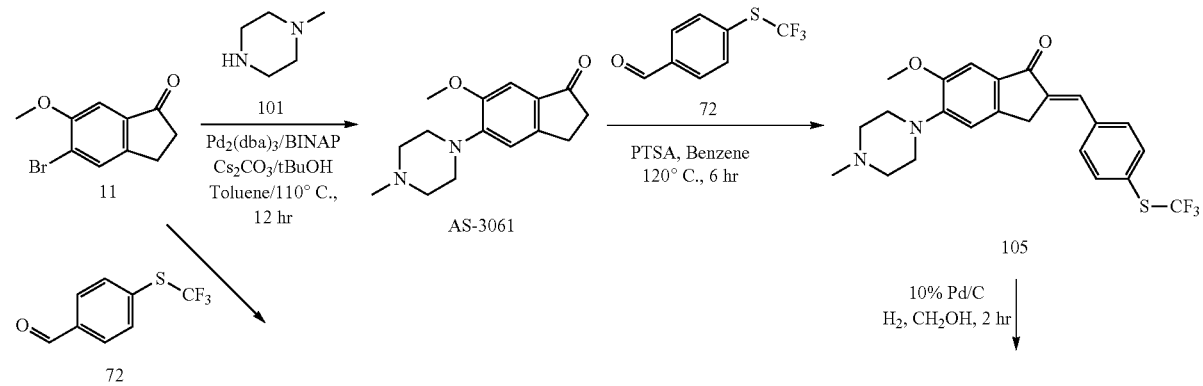

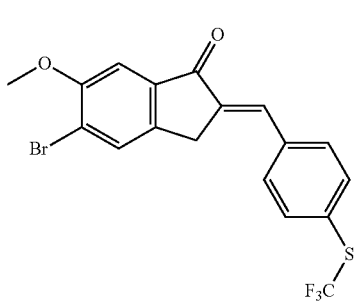

101

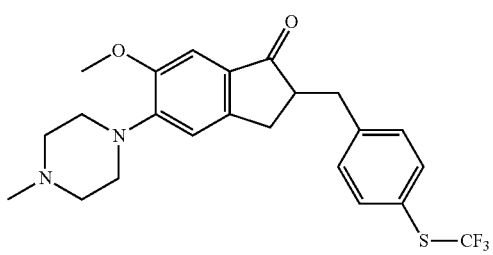

102

104

106

To a solution of 5-bromo-6-methoxy-2, 3-dihydro-1H-inden-1-one 11 (250 mg, 1.04 mol) and N-methylpiperazine (125 mg, 1.248 mol) in toluene 15 mL was added cesium carbonate (677 mg, 2.08 mol). The reaction was degassed and purged with nitrogen for 10 min. $Pd_2(dba)_3$ (4.7 mg, 0.052 mol) and BINAP (6.4 mg, 0.104 mol) was added and again degassed and purged with nitrogen for another 10 min. The reaction was heated to 110° C. overnight under sealed conditions. The reaction was diluted with chloroform and filtered through celite bed. The organic layer was concentrated to get the crude compound AS-3061 and was purified through flash chromatography by using 100-200 mesh silica gel eluting the compound at 2% methanol in chloroform as pale yellow coloured solid compound 6-methoxy-5-(4-methylpiperazin-1-yl)-2,3-dihydro-1H-inden-1-one AS-3061. $^1$HNMR (400 MHz, $CDCl_3$) δ ppm 7.24 (s, 1H), 7.16 (s, 1H), 6.90 (s, 1H), 4.06 (m, 1H), 3.92 (s, 3H), 3.89 (s, 1H), 3.70 (s, 3H), 3.50 (m, 2H), 3.29 (s, 4H), 3.01 (m, 4H), 2.62 (m, 6H), 2.42 (s, 3H); MS (ESI) m/z 260.9 (M+H).

To a solution of 11 (250 mg, 1.04 mol) in toluene 15 mL was added 4-((trifluoromethyl) thio) benzaldehyde 72 (235 mg, 1.144 mol). PTSA (357 mg, 2.08 mol) was added to the reaction mass, which was stirred at 120° C. for 6h, diluted with ethyl acetate and washed with water (3×25 mL). The organic layer was dried over sodium sulphate and concentrated to get the crude compound 104 which was purified through flash chromatography by using 100-200 mesh silica gel. The compound 104 was eluted at 10% ethyl acetate in hexane to afford yellow coloured solid (E)-5-bromo-6-methoxy-2-(4-((trifluoromethyl)thio)benzylidene)-2,3-dihydro-1H-inden-1-one 104.

The 104 (125 mg, 0.467 mol) was dissolved in methanol 25 mL, Pt/C 10 mg added and the reaction stirred under hydrogen balloon for 6h, then filtered through celite bed and washed with excess methanol. The organic layer was concentrated to get the crude compound (E)-6-methoxy-5-(4-methylpiperazin-1-yl)-2-(4-((trifluoromethyl) thio) benzylidene)-2, 3-dihydro-1H-inden-1-one 105 and was purified by flash chromatography using 100-200 mesh silica gel. The compound was eluted at 12% ethyl acetate in hexane as half white coloured solid compound 105.

To a solution of 105 (75 mg, 0.174 mol) and N-methyl piperazine (20.9 mg, 0.209 mol) in toluene 15 mL was added cesium carbonate (113.3 mg, 0.348 mol). The reaction was degassed and purged with nitrogen for 10 min. $Pd_2(dba)_3$ (7.96 mg, 0.0087 mol) and BINAP (10.8 mg, 0.0174 mol) was added and again degassed and purged with nitrogen for another 10 min. The reaction was heated to 110° C. overnight under sealed conditions. The reaction was diluted with chloroform and filtered through celite bed. The organic layer was concentrated to get the crude compound 106 and was purified through flash chromatography by using 100-200 mesh silica gel eluting the compound at 5% methanol in chloroform as brown coloured solid 6-methoxy-5-(4-methylpiperazin-1-yl)-2-(4-((trifluoromethyl) thio)benzyl)-2,3-dihydro-1H-inden-1-one 106. $^1$HNMR (400 MHz, $CDCl_3$) δ ppm 7.57 (d, 2H), 7.28 (bs, 2H), 7.20 (s, 1H), 6.90 (s, 1H), 3.91 (s, 3H), 3.70 (bs, 4H), 3.35 (d, 2H), 2.99 (bs, 5H), 2.73 (bs, 3H); MS (ESI) m/z 451.0 (M+H).

Example 31: 6-methoxy-5-(4-methylpiperazin-1-yl)-2-((3-(trifluoromethyl) pyridin-2-yl) methyl)-2, 3-dihydro-1H-inden-1-one (113)

Scheme 33

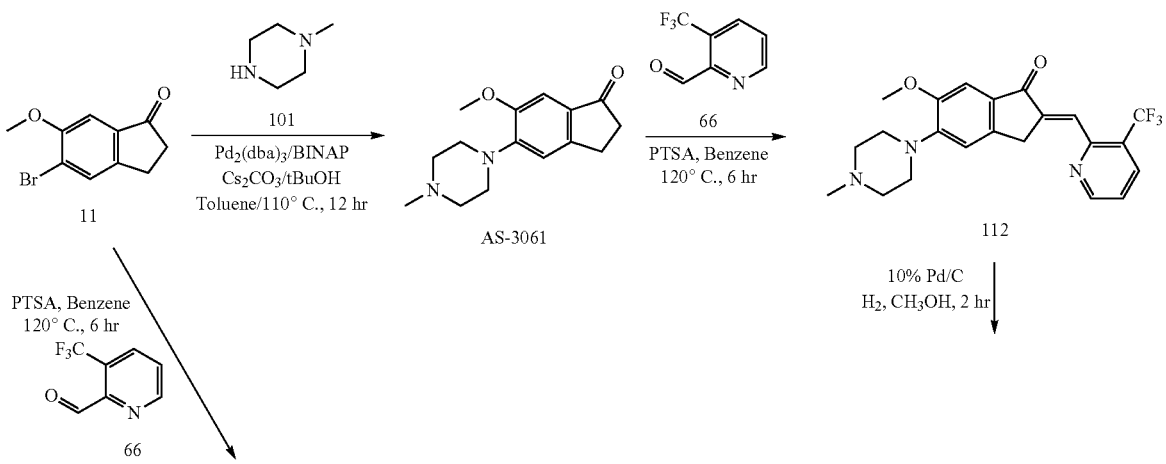

103
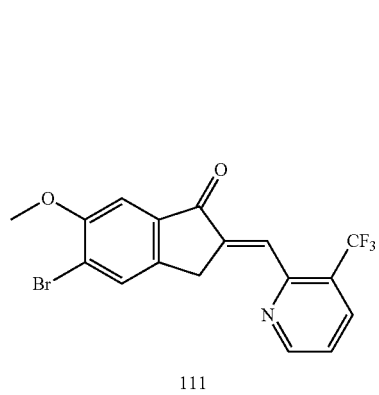
111
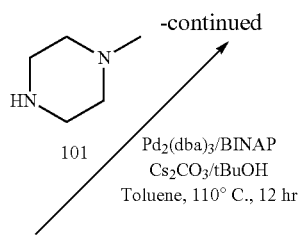
101
Pd₂(dba)₃/BINAP
Cs₂CO₃/tBuOH
Toluene, 110° C., 12 hr
-continued
104
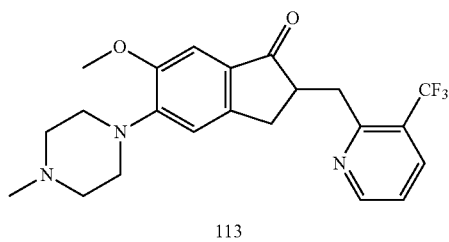
113
Example 32: 6-methoxy-5-(piperazin-1-yl)-2-(4-((trifluoromethyl) thio) benzyl)-2, 3-dihydro-1H-inden-1-one (117)
Scheme 34
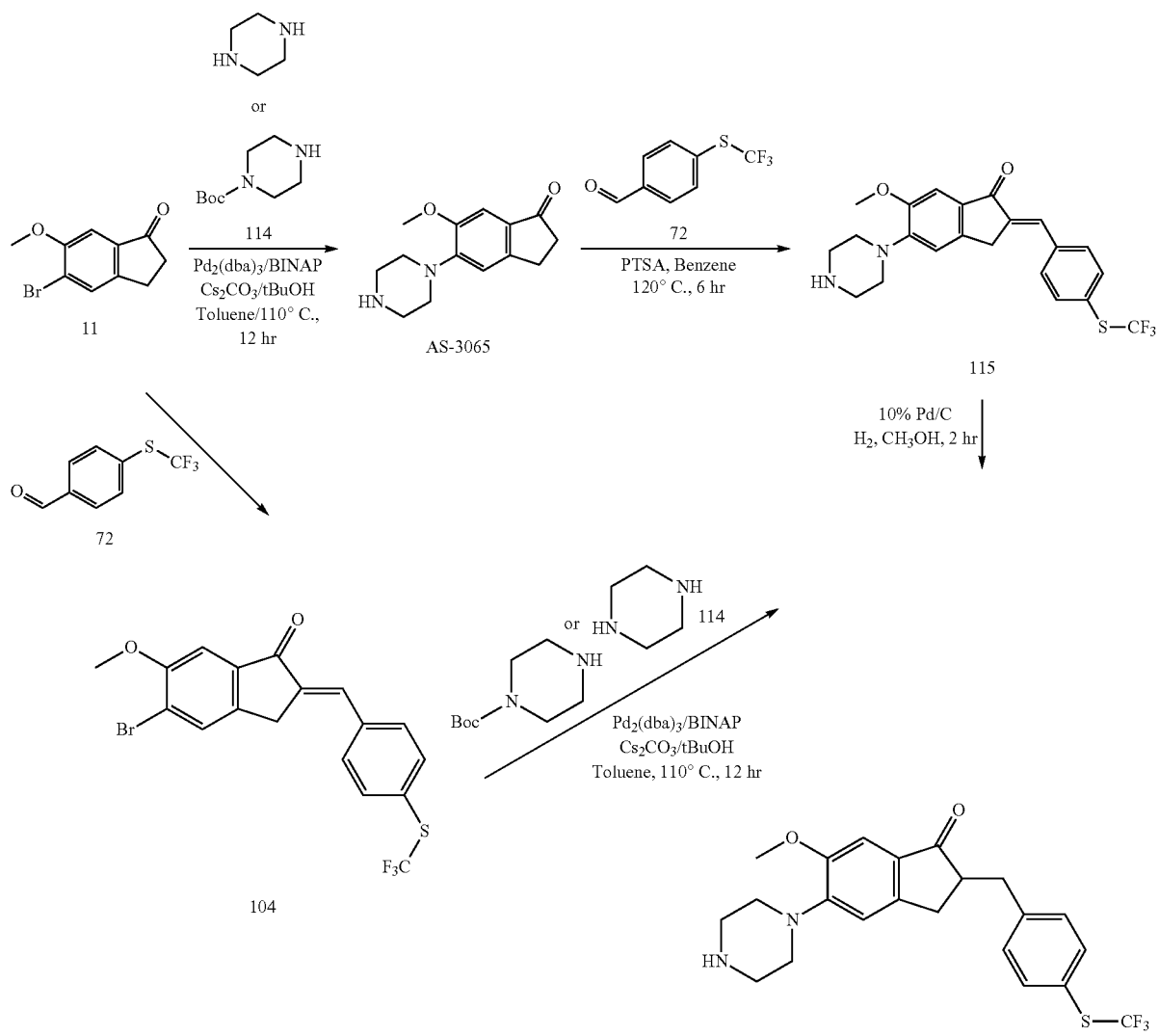

To a solution of 5-bromo-6-methoxy-2,3-dihydro-1H-inden-1-one 11 (250 mg, 1.04 mol), piperazine (107 mg, 1.248 mol) and/or Boc-piperazine in toluene 15 mL was added cesium carbonate (677 mg, 2.08 mol). The reaction was degassed and purged with nitrogen for 10 min. Pd$_2$(dba)$_3$ (4.7 mg, 0.052 mol) and BINAP (6.4 mg, 0.104 mol) was added and again degassed and purged with nitrogen for another 10 min. The reaction mixture was heated to 110° C. overnight under sealed conditions. After completion, the reaction was diluted with chloroform and filtered through celite bed. The organic layer was concentrated to get the crude compound and was purified through flash chromatography by using 100-200 mesh silica gel eluting the compound AS-3065 at 4% methanol in chloroform as pale yellow coloured solid compound 6-methoxy-5-(piperazin-1-yl)-2,3-dihydro-1H-inden-1-one AS-3065. $^1$HNMR (400 MHz, CDCl$_3$) δ ppm 7.17 (s, 1H), 6.90 (s, 1H), 3.89 (s, 3H), 3.21 (m, 4H), 3.15 (m, 4H), 3.035 (m, 2H), 2.67 (m, 2H).

Example 41: 6-methoxy-5-(4-methylpiperidin-1-yl)-2-(4-((trifluoromethyl) thio) benzyl)-2, 3-dihydro-1H-inden-1-one (140)

(dba)$_3$ (4.7 mg, 0.052 mol) and BINAP (6.7 mg, 0.104 mol) was added and again degassed and purged with nitrogen for another 10 min. The reaction was heated to 110° C. overnight under sealed conditions. After completion, the reaction was diluted with chloroform and filtered through celite bed. The organic layer was concentrated to get the crude compound AS-3070 which was purified through flash chromatography by using 100-200 mesh silica gel eluting the compound at 25% ethyl acetate in hexane as pale yellow coloured solid 6-methoxy-5-(4-methylpiperidin-1-yl)-2,3-dihydro-1H-inden-1-one AS-3070. $^1$HNMR (400 MHz, CDCl$_3$) δ ppm 7.14 (s, 1H), 6.90 (s, 1H), 3.88 (s, 3H), 3.60 (d, 2H), 3.00 (m, 2H), 2.64 (m, 4H), 1.73 (m, 2H), 1.41 (m, 3H), 0.99 (m, 3H).

To a solution of 5-bromo-6-methoxy-2, 3-dihydro-1H-inden-1-one 11 (250 mg, 0.1037 mmol) in benzene was added 4-((trifluoromethyl) thio) benzaldehyde 72 (213 mg, 0.103 mmol). PTSA (395 mg, 0.207 mmol) was added, the reaction mass was stirred at 120° C. for 6h, then diluted with ethyl acetate and washed with water (3×25 mL). The organic layer was dried over sodium sulphate and concentrated to get the crude compound 104 and was purified through flash

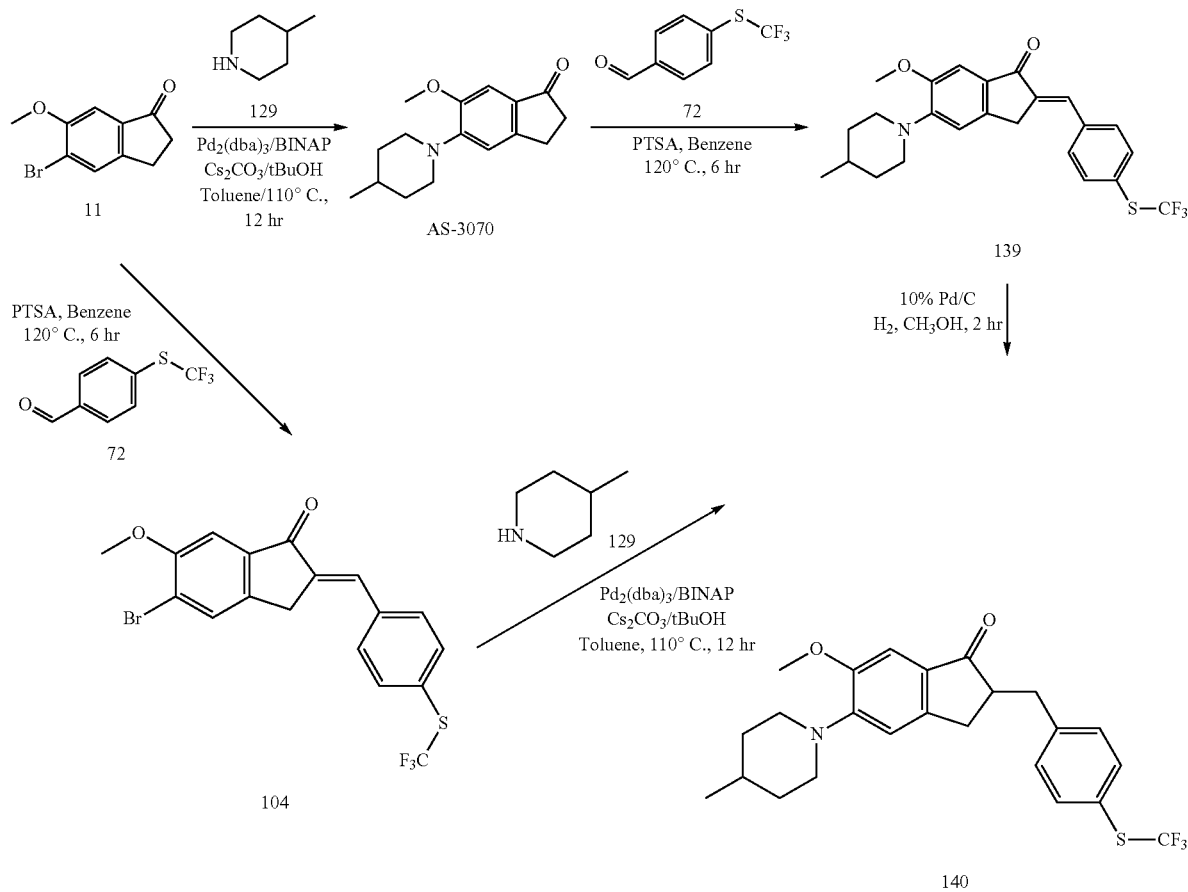

Scheme 43 chromatography by using 100-200 mesh silica gel. The compound 104 was eluted at 30% ethyl acetate in hexane to afford yellow coloured solid.

To a solution of 104 (150 mg, 0.348 mmol) and 4-methylpiperidine (69 mg, 0.696 mmol) in toluene and tBuOH To a solution of compound 5-bromo-6-methoxy-2, 3-dihydro-1H-inden-1-one 11 (250 mg, 1.04 mol) and 4-methylpiperidine 129 (120 mg, 1.248 mol) in toluene 15 mL was added cesium carbonate (677 mg, 2.08 mol). The reaction was degassed and purged with nitrogen for 10 min, Pd$_2$ (8:2, 10 mL) was added cesium carbonate 228 mg, 0.696). The reaction was degassed and purged with nitrogen for 10 min. Pd$_2$(dba)$_3$ (15.9 mg, 0.0174 mmol) and BINAP (32.4 mg, 0.15 m·mol) was added and again degassed and purged with nitrogen for another 10 min. The reaction was heated to 110° C. for overnight under sealed condition. The reaction was diluted with chloroform and filtered through celite bed. The organic layer was concentrated to get the crude compound 139 which was purified through flash chromatography by using 100-200 mesh silica gel eluting the compound at 10% ethyl acetate in hexane as pale yellow coloured solid (E)-6-methoxy-5-(4-methylpiperidin-1-yl)-2-(4-((trifluoromethyl)thio)benzylidene)-2,3-dihydro-1H-inden-1-one 139.

The 139 (80 mg, 0.178 mmol) was dissolved in methanol 50 mL and Raney-Nickel (8 mg) added and the reaction stirred under hydrogen balloon for 2h. The reaction was filtered through celite bed and washed with excess methanol. The organic layer was concentrated to get the crude compound 140 and purified by flash chromatography using 100-200 mesh silica gel. The compound 140 was eluted at 8% ethyl acetate in hexane as half white coloured solid compound 6-methoxy-5-(4-methylpiperidin-1-yl)-2-(4-((trifluoromethyl)thio)benzyl)-2,3-dihydro-1H-inden-1-one 140. $^1$HNMR (400 MHz, CDCl$_3$) δ ppm 7.27 (m, 3H), 7.11 (m, 4H), 6.81 (s, 1H), 3.89 (s, 3H), 3.60 (bs, 2H), 3.37 (dd, 1H), 2.94 (m, 2H), 2.59 (m, 4H), 0.94 (m, 3H), 0.86 (m, 4H); MS (ESI) m/z 450.1 (M+H).

Example 42: 6-methoxy-5-(4-methylpiperidin-1-yl)-2-((3-(trifluoromethyl) pyridin-2-yl) methyl)-2,3-dihydro-1H-inden-1-one (142)

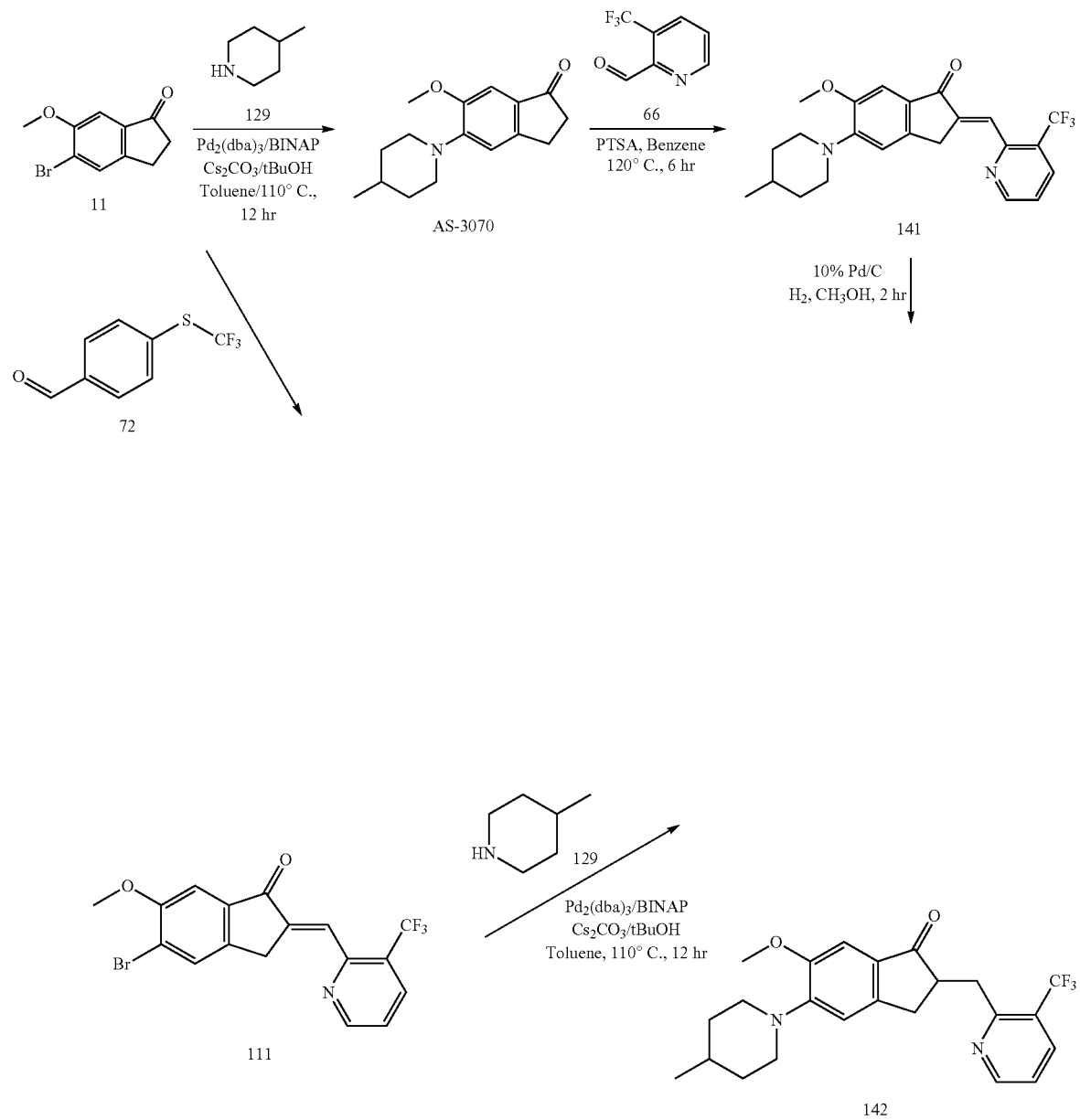

Example 43: 6-methoxy-5-((1-methylpiperidin-4-yl)amino)-2-(4-((trifluoromethyl) thio) benzyl)-2, 3-dihydro-1H-inden-1-one (144)

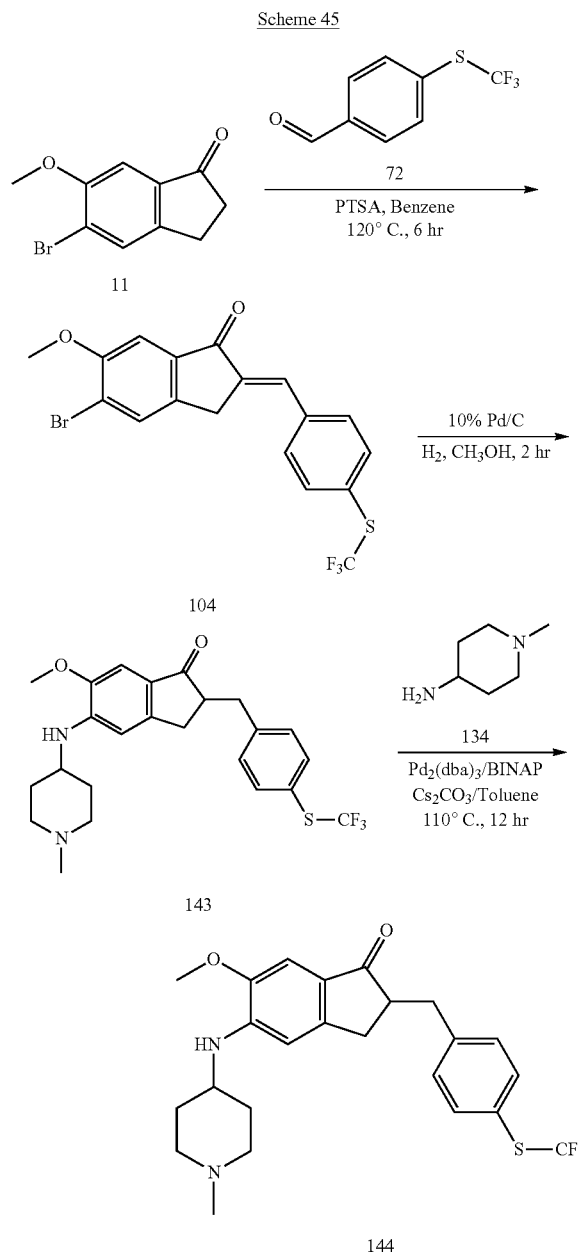

To a solution of 11 (250 mg, 1.04 mol) in toluene 15 mL was added 4-((trifluoromethyl) thio) benzaldehyde 72 (235 mg, 1.144 mol). PTSA (357 mg, 2.08 mol) was added, the reaction mixture stirred at 120° C. for 6h, diluted with ethyl acetate and washed with water (3×25 mL). The organic layer was dried over sodium sulphate and concentrated to get the crude compound 104 and was purified through flash chromatography by using 100-200 mesh silica gel. The resulting compound (E)-5-bromo-6-methoxy-2-(4-(((trifluoromethyl)thio)benzylidene)-2,3-dihydro-1H-inden-1-one 104 was eluted at 10% ethyl acetate in hexane to afford yellow coloured solid.

The 104 (125 mg, 0.467 mol) was dissolved in methanol 25 mL, Pt/C 10 mg added, the reaction stirred under hydrogen balloon for 6h, filtered through celite bed and washed with excess methanol. The organic layer was concentrated to get the crude compound 143 and was purified by flash chromatography using 100-200 mesh silica gel. The compound 5-bromo-6-methoxy-2-(4-(((trifluoromethyl)thio)benzyl)-2,3-dihydro-1H-inden-1-one 143 was eluted at 12% ethyl acetate in hexane as half white coloured solid.

To a solution of 143 (75 mg, 0.174 mol) and 1-methylpiperidin-4-amine 134 (23.8 mg, 0.0208 mol) in toluene 15 mL was added cesium carbonate (113.3 mg, 0.348 mol). The reaction was degassed and purged with nitrogen for 10 min. $Pd_2(dba)_3$ (7.96 mg, 0.0087 mol) and BINAP (10.8 mg, 0.0174 mol) was added and again degassed and purged with nitrogen for another 10 min. The reaction was heated to 110° C. overnight under sealed conditions. The reaction was diluted with chloroform and filtered through celite bed. The organic layer was concentrated to get the crude compound 144 and was purified through flash chromatography by using 100-200 mesh silica gel eluting the compound at 7.5% methanol in chloroform as brown coloured solid 6-methoxy-5-((1-methylpiperidin-4-yl)amino)-2-(4-(((trifluoromethyl) thio) benzyl)-2, 3-dihydro-1H-inden-1-one 144. $^1$HNMR (400 MHz, $CDCl_3$) δ ppm 7.55 (bs, 2H), 7.28 (bs, 2H), 7.08 (s, 1H), 6.42 (s, 1H), 4.99 (s, 1H), 3.89 (s, 3H), 3.37 (m, 4H), 2.84 (m, 6H), 2.66 (m, 3H), 2.09 (m, 4H); MS (ESI) m/z 465.0 (M+H).

Example 47: 6-methoxy-5-(4-methylpiperidin-1-yl)-2-(3-(trifluoromethyl) benzyl)-2, 3-dihydro-1H-inden-1-one (146)

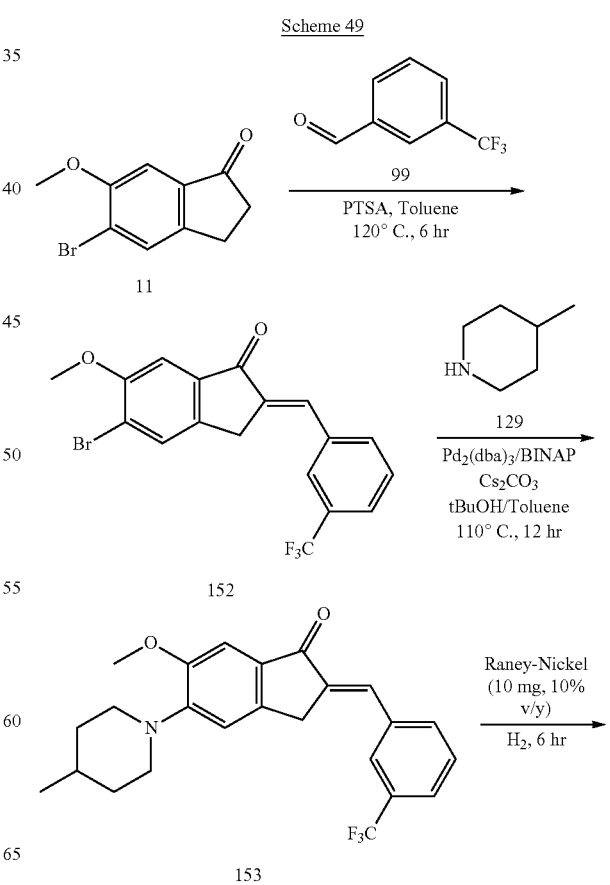

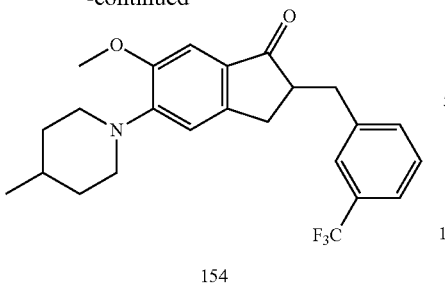

154

To a solution of 11 (200 mg, 0.829 mmol) in toluene was added 3-(trifluoromethyl) benzaldehyde 99 (158.86 mg, 0.9128 mmol). PTSA (285.5 mg, 172.20 mmol) was added to the reaction mass, then stirred at 120° C. for 6h, diluted with ethyl acetate and washed with water (3×25 mL). The organic layer was dried over sodium sulphate and concentrated to get the crude compound 152 which was purified through flash chromatography by using 100-200 mesh silica gel. The compound (E)-5-bromo-6-methoxy-2-(3-(trifluoromethyl)benzylidene)-2,3-dihydro-1H-inden-1-one 152 was eluted at 30% ethyl acetate in hexane to afford yellow coloured solid.

To a solution of 152 (120 mg, 0.3007 mmol) and 4-methylpiperidine 129 (60.2 mg, 0.6015 mmol) in toluene was added cesium carbonate (197.2 mg, 0.6015 mmol). The reaction was degassed and purged with nitrogen for 10 min. $Pd_2(dba)_3$ (13.7 mg, 0.0150 mmol) and BINAP (28.1 mg, 0.0451 mmol) was added and again degassed and purged with nitrogen for another 10 min. The reaction was heated to 110° C. overnight under sealed conditions. The reaction was diluted with chloroform and filtered through celite bed. The organic layer was concentrated to get the crude compound 153 which was purified through flash chromatography by using 100-200 mesh silica gel eluting the compound (E)-6-methoxy-5-(4-methylpiperidin-1-yl)-2-(3-(trifluoromethyl) benzylidene)-2,3-dihydro-1H-inden-1-one 153 at 25% ethyl acetate in hexane as pale yellow coloured solid.

The 153 (100 mg, 0.240 mmol) was dissolved in methanol and Raney-Nickel (10 mg, 10% v/v) added and the reaction stirred under hydrogen balloon for 6h. The reaction was filtered through celite bed and washed with excess methanol. The organic layer was concentrated to get the crude compound 154 which was purified by flash chromatography using 100-200 mesh silica gel. The compound 154 was eluted at 20% ethyl acetate in hexane as half white coloured solid compound 6-methoxy-5-(4-methylpiperidin-1-yl)-2-(3-(trifluoromethyl) benzyl)-2,3-dihydro-1H-inden-1-one 154. $^1$HNMR (400 MHz, $CDCl_3$) δ ppm 7.40 (m, 4H), 7.15 (s, 1H), 6.82 (s, 1H), 3.89 (s, 3H), 3.60 (s, 2H), 3.41 (dd, 1H), 2.94 (m, 2H), 2.62 (m, 4H), 0.92 (m, 4H), 0.85 (m, 3H); MS (ESI) m/z 418.0 (M+H).

Example 48: 6-methoxy-5-(4-methylpiperazin-1-yl)-2-(3-(trifluoromethyl) benzyl)-2, 3-dihydro-1H-inden-1-one (156)

Scheme 50

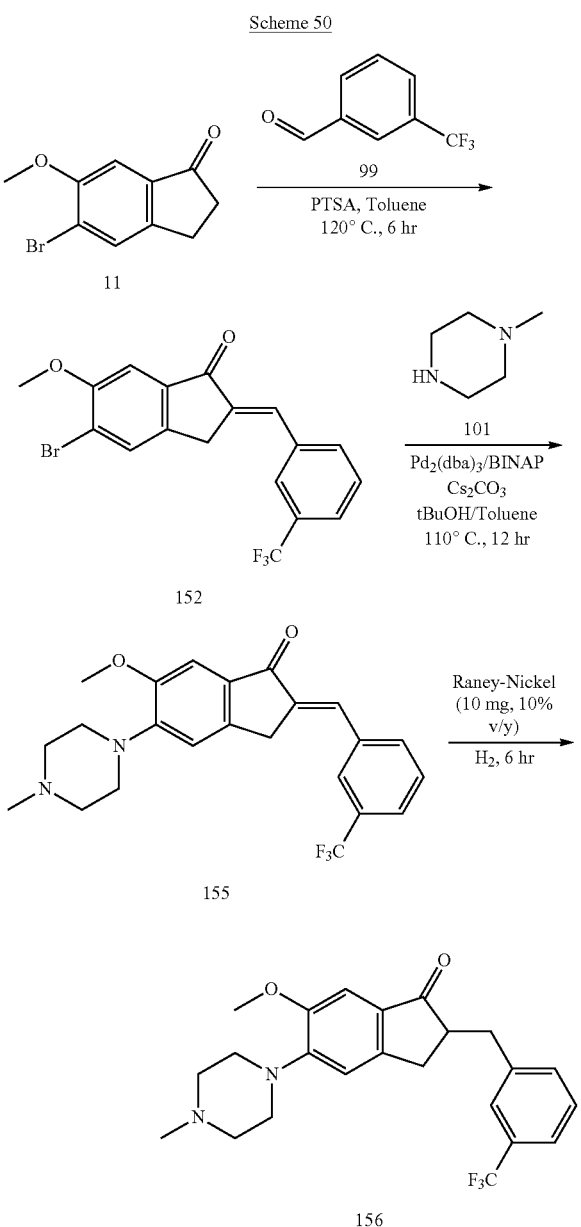

A solution of 11 (200 mg, 0.829 mmol) in toluene was added 3-(trifluoromethyl) benzaldehyde 99 (158.86 mg, 0.9128 mmol). PTSA (285.5 mg, 172.20 mmol) was added to the reaction mass. The reaction was stirred at 120° C. for 6h. The reaction mass was diluted with ethyl acetate and washed with water (3×25 mL). The organic layer was dried over sodium sulphate and concentrated to get the crude compound 152 which was purified through flash chromatography by using 100-200 mesh silica gel. The compound (E)-5-bromo-6-methoxy-2-(3-(trifluoromethyl)benzylidene)-2,3-dihydro-1H-inden-1-one 152 was eluted at 30% ethyl acetate in hexane to afford yellow coloured solid.

To a solution of 152 (120 mg, 0.3009 mmol) and 4-methylpiperazine (60.1 mg, 0.6105 mmol) in toluene was added cesium carbonate (197.2 mg, 0.6015 mmol). The reaction was degassed and purged with nitrogen for 10 min. $Pd_2(dba)_3$ (13.7 mg, 0.0150 mmol) and BINAP (28.0 mg, 0.0451 mmol) was added and again degassed and purged with nitrogen for another 10 min. The reaction was heated to 110° C. overnight under sealed conditions. The reaction was diluted with chloroform and filtered through celite Bed. The organic layer was concentrated to get the crude compound 155 which was purified through flash chromatography by using 100-200 mesh silica gel eluting the compound at 25% ethyl acetate in hexane as pale yellow coloured solid (E)-6-methoxy-5-(4-methylpiperazin-1-yl)-2-(3-(trifluoromethyl)benzylidene)-2,3-dihydro-1H inden-1-one 155.

The 155 (100 mg, 0.241 mmol) was dissolved in methanol and Raney-Nickel (10 mg, 10% v/v) added and the reaction stirred under hydrogen balloon for 6h. The reaction was filtered through celite bed and washed with excess methanol. The organic layer was concentrated to get the crude product 156 which was purified by flash chromatography using 100-200 mesh silica gel. The compound 156 was eluted at 20% ethyl acetate in hexane as half white coloured solid 6-methoxy-5-(4-methylpiperazin-1-yl)-2-(3-(trifluoromethyl) benzyl)-2,3-dihydro-1H-inden-1-one 156. $^1$HNMR (400 MHz, $CDCl_3$) δ ppm 7.42 (m, 4H), 7.17 (s, 1H), 6.83 (s, 1H), 3.41 (dd, 1H), 3.21 (bs, 4H), 3.03 (m, 1H), 2.95 (m, 1H), 2.68 (m, 2H), 2.61 (bs, 4H), 2.35 (s, 3H); MS (ESI) m/z 419.0 (M+H).

Example 49: 2-(2-chloro-5-(trifluoromethyl) benzyl)-6-methoxy-5-morpholino-2,3-dihydro-1H-inden-1-one (158)

Scheme 51

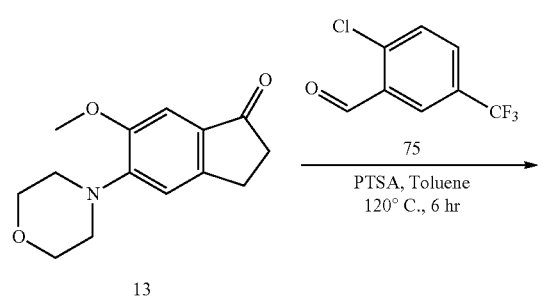

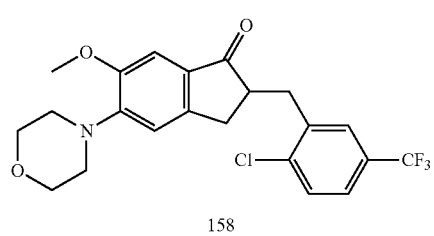

To a solution of 6-methoxy-5-morpholino-2, 3-dihydro-1H-inden-1-one 13 (0.120 mg, 0.485 mmol) in toluene (10 mL) was added 2-chloro-5-(trifluoromethyl) benzaldehyde 75 (0.101 mg, 0.485 mmol). PTSA (0.184 mg, 0.971 mmol) was added to the reaction mass, reaction stirred at 100° C. for 6h, diluted with ethyl acetate and washed with water (3×25 mL). The organic layer was dried over sodium sulphate and concentrated to get the crude compound 157 which was purified through flash chromatography by using 100-200 mesh silica gel. The compound was eluted at 15% ethyl acetate in hexane to afford yellow coloured solid (E)-2-(2-chloro-5-(trifluoromethyl) benzylidene)-6-methoxy-5-morpholino-2, 3-dihydro-1H-inden-1-one 157.

The 157 (100 mg, 0.228 mmol) was dissolved in methanol and Pd/C (40 mg) added, the reaction stirred under hydrogen balloon for 6h, filtered through celite bed and washed with excess methanol. The organic layer was concentrated to get the crude compound 158 which was purified by flash chromatography using 100-200 mesh silica gel. The compound was eluted at 10% ethyl acetate in hexane as half white coloured solid 2-(2-chloro-5-(trifluoromethyObenzyl)-6-methoxy-5-morpholino-2,3-dihydro-1H-inden-1-one 158. $^1$HNMR (400 MHz, $CDCl_3$) δ ppm 7.43 (m, 3H), 7.20 (s, 1H), 6.84 (s, 1H), 3.89 (m, 7H), 3.54 (dd, 1H), 3.14 (m, 4H), 3.07 (m, 2H), 2.75 (m, 2H); MS (ESI) m/z 440.0 (M+H).

Example 50: 6-methoxy-5-(piperazin-1-yl)-2-((3-(trifluoromethyl) pyridin-2-yl) methyl)-2, 3-dihydro-1H-inden-1-one (164)
Scheme 52
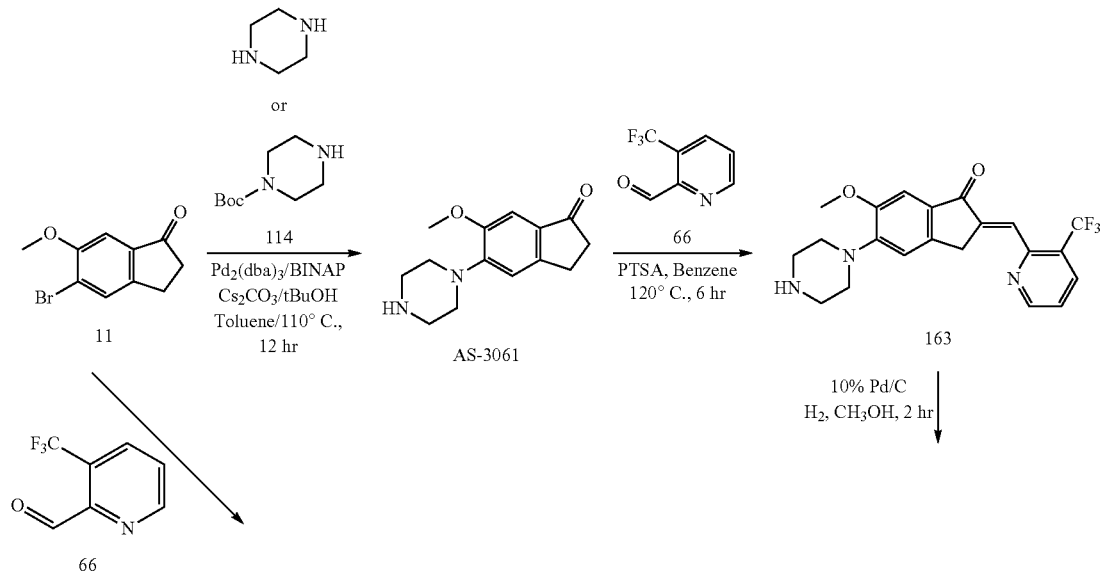
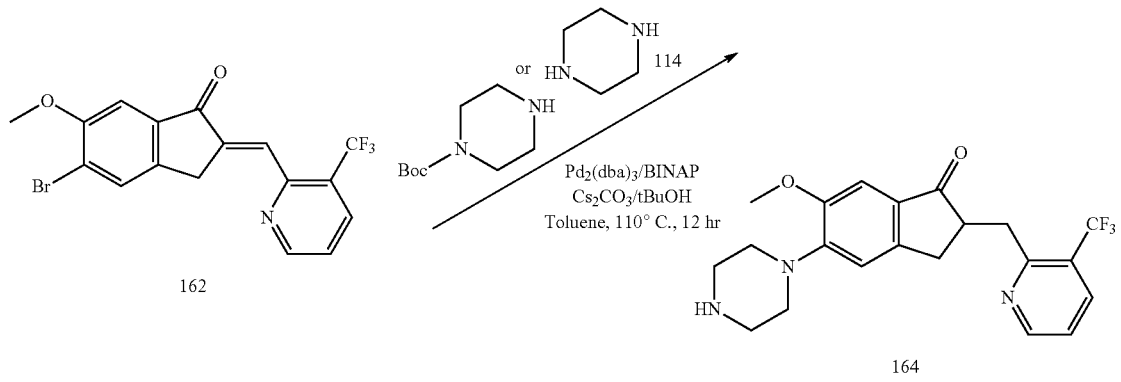

Example 51: 4,5-dimethoxy-2-(4-((trifluoromethyl)thio)benzyl)-2,3-dihydro-1H-inden-1-one (167)

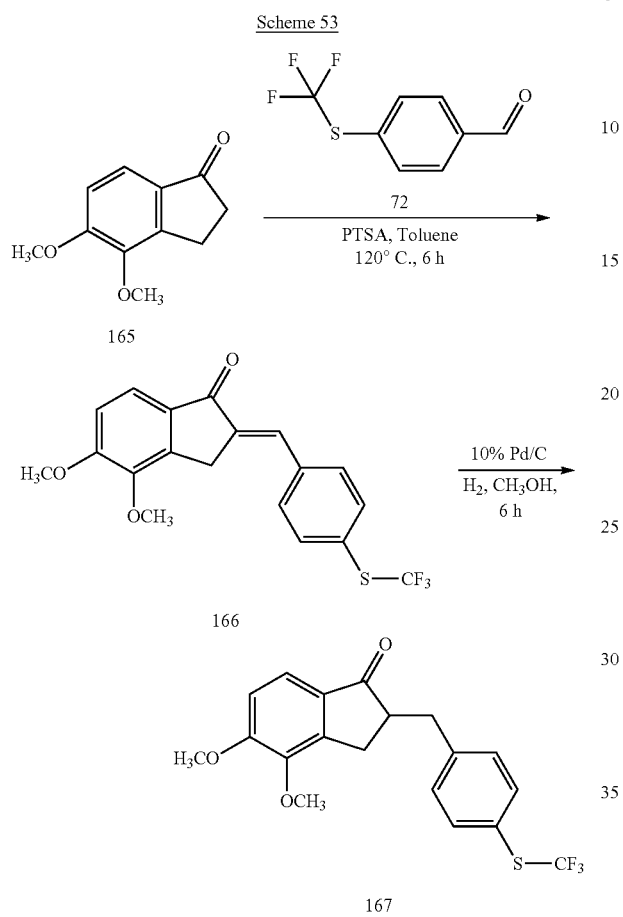

To a solution of 4,5-dimethoxy-2,3-dihydro-1H-inden-1-one (165) (100 mg, 0.520 mmol) in toluene 15 mL was added 4-((trifluoromethyl)thio)benzaldehyde (72) (118.4 mg, 0.572 mmol) and PTSA (178.9 mg, 1.414 mmol). The reaction was stirred at 120° C. for 6h. The resulting reaction mixture was diluted with ethyl acetate and washed with water (3×25 mL). The organic layer was dried over sodium sulphate and concentrated to get the crude, which was purified through flash chromatography by using 100-200 mesh silica gel.

The compound was eluted at 25% ethyl acetate in hexane to afford yellow coloured solid of (E)-4,5-dimethoxy-2-(4-((trifluoromethyl)thio)benzylidene)-2,3-dihydro-1H-inden-1-one intermediate 166.

The 166 (85 mg, 0.223 mmol) was dissolved in methanol 25 ml. Pd/C 20 mg was added and the reaction stirred under $H_2$ balloon for 6h. The reaction was filtered through Celite bed and washed with excess methanol. The organic layer was concentrated to get the crude compound 4,5-dimethoxy-2-(4-((trifluoromethyl)thio)benzyl)-2,3-dihydro-1H-inden-1-one 167, which was purified by flash chromatography using 100-200 mesh silica gel. The resulting compound 167 was eluted at 20% ethyl acetate in hexane as half white coloured solid. $^1$HNMR (400 MHz, CDCl$_3$) δ ppm 7.56 (m, 3H, 7.29 (m, 2H), 6.96 (d, 1H), 3.94 (s, 3H), 3.85 (s, 3H), 3.37 (m, 1H), 3.17 (m, 1H), 2.95 (m, 1H), 2.71 (m, 2H); MS (ESI) m/z 382.9 (M+H).

Example 52: 4,5-dimethoxy-2-((3-(trifluoromethyl)pyridin-2-yl)methyl)-2,3-dihydro-1H-inden-1-one (169)

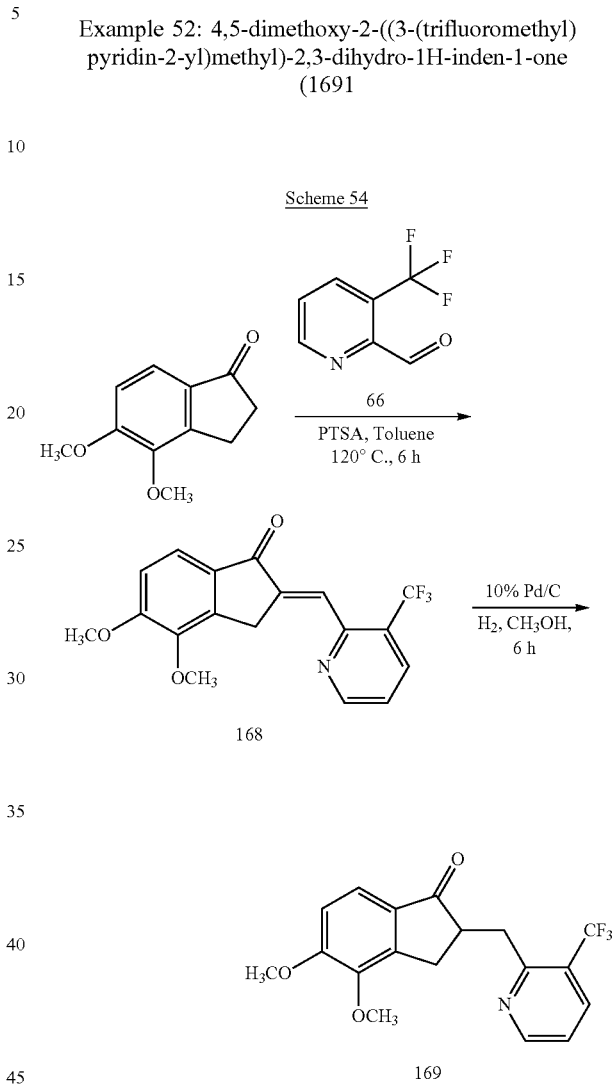

To a solution of 165 (100 mg, 0.518 mmol) in toluene 15 ml was added 66 (99.7 mg, 0569 mmol). PTSA (196.8 mg 1.03 mmol) was added to the reaction mass, which was then stirred at 120° C. for 12h. The reaction mass was diluted with ethyl acetate and washed with water (3×25 ml.). The organic layer was dried over sodium sulphate and concentrated to get the crude, which was used in the next step without further purification.

The 168 (100 mg) was dissolved in methanol 25 ml, and Pd/C 15 mg added, and the reaction stirred under $H_2$ balloon for 6h. The reaction was filtered through celite bed and washed with excess methanol. The organic layer was concentrated to get the crude 169 and was purified by flash chromatography using 100-200 mesh silica gel. The compound was eluted at 20% ethyl acetate in hexane as half white coloured solid 168. $^1$H NMR (400 MHz, CDCl$_3$) δ ppm 8.64 (d, 1H), 7.91 (d, 1H), 7.56 (d, 1H), 6.97 (d, 1H), 7.11 (d, 1H), 3.86 (s, 6H), 3.66 (d, 1H), 3.43 (m, 1H), 3.32 (m, 1H), 3.17 (m, 1H), 2.74 (dd, 1H); MS-ES+351.9.

119

Example 53: 5-chloro-6-methoxy-2-(4-((trifluoromethyl)thio)benzyl)-2,3-dihydro-1H-inden-1-one (172)

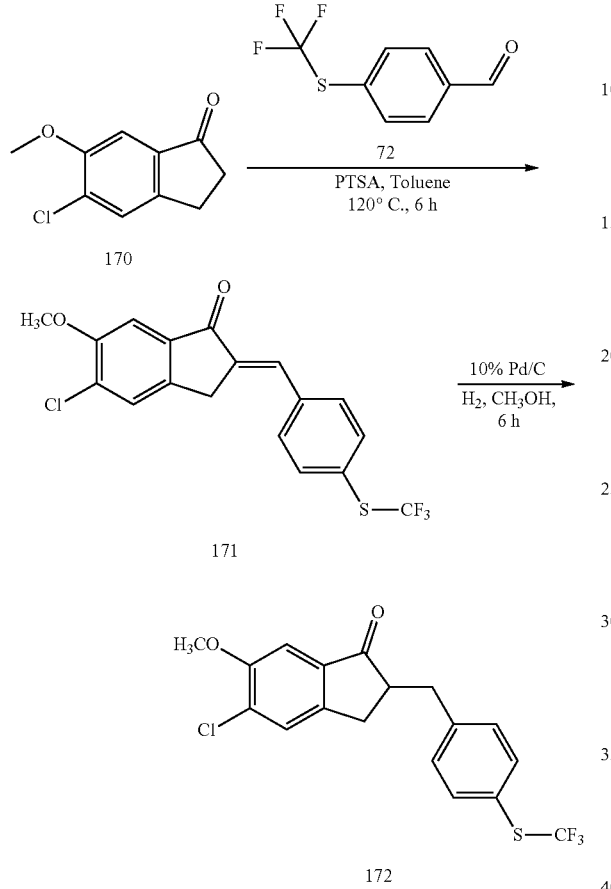

To a solution of 5-chloro-6-methoxy-2,3-dihydro-1H-inden-1-one 170 (100 mg, 0.510 mmol) in toluene 15 mL was added 4-((trifluoromethyl)thio)benzaldehyde 72 (98.4 mg, 0.561 mmol). PTSA (175.9 mg, 1.2 mmol) was added to the reaction mass, which was stirred at 120° C. for 6h. The reaction mass was diluted with ethyl acetate and washed with water (3×25 mL). The organic layer was dried over sodium sulphate and concentrated to get the crude (E)-5-chloro-6-methoxy-2-(4-((trifluoromethyl)thio)benzylidene)-2,3-dihydro-1H-inden-1-one (171), which was purified through flash chromatography by using 100-200 mesh silica gel. The compound was eluted at 22% ethyl acetate in hexane to afford yellow coloured solid.

The compound 171 (85 mg, 0.195 mmol) was dissolved in methanol 25 mL and Pt/C (40 mg) and the reaction stirred under $H_2$ balloon for 6h. The reaction was filtered through celite bed and washed with excess methanol. The organic layer was concentrated to get the crude. The crude was purified by flash chromatography using 100-200 mesh silica gel. The compound was eluted at 25% ethylacetate in hexane as half white coloured solid 172. $^1$H NMR (400 MHz, CDCl$_3$) δ ppm 7.57 (d, 2H), 7.43 (s, 1H), 7.27 (d, 2H), 7.25 (s, 1H), 3.94 (s, 3H), 3.37 (dd, 1H), 3.11 (m, 1H), 2.99 (m, 1H), 2.72 (m, 2H); MS-ES+386.8.

120

Example 54: 5-chloro-6-methoxy-2-((3-(trifluoromethyl)pyridin-2-yl)methyl)-2,3-dihydro-1H-inden-1-one (174)

Scheme 56

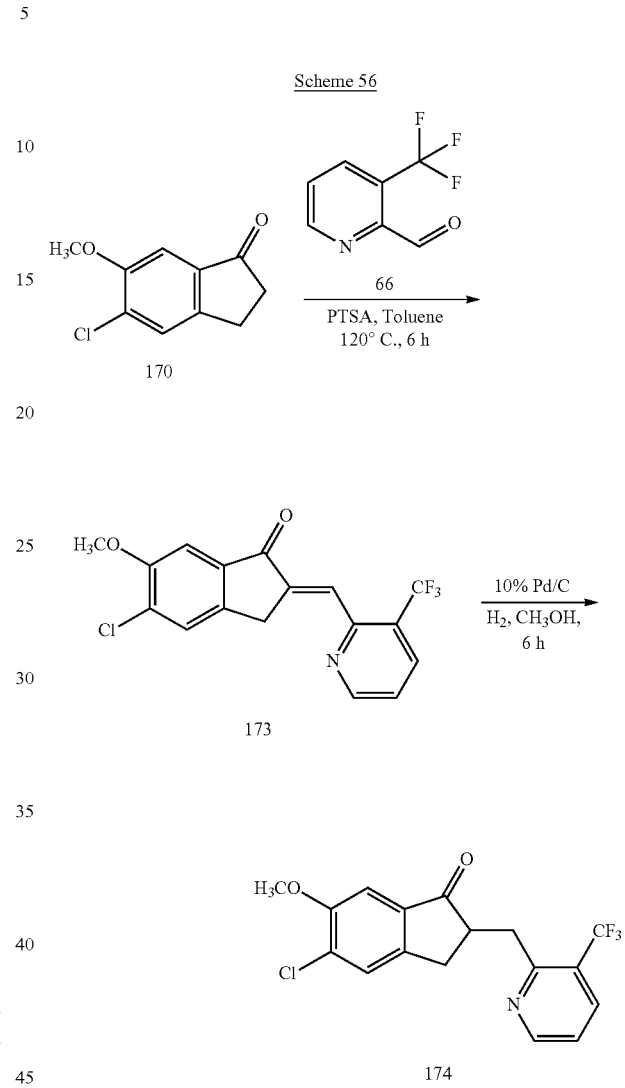

To a solution of 170 (150 mg, 0.7769 mmol) in toluene 15 ml was added 66 (203.9 mg, 1.165 mmol). PTSA (443.06 mg, 0.2337 mmol) was added to the reaction mass, which was stirred at 120° C. for 6h. The reaction mass was diluted with ethyl acetate and washed with water (3×25 ml). The organic layer was dried over sodium sulphate and concentrated to get the crude, used for the next step without further purification.

The 173 (50 mg) was dissolved in methanol 25 ml. Pt/C 10 mg was added and the reaction stirred under $H_2$ balloon for 6h. The reaction was filtered through celite bed and washed with excess methanol. The organic layer was concentrated to get the crude. The crude was purified by flash chromatography using 100-200 mesh silica gel. The compound 174 was eluted at 20% ethyl acetate in hexane as half white coloured solid 174. $^1$HNMR (400 MHz, CDCl$_3$) δ ppm 8.57 (d, 1H), 7.91 (d, 1H), 7.43 (s, 1H), 7.29 (s, 1H), 7.23 (d, 1H), 3.95 (s, 3H), 3.64 (dd, 1H), 3.40 (m, 1H), 3.23 (m, 2H), 2.75 (dd, 1H); MS-ES+357.8.

Example 55: 4-chloro-5-methoxy-2-(4-((trifluoromethyl)thio)benzyl)-2,3-dihydro-1H-inden-1-one (177)

Example 56: 4-chloro-5-methoxy-2-((3-(trifluoromethyl)pyridin-2-yl)methyl)-2,3-dihydro-1H-inden-1-one (179)

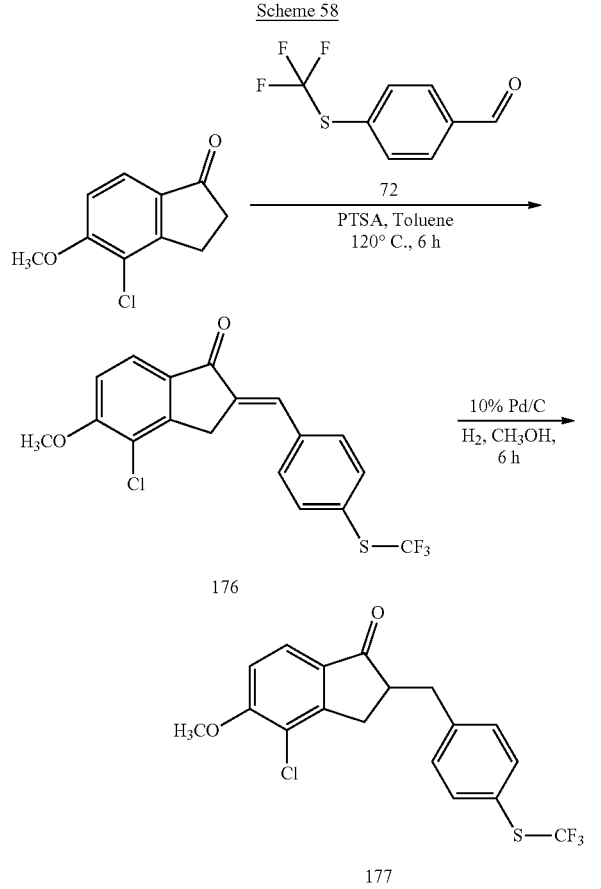

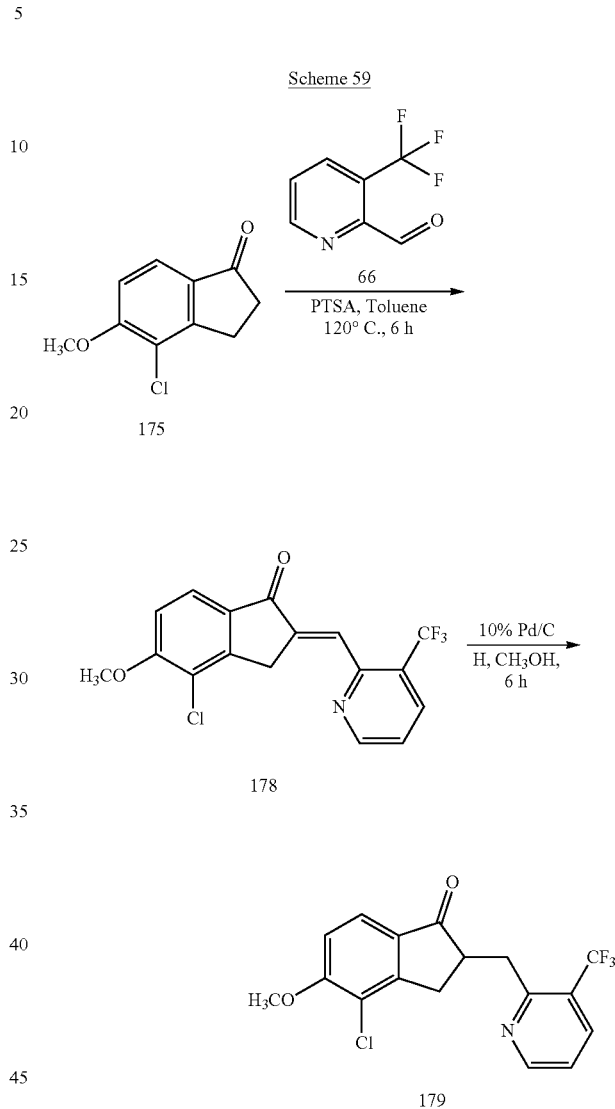

To a solution of 4-chloro-5-methoxy-2,3-dihydro-1H-inden-1-one 175 (100 mg, 0.510 mmol) in toluene 15 mL was added compound 72 (123.4 mg, 0.607 mmol). PTSA (230.9 mg, 1.214 mmol) was added to the reaction mass, and stirred at 120° C. for 6h. The reaction mass was diluted with ethyl acetate and washed with water (3×25 mL). The organic layer was dried over sodium sulphate and concentrated to get the crude 176, which was purified through flash chromatography by using 100-200 mesh silica gel. The compound was eluted at 24% ethyl acetate in hexane to afford yellow coloured solid.

The (E)-4-chloro-5-methoxy-2-(4-((trifluoromethyl)thio) benzylidene)-2,3-dihydro-1H-inden-1-one 176 (75 mg, 0.195 mmol) was dissolved in methanol 25 ml to which was added Pt/c 40 mg and the reaction stirred under $H_2$ balloon for 6h. The reaction was filtered through celite bed and washed with excess methanol. The organic layer was concentrated to get the crude, which was purified by flash chromatography using 100-200 mesh silica gel. The final compound 177 was eluted at 20% ethylacetate in hexane as half white coloured solid. $^1$H NMR (400 MHz, CDCl$_3$) δ ppm 7.69 (d, 1H), 7.58 (d, 2H), 7.29 (d, 2H), 6.98 (d, 1H), 3.99 (s, 3H), 3.38 (dd, 1H), 3.18 (dd, 1H), 2.99 (m, 1H), 2.73 (m, 1H); MS-ES+386.8.

To a solution of 175 (100 mg, 0.776 mmol) in toluene 15 ml was added 66 (203.9 mg, 1.16 mmol). PTSA (452 mg, 2.303 mmol) was added to the reaction mass and stirred at 120° C. for 6h. The reaction mass was diluted with ethyl acetate and washed with water (3×25 ml). The organic layer was dried over sodium sulphate and concentrated to get the crude 178, used in the next step without further purification The 178 (70 mg) was dissolved in methanol 25 ml, Pt/C 10 mg added, and the reaction stirred under $H_2$ balloon for 6h. The reaction was filtered through celite bed and washed with excess methanol. The organic layer was concentrated to get the crude, which was purified by flash chromatography using 100-200 mesh silica gel. The compound 179 was eluted at 20% ethyl acetate in hexane as half white coloured solid 179. $^1$H NMR (400 MHz, CDCl$_3$) δ ppm 8.60 (d, 1H), 7.91 (d, 1H), 7.72 (d, 1H), 7.24 (d, 1H), 6.99 (d, 1H), 4.00 (s, 3H), 3.66 (dd, 1H), 3.44 (m, 1H), 3.24 (m, 2H), 2.75 (dd, 1H); MS-ES+355.8.

Example 57: 5-methoxy-2-(4-((trifluoromethyl)thio)benzyl)-2,3-dihydro-1H-inden-1-one (182)

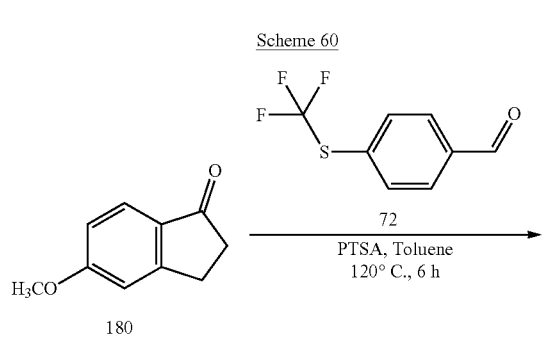

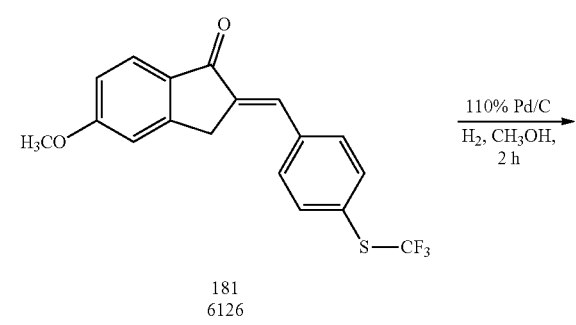

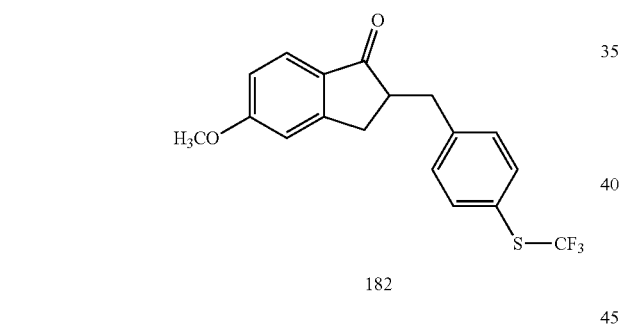

To a solution of 180 (100 mg, 0.617 mmol) in toluene 15 mL was added 72 (139.4 mg, 0.6787 mmol). PTSA (212.9 mg, 1.234 mmol) was added to the reaction mass, and stirred at 120° C. for 6h. The reaction mass was diluted with ethyl acetate and washed with water (3×25 mL). The organic layer was dried over sodium sulphate and concentrated to get the crude, which was purified through flash chromatography by using 100-200 mesh silica gel. The compound was eluted at 15% ethyl acetate in hexane to afford 181 as a yellow solid.

The 181 (90 mg, 0.270 mmol) was dissolved in methanol 25 mL, Pd/C 15 mg added, and the reaction stirred under $H_2$ balloon for 6h. The reaction was filtered through celite bed and washed with excess methanol. The organic layer was concentrated to get the crude, which was purified by flash chromatography using 100-200 mesh silica gel. The compound was eluted at 20% ethyl acetate in hexane as half white coloured solid 182. $^1$H NMR (400 MHz, CDCl$_3$) δ ppm 7.70 (d, 1H), 7.56 (d, 2H), 7.28 (d, 2H), 6.89 (m, 1H), 6.83 (m, 1H), 3.86 (s, 3H), 3.38 (dd, 1H), 3.13 (dd, 1H), 2.96 (m, 1H), 2.70 (m, 2H); MS-ES+352.9.

Example 58: 5-methoxy-2-((3-(trifluoromethyl)pyridin-2-yl)methyl)-2,3-dihydro-1H-inden-1-one (184)

A solution of 180 (100 mg, 0.617 mmol) in toluene 15 ml was added 66 (151.2 mg, 0.864 mmol). PTSA (234.5 mg, 1.234 mmol) was added to the reaction mass. The reaction was stirred at 120° C. for 6h. The reaction mass was diluted with ethyl acetate and washed with water (3×25 mL). The organic layer was dried over sodium sulphate and concentrated to get the crude 183, used the next step without further purification.

The 183 (100 mg) was dissolved in methanol 25 ml, Pd/C 10 mg added, and the reaction stirred under $H_2$ balloon for 6h. The reaction was filtered through celite bed and washed with excess methanol. The organic layer was concentrated to get the crude, which was purified by flash chromatography using 100-200 mesh silica gel. The compound 184 was eluted at 12% ethyl acetate in hexane as half white coloured solid 184. $^1$HNMR (400 MHz, CDCl$_3$) δ ppm 8.64 (d, 1H), 7.91 (d, 1H), 7.72 (d, 1H), 6.90 (d, 1H), 6.85 (s, 1H), 3.87 (s, 3H), 3.65 (dd, 1H), 3.42 (m, 1H), 3.27 (m, 1H), 3.15 (m, 1H), 2.79 (dd, 1H); MS-ES+321.8.

Example 59: 6-methoxy-3-oxo-2-(4-((trifluoromethyl)thio)benzyl)-2,3-dihydro-1H-inden-5-yl ethanesulfonate (188)

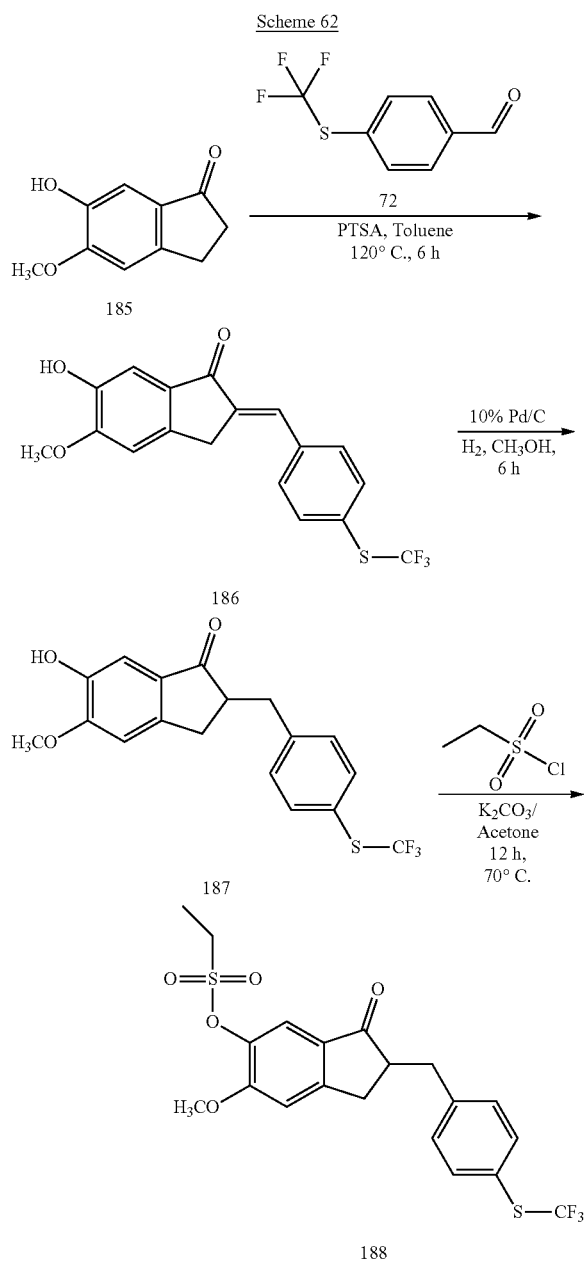

To a solution of 185 (50 mg, 0.280 mmol) in toluene 15 mL was added 72 (34.4 mg, 0.280 mmol). PTSA (94.129 mg, 0.561 mmol) was added to the reaction mass and stirred at 120° C. for 6h. The reaction mass was diluted with ethyl acetate and washed with water (3×25 mL). The organic layer was dried over sodium sulphate and concentrated to get the crude, which was purified through flash chromatography by using 100-200 mesh silica gel. The compound 186 was eluted at 30% ethyl acetate in hexane to afford yellow coloured solid.

The 186 (70 mg 0.195 mmol) was dissolved in methanol 25 mL, Pd/C 30 mg added, and the reaction stirred under $H_2$ balloon for 6h. The reaction was filtered through celite bed and washed with excess methanol. The organic layer was concentrated to get the crude 187 which was purified by flash chromatography using 100-200 mesh silica gel. The compound 187 was eluted at 20% ethyl acetate in hexane as half white coloured solid. $^1$H NMR (400 MHz, CDCl$_3$) δ ppm 7.56 (d, 2H), 7.28 (d, 2H), 6.80 (s, 1H), 5.67 (s, 1H), 3.96 (s, 3H), 3.36 (dd, 1H), 3.07 (dd, 1H), 2.94 (m, 1H), 2.70 (m, 2H); MS-ES+368.9.

The 187 (50 mg, 0.1366 mmol) was dissolved in acetone and $K_2CO_3$ (37.7 mg, 0.2732 mmol) added followed by ethane sulfonyl chloride (50 mg, 0.1366 mmol). The reaction was stirred for 12h at 70° C., then diluted with ethyl acetate and washed with water (3×50 ml). The organic layer was concentrated to get the crude 188 which was purified by flash chromatography using 100-200 mesh silica gel. The compound was eluted at 15% ethyl acetate in hexane as half white coloured solid 188. $^1$HNMR (400 MHz, CDCl$_3$) δ ppm 7.65 (s, 1H), 7.57 (d, 2H), 7.27 (d, 2H), 6.94 (s, 1H), 3.95 (s, 3H), 3.35 (m, 3H), 3.14 (m, 1H), 2.99 (m, 1H), 2.71 (m, 2H), 1.57 (m, 3H); MS-ES+460.8.

Example 60: 6-methoxy-3-oxo-2-((3-(trifluoromethyl)pyridin-2-yl)methyl)-2,3-dihydro-1H-inden-5-yl ethanesulfonate (191)

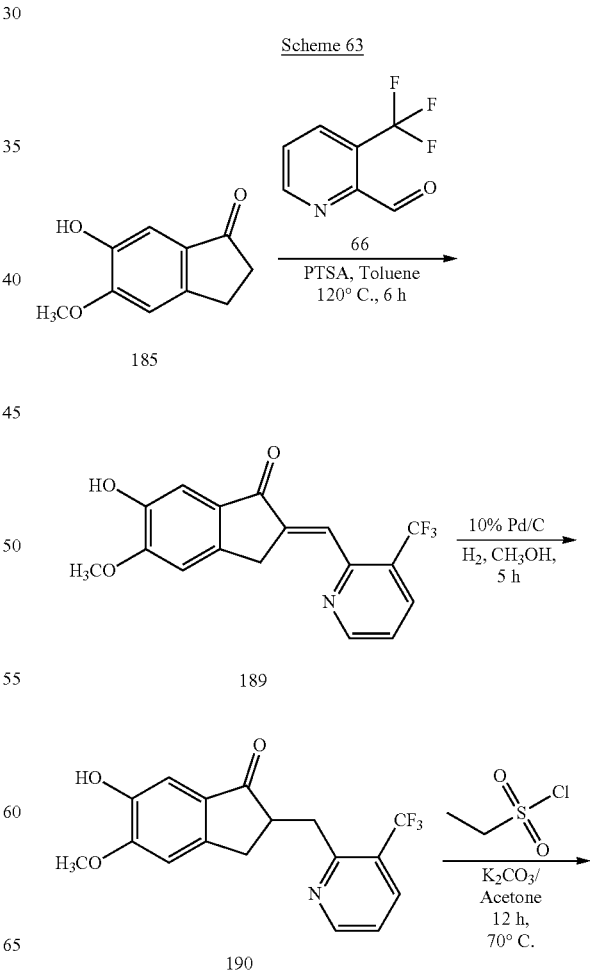

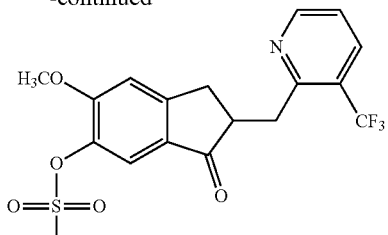

191

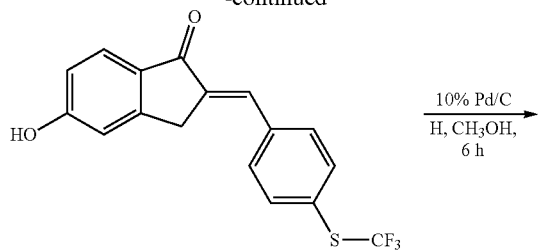

192

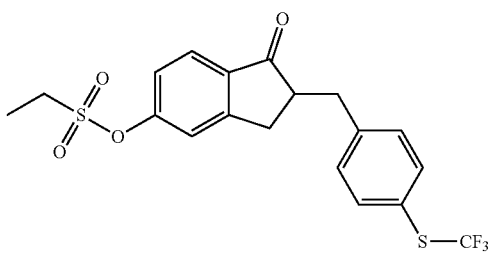

193

194

To a solution of 185 (50 mg, 0.2808 mmol) in toluene 15 ml was added 66 (68.8 mg, 0.393 mmol). PTSA (106.7 mg, 0.561 mmol) was added to the reaction mass and stirred at 120° C. for 6h. The reaction mass was diluted with ethyl acetate and washed with water (3×25 ml.). The organic layer was dried over sodium sulphate and concentrated to get the crude 189, which was used for next step without further purification.

The 189 (50 mg) was dissolved in methanol 25 ml, Pd/C 10 mg added, and the reaction stirred under $H_2$ balloon for 6h. The reaction was filtered through celite bed and washed with excess methanol. The organic layer was concentrated to get the crude 190, which was purified by flash chromatography using 100-200 mesh silica gel. The compound was eluted at 20% ethyl acetate in hexane as half white coloured solid 190. $^1$HNMR (400 MHz, CDCl$_3$) δ ppm 8.64 (d, 1H), 7.91 (d, 1H), 7.29 (s, 1H), 6.82 (s, 1H), 3.97 (s, 3H), 3.64 (dd, 1H), 3.43 (m, 1H), 3.13 (m, 2H), 2.74 (dd, 1H); MS-ES+337.8.

The 190 (40 mg, 0.108 mmol) was dissolved in acetone, $K_2CO_3$ (29.9 mg, 0.217 mmol) added, followed by ethane sulfonyl chloride (16.6 mg, 0.103 mmol). The reaction was stirred for about 12h at 70° C. The reaction mass was diluted with ethyl acetate and washed with water (3×50 mL). The organic layer was concentrated to get the crude 191, which was purified by flash chromatography using 100-200 mesh silica gel. The compound was eluted at 14% ethyl acetate in hexane as half white coloured solid 191. $^1$H NMR (400 MHz, CDCl$_3$) δ ppm 8.60 (d, 1H), 7.91 (d, 1H), 7.67 (s, 1H), 7.27 (s, 1H), 6.96 (s, 1H), 3.95 (s, 3H), 3.65 (dd, 1H), 3.42 (m, 2H), 3.20 (m, 2H), 2.82 (dd, 1H), 1.57 (m, 2H), 1.20 (m, 3H); MS-ES+429.8.

Example 61: 1-oxo-2-(4-(((trifluoromethyl)thio)benzyl)-2,3-dihydro-1H-inden-5-yl ethanesulfonate (194)

Scheme 64

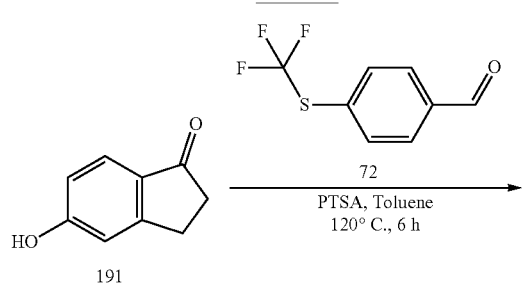

191

To a solution of 191 (250 mg, 1.688 mmol) in toluene 15 mL was added 72 (382.5 mg, 1.858 mmol). PTSA (641.7 mg, 3.376 mmol) was added to the reaction mass, then stirred at 120° C. for 6h, diluted with ethyl acetate, and washed with water (3×25 mL). The organic layer was dried over sodium sulphate and concentrated to get the crude, which was purified through flash chromatography by using 100-200 mesh silica gel. The compound was eluted at 30% ethyl acetate in hexane to afford yellow coloured solid 192.

The 192 (250 mg, 0.744 mmol) was dissolved in methanol 25 mL, Pd/C 10 mg added, and the reaction stirred under $H_2$ balloon for 6h. The reaction was filtered through celite bed and washed with excess methanol. The organic layer was concentrated to get the crude, which was purified by flash chromatography using 100-200 mesh silica gel. The compound was eluted at 20% ethylacetate in hexane as half white coloured solid 193. $^1$H NMR (400 MHz, CDCl$_3$) δ ppm 7.69 (d, 1H), 7.56 (d, 2H), 7.28 (d, 2H), 6.79 (d, 2H), 5.46 (s, 1H), 3.38 (dd, 1H), 3.11 (dd, 1H), 2.97 (m, 1H), 2.70 (m, 2H); MS-ES+336.9.

The 193 (100 mg, 0.295 mmol) was dissolved in acetone and $K_2CO_3$ (62 mg, 0.442 mmol) added, followed by ethane sulfonyl chloride (42 mg, 0.324 mmol). The reaction was stirred for about 12h at 70° C. The reaction mass was diluted with acetate and washed with water (3×50 mL). The organic layer was concentrated to get the crude, which was purified by flash chromatography using 100-200 mesh silica gel. The compound was eluted at 20% ethyl acetate in hexane as half white coloured solid 194. $^1$HNMR (400 MHz, CDCl$_3$) δ ppm 7.81 (d, 1H), 7.58 (d, 2H), 7.34 (s, 1H) 7.26 (m, 3H), 3.33 (m, 3H), 3.21 (m, 2H), 3.02 (m, 1H), 2.75 (m, 2H), 1.56 (m, 4H), 1.28 (m, 3H); MS-ES+429.0.

Example 62: 6-methoxy-3-oxo-2-((3-(trifluoromethyl)pyridin-2-yl)methyl)-2,3-dihydro-1H-inden-5-yl ethanesulfonate (197)

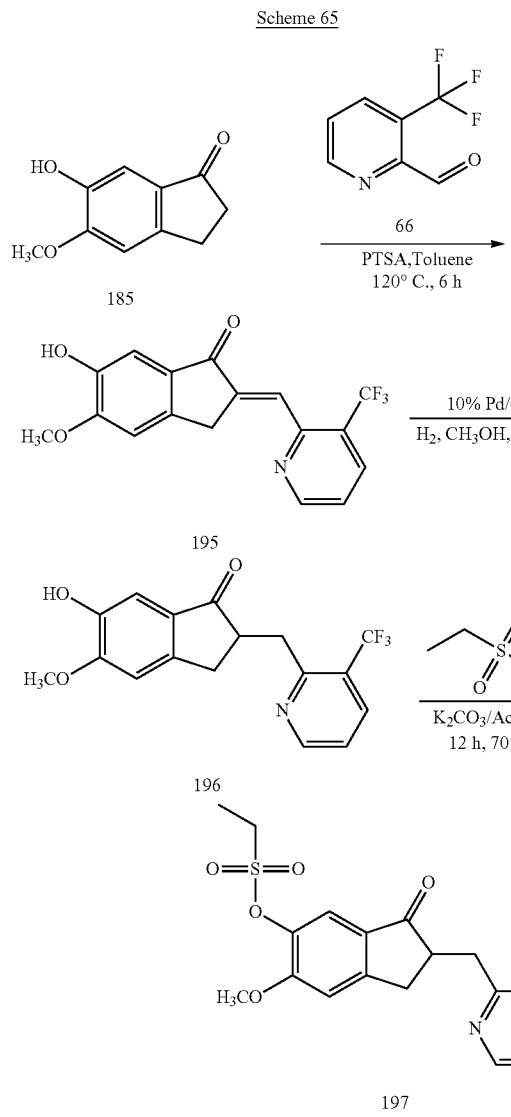

To a solution of 185 (100 mg, 0.6754 mmol) in toluene 15 mL was added 66 (130.09 mg, 0.742 mmol). PTSA for 6h. The reaction mass was diluted with ethyl acetate and washed with water (3×25 mL). The organic layer was dried over sodium sulphate and concentrated to get the crude 195, which was used for next step without further purification.

The 195 (100 mg) was dissolved in methanol 25 ml, Pd/C 20 mg added, and the reaction stirred under H₂ balloon for 6h. The reaction was filtered through celite bed and washed with excess methanol. The organic layer was concentrated to get the crude 196, which was purified by flash chromatography using 100-200 mesh silica gel. The compound 196 was eluted at 20% ethyl acetate in hexane as half white coloured solid 196. $^1$HNMR (400 MHz, CDCl$_3$) δ ppm 10.4 (s, 1H), 8.74 (d, 1H), 8.14 (d, 1H), 7.49 (m, 2H), 6.81 (m, 2H), 3.45 (dd, 1H), 3.18 (m, 2H), 3.01 (m, 1H), 2.77 (dd, 1H); MS-ES+307.8.

The 196 (40 mg, 0.1299 mmol) was dissolved in acetone, K$_2$CO$_3$ (35.7 mg, 0.259 mmol) added, followed by ethane sulfonyl chloride (33.1 mg, 0.259 mmol). The reaction was stirred for about 12h at 70° C. The reaction mass was diluted with acetate and washed with water (3×50 ml) the organic layer was concentrated to get the crude 197, which was purified by flash chromatography using 100-200 mesh silica gel. The compound was eluted at 20% ethyl acetate in hexane as half white coloured solid 197. $^1$HNMR (400 MHz, CDCl$_3$) δ ppm 8.56 (d, 1H), 7.91 (d, 1H), 7.83 (d, 1H), 7.35 (s, 1H), 7.27 (s, 1H), 3.64 (dd, 1H), 3.41 (m, 1H), 3.31 (m, 4H), 2.88 (m, 1H), 1.57 (m, 4H), 1.23 (m 3H); MS-ES+ 399.9.

Example 63: 6-methoxy-5-(2-(trifluoromethoxy)phenyl)-2-((3-(trifluoromethyl)pyridin-2-yl)methyl)-2,3-dihydro-1H-inden-1-one (213)

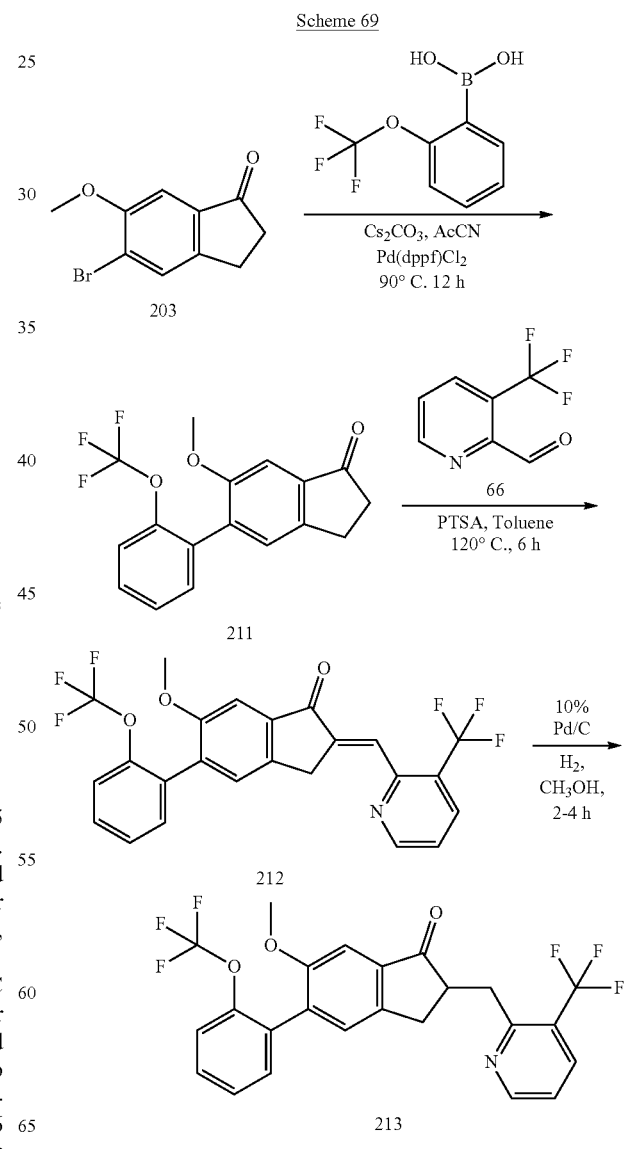

To a solution of 203 (100 mg, 0.414 mmol) and (2-(trifluoromethoxy)phenyl) boronic acid (85.32 mg, 0.414 mmol) in acetonitrile was added cesium carbonate (271 mg, 0.826 mmol). The reaction was degassed and purged with $N_2$ for 10 min. Pd(dppf)Cl$_2$ (16.88 mg, 0.02 mmol) was added to the reaction, then degassed and purged with nitrogen for another 10 min. The reaction was heated to 90° C. under sealed condition overnight. The reaction mixture was allowed to cool to rt, and diluted with chloroform. The organic layer was filtered through celite plug and concentrated to get the crude, which was purified through flash chromatography by using 100-200 mesh silica gel. The compound 211 was eluted in 5% ethyl acetate in hexane as half white solid 211.

To a solution of 211 (150 mg, 0.465 mmol) and 66 (122 mg, 0.698 mmol) in toluene 15 mL was added PTSA (177 mg, 0.9314 mmol). The reaction was stirred at 120° C. for 6h, diluted with ethyl acetate and washed with water (3×25 mL). The organic layer was dried over sodium sulphate and concentrated to get the crude 212, which was purified through flash chromatography by using 100-200 mesh silica gel. The compound 212 was eluted at 10% ethyl acetate in hexane to afford yellow coloured solid.

The 212 (70 mg, 0.145 mmol) was dissolved in methanol 25 mL and Pd/C 10 mg added. The reaction was stirred under H$_2$ balloon for 6h, then filtered through celite bed and washed with excess methanol. The organic layer was concentrated to get the crude 213 which was purified by flash chromatography using 100-200 mesh silica gel. The compound 213 was eluted at 12% ethyl acetate in hexane as half white coloured solid. $^1$HNMR (400 MHz, CDCl$_3$) δ ppm 8.16 (d, 1H), 7.92 (d, 1H), 7.41 (m, 1H), 7.34 (m, 4H), 7.24 (m, 2H), 3.82 (s, 3H), 3.68 (dd, 1H), 3.49 (m, 1H), 3.26 (m, 1H), 2.79 (dd, 1H); MS-ES+482.0.

Example 64: 5-(2-fluoro-4-(trifluoromethoxy)phenyl)-6-methoxy-2-((3-(trifluoromethyl)pyridin-2-yl)methyl)-2,3-dihydro-1H-inden-1-one (216)

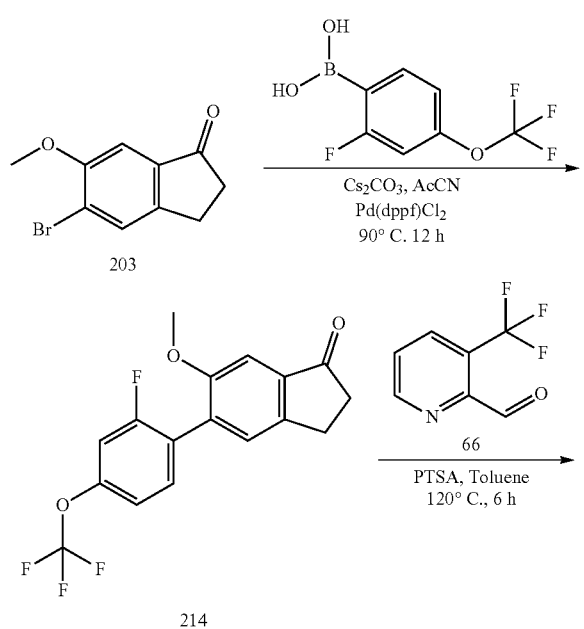

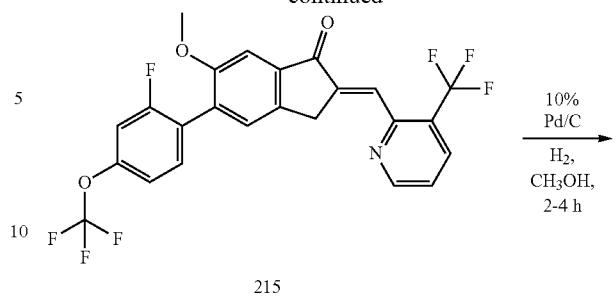

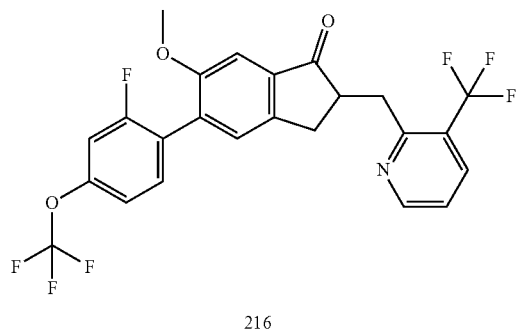

To a solution of 203 (100 mg, 0.414 mmol) and (2-fluoro-4-(trifluoromethoxy)phenyl)boronic acid (101.8 mg, 0.456 mmol) in acetonitrile was added cesium carbonate (272.1 mg, 0.829 mmol). The reaction was degassed and purged with nitrogen for 10 min. Pd(dppf)Cl$_2$ (16.9 mg, 0.020 mmol) was added to the reaction, which was then degassed and purged with nitrogen for another 10 min. The reaction was heated to 90° C. under sealed condition overnight, then allowed to cool to rt, and diluted with chloroform. The organic layer was filtered through celite plug and concentrated to get the crude 214, which was purified through flash chromatography by using 100-200 mesh silica gel. The compound was eluted in 5% ethyl acetate in hexane as half white solid 214.

To a solution of 214 (110 mg, 0.322 mmol)) in toluene 15 ml was added 66 (84.9 mg, 0.483 mmol). PTSA (122.4 mg, 0.644 mmol) was added to the reaction mass, which was stirred at 120° C. for 6h. The reaction mass was diluted with ethyl acetate and washed with water (3×25 mL). The organic layer was dried over sodium sulphate and concentrated to get the crude 215, which was purified through flash chromatography by using 100-200 mesh silica gel. The compound was eluted at 10% ethyl acetate in hexane to afford yellow coloured solid 215.

The 215 (65 mg, 0.130 mmol) was dissolved in methanol 25 mL, Pd/C 10 mg added, and the reaction stirred under H$_2$ balloon for 6h, filtered through celite bed and washed with excess methanol. The organic layer was concentrated to get the crude 216, which was purified by flash chromatography using 100-200 mesh silica gel. The compound 216 was eluted at 12% ethyl acetate in hexane as half white coloured solid. $^1$HNMR (400 MHz, CDCl$_3$) δ ppm 8.63 (d, 1H), 7.92 (d, 1H), 7.36 (m, 2H), 7.28 (m, 2H), 7.06 (m, 2H), 3.86 (s, 3H), 3.68 (dd, 1H), 3.48 (m, 1H), 3.26 (m, 2H), 2.80 (dd, 1H); MS-ES+500.1.

Example 65: 6-methoxy-5-(4-methylpiperazin-1-yl)-2-((3-(trifluoromethyl)pyridin-2-yl)methyl)-2,3-dihydro-1H-inden-1-one (250)

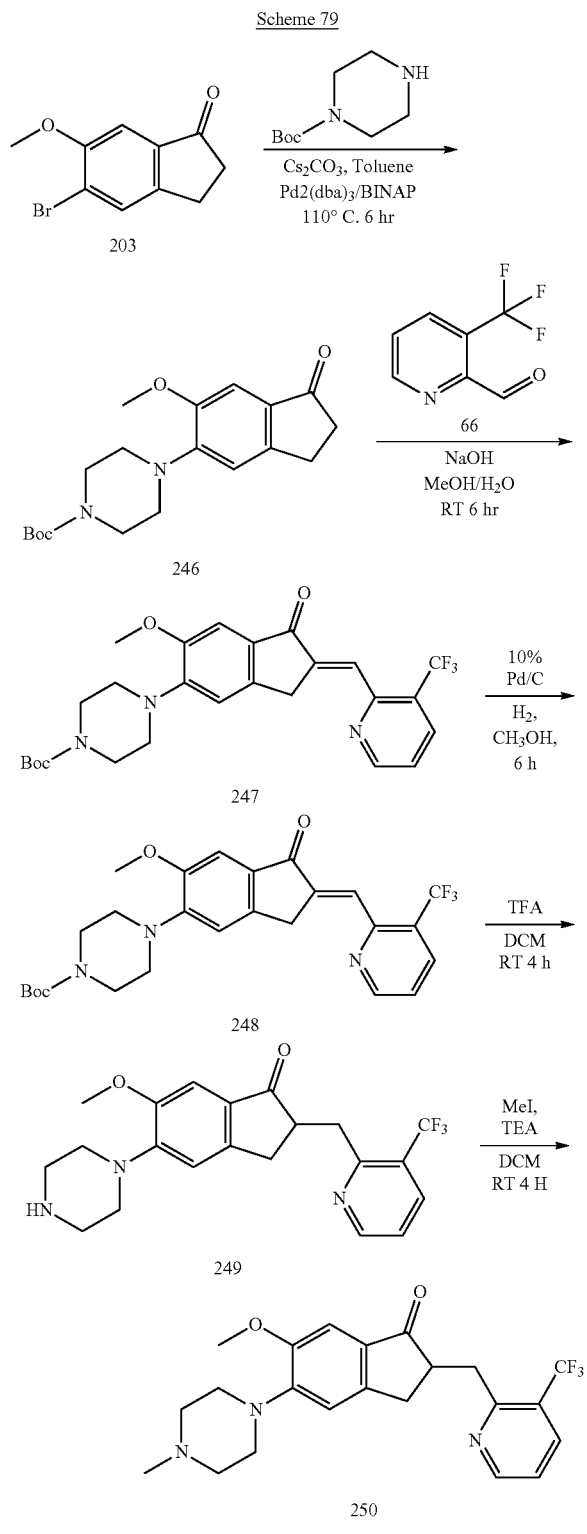

To a solution of 203 (1.0 g, 0.0041 mmol) and tert-butyl piperazine-1-carboxylate (960 mg, 0.00518 mmol) in toluene 15 ml was added cesium carbonate (2.69 g, 0.0082 mmol). The reaction was degassed and purged with $N_2$ for 10 min. $Pd_2(dba)_3$ (112 mg, 0.000123 mmol) and BINAP (153 mg, 0.000246 mmol) was added and again degassed and purged with nitrogen for another 10 min. The reaction was heated to 110° C. overnight under sealed condition, then diluted with chloroform and filtered through celite bed. The organic layer was concentrated to get the crude 246, which was purified through flash chromatography by using 100-200 mesh silica gel eluting the compound at 25% Ethyl acetate in hexane as pale yellow coloured solid 246.

To a solution of 246 (0.42 g, 0.0012 mmol) in MeOH/$H_2O$ was added 66 (233 mg, 0.00133 mmol) and sodium hydroxide (96 mg, 0.0024 mmol). The reaction was stirred at RT for 6h, diluted with chloroform, and washed with water (3×25 mL). The organic layer was dried over sodium sulphate and concentrated to get the crude, which was purified through flash chromatography by using 100-200 mesh silica gel. The compound 247 was eluted at 30% ethyl acetate in hexane to afford yellow coloured solid 247.

The 247 (400 mg, 0.0009 mmol) was dissolved in methanol 25 mL and Pd/C 40 mg added and the reaction stirred under $H_2$ balloon for 6h. The reaction was filtered through celite bed and washed with excess methanol. The organic layer was concentrated to get the crude 248, which was purified by flash chromatography using 100-200 mesh silica gel. The compound was eluted at 20% ethyl acetate in hexane as half white coloured solid 248.

To a solution 248 (300 mg, 0.0059 mmol) in DCM was added trifluoroacetic acid 3 ml and kept stirring for 4h at RT. After completion of the reaction, solvent was evaporated, and remainder diluted with water. The aqueous layer was washed with ethyl acetate and kept aside. The aqueous layer pH was adjusted to 9-10, then extracted with chloroform twice. The combined organic layer was dried over sodium sulphate and concentrated to get the crude 249, which was titurated with hexane at 5° C. to get pale yellow coloured solid 249.

A solution of 249 (0.15 g, 0.00037 mmol) was dissolved in DCM. Triethyl amine (56 mg, 0.00055 mmol) was added to the reaction followed by methyl iodide (50 mg, 0.00044 mmol) and kept stirring at RT for 4h. After completion of the reaction, it was diluted with DCM and washed with water twice. The organic layer was died over sodium sulphate and concentrated to get the crude 250, which was purified through flash chromatography using neutral alumina eluting the compound at 2% MeOH in chloroform as thick sticky solid 250. $^1$HNMR (400 MHz, CDCl$_3$) δ ppm 8.65 (d, 1H), 7.91 (d, 1H), 7.27 (d, 1H), 7.20 (s, 1H), 6.90 (s, 1H), 3.90 (m, 4H), 3.64 (dd, 1H), 3.42 (m, 1H), 3.03 (m, 4H), 2.65 (m, 4H), 2.36 (m, 4H); MS-ES+420.0.

Example 66: 5-(4-(2-hydroxyethyl)piperazin-1-yl)-6-methoxy-2-((3-(trifluoromethyl)pyridin-2-yl)methyl)-2,3-dihydro-1H-inden-1-one (251)

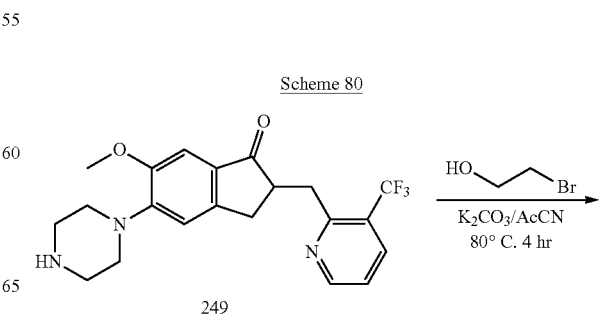

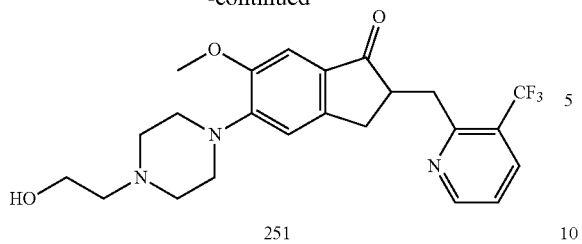

251

To a stirred solution of 249 (150 mg, 0.00037 mmol) in acetonitrile was added potassium carbonate (100 mg, 0.00074 mmol) then 2-bromo ethanol (57 mg, 0.00046 mmol). The stirred reaction mixture was heated to 80° C. for 4h. After completion of the reaction, it was filtered through celite bed and washed with chloroform. The organic layer was concentrated to get the crude 251, which was purified through flash chromatography using neutral alumina by eluting the compound at 2% methanol in chloroform to yield compound 251. $^1$HNMR (400 MHz, CDCl$_3$) δ ppm 8.65 (d, 1H), 7.91 (d, 1H), 7.20 (m, 2H), 6.84 (s, 1H), 3.89 (m, 5H), 3.66 (m, 4H), 3.43 (m, 1H), 3.12 (m, 4H), 3.03 (m, 1H), 2.72 (m, 4H), 2.63 (m, 3H); MS-ES+450.0.

Example 67: 2-((5-(1,1,1,3,3,3-hexafluoro-2-hydroxypropan-2-yl)pyridin-3-yl)methyl)-6-methoxy-5-morpholino-2,3-dihydro-1H-inden-1-one (245)

Scheme 78

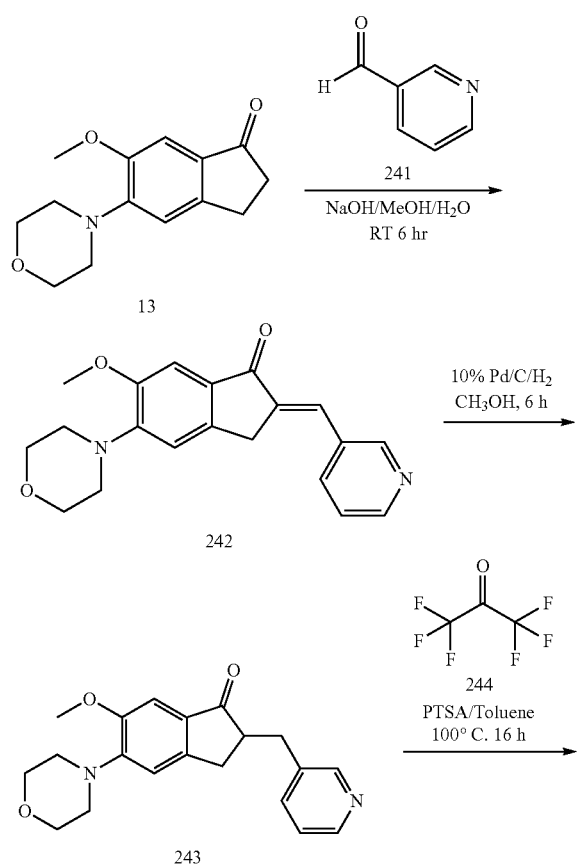

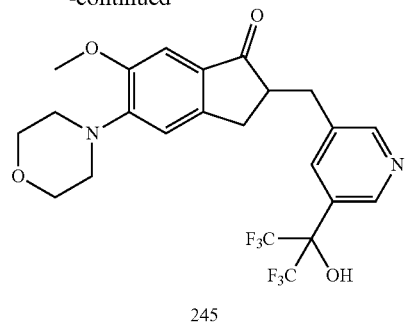

245

To a solution of 13 (0.1 g, 0.404 mmol) in MeOH/H$_2$O (1:1) was added nicotinaldehyde 241 (0.052 g, 0.484 mmol) and NaOH (0.032 g, 0.808 mmol). The reaction was stirred at RT for 6h, diluted with chloroform and washed with water (3×25 mL). The organic layer was dried over sodium sulphate and concentrated to get the crude, which was purified through flash chromatography by using 100-200 mesh silica gel. The compound 242 was eluted at 30% ethyl acetate in hexane to afford yellow coloured solid (E)-6-methoxy-5-morpholino-2-(pyridin-3-ylmethylene)-2,3-dihydro-1H-inden-1-one 242.

The 242 (0.1 g 0.297 mmol) was dissolved in methanol 25 ml and Pd/C 40 mg added. The reaction was stirred under H$_2$ balloon for 6h. The reaction was filtered through celite bed and washed with excess methanol. The organic layer was concentrated to get the crude which was purified by flash chromatography using 100-200 mesh silica gel. The compound 243 was eluted at 20% ethyl acetate in hexane as half white coloured solid 6-methoxy-5-morpholino-2-(pyridin-3-ylmethyl)-2,3-dihydro-1H-inden-1-one 243. $^1$HNMR (400 MHz, CDCl$_3$) δ ppm 8.47 (m, 2H), 7.56 (d, 1H), 7.22 (m, 1H), 7.17 (s, 1H), 6.84 (s, 1H), 3.89 (m, 3H), 3.87 (m, 4H), 3.30 (dd, 1H), 3.07 (m, 4H), 2.99 (m, 1H), 2.95 (m, 1H), 2.70 (m, 2H).

To a stirred solution of 243 (0.08 g, 0.236 mmol) in toluene was added PTSA (0.090 g, 0.472 mmol) and kept stirring at 120° C. Hexafluoroacetone 244 (0.129 g, 0.590 mmol) was added to the reaction and heated to 100° C. for 16h. Reaction was cooled to RT, diluted with water, extracted with ethyl acetate twice, the organic layer dried over sodium sulphate and concentrated to get the crude, which was purified through flash chromatography by using 100-200 mesh silica gel eluting the compound at 30% ethyl acetate in hexane as thick sticky solid 2-((5-(1,1,1,3,3,3-hexafluoro-2-hydroxypropan-2-yl)pyridin-3-yl)methyl)-6-methoxy-5-morpholino-2,3-dihydro-1H-inden-1-one 245. $^1$HNMR (400 MHz, CDCl$_3$) δ ppm 7.06 (m, 2H), 6.88 (s, 1H), 6.90 (s, 1H), 6.123 (s, 1H), 3.88 (m, 7H), 3.49 (m, 1H), 3.08 (m, 2H), 3.03 (m, 6H), 2.29 (m, 2H).

Example 68: 2-((5-(1,1,1,3,3,3-hexafluoro-2-hy-droxypropan-2-yl)pyridin-3-yl)methyl)-6-methoxy-5-(4-methylpiperazin-1-yl)-2,3-dihydro-1H-inden-1-one (256)

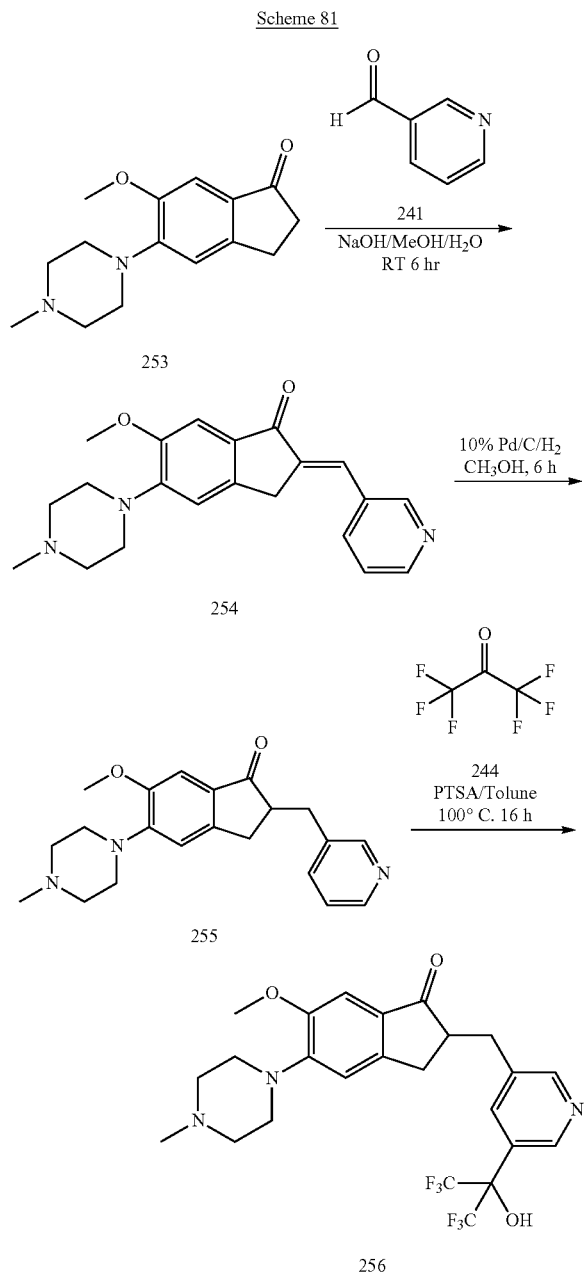

acetate in hexane to afford yellow coloured solid (E)-6-methoxy-5-(4-methylpiperazin-1-yl)-2-(pyridin-3-ylmethylene)-2,3-dihydro-1H-inden-1-one 254.

The 254 (0.08 g, 0.229 mmol) was dissolved in methanol 25 ml, Pd/C 20 mg added and the reaction stirred under H₂ balloon for 6h. The reaction was filtered through celite bed and washed with excess methanol. The organic layer was concentrated to get the crude, which was purified by flash chromatography using 100-200 mesh silica gel. The compound was eluted at 20% ethyl acetate in hexane as half white coloured solid 6-methoxy-5-(4-methylpiperazin-1-yl)-2-(pyridin-3-ylmethyl)-2,3-dihydro-1H-inden-1-one 255.

To a stirred solution of 255 (0.05 g, 0.142 mmol) in toluene was added PTSA (0.054 g, 0.284 mmol) and kept stirring at 120° C. Hexafluoroacetone 244 (0.078 g, 0.356 mmol) was added to the reaction and kept at temperature and stirred for 16h. Reaction was then cooled to RT, diluted with water, and extracted with ethyl acetate twice, The organic layer was dried over sodium sulphate and concentrated to get the crude, which was purified through flash chromatography by using 100-200 mesh silica gel and eluting the compound at 30% ethyl acetate in hexane as thick sticky solid 2-((5-(1,1,1,3,3,3-hexafluoro-2-hydroxypropan-2-yl)pyridin-3-yl)methyl)-6-methoxy-5-(4-methylpiperazin-1-yl)-2,3-dihydro-1H-inden-1-one 256.

Example 69: 5-(1,1,1,3,3,3-hexafluoro-2-hydroxypropan-2-yl)nicotinaldehyde (259)

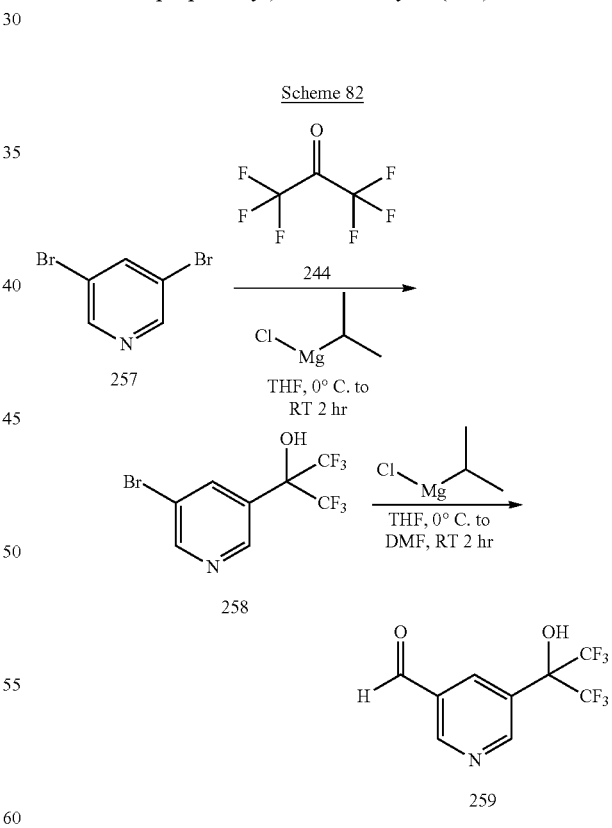

To a solution of 6-methoxy-5-(4-methylpiperazin-1-yl)-2,3-dihydro-1H-inden-1-one 253 (0.1 g, 0.384 mmol) in MeOH/H₂O (1:1) was added nicotinaldehyde (0.049 g, 0.461 mmol) and NaOH (0.03 g, 0.768 mmol) was added to the reaction mass, which was then stirred at RT for 6h. The reaction mass was diluted with chloroform and washed with water (3×25 mL). The organic layer was dried over sodium sulphate and concentrated to get the crude, which was purified through flash chromatography by using 100-200 mesh silica gel. The compound was eluted at 30% ethyl To a stirred solution of 3,5-dibromo pyridine 257 (1.09 g, 4.60 mmol) in dry THF cooled to 0° C., was added isopropyl magnesium chloride (2.4 mL, 4.8 mmol) drop wise while stirring for 10 min. Hexafluoroacetone (CF₃—CO—CF₃) 244 was added to the resulting reaction and continued stirring for another 2h. After completion of the starting materials, the reaction was quenched with saturated ammonium chloride solution. The organic layer was separated and aqueous phase was extracted again with diethyl ether, the combined organic layer was dried over sodium sulphate and concentrated to get the crude 2-(5-bromopyridin-3-yl)-1,1,1,3,3,3-hexafluoropropan-2-ol 258. The crude was purified through silica gel by using 100-200 mesh silica gel by eluting the compound at 20:5 ethyl acetate in hexane as thick oil of compound 258.

To a stirred solution of 258 (0.347 g, 1.07 mmol) in dry THF, cooled to 0° C., was added isopropyl magnesium chloride (1.2 mL, 2.4 mmol) drop wise and stirred for 10 min followed by the addition of DMF (0.015 ml, 1.94 mmol) to the reaction and stirred for additional 2h. After completion of the reaction, it was quenched with saturated ammonium chloride solution. The organic layer was separated and aqueous phase was extracted again with diethyl ether, the combined organic layer was dried over sodium sulphate and concentrated to get the crude compound 5-(1,1,1,3,3,3-hexafluoro-2-hydroxypropan-2-yl)nicotinaldehyde 259 used directly to proceed for the next step.

Example 70: 6-(1,1,1,3,3,3-hexafluoro-2-hydroxypropan-2-yl)picolinaldehyde (262)

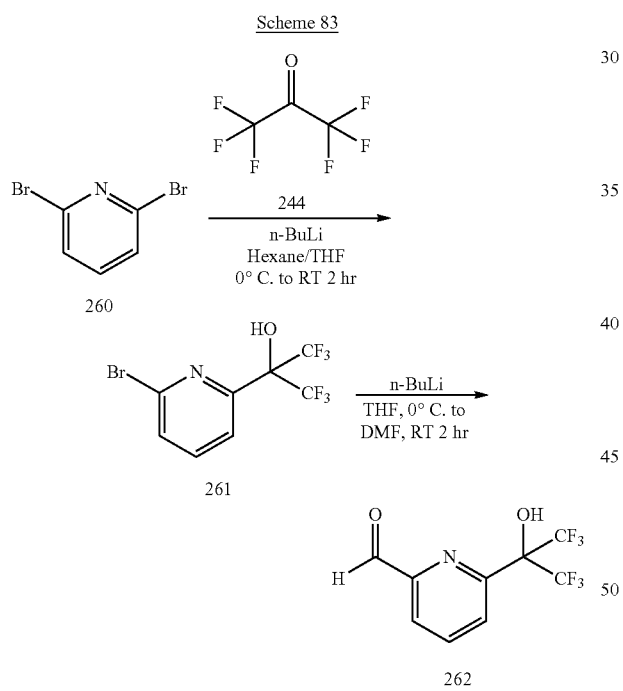

To a stirred solution of 2,6-dibromo pyridine 260 (2.37 g, 10 mmol) in dry THF, cooled to 0° C., n-BuLi 1.4 mmol in hexane (7.9 ml, 11 mmol) was added drop wise, and stirred for 10 min. Then hexafluoroacetone (CF₃—CO—CF₃) 244 was added to the reaction mixture and continued stirring for another 2h. After completion of the reaction, it was quenched with saturated ammonium chloride solution. The organic layer was separated and aqueous phase was extracted again with diethyl ether, the combined organic layer was dried over sodium sulphate and concentrated to get the crude compound 2-(6-bromopyridin-2-yl)-1,1,1,3,3,3-hexafluoropropan-2-ol 261, which was purified through 100-200 mesh silica gel by eluting the compound at 15% Ethylacetate in hexane to get the thick oil compound 261.

To a stirred solution of 261 (0.5 g, 1.54 mmol) in dry THF, cooled to 0° C., n-BuLi (0.118 g, 1.85 mmol) was added drop wise and continued stirring for 10 min. Then DMF (0.224 g, 3.08 mmol) was added to the reaction mixture while stirring for another 2h. After completion of the reaction, it was quenched with saturated ammonium chloride solution. The organic layer was separated and aqueous phase was extracted again with diethyl ether, the combined organic layer was dried over sodium sulphate and concentrated to get the crude compound 6-(1,1,1,3,3,3-hexafluoro-2-hydroxypropan-2-yl)picolinaldehyde 262.

Example 71: 2-((5-(1,1,1,3,3,3-hexafluoro-2-hydroxypropan-2-yl)pyridin-3-yl)methyl)-6-methoxy-5-morpholino-2,3-dihydro-1H-inden-1-one (264)

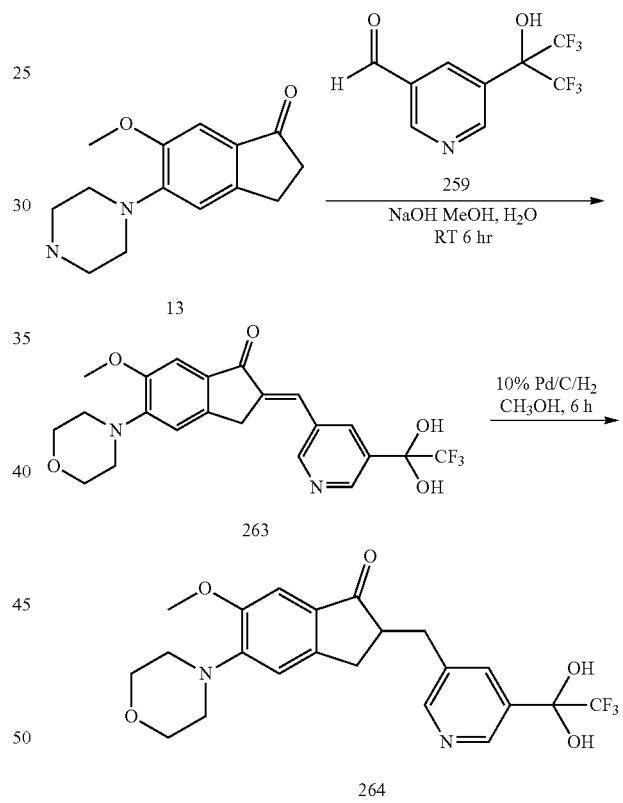

To a solution of 13 (0.1 g, 0.40 mmol)), MeOH/H₂O (1:1), was added 5-(1,1,1,3,3,3-hexafluoro-2-hydroxypropan-2-yl) nicotinaldehyde 259 (0.132 g, 0.485 mmol) and NaOH (0.032 g, 0.80 mmol). The reaction was stirred at RT for 6h. The reaction mass was diluted with chloroform and washed with water (3×25 ml). The organic layer was dried over sodium sulphate and concentrated to get the crude 263, which was purified through flash chromatography by using 100-200 mesh silica gel. The compound was eluted at 30% ethyl acetate in hexane to afford yellow coloured solid (E)-2-((5-(1,1,1,3,3,3-hexafluoro-2-hydroxypropan-2-yl)pyridin-3-yl)methylene)-6-methoxy-5-morpholino-2,3-dihydro-1H-inden-1-one 263.

The 263 (50 mg, 0.090 mmol) was dissolved in methanol 25 ml, Pd/C 40 mg added, and the reaction stirred under $H_2$ balloon for 6h. The reaction was filtered through celite bed and washed with excess methanol. The organic layer was concentrated to get the crude, which was purified by flash chromatography using 100-200 mesh silica gel. The crude compound 264 was eluted at 20% ethyl acetate in hexane as half white coloured solid 2-((5-(1,1,1,3,3,3-hexafluoro-2-hydroxypropan-2-yl)pyridin-3-yl)methyl)-6-methoxy-5-morpholino-2,3-dihydro-1H-inden-1-one 264.

Example 72: 2-((6-(1,1,1,3,3,3-hexafluoro-2-hydroxypropan-2-yl)pyridin-2-yl)methyl)-6-methoxy-5-morpholino-2,3-dihydro-1H-inden-1-one (266)

The 265 (50 mg 0.1 mmol) was dissolved in methanol 25 ml, Pd/C 40 mg added, and the reaction stirred under $H_2$ balloon for 6h. The reaction was filtered through celite bed and washed with excess methanol. The organic layer was concentrated to get the crude 266 and was purified by flash chromatography using 100-200 mesh silica gel. The 266 compound was eluted at 20% ethyl acetate in hexane as half white coloured solid 2-(((6-(1,1,1,3,3,3-hexafluoro-2-hydroxypropan-2-yl)pyridin-2-yl)methyl)-6-methoxy-5-morpholino-2,3-dihydro-1H-inden-1-one 266.

Example 73: 2-((5-(1,1,1,3,3,3-hexafluoro-2-hydroxypropan-2-yl)-3-(trifluoromethyl)pyridin-2-yl)methyl)-6-methoxy-5-morpholino-2,3-dihydro-1H-inden-1-one (268)

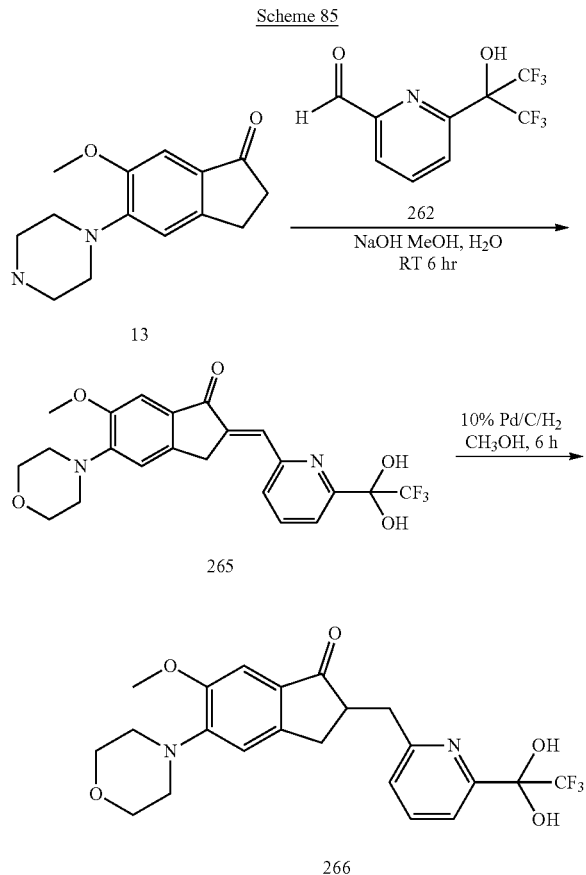

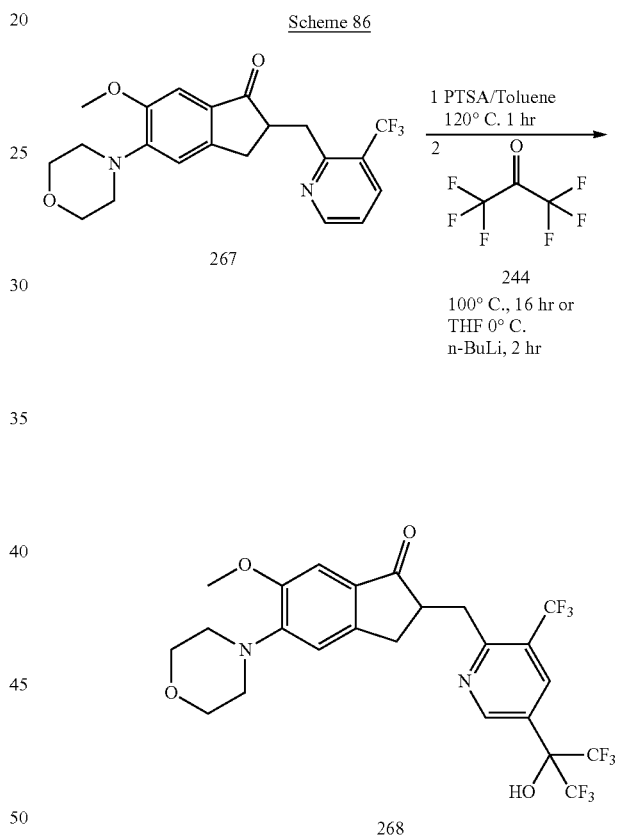

To a solution of 13 (0.1 g, 0.40 mmol)) in MeOH/$H_2O$ (1:1) was added 6-(1,1,1,3,3,3-hexafluoro-2-hydroxypropan-2-yl)picolinaldehyde 262 (0.132 g, 0.485 mmol), NaOH (0.032 g, 0.80 mmol), and the reaction stirred at RT for 6h. The reaction mass was diluted with chloroform and washed with water (3×25 ml). The organic layer was dried over sodium sulphate and concentrated to get the crude, which was purified through flash chromatography by using 100-200 mesh silica gel. The compound 265 was eluted at 30% ethyl acetate in hexane to afford yellow coloured solid (E)-2-((6-(1,1,1,3,3,3-hexafluoro-2-hydroxypropan-2-yl)pyridin-2-yl)methylene)-6-methoxy-5-morpholino-2,3-dihydro-1H-inden-1-one 265.

To a stirred solution of 267 (0.1 g, 0.245 mmol) in toluene was added PTSA (0.094 g, 0.490 mmol) and kept stirring at 120° C. for 1 h. After the addition of hexafluoroacetone 244 (0.134 g, 0.614 mmol), the reaction was heated to 100° C. for 16h. After completion of the reaction, it was cooled to RT, diluted with water, and extracted with ethyl acetate twice. The organic layer was dried over sodium sulphate and concentrated to get the crude compound 268, which was purified through flash chromatography by using 100-200 mesh silica gel eluting the compound at 30% ethyl acetate in hexane as thick sticky solid compound 2-((5-(1,1,1,3,3,3-hexafluoro-2-hydroxypropan-2-yl)-3-(trifluoromethyl)pyridin-2-yl)methyl)-6-methoxy-5-morpholino-2,3-dihydro-1H-inden-1-one 268.

Example 74: 2-(2-(1,1,1,3,3,3-hexafluoro-2-hydroxypropan-2-yl)-5-(trifluoromethyl)benzyl)-6-methoxy-5-morpholino-2,3-dihydro-1H-inden-1-one (270)

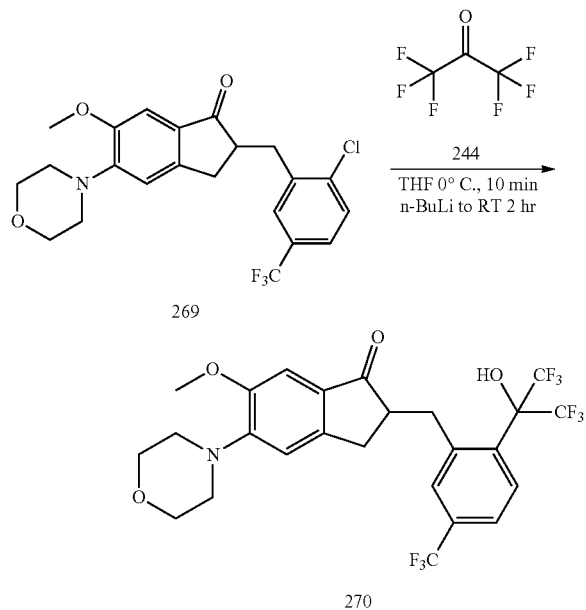

To a stirred solution of 2-(2-chloro-5-(trifluoromethyObenzyl)-6-methoxy-5-morpholino-2,3-dihydro-1H-inden-1-one 269 (0.1 g, 0.226 mmol) in dry THF, cooled to 0° C., n-BuLi (0.021 g, 0.339 mmol) was added drop wise and the solution stirred for 10 min. Then hexafluoroacetone 244 (0.10 g, 0.453 mmol) was added to the reaction and stirred for another 2h. After completion of the reaction, it was quenched with saturated ammonium chloride solution. The organic layer was separated and aqueous phase was extracted again with diethyl ether, the combined organic layer was dried over sodium sulphate and concentrated to get the crude 270, which was purified through 100-200 mesh silica gel by eluting with 15% ethyl acetate in hexane to give 20 mg of compound 2-(2-(1,1,1,3,3,3-hexafluoro-2-hydroxypropan-2-yl)-5-(trifluoromethyObenzyl)-6-methoxy-5-morpholino-2,3-dihydro-1H-inden-1-one 270.

Additional Examples of Usage Method

Example 75

Structural Modelling of RORγt:

The compounds of Formula I provided in TABLE 1A & 1B were designed using a crystal structures of RORγt. Nuclear hormone receptor superfamily RORα/γ contains a signature type II zinc finger DNA binding motif and a ligand binding hydrophobic pocket. Three subtypes; RORα, -β, and -γ (NR1F1-3 or RORA-C), have been identified with unique tissue distributions and biological function. In the thymus, RORα and two isoforms, γ1 and γ2 (RORγt/RORγT), have been identified with RORγt distinct from the RORγ1 isoform in that it lacks the amino terminus of RORγ1. A sequence of ROR-γt (NP_001001523, 1-497) search with in the rcsb.org provided the 6 homologues X-ray crystal structure templates and 3B0W is selected for FFDD strategy lead to the discovery of substituted 2, 3-dihydro-1H-inden-1-one containing RORγ antagonists depicted in FIG. 1 and its analogues.

In Vitro Inhibition Assays

Example 76

TR-FRET RORγt Binding Assay:

RORγ-LBD contains a 6-His and GST tag peptide from SRC1-2 an aminoterminal biotinyl-CPSSHSSLTERH-KILHRLLQEGSPS was employed and the 6-His-(GST) RORγ-LBD was used which expressed and purified from baculovirus infected Sf-21 insect cells from Invitrogen and purified using glutathione sepharose. The assay protocol included 504 of TR-FRET buffer 50 mM KCl, 50 mM TRIS, 1 mM Na-EDTA, 0.1 mM DTT, (pH 7.0); 10 nM of 6-His(GST)RORgamma-LBD, 1 nM Anti-6-His-Eu, 0.1 μM of SRC1_2 peptide and Strep-APC 10 nM. The peptide binding due to dose-curves of compounds was added the 0.1% DMSO. Fluorescence at wavelength 340 nm was read in each well of 94 well plates using an Envision fluorescence reader in Time Resolved mode after overnight incubation at 4° C. Dose-response data and $IC_{50}$ values are provided in the TABLE 3.

Example 77

Effects of the Test Compounds on the RORγt-Activated IL-17A Prom/LUCPorter™ HEK 293 Cells:

Antagonistic (or inverse agonistic) effects of the test compounds on the RORγt-activated IL-17A Prom/LUC-Porter™ HEK 293 cells were analyzed and IC50 of each compound was evaluated. The IL-17A Prom/LUCPorter™ HEK 293 cell line (IMGENEX, IML-301) was plated in 96-well white plates at 0.75×105 cells per well for overnight. Cells were transfected with the RORγt plasmid (IMGENEX, IMP-122) for 6h. Cells were treated with a series of 8 point concentrations of each compound (100, 33.33, 11.11, 3.70, 1.23, 0.41, 0.14 and 0.0457 μM) for 16h. Luciferase activity was analyzed using the luciferase reporter assay reagent (IMGENEX, LS100). The data were analyzed using Excel and Prism software. Percent activity was defined as 100×(1−(Well−Control A)/(Control B−Control A)), where Control A was the wells containing cells transfected with RORγt and Control B was the wells containing non-transfected cells. Both Controls A and B were treated with vehicle alone.

Figure 2A:
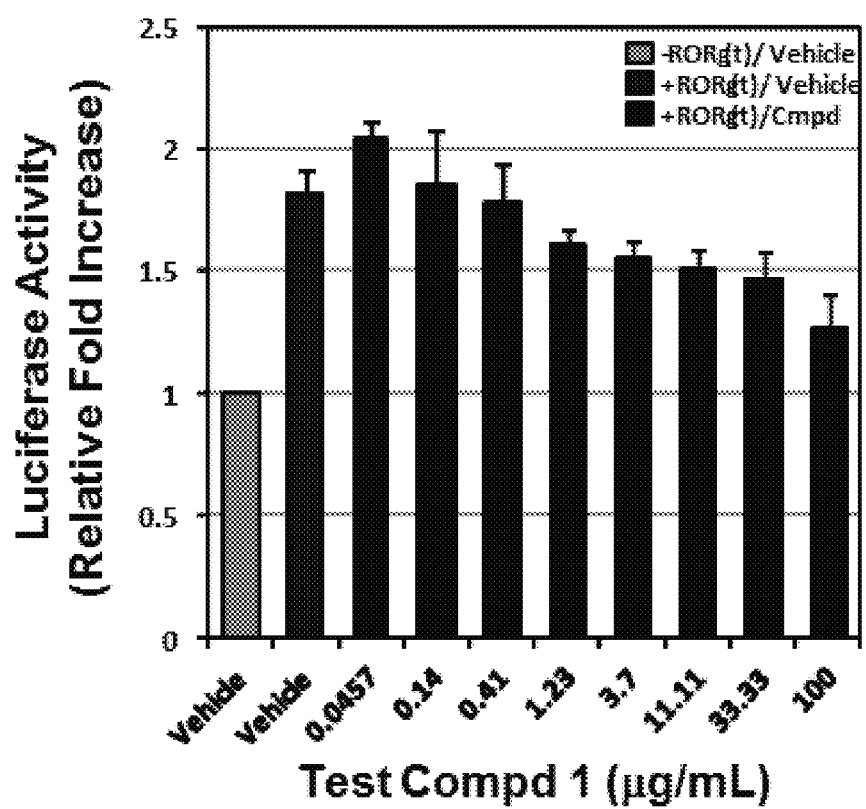
FIG. 2A: Effect of substituted 2, 3-dihydro-1H-inden-1-one series containing RORg antagonists on RORγt-mediated IL-17A promoter activity.
Figure 2B:
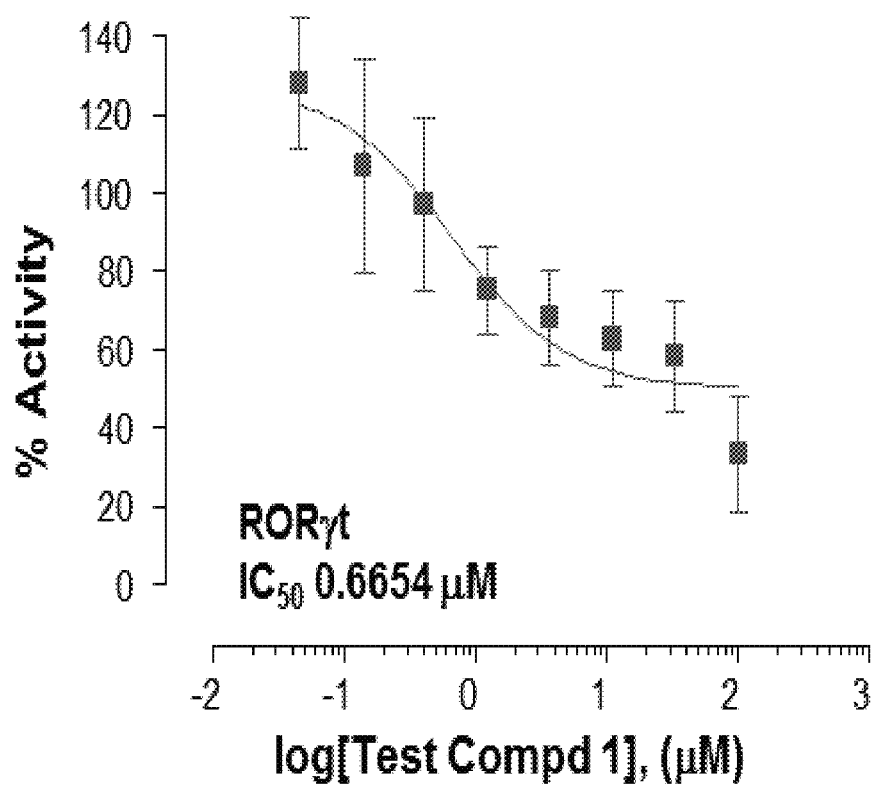
FIG. 2B: RORγt-mediated IL-17A Dose-response curve.
Figure 3A:
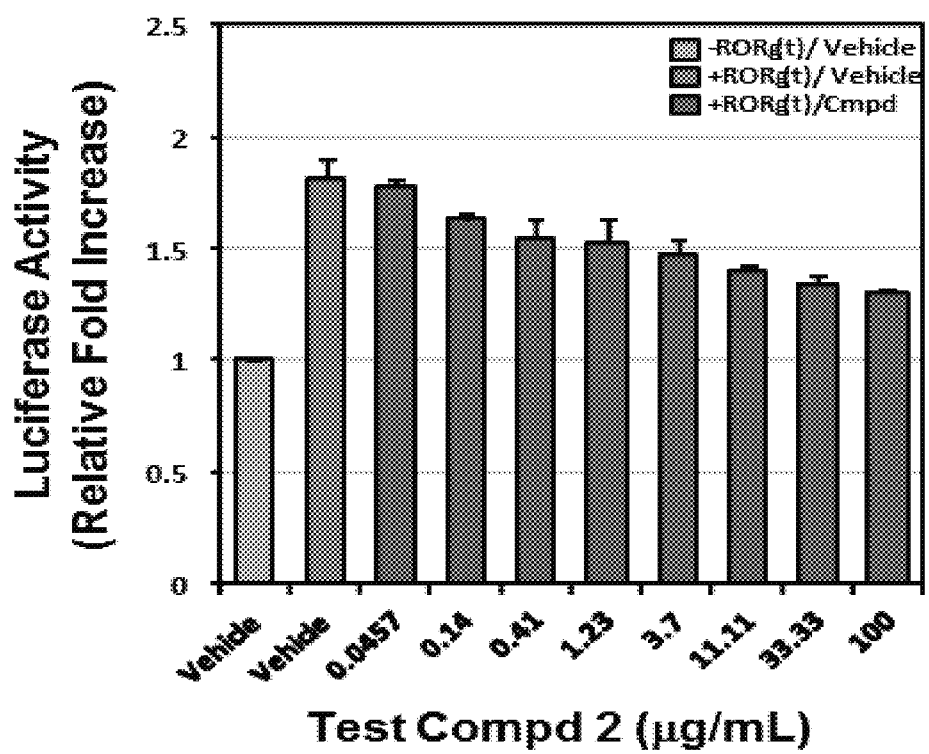
FIG. 3A: Effect of substituted 2, 3-dihydro-1H-inden-1-one series RORg antagonists on RORγt-mediated IL-17A promoter activity.
Figure 3B:
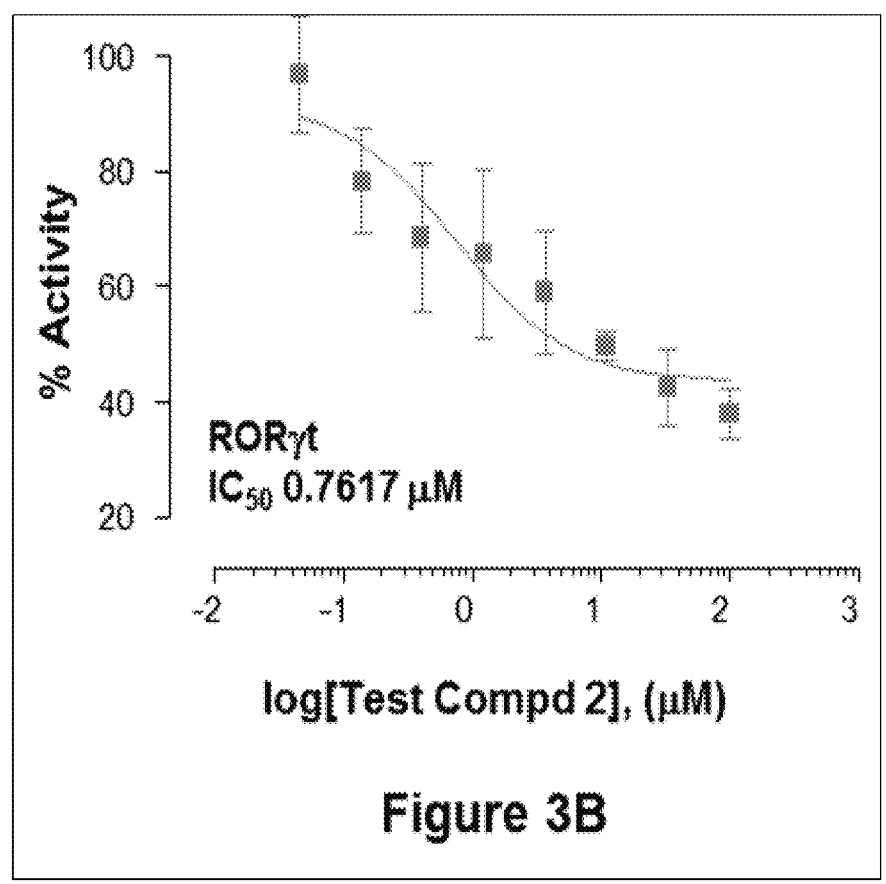
FIG. 3B: RORγt-mediated IL-17A Dose-response curve.

$IC_{50}$ evaluation of selected compound from the TABLE 1 on RORγt-mediated IL-17A promoter activity and its 10 dose-response curve is given in FIGS. 2 and 3.

Example 78

Cytokine IL-17 Estimation by HTRF:

The assay was designed to assess the potency of test compounds on IL-17 cytokine release from CD4+ T cells. In order to aid in the identification of potent inhibitors, the $IC_{50}$'s determined for the test compounds IL-17 release from CD4+ T cells through the generation of 10 point Dose Response Curves (DRC). Assay methods used to quantify IL-17 secretion is HTRF (Homogenous Time Resolved Fluorescence). IL-17 secreted is detected by anti-IL-17 MAb labeled with XL665, the second MAb labeled with Cryptate, which binds to specific epitopes of human IL-17. Upon close proximity of both acceptor and donor energy transfer (FRET) occurs. This technique has been further enhanced by using long-lived labels combined with the detection on a time-resolved fluorescence basis, allowing maximization of prompt fluorescence interferences.

The assay was performed according to manufacturer's instruction. All the reagents were reconstituted according to instructions provided. The reagents were dispensed into a half area 96-well plate in the following order: 104 standard or sample, IL-17 MAbXL665 and 5 µL IL-17 Cryptate. For the negative control, the standard or sample is replaced by 104 of diluent. The plate is covered with a plate sealer and incubated at rt for 2h. Following incubation, the plate sealer is removed and the plate is read using HTRF protocol on Envision Microplate reader. All of the data analysis was carried out using Microsoft Excel (2010) and $IC_{50}$ was determined using GraphPad Prism 4 software. % Inhibition of the test compounds were determined utilizing the following formula:

% Inhibition=100−(100*(Average Test Compound Counts−Average Negative Control Counts)/(Average Positive Control Counts−Average Negative Control Counts)).

Dose-response data and $IC_{50}$ values are provided in the TABLE 3.

TABLE 3

List of substituted 2, 3-dihydro-1H-inden-1-one containing compounds and corresponding RORγt antagonistic, cellular and IL-17 inhibition results*

| Example ID | RORγt Binding | RORγt Cell Specific | IL-17 Inhibition |
|---|---|---|---|
| 16 | ** | ** | ** |
| 20 | ** | * | ** |
| 23 | *** | ** | *** |
| 25 | NA | * | NA |
| 28 | ** | * | ** |
| 31 | ** | * | ** |
| 34 | NA | NA | NA |
| 30 | * | * | ** |
| 32 | *** | *** | ** |
| 37 | *** | *** | *** |
| 39 | NA | NA | NA |
| 42 | ** | NA | ** |
| 44 | NA | NA | * |
| 47 | ** | ** | ** |
| 50 | *** | ** | ** |
| 53 | ** | ** | ** |
| 56 | ** | ** | ** |
| 59 | ** | * | ** |
| 62 | ** | ** | *** |
| 65 | * | ** | ** |
| 68 | *** | *** | *** |
| 71 | * | * | ** |
| 74 | * | * | ** |
| 77 | ** | ** | ** |
| 80 | ** | ** | ** |
| 83 | ** | ** | ** |
| 86 | ** | ** | ** |
| 89 | ** | ** | *** |
| 92 | ** | ** | ** |
| 95 | ** | ** | ** |
| 98 | NA | NA | NA |
| 103 | *** | ** | ** |
| 106 | *** | ** | ** |
| 110 | *** | *** | ** |
| 113 | *** | *** | ** |
| 117 | *** | ** | ** |
| 120 | NA | NA | NA |
| 123 | ** | ** | ** |
| 125 | ** | ** | ** |
| 128 | ** | ** | ** |
| 131 | ** | ** | ** |
| 133 | ** | ** | ** |
| 136 | NA | NA | NA |
| 138 | NA | NA | NA |
| 140 | *** | ** | * |
| 142 | ** | ** | *** |
| 144 | ** | ** | ** |
| 146 | ** | ** | *** |
| 149 | *** | * | ** |
| 151 | ** | ** | ** |
| 154 | ** | ** | *** |
| 156 | * | *** | ** |
| 158 | *** | ** | *** |
| 161 | ** | *** | ** |
| 164 | *** | ** | *** |
| 167 | ** | ** | *** |
| 169 | ** | ** | *** |
| 172 | ** | ** | *** |
| 174 | ** | ** | *** |
| 177 | *** | ** | *** |
| 179 | *** | ** | *** |
| 182 | ** | ** | *** |
| 184 | *** | ** | *** |
| 187 | ** | ** | *** |
| 188 | *** | ** | *** |
| 190 | *** | ** | *** |
| 191 | *** | *** | *** |
| 193 | *** | *** | *** |
| 194 | *** | *** | *** |
| 196 | *** | ** | ** |
| 197 | *** | *** | *** |
| 200 | NA | NA | NA |
| 202 | NA | NA | NA |
| 206 | NA | NA | NA |
| 209 | NA | NA | NA |
| 213 | *** | ** | *** |
| 216 | ** | ** | *** |
| 220 | NA | NA | NA |
| 225 | NA | NA | NA |
| 229 | *** | *** | *** |
| 232 | *** | *** | *** |
| 236 | ** | ** | *** |
| 240 | *** | *** | *** |
| 242 | *** | *** | *** |
| 245 | ** | *** | ** |
| 249 | ** | *** | ** |
| 250 | ** | *** | ** |
| 251 | *** | *** | *** |
| 256 | *** | *** | *** |
| 264 | *** | *** | *** |
| 266 | *** | *** | *** |
| 268 | *** | *** | *** |
| 270 | NA | NA | NA |

*RORγt antagonistic, cellular and IL-17 inhibition activity result for selected compounds
*** <0.5 µM,
** >1.0 µM,
* >10 µM
NA = Not Available In Vivo Models Experiment Example 79

Efficacy of substituted 2, 3-dihydro-1H-inden-1-one containing selected compounds on Inhibition of Anti-CD3e Antibody induced $CD4^+$T cell Cytokine-IL-17 Production in Male BALB/c Mice In Vivo Mice Cytokine IL-17 by ELISA Method:

A quantitative analysis of mouse IL-17 sandwich ELISA was conducted from the collected serum samples (Mouse IL-17 ELISA Ready-DuoSet ELISA kit, from R&D Systems, USA). The serum samples tested were collected from mice after 1.5 h of anti-CD3e antibody challenge, before antibody challenge, the mice were treated with different doses of test compounds or Dexamethasone as mentioned above in experimental design. The capture antibody was diluted in coating buffer (1×PBS) and transferred into each well. The plate was sealed and incubated overnight at RT. The following day the wells of the plate were aspirated and washed (3 times), allowing a one minute soak time in each step. The plate was blocked using 1% BSA in PBS, sealed, and incubated in ambient conditions for not less than one hour. After the incubation period, the plate was washed as described above, and the standards and serum samples were added to the appropriate wells and incubated for two hours at RT. The samples were diluted in a 1:10 ratio with 1% BSA in PBS (reagent diluent). After two hours, well were washed as mentioned above three times and added the detection min at 4±2° C. The plasma was separated within 30 min of scheduled time and stored below −60° C. until bio-analysis. The plasma samples were analyzed for selected test EXAMPLES using a fixed-for purpose liquid chromatographic tandem mass spectrometric detection (LC-MS/MS) method with a lower limit of quantification of 2.21 ng/mL. The pharmacokinetic parameters for select EXAMPLES were calculated using the non-compartmental analysis tool of validated WinNonlin® software (Version 5.2).

Pharmacokinetic parameters (mean±SD; n=3) of 7 following intravenous bolus and oral gavage administration of 7 solution in male Sprague Dawley rats are shown in TABLE 4 below:

TABLE 4

Rat PK: The pharmacokinetic profiles of substituted 2,3-dihydro-1H-inden-1-one containing compounds following intravenous bolus administration and oral gavage in male Sprague Dawley rats.

| Formulation | Group | Route/Dose (mg/kg) | $T_{max}$ (h) | $C_{max}$ (ng/mL) | $AUC_{last}$ (ng · h/mL) | $AUC_{inf}$ (ng · h/mL) | CL (mL/min/kg) | $V_{35}$ (L/kg) | $T_{1/2}$ (h) | $F^a$ |
|---|---|---|---|---|---|---|---|---|---|---|
| Solution | 1 | IV/2 | n/a | 1937.82 ± 481.94 | 571.57 ± 57.37 | 589.36 ± 63.88 | 56.98 ± 5.85 | 7.18 ± 2.00 | 6.63 ± 4.92 | 19 |
| | 2 | PO/10 | $2.00^c$ (1.00-2.00) | 176.16 ± 22.73 | 552.65 ± 123.98 | 557.70 ± 124.96 | n/a | n/a | n/a | |

$^a AUC_{inf}$ and nominal doses were used for bioavailability (F) calculation;
$^b$ back extrapolated concentration at time zero;
$^c T_{max}$ reported as median (min-max); n/a: not applicable antibody and incubated for two hours. After washing (as mentioned above), the HRP enzyme is added and incubated for 20 min and washed again and added substrate according to the manufacturer's instructions and incubated for 30 min/until blue color develops. The plate was read at 450/570 nm using the Microplate Absorbance Reader (SpectraMax; M3). Statistics: One-Way ANOVA was performed followed by Dunnett's multiple comparison test. Percent inhibition of cytokine production was calculated for all groups compared to positive control.

Figure 4:
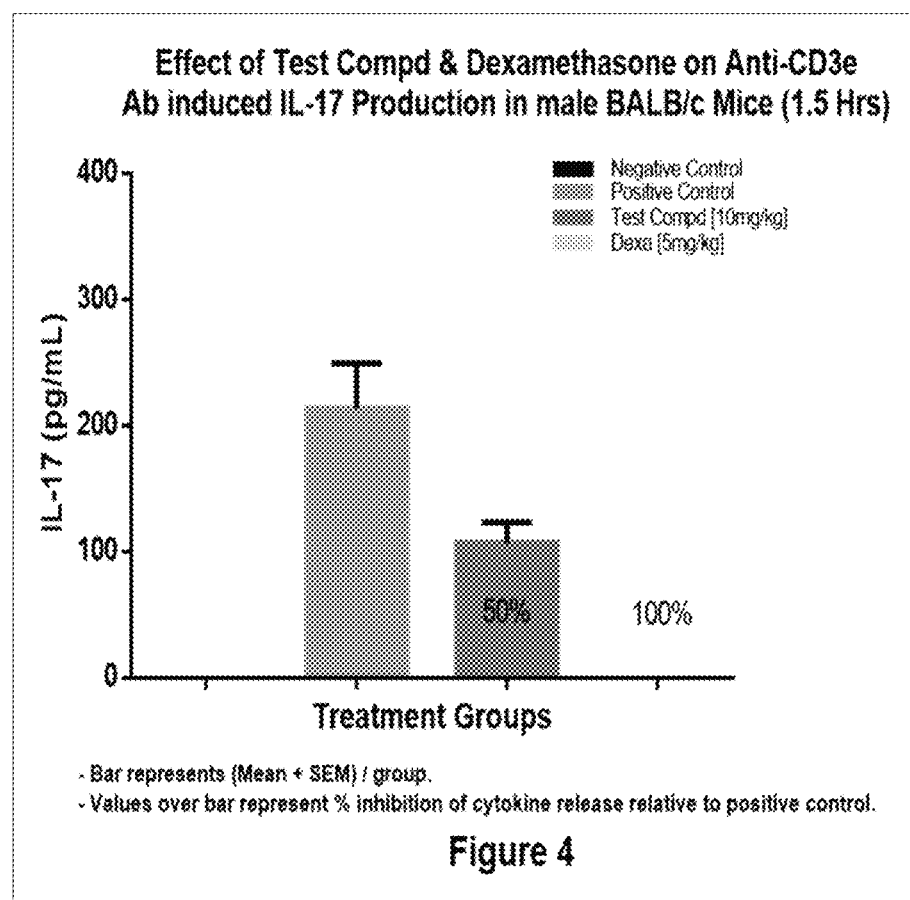
FIG. 4: Cytokine IL-17 inhibition by substituted 2, 3-dihydro-1H-inden-1-one series.

IL-17 production: Intravenous administration of 5 ug/animal anti-CD3e antibody to each mice resulted in significant elevation of IL-17 production at 1.5 h time point compared to negative control group. Oral administration of test compounds 10 mg/kg, 20 mins prior to antibody administration resulted in 50% respectively. Dexamethasone treatment showed 94%, respectively, reduction in IL-17 production when compared to positive control group. Data is shown in FIG. 4.

Example 80

Pharmacokinetic Experiments:

The bio-availability and pharmacokinetics of some compounds of the present invention were examined in male Sprague Dawley rats. A total of 6 male rats were used in the study. The study was performed using parallel design (n=3) with serial sampling.

Dose formulations were prepared on the day of doing. Blood samples were collected at 0.083 (only IV), 0.25, 0.5, 1, 2, 4, 8 and 24 h post-dose. At each time point, approximately 0.2 mL of blood was withdrawn from each cannulated rat through jugular vein and transferred to a pre-labeled microfuge tube containing 20 μL of 200 mm K2EDTA per mL of blood. Following collection of blood sample, equal volume of heparinized saline was flushed into jugular vein of rat. The blood samples were centrifuged at 5000 g for 5

Example 81: Assessment of the Potency of Test Compounds on IL-17 Release from CD4+ T cells: We have established robust in vitro cell-based HTRF assay for the activation and stimulation of CD4+T lymphocytes to T helper 17 (Th17) cell differentiation and IL-17 production. The test compounds are selective small-molecule inhibitors of RORγt, was found to inhibit IL-17 production, with an $IC_{50}$ of 220 nM to 1.2 μM. The assay quantification was performed using a standard Dex and SB203589 reported to inhibit IL-17, with an $IC_{50}$ of 14 & 37 nM respectively. These series of compounds dose dependently inhibited CD4$^+$T cell pool and exhausted IL-17 release from mouse splenocytes.

Figure 5:
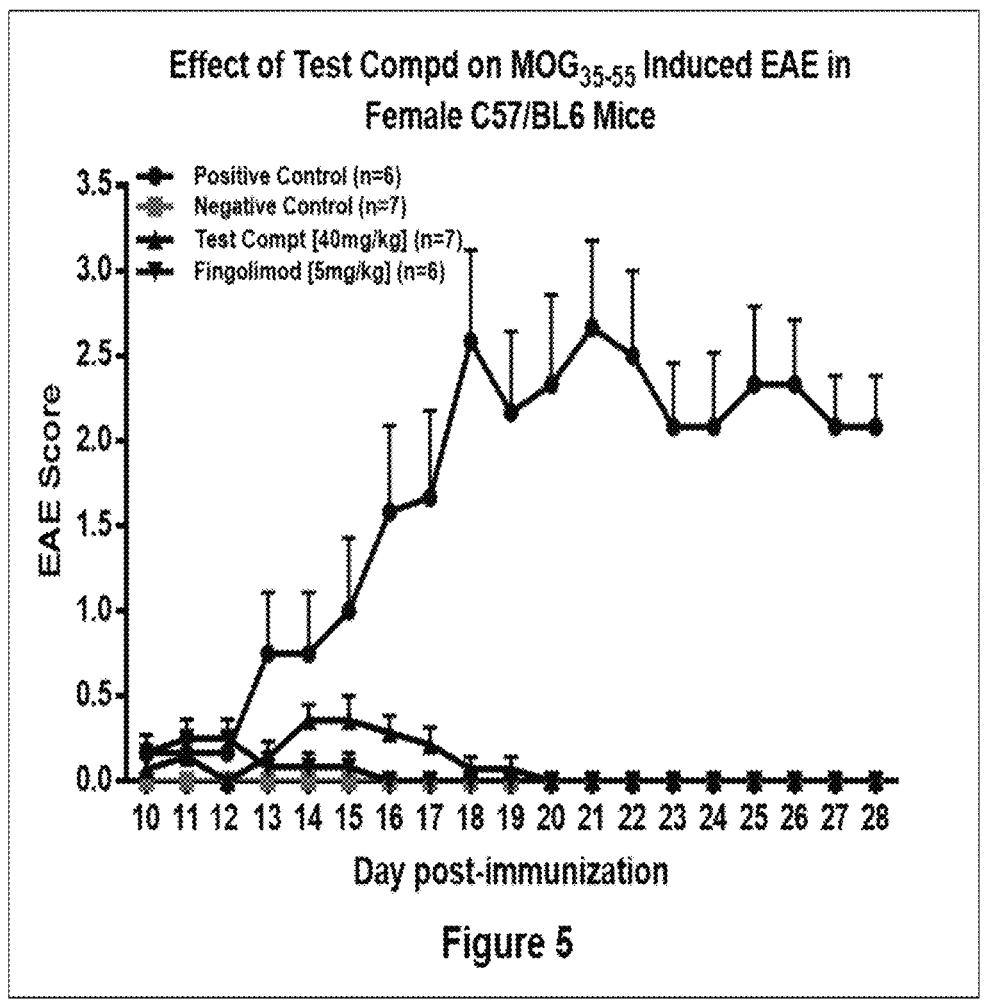
FIG. 5: Effect of Test Compound on MOG35-55 Induced EAE in Female C57/BL6 Mice.
Figure 6:
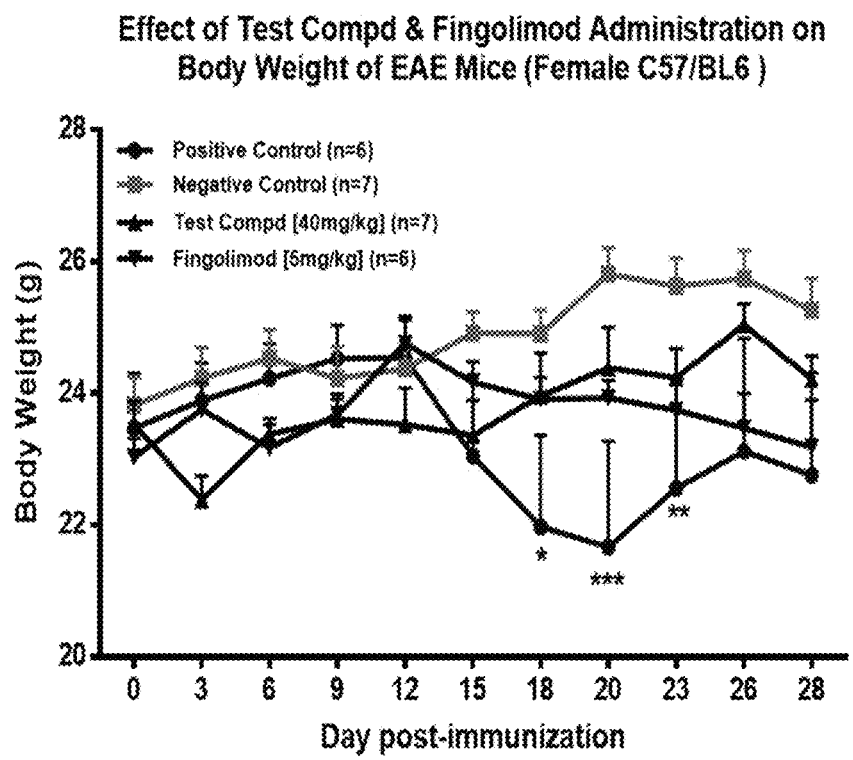
FIG. 6: Effect of Test Compound & Fingolimod Administration on Body Weight of EAE Mice (Female C57/BL6).

Example 82: Efficacy of dihydro-1H-inden-1-one class analogues in $MOG_{35-55}$ Induced EAE in Female C57BL/6 Mice To establish the in vivo proof-of-concept in chronic mouse MOG EAE model, the lead dihydro-1H-inden-1-one class analogues was administered orally for QD 28 days as a prophylactic treatment where the disease severity was successfully controlled for dihydro-1H-inden-1-one class analogues and control Fingolimod (FIG. 5). The cumulative EAE scores (Scale: 0-3.5) of 0.2, 0.0, 0.4, 0.7, 0.1 on days 9-18 (p=0.001) and reached to 0 on day 18 to until day $28^{th}$ (p=0.001) for dihydro-1H-inden-1-one class analogues and similar scores observed for Fingolimod as well (FIG. 6). The results are striking for this study, whereas the positive control (disease mice) with an EAE score of >3.0 (>95% disease incidence). The dihydro-1H-inden-1-one class treated mice was well tolerated through put the study with optimal body conditions and had no signs of Clinical Chemistry changes or toxicity events observed throughout the study. All the mice in the treatment groups are similar body weights to that of vehicle treated group. Oral dihydro-1H- inden-1-one class analogues treatment from this study provided a compelling evidence of its RORγt antagonistic activity, translating cellular efficacy in to in vivo further supports these series of compounds for MS and other indications claimed. All references are incorporated by reference herein in their entireties.

REFERENCES

1. Kipp, M. van der Valk, P. Amor, S. (2012). Pathology of multiple sclerosis. CNS Neurol Disord Drug Targets 11(5): 506-517. PMID: 12858058.
2. Kieseier, B. C. and H. P. Hartung (2003). Multiple paradigm shifts in multiple sclerosis. Curr Opin Neurol 16(3): 247-252. PMID: 22583433.
3. Steinman, L. (2013). Multiple sclerosis: a coordinated immunological attack against myelin in the central nervous system. Cell 85, 299-302. PMID: 8616884
4. Pottgen, J. Dziobek, I. Reh, S. Heesen, C. Gold, S. M. (2013). Impaired social cognition in multiple sclerosis." J Neurol Neurosurg Psychiatry 84(5): 523-528. PMID: 23315621.
5. Kallaur, A. P. Oliveira, S. R. Colado Simao, A. N. Delicato de Almeida, E. R. Kaminami Morimoto, H. Lopes, J. de Carvalho Jennings Pereira, W. L. Marques Andrade, R. Muliterno Pelegrino, L. Donizete Borelli, S. Kaimen-Maciel, D. R. Reiche, E. M. 2013). Cytokine profile in relapsing remitting multiple sclerosis patients and the association between progression and activity of the disease. Mol Med Rep 7(3): 1010-1020. PMID: 23292766
6. Glass, C. K. and K. Saijo (2010). Nuclear receptor transrepression pathways that regulate inflammation in macrophages and T cells. Nat Rev Immunol 10(5): 365-376. PMID: 20414208
7. Lopez-Diego, R. S. and H. L. Weiner (2008). Novel therapeutic strategies for multiple sclerosis—a multifaceted adversary. Nat Rev Drug Discov 7(11): 909-925. PMID: 18974749.
8. Ali, R. Nicholas, R. S. Muraro, P. A. (2013). Drugs in development for relapsing multiple sclerosis. Drugs 73(7): 625-650. PMID: 23609782
9. The M S Disease-Modifying Medications, General Information. 2013 Multiple Sclerosis Society and ms-coalition.org/EmergingTherapies.
10. Vermersch, P. Benrabah, R. Schmidt, N. Zephir, H. Clavelou, P. Vongsouthi, C. Dubreuil, P. Moussy, A. Hermine, O. (2012). Masitinib treatment in patients with progressive multiple sclerosis: a randomized pilot study. BMC Neurol 12: 36. PMID: 22691628
11. Ivanov., I I, McKenzie, B. S. Zhou, L. Tadokoro, C. E. Lepelley, A. Lafaille, J. J. Cua, D. J. Littman, D. R. (2006). The orphan nuclear receptor RORgammat directs the differentiation program of proinflammatory IL-17+T helper cells. Cell 126(6): 1121-1133. PMID: 16990136
12. Wang, Y. Kumar, N. Solt, L. A. Richardson, T. I. Helvering, L. M. Crumbley, C. Garcia-Ordonez, R. D. Stayrook, K. R. Zhang, X. Novick, S. Chalmers, M. J. Griffin, P. R. Burris, T. P. (2010). Modulation of retinoic acid receptor-related orphan receptor alpha and gamma activity by 7-oxygenated sterol ligands. Journal of Biological Chemistry 285(7): 5013-5025. PMID: 19965867
13. Kryczek, I, Wei, S, Zou, L, Altuwaijri, S, Szeliga, W, Kolls, J, Chang, A, Zou, W. (2007). Cutting edge: Th17 and regulatory T cell dynamics and the regulation by IL-2 in the tumor microenvironment. J. Immunol. 178, 6730-6733. PMID: 17513719
14. Hu, Y. Shen, F. Crellin, N. K. Ouyang, W. (2011). The IL-17 pathway as a major therapeutic target in autoimmune diseases. Ann N Y Acad Sci 1217: 60-76. PMID: 21155836
15. Tesmer, L. A. Lundy, S. K. Sarkar, S. Fox, D. A. (2008). Th17 cells in human disease. Immunol Rev 223: 87-113. PMID: 18613831
16. Rauen, T. Juang, Y. T. Hedrich, C. M. Kis-Toth, K. Tsokos, G. C. (2012). A novel isoform of the orphan receptor RORgammat suppresses IL-17 production in human T cells. Genes Immun 13(4): 346-350. PMID: 22237416
17. Kamenecka, T. M, Lyda, B, Ra, M, Chang, M. R, Griffin, P. R. (2013) Synthetic modulators of the retinoic acid receptor-related orphan receptors. Med. Chem. Commun. 4, 764-776
18. Fragment-Field Drug Design (FFDD) (2011), Proprietary empirical driven fragment fields, Arrien Pharmaceuticals, USA.
19. www.clinicaltrials.gov/multiple sclerosis
20. (a) Kumar, N. Lyda, B. Chang, M. R. Lauer, J. L. Solt, L. A. Burris, T. P. Kamenecka, T. M. Griffin, P. R. (2012). Identification of SR2211: a potent synthetic RORgamma-selective modulator. ACS Chem Biol 7(4): 672-677. PMID: 22292739. (b) Kumar, N. Solt, L. A. Conkright, J. J. Wang, Y. Istrate, M. A. Busby, S. A. Garcia-Ordonez, R. D. Burris, T. P. Griffin, P. R. (2010). The benzenesulfoamide T0901317 [N-(2,2,2-trifluoroethyl)-N-[4-[2,2,2-trifluoro-1-hydroxy-1-(trifluoromethyl)ethyl]phenyl] benzenesulfonamide] is a novel retinoic acid receptor-related orphan receptor-alpha/gamma inverse agonist. Molecular Pharmacology 77(2): 228-236. PMID: 19887649. (c) Khan, P. M. El-Gendy Bel, D. Kumar, N. Garcia-Ordonez, R. Lin, L. Ruiz, C. H. Cameron, M. D. Griffin, P. R. Kamenecka, T. M. (2013). Small molecule amides as potent ROR-gamma selective modulators. Bioorganic & Medicinal Chemistry Letters 23(2): 532-536. PMID: 23232056 (d) Huh, J. R, Englund, E. E, Wang, H, Huang, R, Huang, P, Rastinejad, F, Inglese, J, Austin, C. P, Ronald L. Johnson, Huang, W, Littman, D. R. (2013) Identification of Potent and Selective Diphenylpropanamide RORγ Inhibitors. ACS Med. Chem. Lett. 4 (1), 79-84.
21. Sheridan, C. (2013). Footrace to clinic heats up for T-cell nuclear receptor inhibitors. Nature Biotechnology 31(5): 370. PMID: 23657373
22. Solt, L. A., Kumar, N., Nuhant, P., Wang, Y, Lauer, J. L., Liu, J., Istrate, M. A., Kamenecka, T. M., Roush, W. R., Vidovic, D., Schurer, S. C., Xu, J., Wagoner, G., Drew, P. D., Griffin, P. R., and Burris, T. P. (2011) Suppression of TH17 differentiation and autoimmunity by a synthetic ROR ligand. Nature 472, 491-494. PMID: 21499262
23. Ransohoff, R. M. (2012). Animal models of multiple sclerosis: the good, the bad and the bottom line. Nat Neurosci 15(8): 1074-1077. PMID: 22837037
24. (a) Jin, L. Martynowski, D. Zheng, S. Wada, T. Xie, W. Li, Y. (2010). Structural basis for hydroxycholesterols as natural ligands of orphan nuclear receptor RORgamma. Mol Endocrinol 24(5): 923-929.
25. Fujita-Sato, S., Ito, S., Isobe, T., Ohyama, T., Wakabayashi, K., Morishita, K., Ando, O., and Isono, F. (2011) Structural basis of digoxin that antagonizes RORgamma t receptor activity and suppresses Th17 cell differentiation and interleukin (IL)-17 production. J. Biol. Chem. 286, 31409-31417. PMID: 21733845
26. Xiao S, Yosef N, Yang J, Wang Y, Zhou L, Zhu C, Wu C, Baloglu E, Schmidt D, Ramesh R, Lobera M, Sundrud M. S, Tsai P. Y, Xiang Z, Wang J, Xu Y, Lin X, Kretschmer K, Rahl P. B, Young R. A, Zhong Z, Hafler D. A, Regev A, Ghosh S, Marson A, Kuchroo V. K. (2014) Small-molecule RORγt antagonists inhibit T helper 17 cell transcriptional network by divergent mechanisms. Immunity. 40 (4): 477-489. PMID: 24745332

27. Wingerchuk D. M, Carter J. L. (2014) Multiple sclerosis: current and emerging disease-modifying therapies and treatment strategies. Mayo Clin Proc. 89 (2):225-240. PMID: 24485135

28. Zhang W, Zhang J, Fang L, Zhou L, Wang S, Xiang Z, Li Y, Wisely B, Zhang G, An G, Wang Y, Leung S, Zhong Z. (2012) Increasing human Th17 differentiation through activation of orphan nuclear receptor retinoid acid-related orphan receptor γ (RORγ) by a class of aryl amide compounds. Mol Pharmacol. 82 (4):583-590. PMID: 22700697

29. Jacob S. L, Daniel J. Cua. (2014) The Emerging Landscape of RORγt Biology. Immunity. 40 (4), 17, 451-452.

30. Skepner J, Ramesh R, Trocha M, Schmidt D, Baloglu E, Lobera M, Carlson T, Hill J, Orband-Miller L A, Barnes A, Boudjelal M, Sundrud M, Ghosh S, Yang J. (2014) Pharmacologic inhibition of RORγt regulates Th17 signature gene expression and suppresses cutaneous inflammation in vivo. J Immunol. 192(6):2564-2575. PMID: 24516292

31. Isono F, Fujita-Sato S, Ito S. (2014) Inhibiting RORγt/Th17 axis for autoimmune disorders. Drug Discov Today. 19 (8): 1205-1211. PMID: 24792721

What is claimed is:

1. A method of synthesizing a compound of formula (I):

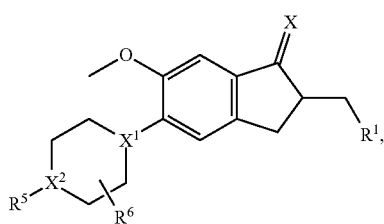
(I)

or a pharmaceutically acceptable salt thereof, wherein:
X is O or S;
$R^1$ is

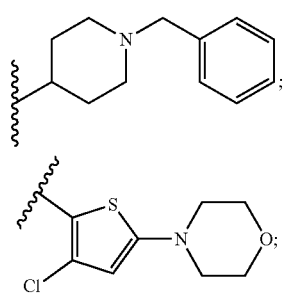

a $C_{1-4}$alkyl optionally substituted with 1-6 independent halo substituents; or a phenyl, pyridinyl, or pyrazolyl, each optionally substituted with 1-5 independent halo, trifluoromethyl, (trifluoromethyl)thio,

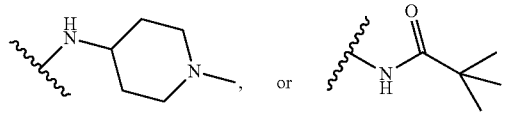

substituents;
$X^1$ is CH or N;
$X^2$ is CH, N or O, wherein at least one of $X^1$ and $X^2$ is not CH;
$R^5$ is absent, halo, or $C_{0-4}$alkyl;
and $R^6$ is halo or $C_{0-4}$alkyl,
the method comprising
reducing a compound of formula (1):

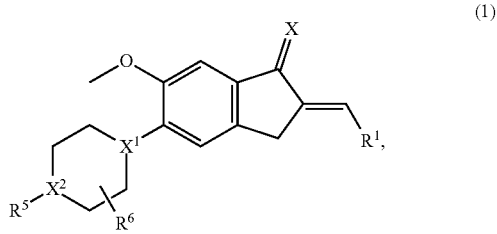
(1)

wherein X, $R^1$, $R^5$, $R^6$, $X^1$ and $X^2$ are the same as formula (I).

2. The method of claim 1, wherein the method further comprises reacting a compound of formula (2):

(2)

with a compound of formula (3):

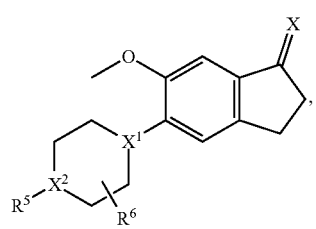
(3)

and
obtaining a compound of formula (1),
wherein X, $R^1$, $R^5$, $R^6$, $X^1$ and $X^2$ are the same as formula (I).

3. The method of claim 1, wherein X is O.
4. The method of claim 2, wherein X is O.
5. The method of claim 3, wherein $R^1$ is phenyl, pyridinyl, or pyrazolyl, optionally substituted with 1-5 independent halo, trifluoromethyl, (trifluoromethyl)thio,

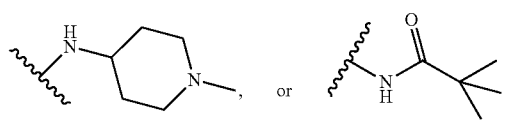

substituents.

6. The method of claim 1, wherein $X^1$ is N.
7. The method of claim 5, wherein $X^1$ is N.
8. The method of claim 1, wherein $X^2$ is O.
9. The method of claim 7, wherein $X^2$ is O.
10. The method of claim 1, wherein $R^6$ is $C_{0-4}$alkyl.
11. The method of claim 9, wherein $R^6$ is $C_{0-4}$alkyl.
12. The method of claim 1, wherein $X^1$ is N; $X^2$ is O; $R^5$ is absent; and $R^6$ is $C_0$alkyl.
13. The method of claim 1, wherein $R^1$ is optionally substituted pyridinyl.
14. The method of claim 11, wherein $R^1$ is optionally substituted pyridinyl.
15. The method of claim 14, wherein pyridinyl is substituted with one trifluoromethyl substituent.
16. The method of claim 1, wherein the compound of formula (1) is:

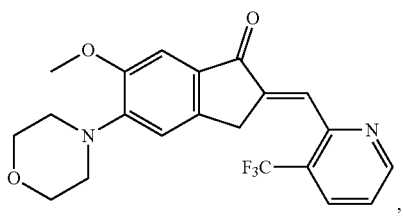 [SMILES: COc1cc2c(cc1N1CCOCC1)C/C(=C\c1ncccc1C(F)(F)F)C2=O]

and the reduction is performed by hydrogenation over palladium on charcoal.

17. The method of claim 2, wherein the compound of formula (3) is:

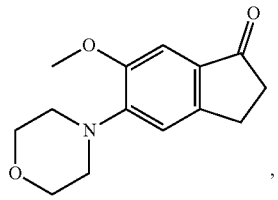 [SMILES: COc1cc2c(cc1N1CCOCC1)CCC2=O]

and the method further comprises reacting a compound of formula (4):

(4)

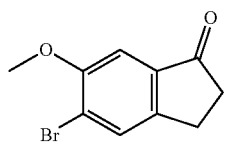

with morpholine.

* * * * *